United States Patent
Huang et al.

(10) Patent No.: US 8,592,383 B2
(45) Date of Patent: Nov. 26, 2013

(54) CYCLOALKYL-FUSED TETRAHYDROQUINOLINES AS CRTH$_2$ RECEPTOR MODULATORS

(75) Inventors: Xianhai Huang, Warren, NJ (US);
Jason Brubaker, Cambridge, MA (US);
Scott L. Peterson, Salem, MA (US);
John W. Butcher, Berlin, MA (US);
Joshua T. Close, Franklin, MA (US);
Michelle Martinez, Medford, MA (US);
Rachel Nicola MacCoss, Oxford (GB);
Joon O. Jung, Newton, MA (US);
Phieng Siliphaivanh, Newton, MA (US); Hongjun Zhang, Newton, MA (US); Robert G. Aslanian, Rockaway, NJ (US); Purakkattle Johny Biju, Piscataway, NJ (US); Li Dong, Roselle Park, NJ (US); Ying Huang, Berkeley Heights, NJ (US); Kevin D. McCormick, Basking Ridge, NJ (US); Anandan Palani, Bridgewater, NJ (US); Ning Shao, Watchung, NJ (US); Wei Zhou, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/523,354

(22) Filed: Jun. 14, 2012

(65) Prior Publication Data
US 2012/0329743 A1    Dec. 27, 2012

Related U.S. Application Data

(60) Provisional application No. 61/498,345, filed on Jun. 17, 2011.

(51) Int. Cl.
| | |
|---|---|
| *C07D 221/16* | (2006.01) |
| *C07D 401/10* | (2006.01) |
| *C07D 413/10* | (2006.01) |
| *A61K 31/473* | (2006.01) |
| *A61K 31/501* | (2006.01) |
| *A61K 31/506* | (2006.01) |
| *A61K 31/5377* | (2006.01) |
| *A61K 31/706* | (2006.01) |
| *A61P 11/00* | (2006.01) |
| *A61P 11/06* | (2006.01) |
| *A61P 37/08* | (2006.01) |
| *C07H 15/26* | (2006.01) |

(52) U.S. Cl.
USPC .............. 514/32; 514/210.18; 514/232.8; 514/252.04; 514/256; 514/290; 536/17.4; 544/126; 544/238; 544/335; 546/79

(58) Field of Classification Search
None
See application file for complete search history.

(56) References Cited

U.S. PATENT DOCUMENTS

| | | | |
|---|---|---|---|
| 5,925,527 A | 7/1999 | Hayes et al. | |
| 6,140,343 A | 10/2000 | DiNinno et al. | |
| 7,037,919 B1 | 5/2006 | Hanada et al. | |
| 7,696,222 B2 | 4/2010 | Wang | |
| 2004/0082609 A1 | 4/2004 | Ghosh et al. | |
| 2004/0180917 A1 | 9/2004 | Husson et al. | |
| 2005/0038070 A1 | 2/2005 | Inman et al. | |
| 2005/0256158 A1 | 11/2005 | Ghosh et al. | |
| 2009/0270414 A1 | 10/2009 | Fecher et al. | |
| 2011/0172263 A1 | 7/2011 | Colucci et al. | |
| 2011/0178115 A1 | 7/2011 | Leblanc et al. | |
| 2011/0201641 A1 | 8/2011 | Wang | |

FOREIGN PATENT DOCUMENTS

| | | |
|---|---|---|
| WO | 02/94840 A2 | 11/2002 |
| WO | 2004/032848 A2 | 4/2004 |
| WO | 2004/035541 A1 | 4/2004 |
| WO | 2004/035543 A1 | 4/2004 |
| WO | 2005/007094 A2 | 1/2005 |
| WO | 2005/007672 A2 | 1/2005 |
| WO | 2005/100321 A1 | 10/2005 |
| WO | 2012/051036 A1 | 4/2012 |
| WO | 2012/087861 A1 | 6/2012 |
| WO | 2012/087872 A1 | 6/2012 |

OTHER PUBLICATIONS

Liu, et al., "Tetrahydroquinoline derivatives as CRTH2 antagonists," Bioorganic & Medicinal Chemistry Letters 19 (2009), pp. 6840-6844.
International Search Report corresponding to PCT/US2012/042336, issued Aug. 27, 2012.

*Primary Examiner* — Janet Andres
*Assistant Examiner* — Timothy R Rozof
(74) *Attorney, Agent, or Firm* — Eric A. Meade; Valerie J. Camara

(57) ABSTRACT

The invention provides certain cycloalkyl-fused tetrahydroquinolines of the Formula (I),

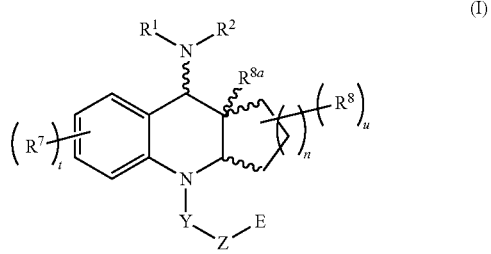

and their pharmaceutically acceptable salts and esters, wherein $R^1$, $R^2$, $R^7$, $R^8$, $R^{8a}$, E, Y, Z, n, u, and t are as defined herein. The invention also provides pharmaceutical compositions comprising such compounds, and methods of using the compounds for treating diseases or conditions associated with uncontrolled or inappropriate stimulation of CRTH$_2$ function.

48 Claims, 1 Drawing Sheet

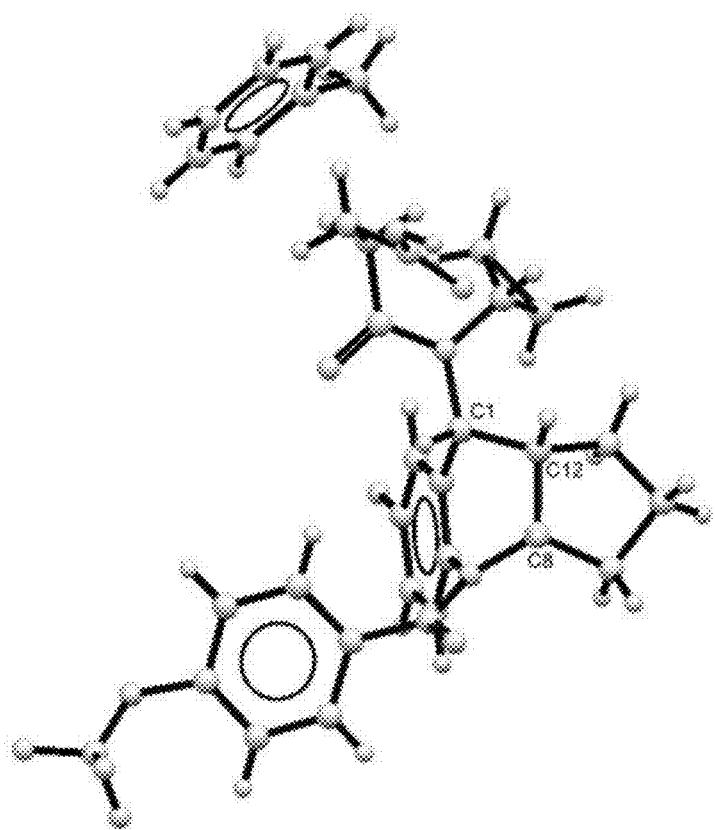

CYCLOALKYL-FUSED TETRAHYDROQUINOLINES AS CRTH$_2$ RECEPTOR MODULATORS

CROSS-REFERENCE TO RELATED APPLICATIONS

This application claims the benefit under 35 U.S.C. 119(e) of U.S. Provisional Application No. 61/498,345, filed Jun. 17, 2011.

FIELD OF THE INVENTION

The present invention relates to certain cycloalkyl-fused tetrahydroquinolines of the Formula (I) (also referred to herein as the "compounds of the Formula (I)"), compositions comprising such compounds, and methods of using such compounds for treating an inflammatory disease, or other disorder mediated by the chemoattractant receptor-homologous molecule expressed on T-helper-type-2 cells (CRTH$_2$).

BACKGROUND OF THE INVENTION

Prostaglandin D$_2$ (PGD$_2$) belongs to a class of chemical mediators which cells synthesize in response to stimuli, such as local tissue damage or hormonal stimuli, or by cellular activation pathways. Cells synthesize PGD$_2$ from arachidonic acid by cyclooxygenase and other specific synthases in the pathway.

Upon stimulation, mast cells release PGD$_2$ in major amounts and this release plays a major role in the etiology of respiratory disease, such as asthma and congestion. PGD$_2$ achieves this effect by binding with either of two G-protein coupled receptors, which are the D-prostanoid (DP) receptor and the CRTH$_2$ receptor. TH-2 cells, eosinophils, and basophils express the CRTH$_2$ receptor, which mediates the chemoattractant effect of PGD$_2$.

Scientific studies support a clear role for PGD$_2$ in an allergic inflammatory response. PGD$_2$ is found at high levels in the bronchoalveolar lavage of asthmatics. Inhalation of PGD$_2$ enhances eosinophilic and lymphocytic airway inflammation in allergic animal models. Evidence obtained by studying CRTH$_2$ knockout mice demonstrates that PGD$_2$ achieves this enhancement by binding to the CRTH$_2$ receptor. Hence, CRTH$_2$ receptor antagonists would be expected to reduce the allergic inflammatory response caused by PGD$_2$, and these compounds would be useful in the treatment or prevention of allergic/immune disorders.

Current drugs of choice for the treatment of chronic inflammatory airway disease, such as asthma or COPD, are synthetic glucocorticoids; examples of these compounds currently indicated for treating these disorders include fluticasone and mometasone. The difficulty with treating patients with this class of compounds is that the compounds possess a number of systemic side-effects; these include adrenal suppression, altered bone metabolism and growth suppression in children. These side effects limit the dose that can be administered on a daily basis to the patient. While a non-steroidal class of therapeutics that inhibit bronchoconstriction exists (CysLT$_1$ antagonists), this class of compounds has limited efficacy in achieving the endpoints of reducing inflammatory and improving in lung function when compared to the glucocorticoids. Therefore, a therapeutic that combines the efficacy of inhaled glucocorticoids without the side effects would be advantageous.

SUMMARY OF THE INVENTION

The present invention provides novel compounds of the Formula (I) as described below and pharmaceutically acceptable salts or esters thereof as well as pharmaceutical compositions containing them. The compounds of Formula (I) are useful in the treatment and prevention of diseases and disorders associated with uncontrolled or inappropriate stimulation of CRTH$_2$ function such as asthma.

BRIEF DESCRIPTION OF THE FIGURE

FIG. 1 shows a perspective view calculated from the crystallographic coordinates of a single crystal X-ray of a monotoluene solvate of 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoic acid, compound 17.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or disorder associated with uncontrolled or inappropriate stimulation of CRTH$_2$ function. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to disease or disorder associated with uncontrolled or inappropriate stimulation of CRTH$_2$ function, refers to reducing the likelihood of disease or disorder associated with uncontrolled or inappropriate stimulation of CRTH$_2$ function.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms (C$_1$-C$_6$ alkyl), 1 to 4 carbon atoms (C$_1$-C$_4$ alkyl), or from 1 to 3 carbon atoms (C$_1$-C$_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)$ $CH_2$—. In one embodiment, an alkylene group has from 1 to about 6 carbon atoms ($C_1$-$C_6$ alkylene). In another embodiment, an alkylene group has from 1 to 3 carbon atoms $C_1$-$C_3$ alkylene). In another embodiment, an alkylene group is branched. In another embodiment, an alkylene group is linear. In one embodiment, an alkylene group is —$CH_2$—. The term "$C_1$-$C_3$ alkylene" refers to an alkylene group having from 1 to 3 carbon atoms. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to 4 carbon atoms. Non-limiting examples of alkenyl groups include ethenyl, propenyl, n-butenyl, 3-methylbut-2-enyl, n-pentenyl, octenyl and decenyl. The term "$C_2$-$C_6$ alkenyl" refers to an alkenyl group having from 2 to 6 carbon atoms. The term "$C_2$-$C_4$ alkenyl" refers to an alkenyl group having from 2 to 4 carbon atoms. Unless otherwise indicated, an alkenyl group is unsubstituted.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to 10 ring carbon atoms. In another embodiment, a cycloalkyl contains from 3 to 7 ring atoms ($C_3$-$C_7$ cycloalkyl). In another embodiment, a cycloalkyl contains from 3 to 6 ring atoms ($C_3$-$C_7$ cycloalkyl). In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. Unless otherwise indicated, a cycloalkyl group is unsubstituted.

The term "halo," as used herein, means —F, —Cl, —Br or —I. In one embodiment, a halo group is —F or —Cl. In another embodiment, a halo group is —F.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group is substituted with from 1 to 3 F atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocyclyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocyclyl group can be joined via a ring carbon or ring nitrogen atom. In one embodiment, a heterocyclyl group is monocyclic and has from about 3 to about 7 ring atoms. In another embodiment, a heterocyclyl group is monocyclic has from about 4 to about 7 ring atoms. In another embodiment, a heterocyclyl group is bicyclic and has from about 7 to about 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. The term "heterocyclyl" also encompasses a heterocyclyl group, as defined above, which is fused to an aryl (e.g., benzene) or heteroaryl ring. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms. Unless otherwise indicated, a heterocyclyl group is unsubstituted.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. In specific embodiments of the ring system, from 1 to 4 of the ring atoms are independently O, S, or N, and the remainder of the ring atoms are carbon atoms. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. Unless otherwise indicated, a heterocyclenyl group is unsubstituted. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like."

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

Esters of the compounds of the invention are also contemplated herein. For example, if a compound of Formula (I) contains a carboxylic acid functional group, a prodrug can comprise an ester formed by the replacement of the hydrogen atom of the acid group with a group such as, for example, $(C_1-C_8)$alkyl, $(C_1-C_6)$alkoxymethyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like. Such esters may antagonize $CRTH_2$ themselves and/or can function as prodrugs of the corresponding carboxylic acids. In one embodiment, the esters are $C_1-C_6$ alkyl esters (e.g., $C_1-C_3$ alkyl esters). In another embodiment, the esters are $C_1-C_3$ alkoxymethyl esters (e.g., methoxymethyl esters).

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, e.g., such as the supercritical fluid chromatography, which methods are well known in the art. Alternatively, any enantiomer of a compound may be obtained by stereoselective synthesis using optically pure starting materials or reagents of known configuration by methods well known in the art.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Compounds of the Invention

In embodiment no. 1, the present invention provides a compound of the Formula (I):

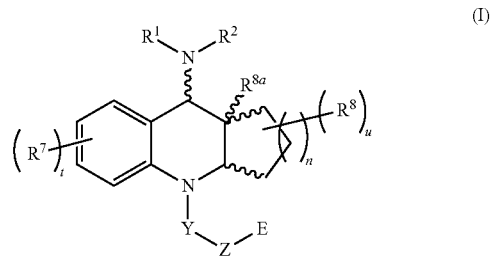

or a pharmaceutically acceptable salt or ester thereof, wherein $R^1$ is (i) H, (ii) $C_1$-$C_4$ alkyl, (iii) $C_2$-$C_4$ alkenyl, (iv) $C_3$-$C_7$ cycloalkyl, (v) —($C_1$-$C_3$ alkylene)-$R^9$ wherein $R^9$ is $C_3$-$C_7$ cycloalkyl, phenyl or a 5- to 6-membered heteroaryl containing 1 to 2 heteroatoms selected from the group consisting of N, O, and S, (vi) phenyl, (vii) —C(O)—$R^5$, wherein $R^5$ is $C_1$-$C_6$ alkyl, $C_3$-$C_6$ cycloalkyl, phenyl, (viii) or a group of the formula

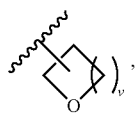

wherein v is 1, 2, or 3;
R² is
(i) -Q-W—V, wherein
Q is —C(O)—, —C(O)O—, —C(O)N(H)—, —C(O)N(C₁-C₆ alkyl)-, —CH₂—, or —S(O)₂—;
W is
(a) C₁-C₈ alkylene, wherein said alkylene of W is unsubstituted or substituted by 1 to 2 fluoro;
(b) —CH=CH—, or
(c) a phenylene of the formula

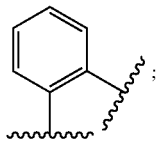

wherein said phenylene is unsubstituted or substituted by 1 to 2 halo;
V is
(a) —CO₂H, or
(b) tetrazolyl, or
(c) a group of the formula

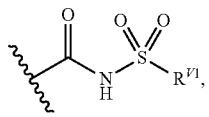

wherein R^{V1} is selected from the group consisting of C₁-C₆ alkyl, C₃-C₆ cycloalkyl, and phenyl;
(ii) -M-CO₂H, wherein
M is

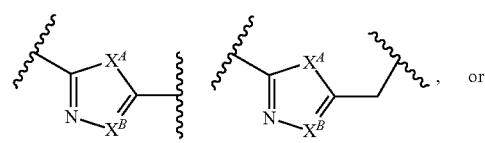

wherein w is 0, 1, 2, or 3;
X^A is S or O;
X^B is N or C(H);
with the proviso that when R¹ is —C(O)—R⁵, then R² is —CH₂—W—V;

Y is —C(O)—, —S(O)₂—, or a group of the formula

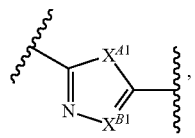

wherein X^{A1} is S or O; and
X^{B1} is N or C(H);
Z is
(i) absent,
(ii) —(C₁-C₆) alkylene-,
(iii) —O—,
(iv) —O—(C₁-C₆ alkylene)-, wherein said —O—(C₁-C₆ alkylene)- of Z is unsubstituted or substituted by 1 to 3 fluoro,
(v) —N(H)—, or
(vi) a group of the formula

wherein r is 1, 2, 3, or 4;
E is
(i) phenyl,
(ii) naphthyl,
(iii) tetrahydronaphthyl,
(iv) indanyl,
(v) 5- to 10-membered mono- or bicyclic heteroaryl containing one to three heteroatoms selected from the group consisting of N, O, and S,
(vi) 5- to 10-membered mono- or bicyclic heterocyclenyl containing one to three heteroatoms selected from the group consisting of N, O, and S,
wherein said phenyl, napthyl, tetrahydronapthyl, indanyl, 5- to 10-membered heteroaryl, or 5- to 10-membered heterocyclenyl of E is unsubstituted or substituted by one to three R⁴ moieties, wherein
each R⁴ is selected from the group consisting of C₁-C₆ alkyl, C₁-C₃ alkoxy, —CN, halo, hydroxyl, C₁-C₃ fluoroalkyl, —O—(C₁-C₃ fluoroalkyl), —S—(C₁-C₃ alkyl), —S—(C₁-C₃ fluoroalkyl), C₃-C₇ cycloalkyl, R^{4a}, —O—R^{4a}, or 5- to 6-membered heterocyclyl containing 1 or 2 heteroatom selected from the group consisting of N, O, and S;
R^{4a} is phenyl or a 5 to 6-membered heteroaryl ring containing one to two heteroatoms selected from the group consisting of N, O, and S;
wherein R^{4a} is unsubstituted or substituted by one to two moieties independently selected from the group consisting of C₁-C₆ alkyl, C₁-C₃ alkoxy, halo, —CN, C₁-C₃ fluoroalkyl, —O—(C₁-C₃ fluoroalkyl), —S—(C₁-C₃ fluoroalkyl), and —SO₂—(C₁-C₃ alkyl),
or, wherein two R⁴ moieties are substituted on vicinal carbon atoms of E, the two R⁴ moieties together with the carbon atoms to which they are attached form a dioxolane ring;
(vii) C₃-C₇ cycloalkyl, or
(viii) C₁-C₆ alkyl;

n is 0, 1, or 2;

each occurrence of $R^7$ is independently halo, $C_1$-$C_3$ fluoroalkyl, hydroxy($C_1$-$C_3$ alkyl), —CN, phenyl, or a 5- to 6-membered heteroaryl containing 1 to 2 heteroatoms selected from the group consisting of N, O, and S, wherein said phenyl or heteroaryl of $R^7$ is independently unsubstituted or substituted with 1 to 2 halo;

t is 0, 1, 2, or 3;

each occurrence of $R^8$ is independently $C_1$-$C_3$ alkyl, $C_2$-$C_3$ alkenyl, or fluoro;

u is 0, 1, or 2; and $R^{8a}$ is H or $C_1$-$C_6$ alkyl.

The compounds of Formulae (IA'), (IA"), (IB), (IB'), (IB"), (IC), (IC'), and (IC") as are described in detail below, are embodiments of the compound of Formula (I).

Described below are further embodiments of the compound of Formula (I).

In embodiment no. 2, $R^1$ is $C_1$-$C_4$ alkyl, $C_3$-$C_7$ cycloalkyl, or —($C_1$-$C_3$ alkylene)-$R^9$, wherein $R^9$ is $C_3$-$C_7$ cycloalkyl, and the remaining variables are as set forth in embodiment no. 1.

In embodiment no. 3, $R^1$ is methyl, ethyl, cyclopropyl, cyclobutyl, —CH$_2$-cyclopropyl, or phenyl, and the remaining variables are as set forth in embodiment no. 1.

In embodiment no 4, $R^2$ is -Q-W—V;

Q is —C(O)—, —C(O)O—, —C(O)N(CH$_3$)— or —CH$_2$—;

W is $C_1$-$C_4$ alkylene; and

V is —CO$_2$H; and the remaining variables are as set forth in any one of embodiment nos. 1-3.

In embodiment no. 5, the group -Q-W—V is selected from the group consisting of:

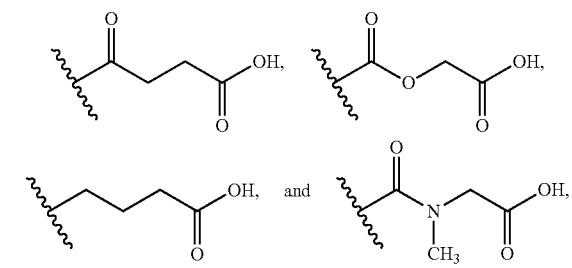

and the remaining variables are as set forth in any one of embodiment nos. 1-3.

In embodiment no. 6, $R^2$ is -Q-W—V;

Q is —C(O)—;

W is $C_1$-$C_4$ alkylene; and

V is a group of the formula

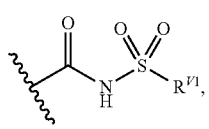

wherein $R^{V1}$ is selected from the group consisting of $C_1$-$C_6$ alkyl and $C_3$-$C_6$ cycloalkyl; and the remaining variables are as set forth in any one of embodiment nos. 1-3.

In embodiment no 7,

W is —CH$_2$CH$_2$—; and $R^{V1}$ is selected from the group consisting of methyl and cyclopropyl; and the remaining variables are as set forth in embodiment no. 6.

In embodiment no. 8, Y is —C(O)— or

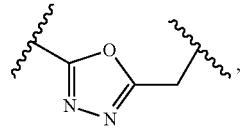 [SMILES: *Cc1nnc(*)o1]

and the remaining variables are as set forth in any one of embodiment nos. 1-7.

In embodiment no. 9, Y is —C(O)—, and the remaining variables are as described are as set forth in any one of embodiment nos. 1-7.

In embodiment no. 10, Y is —Y—Z is selected from the group consisting of —C(O)—, C(O)O—CH$_2$—, —C(O)O—C(H)(CH$_3$)—, and

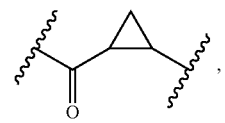 [SMILES: *C(=O)C1CC1*]

and the remaining variables are as set forth in any one of embodiment nos. 1-7.

In embodiment no. 11, E is phenyl, thienyl,

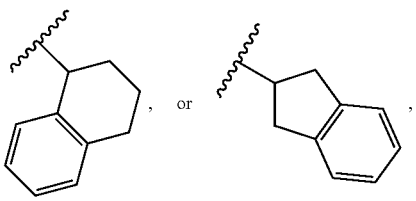

wherein E is unsubstituted or substituted by one to two moieties independently selected from the group consisting of methyl, fluoro, trifluoromethoxy, —O-phenyl, and thiazolyl, and the remaining variables are as set forth in any one of embodiment nos. 1-10.

In embodiment no. 12, said ester is a $C_1$-$C_6$ alkyl carboxylic acid ester, and the remaining variables are as described in any one of embodiment nos. 1-11. For example, when V is —CO$_2$H, said ester can be a methyl carboxylic acid ester, i.e., —CO$_2$CH$_3$, or ethyl carboxylic acid ester, i.e., —CO$_2$CH$_2$CH$_3$.

In embodiment no. 13, each occurrence of $R^7$ is independently chloro or fluoro; and t is 0, 1, or 2, and the remaining variables are as set forth in any one of embodiment nos. 1-12.

In embodiment no. 14, n is 0 (such that a cyclobutyl ring is formed) or 1, and the remaining variables are as set forth in any one of embodiment nos. 1-11.

In embodiment no. 15, n is 0 or 1, $R^8$ is methyl, and the remaining variables are as set forth in any one of embodiment nos. 1-14.

In embodiment no. 16, $R^{8a}$ is H or methyl, and the remaining variables are as set forth in any one of embodiment nos. 1-15.

In embodiment no. 17, $R^{8a}$ is H, and the remaining variables are as set forth in any one of embodiment nos. 1-15.

In embodiment no. 18, the bond joining the substituent $N(R^1)(R^2)$ to the tetrahydroquinoline in the tricyclic core of Formula (I) and the bond on the vicinal carbon atom which joins the cycloalkyl ring to the tetrahydroquinoline are on the same side of the plane of the tetrahydroquinoline, or are cis to each other. In addition, the bonds joining the cycloalkyl ring to the tetrahydroquinoline are on the same side of the plane of the tetrahydroquinoline, or are cis to each other. Such a configuration in the central tricyclic core of the compound of the Formula (I) is referred to hereinafter as a "cis, cis" configuration. The variables are as set forth in any one of embodiment nos. 1-17.

In one embodiment of a compound having a cis,cis configuration, i.e., embodiment no. 19, the compound of the Formula (I) has the Formula (IA')

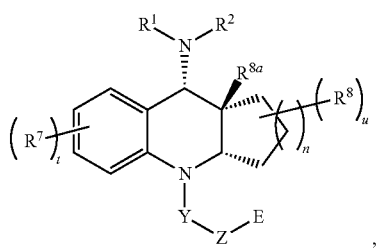
(IA')

and the variables $R^1$, $R^2$, $R^7$, $R^8$, $R^{8a}$, Y, Z, E, n, u, and t are as set forth in any one of embodiment nos. 1-17.

In embodiment no. 20, the compound of the Formula (I) has the Formula (IA")

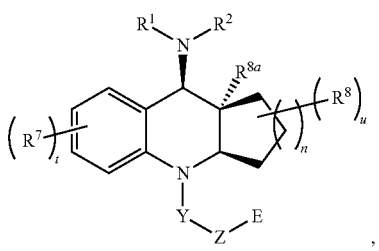
(IA")

and the variables $R^1$, $R^2$, $R^7$, $R^8$, $R^{8a}$, Y, Z, E, n, u, and t are as set forth in any one of embodiment nos. 1-17.

In embodiment no. 21, the present invention provides a compound of the Formula (I) as described in any one of embodiment nos. 1-11 and 13-20, or a pharmaceutically acceptable salt thereof.

In embodiment no. 22, the compound of the Formula (I) has the Formula (IB)

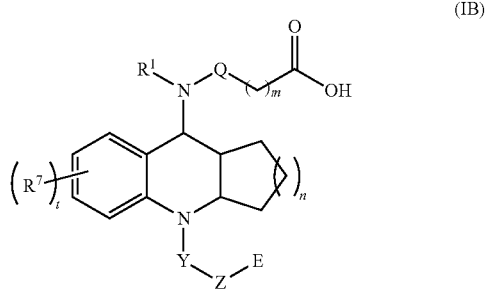
(IB)

wherein
$R^1$ is H, $C_1$-$C_4$ alkyl, cyclopropyl, cyclobutyl, —$CH_2$-cyclopropyl, —$CH_2$-cyclobutyl, or phenyl;
Q is —C(O)—, —C(O)O—, —C(O)N(CH$_3$)—, or —CH$_2$—;
m is 1 or 2;
Y is —C(O)— or

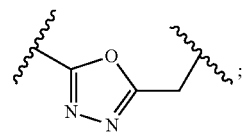 [SMILES: *Cc1nnc(*)o1]

Z is absent, —(C$_1$-C$_3$) alkylene-, —OCH$_2$—, —OCH(CH$_3$)—, or a group of the formula

E is phenyl, thienyl,

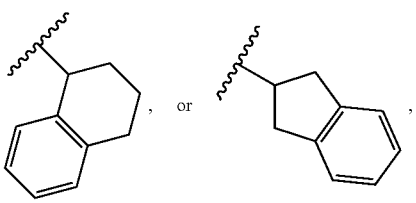 [SMILES: *C1CCCc2ccccc21 ; *C1Cc2ccccc2C1], or wherein E is unsubstituted or substituted by one to two $R^4$ moieties independently selected from the group consisting of C$_1$-C$_3$ alkyl, fluoro, trifluoromethoxy, —S—CF$_3$, —O-phenyl, and thiazolyl;
n is 0 or 1;
each occurrence of $R^7$ is independently chloro or fluoro; and
t is 0, 1, or 2.

In embodiment no. 23, $R^1$ is H, $C_1$-$C_2$ alkyl, cyclopropyl, cyclobutyl, —CH$_2$-cyclopropyl, or —CH$_2$-cyclobutyl, and the remaining variables are as set forth in embodiment no. 22.

In embodiment no. 24, $R^1$ is cyclopropyl and the remaining variables are as set forth in embodiment no. 22.

In embodiment no. 25, the group

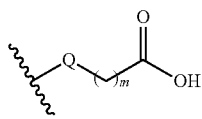

(wherein the truncated bond joins with the nitrogen atom bearing $R^1$) is selected from the group consisting of

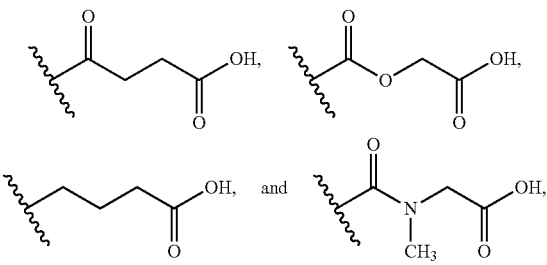

and the remaining variables are as set forth in any one of embodiment nos. 22-24.

In embodiment no. 26, n is 1, and the remaining variables are as set forth in any one of embodiment nos. 22-25.

In embodiment no. 27, n is 0, and the remaining variables are as set forth in any one of embodiment nos. 22-25.

In embodiment no. 28, Y is —C(O)—, Z is absent, and the remaining variables are as set forth in any one of embodiment nos. 22-27.

In embodiment no. 29, Y is —C(O)—, Z is —($C_1$-$C_3$) alkylene-, and the remaining variables are as set forth in any one of embodiment nos. 22-27.

In embodiment no. 30, Y is

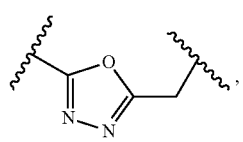 [SMILES: *Cc1nnc(*)o1]

Z is absent, and the remaining variables are as set forth in any one of embodiment nos. 22-27.

In embodiment no. 31, the bond joining the group

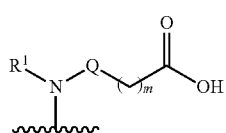

to the central piperidine ring and the bonds joining the cycloalkane ring to the piperidine ring in the compound of Formula (IB) are disposed in a cis, cis configuration, and the variables $R^1$, $R^7$, Q, Y, Z, E, m, n, and t are as set forth in any one of embodiment nos. 22-30. For instance, in one alternative, the compound of the Formula (IB) has the Formula (IB')

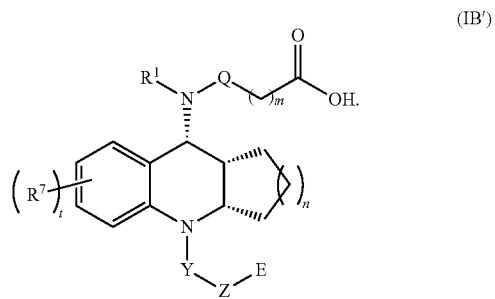

In another alternative, the compound of the Formula (IB) has the Formula (IB")

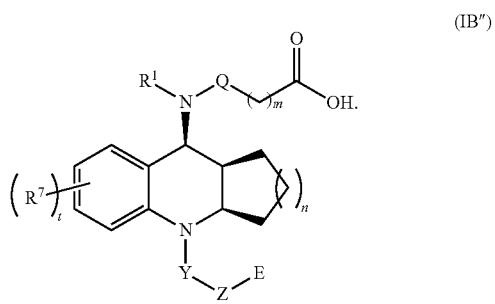

In embodiment no. 32, the compound of the Formula (I) has the Formula (IC)

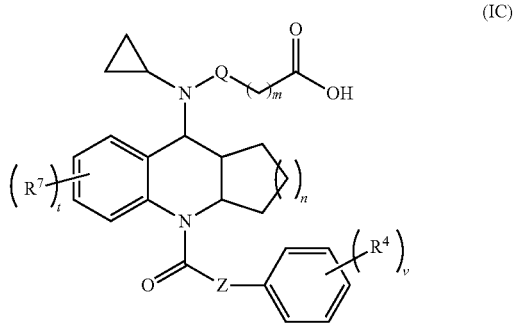

wherein
Q is —C(O)—, —C(O)O—, or —$CH_2$—;
m is 1 or 2;
Z is absent or —$OCH_2$—;
each occurrence of $R^4$ is independently $C_1$-$C_3$ alkyl, fluoro, trifluoromethoxy, or —S—$CF_3$;
v is 0, 1, or 2;
n is 0 or 1;
each occurrence of $R^7$ is independently chloro or fluoro; and
t is 0, 1, or 2.

In embodiment no. 33, the group

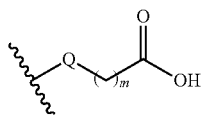

is selected from the group consisting of:

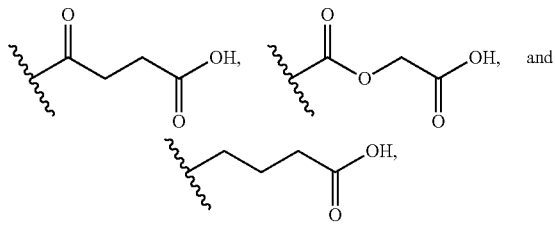

and the remaining variables are as set forth for embodiment no. 32.

In embodiment no. 34, Z is absent and the remaining variables are as set forth for any one of embodiment nos. 32 and 33.

In embodiment no. 35, Z is —OCH$_2$— and the remaining variables are as set forth for any one of embodiment nos. 32 and 33.

In embodiment no. 36, n is 1 and the remaining variables are as set forth for any one of embodiment nos. 32-35.

In embodiment, no. 37, the bond joining the group

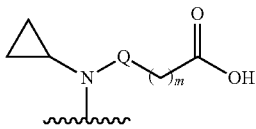

to the central piperidine ring and the bonds joining the cycloalkane ring to the piperidine ring in the compound of Formula (IC) are disposed in a cis, cis configuration, and the variables R$^4$, R$^7$, Q, m, n, t, and v are as described in any one of embodiment nos. 32-36. For instance, in one alternative, the compound of the Formula (IC) has the Formula (IC')

(IC')

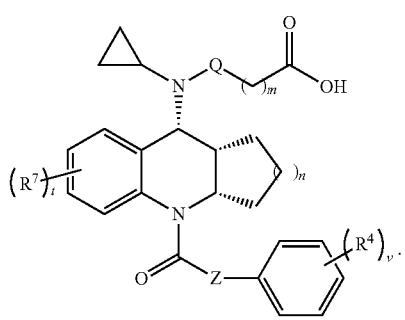

In another alternative, the compound of the Formula (IC) has the Formula (IC")

(IC")

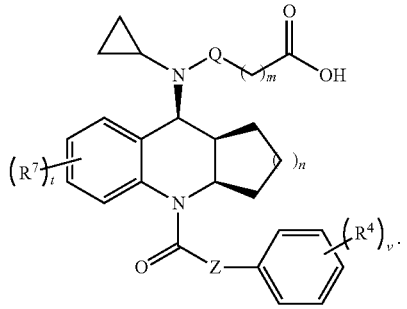

In embodiment no. 38, the compound has the Formula (IC'), wherein
Q is —C(O)— or —CH$_2$—;
m is 2;
R$^7$ is F;
t is 0 or 1
R$^4$ is —OCF$_3$ or halo;
v is 0 or 1; and
Z is absent (such that the carbonyl of Y is directly bonded to the phenyl of E).

In embodiment no. 39, the compound has the Formula (I), wherein
Z is
(i) absent,
(ii) —(C$_1$-C$_6$) alkylene-,
(iii) —O—,
(iv) —O—(C$_1$-C$_6$ alkylene)-,
(v) —N(H)—, or
(vi) a group of the formula

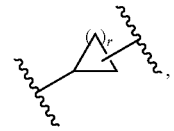

wherein r is 1, 2, 3, or 4;
E is
(i) phenyl,
(ii) naphthyl,
(iii) tetrahydronapthyl,
(iv) indanyl,
(v) 5- to 10-membered mono- or bicyclic heteroaryl containing one to three heteroatoms selected from the group consisting of N, O, and S,
(vi) 5- to 10-membered mono- or bicyclic heterocyclenyl containing one to three heteroatoms selected from the group consisting of N, O, and S,
wherein said phenyl, napthyl, tetrahydronapthyl, indanyl, 5- to 10-membered heteroaryl, or 5- to 10-membered heterocyclenyl of E is unsubstituted or substituted by one to three R$^4$ moieties, wherein
each R$^4$ is selected from the group consisting of C$_1$-C$_6$ alkyl, C$_1$-C$_3$ alkoxy, —CN, halo, C$_1$-C$_3$ fluoroalkyl, —O—(C$_1$-C$_3$ fluoroalkyl), —S—(C$_1$-C$_3$ fluoroalkyl), C$_3$-C$_7$ cycloalkyl, R$^{4a}$, —O—R$^{4a}$, or 5- to 6-membered heterocyclyl containing 1 or 2 heteroatom selected from the group consisting of N, O, and S;
R$^{4a}$ is phenyl or a 5 to 6-membered heteroaryl ring containing one to two heteroatoms selected from the group consisting of N, O, and S;

wherein $R^{4a}$ is unsubstituted or substituted by one to two moieties independently selected from the group consisting of $C_1$-$C_6$ alkyl, $C_1$-$C_3$ alkoxy, halo, —CN, $C_1$-$C_3$ fluoroalkyl, —O—($C_1$-$C_3$ fluoroalkyl), —S—($C_1$-$C_3$ fluoroalkyl), and —$SO_2$—($C_1$-$C_3$ alkyl), or, wherein two $R^4$ moieties are substituted on vicinal carbon atoms of E, the two $R^4$ moieties together with the carbon atoms to which they are attached form a dioxolane ring;

(vii) $C_3$-$C_7$ cycloalkyl, or
(viii) $C_1$-$C_6$ alkyl;

each occurrence of $R^7$ is independently halo, $C_1$-$C_3$ fluoroalkyl, —CN, phenyl, or a 5- to 6-membered heteroaryl containing 1 to 2 heteroatoms selected from the group consisting of N, O, and S, wherein said phenyl or heteroaryl of $R^7$ is independently unsubstituted or substituted with 1 to 2 halo; and the remaining variables are as described in embodiment no. 1.

In embodiment no. 40, the invention also provides any one of the compounds specified in Tables A and B in the Examples section below, which tables include compounds 7, 9, 9A, 9B, 10, 11, 11A, 11B, 11C, 12, 12B, 12C, 12D, 12E, 13, 13C, 13D, 13E, 14, 14C, 14D, 14E, 14F, 14G, 14H, 14i, 14K, 14L, 14N, 14o, 14P, 15, 16, 16A, 16B, 16C, 16D, 16E, 17, 17G, 17H, 17i, 17J, 17K, 17L, 17M, 17N, 17o, 17P, 17Q, 17R, 17S, 17T, 17U, 17V, 17W, 17X, 17Y, 17Z, 17AA, 17AB, 17AC, 17AD, 17AE, 17AF, 17AG, 17AH, 17Ai, 17AJ, 17AK, 17AL, 17AM, 17AN, 17Ao, 17AP, 17AQ, 17AR, 17AS, 17AT, 17AU, 17AV, 17AW, 17AX, 17AY, 17AZ, 17BA, 17BB, 17BC, 17BD, 17BE, 17BF, 17BG, 17BH, 17Bi, 17BJ, 17BK, 17BL, 17BM, 17BN, 17Bo, 17BP, 17BQ, 17BR, 17BS, 17BT, 17BU, 17BV, 17BW, 17BX, 17BY, 17BZ, 17CA, 17CB, 17CC, 17CD, 17CE, 17CF, 17CG, 17CH, 17Ci, 17CJ, 17CK, 17CL, 17CM, 17CN, 17Co, 17CP, 17CQ, 17CR, 17CS, 17CT, 17CU, 17CV, 17CW, 17CX, 17CY, 17CZ, 17DA, 17 DB, 17DC, 17DD, 17DE, 17DF, 17DG, 17DH, 17Di, 17DJ, 17DK, 17DL, 17DN, 17Do, 18, 18C, 18D, 18E, 18F, 18G, 18H, 18i, 18J, 18K, 18L, 18M, 18N, 18o, 18P, 18Q, 18R, 18S, 18T, 19, 20, 21, 21A, 21B, 21C, 21D, 21E, 21F, 21G, 21H, 21i, 21J, 21K, 21L, 22, 22A, 22D, 22E, 22F, 22G, 22H, 22i, 22J, 22K, 22L, 22M, 22N, 22o, 22P, 22Q, 22R, 22S, 22T, 22U, 22V, 22W, 22X, 22Y, 23, 23B, 23C, 23D, 23E, 23F, 23G, 23H, 23i, 24, 24B, 24C, 24D, 25, 26, 27, 27A, 27B, 27C, 27D, 27E, 27F, 27G, 27H, 27i, 27J, 27K, 27L, 27M, 27N, 27o, 27P, 27Q, 27R, 27S, 28, 29, 30, 31, 32, 32C, 32D, 32E, 32F, 32G, 32H, 32i, 32J, 32K, 32L, 32M, 32N, 32o, 32P, 32Q, 32R, 32S, 32T, 32U, 33, 34, 35, 35D, 35E, 35F, 35G, 35H, 35i, 35J, 35K, 36, 36A, 36B, 36C, 37, 38, 38D, 38E, 38F, 38G, 39, 40, 41, 42, 43, 43B, 43C, 44, 44B, 44C, 44D, 44E, 44F, 45, 46, 47, 47D, 47E, 47F, 47G, 48, 48C, 49, 49B, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 156, 157, 158, 159, 160, 161, 162, 163, 164, 165, 166, 167, 168, 169, 170, 171, 172, 173, and 174, or a pharmaceutically acceptable salt thereof. The structures of these compounds are set forth in the Examples section below.

In embodiment no. 41, the invention provides a compound selected from the group consisting of:

4-[{cis,cis-4-[(benzyloxy)carbonyl]-2,3,3a,4,9,9a-hexahydro-1H-cyclopenta[b]quinolin-9-yl}(cyclopropyl)amino]-4-oxobutanoic acid;

4-[{cis,cis-4-[(benzyloxy)carbonyl]-2,3,3a,4,9,9a-hexahydro-1H-cyclopenta[b]quinolin-9-yl}(phenyl)amino]-4-oxobutanoic acid;

4-{ethyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-[{cis,cis-4-[(benzyloxy)carbonyl]-6-fluoro-2,3,3a,4,9,9a-hexahydro-1H-cyclopenta[b]quinolin-9-yl}(cyclopropyl)amino]-4-oxobutanoic acid;

4-{cyclopropyl[cis,cis-6-fluoro-4-[(4-phenoxyphenyl)carbonyl]-2,3,3a,4,9,9a-hexahydro-1H-cyclopenta[b]quinolin-9-yl}amino)-4-oxobutanoic acid;

4-{cyclopropyl[cis,cis-3-{[4-(trifluoromethoxy)phenyl]carbonyl}-1,2,2a,3,8,8a-hexahydrocyclobuta[b]quinolin-8-yl]amino}-4-oxobutanoic acid;

({cyclopropyl[cis,cis-4-{[4-(trifluoromethoxy)phenyl]carbonyl}-2,3,3a,4,9,9a-hexahydro-1H-cyclopenta[b]quinolin-9-yl]carbamoyl}oxy)acetic acid;

3-(phenylmethyl)cis,cis-8-[(3-carboxy-1-oxopropyl)cyclopropylamino]-5-fluoro-2,2a,8,8a-tetrahydrocyclobuta[b]quinoline-3(1H)-carboxylate;

4-(phenylmethyl)cis,cis-9-[(3-carboxy-1-oxopropyl)cyclopropylamino]-6-chloro-1,2,3,3a,9,9a-hexahydro-4H-cyclopenta[b]quinoline-4-carboxylate;

4-(phenylmethyl)cis,cis-9-[(3-carboxy-1-oxopropyl)cyclopropylamino]-7-fluoro-1,2,3,3a,9,9a-hexahydro-4H-cyclopenta[b]quinoline-4-carboxylate;

4-[cyclopropyl[(cis,cis)-7-fluoro-2,3,3a,4,9,9a-hexahydro-4-[4-(trifluoromethoxy)benzoyl]-1H-cyclopenta[b]quinolin-9-yl]amino]-4-oxobutanoic acid;

4-[[cis,cis-2,3,3a,4,9,9a-hexahydro-4-[4-(trifluoromethoxy)benzoyl]-1H-cyclopenta[b]quinolin-9-yl]methylamino]-4-oxobutanoic acid;

4-[(cyclobutylmethyl) [cis,cis-2,3,3a,4,9,9a-hexahydro-4-[4-(trifluoromethoxy)benzoyl]-1H-cyclopenta[b]quinolin-9-yl]amino]-4-oxobutanoic acid;

4-[cyclopropyl[cis,cis-2,3,3a,4,9,9a-hexahydro-4-(3-phenoxybenzoyl)-1H-cyclopenta[b]quinolin-9-yl]amino]-4-oxo-butanoic acid;

4-(cyclopropyl(cis,cis-4-(thiophene-2-carbonyl)-2,3,3a,4,9,9a-hexahydro-1H-cyclopenta[b]quinolin-9-yl)amino)-4-oxobutanoic acid;

[[[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]carbonyl]oxy]acetic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]-4-oxobutanoic acid;

deuterated-4-[cyclopropyl[cis,cis-2,3,3a,4,9,9a-hexahydro-4-[4-(trifluoromethoxy)benzoyl]-1H-cyclopenta[b]quinolin-9(R)-yl-(d)]amino]-4-oxobutanoic acid;

4-[[(cis,cis)-6-chloro-2,3,3a,4,9,9a-hexahydro-4-[4-(trifluoromethoxy)benzoyl]-1H-cyclopenta[b]quinolin-9-yl]cyclobutylamino]-4-oxobutanoic acid;

4-[[(cis,cis)-6-chloro-2,3,3a,4,9,9a-hexahydro-4-[4-(trifluoromethoxy)benzoyl]-1H-cyclopenta[b]quinolin-9-yl]cyclopropylamino]-4-oxobutanoic acid;

4-[[(cis,cis)-6-chloro-2,3,3a,4,9,9a-hexahydro-4-[(trans-2-phenylcyclopropyl)carbonyl]-1H-cyclopenta[b]quinolin-9-yl]cyclopropylamino]-4-oxobutanoic acid;

4-[cyclobutyl[(cis,cis)-2,3,3a,4,9,9a-hexahydro-4-[4-(trifluoromethoxy)benzoyl]-1H-cyclopenta[b]quinolin-9-yl]amino]-4-oxobutanoic acid;

4-[[(cis,cis)-6-chloro-2,3,3a,4,9,9a-hexahydro-4-[(1,2,3,4-tetrahydro-1-naphthalenyl)carbonyl]-1H-cyclopenta[b]quinolin-9-yl]cyclopropylamino]-4-oxobutanoic acid;

4-[[(cis,cis)-6-chloro-4-[(2,3-dihydro-1H-inden-2-yl)carbonyl]-2,3,3a,4,9,9a-hexahydro-1H-cyclopenta[b]quinolin-9-yl]cyclopropylamino]-4-oxobutanoic acid;

4-[[(cis,cis)-6-chloro-2,3,3a,4,9,9a-hexahydro-4-[(1,2,3,4-tetrahydro-2-naphthalenyl)carbonyl]-1H-cyclopenta[b]quinolin-9-yl]cyclopropylamino]-4-oxobutanoic acid;

4-[cyclopropyl[cis,cis-2,3,3a,4,9,9a-hexahydro-4-[3-(5-thiazolyl)benzoyl]-1H-cyclopenta[b]quinolin-9-yl]amino]-4-oxobutanoic acid;

4-[(2,4-difluorophenyl)methyl](cis,cis)-9-[[(carboxymethoxy)carbonyl]cyclopropylamino]-1,2,3,3a,9,9a-hexahydro-4H-cyclopenta[b]quinoline-4-carboxylate;

4-[1-(4-fluorophenyl)ethyl](cis,cis)-9-[(3-carboxy-1-oxopropyl)cyclopropylamino]-1,2,3,3a,9,9a-hexahydro-4H-cyclopenta[b]quinoline-4-carboxylate;

4-(1,2,3,4-tetrahydro-2-naphthalenyl)(cis,cis)-9-[(3-carboxy-1-oxopropyl)cyclopropylamino]-7-fluoro-1,2,3,3a,9,9a-hexahydro-4H-cyclopenta[b]quinoline-4-carboxylate;

4-[cyclopropyl[(cis,cis)-6-fluoro-1,2,2a,3,8,8a-hexahydro-3-[4-(trifluoromethoxy)benzoyl]cyclobuta[b]quinolin-8-yl]amino]-4-oxobutanoic acid;

3-(phenylmethyl)(cis,cis)-8-[(3-carboxy-1-oxopropyl)cyclopropylamino]-5-chloro-2,2a,8,8a-tetrahydrocyclobuta[b]quinoline-3(1H)-carboxylate;

4-[[(cis,cis)-5-chloro-1,2,2a,3,8,8a-hexahydro-3-[4-(trifluoromethoxy)benzoyl]cyclobuta[b]quinolin-8-yl]cyclopropylamino]-4-oxobutanoic acid;

3-(phenylmethyl)(cis,cis)-8-[(3-carboxy-1-oxopropyl)cyclopropylamino]-2,2a,8,8a-tetrahydrocyclobuta[b]quinoline-3(1H)-carboxylate;

4-[cyclopropyl[(cis,cis)-1,2,2a,3,8,8a-hexahydro-3-[4-(trifluoromethoxy)benzoyl]cyclobuta[b]quinolin-8-yl]amino]-4-oxobutanoic acid;

4-(phenylmethyl)(cis,cis)-9-[[(carboxymethoxy)carbonyl]cyclopropylamino]-1,2,3,3a,9,9a-hexahydro-4H-cyclopenta[b]quinoline-4-carboxylate;

4-(phenylmethyl)(cis,cis)-9-[[(carboxymethoxy)carbonyl]cyclopropylamino]-7-fluoro-1,2,3,3a,9,9a-hexahydro-4H-cyclopenta[b]quinoline-4-carboxylate;

[[[cyclopropyl[(cis,cis)-1,2,2a,3,8,8a-hexahydro-3-[4-(trifluoromethoxy)benzoyl]cyclobuta[b]quinolin-8-yl]amino]carbonyl]oxy]acetic acid;

[[[cyclopropyl[(cis,cis)-3-(3,4-difluorobenzoyl)-1,2,2a,3,8,8a-hexahydrocyclobuta[b]quinolin-8-yl]amino]carbonyl]oxy]acetic acid;

[[[cyclopropyl[(cis,cis)-7-fluoro-2,3,3a,4,9,9a-hexahydro-4-[4-(trifluoromethoxy)benzoyl]-1H-cyclopenta[b]quinolin-9-yl]amino]carbonyl]oxy]acetic acid;

4-(phenylmethyl)(cis,cis)-9-[[(2(S)-carboxy-1-azetidinyl)carbonyl]cyclopropylamino]-1,2,3,3a,9,9a-hexahydro-4H-cyclopenta[b]quinoline-4-carboxylate;

N-[[cyclopropyl[(cis,cis)-2,3,3a,4,9,9a-hexahydro-4-[4-(trifluoromethoxy)benzoyl]-1H-cyclopenta[b]quinolin-9-yl]amino]carbonyl]-N-methylglycine;

[[[cyclopropyl[cis,cis-2,3,3a,4,9,9a-hexahydro-4-[5-[[4-(trifluoromethoxy)phenyl]methyl]-1,3,4-oxadiazol-2-yl]-1H-cyclopenta[b]quinoline-9-yl]amino]carbonyl]oxy]acetic acid;

2-[ethyl[cis,cis-2,3,3a,4,9,9a-hexahydro-4-[4-(trifluoromethoxy)benzoyl]-1H-cyclopenta[b]quinolin-9-yl]amino]-4-oxazolecarboxylic acid;

3-(phenylmethyl)cis,cis-8-[(3-carboxypropyl)cyclopropylamino]-5-fluoro-2,2a,8,8a-tetrahydrocyclobuta[b]quinoline-3(1H)-carboxylate;

4-[cyclopropyl[cis,cis-2,3,3a,4,9,9a-hexahydro-4-[4-(trifluoromethoxy)benzoyl]-1H-cyclopenta[b]quinolin-9-yl]amino]butanoic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]butanoic acid;

4-[cyclopropyl[(cis,cis)-2,3,3a,4,9,9a-hexahydro-4-[4-[(trifluoromethyl)thio]benzoyl]-1H-cyclopenta[b]quinolin-9-yl]amino]-4-oxobutanoic acid;

4-(ethyl((cis,cis)-3-(4-(trifluoromethylthio)benzoyl)-1,2,2a,3,8,8a-hexahydrocyclobuta[b]quinolin-8-yl)amino)-4-oxobutanoic acid;

4-(ethyl((cis,cis)-3-(4-ethylbenzoyl)-1,2,2a,3,8,8a-hexahydrocyclobuta[b]quinolin-8-yl)amino)-4-oxobutanoic acid;

3-(phenylmethyl) 8-[(3-carboxy-1-oxopropyl)cyclopropylamino]-5,6-difluoro-2,2a,8,8a-tetrahydro-cyclobuta[b]quinoline-3(1H)-carboxylate;

4-[cyclopropyl[(cis,cis)-5,6-dichloro-1,2,2a,3,8,8a-hexahydro-3-[4-(trifluoromethoxy)benzoyl]cyclobuta[b]quinolin-8-yl]amino]-4-oxobutanoic acid;

4-(cyclopropyl((cis,cis)-5,6-difluoro-3-(4-(trifluoromethoxy)benzoyl)-1,2,2a,3,8,8a-hexahydrocyclobuta[b]quinolin-8-yl)amino)-4-oxobutanoic acid;

4-[cyclopropyl[(cis,cis)-6-fluoro-2,3,3a,4,9,9a-hexahydro-4-[4-(trifluoromethoxy)benzoyl]-1H-cyclopenta[b]quinolin-9-yl]amino]-4-oxo-butanoic acid; and (R)-1-(((cis,cis)-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid;

4-(cyclopropyl(cis,cis-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid; and 4-(cyclopropyl(cis,cis-7-fluoro-4-(4-(trifluoromethoxy)benzoyl)-2,3,3a,4,9,9a-hexahydro-1H-cyclopenta[b]quinolin-9-yl)amino)butanoic acid;

or a pharmaceutically acceptable salt thereof.

In embodiment no. 42, the invention provides a compound selected from the group consisting of:

4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-[cyclopropyl[cis,cis-7-fluoro-2,3,3a,4,9,9a-hexahydro-4-[4-(trifluoromethoxy)benzoyl]-1H-cyclopenta[b]quinolin-9-yl]amino]-4-oxobutanoic acid;

4-[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]-4-oxobutanoic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]-4-oxobutanoic acid;

4-[cyclopropyl[cis,cis-6-fluoro-1,2,2a,3,8,8a-hexahydro-3-[4-(trifluoromethoxy)benzoyl]cyclobuta[b]quinolin-8-yl]amino]-4-oxobutanoic acid;

3-(phenylmethyl)(cis,cis)-8-[(3-carboxy-1-oxopropyl)cyclopropylamino]-5-chloro-2,2a,8,8a-tetrahydrocyclobuta[b]quinoline-3(1H)-carboxylate;

3-(phenylmethyl)(cis,cis)-8-[(3-carboxy-1-oxopropyl)cyclopropylamino]-2,2a,8,8a-tetrahydrocyclobuta[b]quinoline-3(1H)-carboxylate;

4-[cyclopropyl[cis,cis-1,2,2a,3,8,8a-hexahydro-3-[4-(trifluoromethoxy)benzoyl]cyclobuta[b]quinolin-8-yl]amino]-4-oxobutanoic acid;

[[[cyclopropyl[cis,cis-3-(3,4-difluorobenzoyl)-1,2,2a,3,8,8a-hexahydrocyclobuta[b]quinolin-8-yl]amino]carbonyl]oxy]acetic acid;

3-(phenylmethyl)cis,cis-8-[(3-carboxypropyl)cyclopropylamino]-5-fluoro-2,2a,8,8a-tetrahydrocyclobuta[b]quinoline-3(1H)-carboxylate;

4-[cyclopropyl[cis,cis-2,3,3a,4,9,9a-hexahydro-4-[4-(trifluoromethoxy)benzoyl]-1H-cyclopenta[b]quinolin-9-yl]amino]butanoic acid;

4-[cyclopropyl[cis,cis-2,3,3a,4,9,9a-hexahydro-4-[[(trifluoromethyl)thio]benzoyl]-1H-cyclopenta[b]quinolin-9-yl]amino]-4-oxobutanoic acid;

(R)-1-((cis,cis-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid;

4-(cyclopropyl(cis,cis-3-(4-((trifluoromethyl)thio)benzoyl)-1,2,2a,3,8,8a-hexahydrocyclobuta[b]quinolin-8-yl)amino)-4-oxobutanoic acid;

4-[ethyl(cis,cis-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-[ethyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid; and 4-(cyclopropyl(cis,cis-7-fluoro-4-(4-(trifluoromethoxy)benzoyl)-2,3,3a,4,9,9a-hexahydro-1H-cyclopenta[b]quinolin-9-yl)amino)butanoic acid;

or a pharmaceutically acceptable salt thereof.

In embodiment no. 43, the invention provides a compound selected from the group consisting of:

4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-{cyclopropyl[[(3aS,9aR)-4-{[4-(trifluoromethoxy)phenyl]carbonyl}-2,3,3a,4,9,9a-hexahydro-1H-cyclopenta[b]quinolin-9(R)-yl]amino}-4-oxobutanoic acid;

4-{cyclopropyl[[(3aR,9aS)-4-{[4-(trifluoromethoxy)phenyl]carbonyl}-2,3,3a,4,9,9a-hexahydro-1H-cyclopenta[b]quinolin-9(S)-yl]amino}-4-oxobutanoic acid;

4-[cyclopropyl[cis,cis-7-fluoro-2,3,3a,4,9,9a-hexahydro-4-[4-(trifluoromethoxy)benzoyl]-1H-cyclopenta[b]quinolin-9-yl]amino]-4-oxobutanoic acid;

4-[cyclopropyl[(3aS,9aR)-7-fluoro-2,3,3a,4,9,9a-hexahydro-4-[4-(trifluoromethoxy)benzoyl]-1H-cyclopenta[b]quinolin-9(R)-yl]amino]-4-oxobutanoic acid;

4-[cyclopropyl[(3aR,9aS)-7-fluoro-2,3,3a,4,9,9a-hexahydro-4-[4-(trifluoromethoxy)benzoyl]-1H-cyclopenta[b]quinolin-9(S)-yl]amino]-4-oxobutanoic acid;

4-[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]-4-oxobutanoic acid;

4-[[(3aS,9aR)-6-chloro-7-fluoro-2,3,3a,4,9,9a-hexahydro-4-[4-(trifluoromethoxy)benzoyl]-1H-cyclopenta[b]quinolin-9(R)-yl]cyclopropylamino]-4-oxobutanoic acid;

4-[[(3aR,9aS)-6-chloro-7-fluoro-2,3,3a,4,9,9a-hexahydro-4-[4-(trifluoromethoxy)benzoyl]-1H-cyclopenta[b]quinolin-9(S)-yl]cyclopropylamino]-4-oxobutanoic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]-4-oxobutanoic acid;

4-[cyclopropyl[(2aS,8aR)-5-fluoro-1,2,2a,3,8,8a-hexahydro-3-[4-(trifluoromethoxy)benzoyl]cyclobuta[b]quinolin-8(R)-yl]amino]-4-oxobutanoic acid;

4-[cyclopropyl[(2aR,8aS)-5-fluoro-1,2,2a,3,8,8a-hexahydro-3-[4-(trifluoromethoxy)benzoyl]cyclobuta[b]quinolin-8(S)-yl]amino]-4-oxobutanoic acid;

4-[cyclopropyl[cis,cis-6-fluoro-1,2,2a,3,8,8a-hexahydro-3-[4-(trifluoromethoxy)benzoyl]cyclobuta[b]quinolin-8-yl]amino]-4-oxobutanoic acid;

4-[cyclopropyl[(2aS,8aR)-6-fluoro-1,2,2a,3,8,8a-hexahydro-3-[4-(trifluoromethoxy)benzoyl]cyclobuta[b]quinolin-8(R)-yl]amino]-4-oxobutanoic acid;

4-[cyclopropyl[(2aR,8aS)-6-fluoro-1,2,2a,3,8,8a-hexahydro-3-[4-(trifluoromethoxy)benzoyl]cyclobuta[b]quinolin-8(S)-yl]amino]-4-oxobutanoic acid;

3-(phenylmethyl)(cis,cis)-8-[(3-carboxy-1-oxopropyl)cyclopropylamino]-5-chloro-2,2a,8,8a-tetrahydrocyclobuta[b]quinoline-3(1H)-carboxylate;

3-(phenylmethyl)(2aS,8aR)-8(R)-[(3-carboxy-1-oxopropyl)cyclopropylamino]-5-chloro-2,2a,8,8a-tetrahydrocyclobuta[b]quinoline-3(1H)-carboxylate;

3-(phenylmethyl)(2aR,8aS)-8(S)-[(3-carboxy-1-oxopropyl)cyclopropylamino]-5-chloro-2,2a,8,8a-tetrahydrocyclobuta[b]quinoline-3(1H)-carboxylate;

3-(phenylmethyl)(cis,cis)-8-[(3-carboxy-1-oxopropyl)cyclopropylamino]-2,2a,8,8a-tetrahydrocyclobuta[b]quinoline-3(1H)-carboxylate;

3-(phenylmethyl)(2aS,8aR)-8(R)-[(3-carboxy-1-oxopropyl)cyclopropylamino]-2,2a,8,8a-tetrahydrocyclobuta[b]quinoline-3(1H)-carboxylate;

3-(phenylmethyl)(2aR,8aS)-8(S)-[(3-carboxy-1-oxopropyl)cyclopropylamino]-2,2a,8,8a-tetrahydrocyclobuta[b]quinoline-3(1H)-carboxylate;

4-[cyclopropyl[cis,cis-1,2,2a,3,8,8a-hexahydro-3-[4-(trifluoromethoxy)benzoyl]cyclobuta[b]quinolin-8-yl]amino]-4-oxobutanoic acid;

4-[cyclopropyl[(2aS,8aR)-1,2,2a,3,8,8a-hexahydro-3-[4-(trifluoromethoxy)benzoyl]cyclobuta[b]quinolin-8(R)-yl]amino]-4-oxobutanoic acid;

4-[cyclopropyl[(2aR,8aS-1,2,2a,3,8,8a-hexahydro-3-[4-(trifluoromethoxy)benzoyl]cyclobuta[b]quinolin-8(S)-yl]amino]-4-oxobutanoic acid;

[[[cyclopropyl[cis,cis-3-(3,4-difluorobenzoyl)-1,2,2a,3,8,8a-hexahydrocyclobuta[b]quinolin-8-yl]amino]carbonyl]oxy]acetic acid;

[[[cyclopropyl[(2aS,8aR)-3-(3,4-difluorobenzoyl)-1,2,2a,3,8,8a-hexahydrocyclobuta[b]quinolin-8(R)-yl]amino]carbonyl]oxy]acetic acid;

[[[cyclopropyl[(2aR,8aS)-3-(3,4-difluorobenzoyl)-1,2,2a,3,8,8a-hexahydrocyclobuta[b]quinolin-8(S)-yl]amino]carbonyl]oxy]acetic acid;

3-(phenylmethyl)cis,cis-8-[(3-carboxypropyl)cyclopropylamino]-5-fluoro-2,2a,8,8a-tetrahydrocyclobuta[b]quinoline-3(1H)-carboxylate;

3-(phenylmethyl)(2aS,8aR)-8(R)-[(3-carboxypropyl)cyclopropylamino]-5-fluoro-2,2a,8,8a-tetrahydrocyclobuta[b]quinoline-3(1H)-carboxylate;

3-(phenylmethyl)(2aR,8aS)-8(S)-[(3-carboxypropyl)cyclopropylamino]-5-fluoro-2,2a,8,8a-tetrahydrocyclobuta[b]quinoline-3(1H)-carboxylate;

4-[cyclopropyl[cis,cis-2,3,3a,4,9,9a-hexahydro-4-[4-(trifluoromethoxy)benzoyl]-1H-cyclopenta[b]quinolin-9-yl]amino]butanoic acid;

4-[cyclopropyl[(3aS,9aR)-2,3,3a,4,9,9a-hexahydro-4-[4-(trifluoromethoxy)benzoyl]-1H-cyclopenta[b]quinolin-9(R)-yl]amino]butanoic acid;

4-[cyclopropyl[(3aR,9aS)-2,3,3a,4,9,9a-hexahydro-4-[4-(trifluoromethoxy)benzoyl]-1H-cyclopenta[b]quinolin-9(S)-yl]amino]butanoic acid;

4-[cyclopropyl[cis,cis-2,3,3a,4,9,9a-hexahydro-4-[4-[(trifluoromethyl)thio]benzoyl]-1H-cyclopenta[b]quinolin-9-yl]amino]-4-oxobutanoic acid;

4-[cyclopropyl[(3aS,9aR)-2,3,3a,4,9,9a-hexahydro-4-[4-[(trifluoromethyl)thio]benzoyl]-1H-cyclopenta[b]quinolin-9(R)-yl]amino]-4-oxobutanoic acid;

4-[cyclopropyl[(3aR,9aS)-2,3,3a,4,9,9a-hexahydro-4-[4-[(trifluoromethyl)thio]benzoyl]-1H-cyclopenta[b]quinolin-9(S)-yl]amino]-4-oxobutanoic acid;

(R)-1-((cis,cis-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid;

(R)-1-(((2aS,8aR)-3-(benzyloxycarbonyl)-5,6-difluoro-1,2,2a,3,8,8a-hexahydrocyclobuta[b]quinolin-8(R)-yl)(cyclopropyl)carbamoyl)azetidine-2-carboxylic acid;

(R)-1-(((2aR,8aS)-3-(benzyloxycarbonyl)-5,6-difluoro-1,2,2a,3,8,8a-hexahydrocyclobuta[b]quinolin-8(S)-yl)(cyclopropyl)carbamoyl)azetidine-2-carboxylic acid;

4-(cyclopropyl(cis,cis-3-(4-((trifluoromethyl)thio)benzoyl)-1,2,2a,3,8,8a-hexahydrocyclobuta[b]quinolin-8-yl)amino)-4-oxobutanoic acid;

4-(cyclopropyl((2aS,8aR)-3-(4-((trifluoromethyl)thio)benzoyl)-1,2,2a,3,8,8a-hexahydrocyclobuta[b]quinolin-8-yl)amino)-4-oxobutanoic acid;

4-(cyclopropyl((2aR,8aS)-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-(ethyl((2aS,8aR)-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-(ethyl((2aR,8aS)-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(ethyl((3aS,9aR)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(ethyl((3aR,9aS)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl((3aS,9aR)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl((3aR,9aS)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid; and 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)butanoic acid;

or a pharmaceutically acceptable salt thereof.

In embodiment no. 44, the invention provides a compound selected from the group consisting of:

4-{cyclopropyl[[(3aS,9aR)-4-{[4-(trifluoromethyl)phenyl]carbonyl}-2,3,3a,4,9,9a-hexahydro-1H-cyclopenta[b]quinolin-9(R)-yl]amino}-4-oxobutanoic acid;

4-[cyclopropyl[(3aS,9aR)-7-fluoro-2,3,3a,4,9,9a-hexahydro-4-[4-(trifluoromethoxy)benzoyl]-1H-cyclopenta[b]quinolin-9(R)-yl]amino]-4-oxobutanoic acid;

4-[[(3aS,9aR)-6-chloro-7-fluoro-2,3,3a,4,9,9a-hexahydro-4-[4-(trifluoromethoxy)benzoyl]-1H-cyclopenta[b]quinolin-9(R)-yl]cyclopropylamino]-4-oxobutanoic acid;

4-[cyclopropyl[(2aS,8aR)-6-fluoro-1,2,2a,3,8,8a-hexahydro-3-[4-(trifluoromethoxy)benzoyl]cyclobuta[b]quinolin-8(R)-yl]amino]-4-oxobutanoic acid;

4-[cyclopropyl[(2aR,8aS)-6-fluoro-1,2,2a,3,8,8a-hexahydro-3-[4-(trifluoromethoxy)benzoyl]cyclobuta[b]quinolin-8(S)-yl]amino]-4-oxobutanoic acid;

4-(ethyl((3aS,9aR)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-[cyclopropyl[(3aS,9aR)-2,3,3a,4,9,9a-hexahydro-4-[4-[(trifluoromethyl)thio]benzoyl]-1H-cyclopenta[b]quinolin-9(R)-yl]amino]-4-oxobutanoic acid; and 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)butanoic acid;

or a pharmaceutically acceptable salt thereof.

The invention also provides a compound of Formula (I) or a pharmaceutically acceptable salt thereof in purified form.

Compositions and Administration

This invention is also directed to pharmaceutical compositions which comprise a therapeutically effective amount of the compound of Formula (I), or a pharmaceutically acceptable salt of said compound and a pharmaceutically acceptable carrier.

A preferred dosage is about 0.001 to 100 mg/kg of body weight/day of the compound of Formula (I). An especially preferred dosage is about 0.01 to 10 mg/kg of body weight/day of a compound of Formula (I), or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Uses of the Compounds

The compounds of Formula (I) bind to $CRTH_2$ and, therefore, are useful in characterizing tissues containing $CRTH_2$, and in identifying further compounds which bind to $CRTH_2$. The general value of the compounds of the invention in binding the $CRTH_2$ receptor can be determined, for example, using the radioligand binding assay described below in the Examples section.

The compounds of Formula (I) can also be useful as modulators of $CRTH_2$ receptor function. In some embodiments, compounds of Formula (I) are antagonists of the $CRTH_2$ receptor. The general value of the compounds of the invention in antagonizing $CRTH_2$ receptor function can be determined, for example, using the chemiluminescent-based cAMP assay, the β-Arrestin assay, or the eosinophil shape change assay described below in the Examples section.

While not being bound by any specific theory, Applicants believe that the compounds of Formula (I) are useful in treating the symptoms of diseases or conditions associated with uncontrolled or inappropriate stimulation of $CRTH_2$ function because of their ability to antagonize the $CRTH_2$ receptor. Accordingly, in one embodiment, the invention provides a method for treating a disease or conditions associated with uncontrolled or inappropriate stimulation of $CRTH_2$ function, comprising administering a therapeutically effective amount of a compound of Formula (I) to a patient in need of such treatment.

Diseases or conditions associated with uncontrolled or inappropriate stimulation of $CRTH_2$ function include (but are not limited to) asthma, congestion, allergic rhinitis, atopic dermatitis, chronic obstructive pulmonary disease ("COPD"), dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Examples of cerebrovascular disorders include stroke.

In certain embodiments, the present invention provides a method for treating asthma, congestion, allergic rhinitis or COPD which comprises administering a therapeutically effective dose of a compound of Formula (I) or a pharmaceutically acceptable salt thereof to a patient in need of such treatment. In a specific embodiment, the disease or condition being treated is asthma. In another embodiment, the disease or condition being treated is COPD.

In addition, compounds of the Formula (I) which act as $CRTH_2$ receptor antagonists can inhibit prostanoid-induced smooth muscle contraction by antagonizing contractile prostanoids or mimicking relaxing prostanoids and hence may be used in the treatment of dysmenorrhea, premature labor and eosinophil related disorders.

In another embodiment, the present invention provides a compound of Formula (I) or a pharmaceutically acceptable salt thereof for use in the manufacture of a medicament for treating a disease or condition selected from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis.

In another embodiment, the present invention provides a compound of Formula (I) or a pharmaceutically acceptable salt thereof for use in treating a disease or condition from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudophedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

In general, the compounds in the invention may be produced by a variety of processes known to those skilled in the art and by know, processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods. Illustrative general synthetic methods are set out below and then specific compounds of the Formula (I) are prepared in the Examples.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented, $^1$H spectra were obtained on either a Varian VXR-400 (400 MHz, 1H), Varian Gemini-300 (300 MHz), Varian Mercury VX-400 (400 MHz), Bruker-Biospin AV-500 (500 MHz) or Bruker Avance DRX-500 (500 MHz), and chemical shifts are reported as ppm with number of protons and multiplicities indicated parenthetically. Where LC/MS data are presented, analyses was performed using a 1200 series Agilent 6140 Quadrupole LCMS with a 1.8 μM Zorbax SB-C18 column (10-95% of MeCN—H$_2$O with 0.1% TFA over 2.7 min, 1 mL/min) or with an Applied Biosystems API-150 mass spectrometer and Gemini C18 column (50×4.6 mm, 10-95% CH$_3$CN—H$_2$O with 0.05% TFA over 5 min, 1 mL/min).

Preparative chiral HPLC separations were generally carried out using supercritical fluid chromatography by eluting a chiral column such as OJ-H, (4.6×250 mm, Chiral Technologies, Inc., West Chester, Pa.) with a mobile phase of isopropanol and supercritical CO$_2$.

The following solvents, reagents, protecting groups, moieties, and other designations may be referred to by their abbreviations in parenthesis:

Me=methyl; Et=ethyl; Pr=propyl; iPr—isopropyl; Bu=butyl; t-Bu=tert-butyl; Ph=phenyl, and Ac=acetyl
μl=microliters
AcOEt or EtOAc=ethyl acetate
AcOH or HOAc=acetic acid
aq=aqueous
Ar=aryl
atm=atmosphere
9-BBN=9-borabicyclo[3.3.1]nonane
Bn=benzyl
Boc or BOC=tert-butoxycarbonyl
Bz=benzoyl
Boc=tert-butoxycarbonyl
cat=catalyst or catalytic
Cbz or CBZ=benyzloxycarbonyl
DBU=1,8-Diaza-7-bicyclo[5.4.0]undecene
DCM=dichloromethane
DCE=dichloroethane
DMAP=4-Dimethylaminopyridine
DIBAL=diisobutylaluminum hydride
DIPEA or Hünig's Base=N,N-diisopropylethylamine
DME=1,2-dimethoxyethane
DMF=dimethylformamide
DMS=dimethylsulfide
DMSO=dimethyl sulfoxide
EDCI or DEC=1-(3-dimethylaminopropyl)-3-ethylcarbodiimide
ee=enantiomeric excess
EDTA=ethylenediaminetetraacetic acid
Et$_2$O=diethyl ether
hd g=grams
h=hour
HMDS=1,1,1,3,3,3-hexamethyldisilazane
HATU=N,N,N',N'-tetramethyl-O-(7-azabenzotriazol-1-yl)uranium hexafluorophosphate
HOBt=1-hydroxybenzotriazole
Im=imidazole
LAH=lithium aluminum hydride
LDA=lithium diisopropylamide
LCMS=liquid chromatography mass spectrometry
LG=leaving group
min=minute
mg=milligrams
mL=milliliters
mmol=millimoles
MeOH: methanol
MS=mass spectrometry
NBS=N-bromosuccimide
NMR=nuclear magnetic resonance spectroscopy
PG=protecting group
Pyr=pyridine
RT or rt=room temperature (ambient, about 25° C.)
sat=saturated
SFC=supercritical fluid chromatography
SM=starting material
TBSC1=t-butyldimethylsilyl chloride
TBS=t-butyldimethyl silyl
TFA=trifluoroacetic acid
TFAA=trifluoroacetic anhydride
THF=tetrahydrofuran
TLC=thin layer chromatography
TMS=trimethylsilyl
Tos or Ts=p-toluenesulfonyl (tosyl)
Tol=toluene
IBMX==3-Isobutyl-1-methylxanthine
HBSS=Hank's balanced salt solution
HEPES=1-[4-(2-Hydroxyethyl)-1-piperazinyl]ethane-2-sulfonic acid The compounds of this invention can be prepared through the general approach outlined in the following schemes. These schemes are being provided to illustrate the present invention. To assist one in this endeavor, the ordinary practitioner would have full knowledge of literature sources such as *Chemical Abstracts*; Beilstein, *Protective Groups in Organic Synthesis* 2$^{nd}$ Edition T. W. Greene, P. G. M. Wuts 1991, Wiley and Sons; *Comprehensive Organic Transformations, Advanced Organic Chemistry etc.*

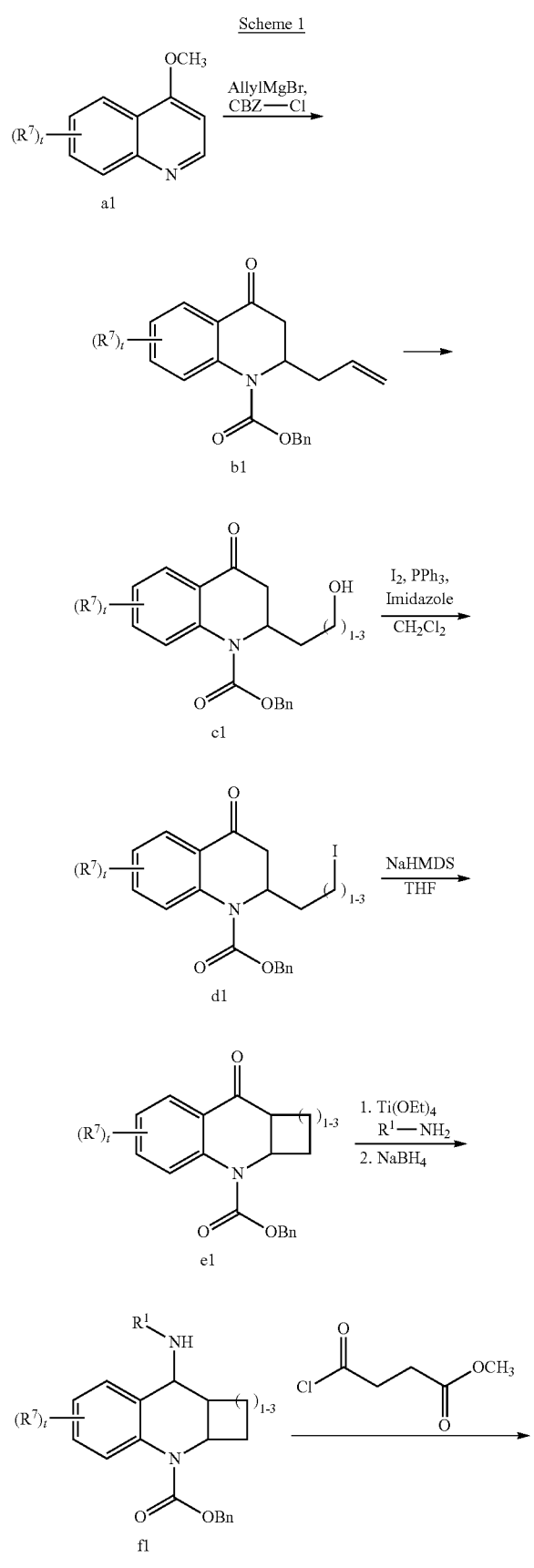

-continued

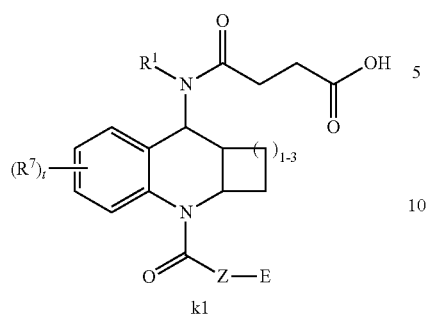

k1

As shown in Scheme 1 above, compounds of the Formula (I) can be prepared from substituted 4-methoxyquinolines a1. Compounds b1 are prepared from a1 in the presence of allylMgBr and CbzCl. The alkene in b1 is used as a key functional group to provide primary alcohol c1 with 2-4 carbon length linkers. The primary alcohols are then converted to iodides d1 before they are cyclized under basic conditions to provide ketones e1. Compounds h1 are obtained from e1 by reductive amination, acylation and hydrolysis. Analogs based on g1 can be synthesized by hydrogenation followed by acylation, carbamate, or urea formation before hydrolysis to give final acids k1.

Scheme 2

For cyclopentyl fused ring compounds, a second route can also be employed as shown Scheme 2 above and Scheme 3 below. Starting from substituted anilines, ethyl 2-oxocyclopentanecarboxylate is condensed with substituted anilines to give the esters (a2). The esters (a2) are hydrolyzed to acids (b2) which undergo Friedel-Crafts reaction to give cyclized products c2. Cbz intermediate d2 and acylated product e2 can be synthesized from c2. Following a similar process as described above for e1-h1 and g1 to k1, further analogs such as h2 and j2 can be prepared from e2. Tertiary amine analogs j2 can be prepared from f2 by reductive amination followed by hydrolysis.

Scheme 3

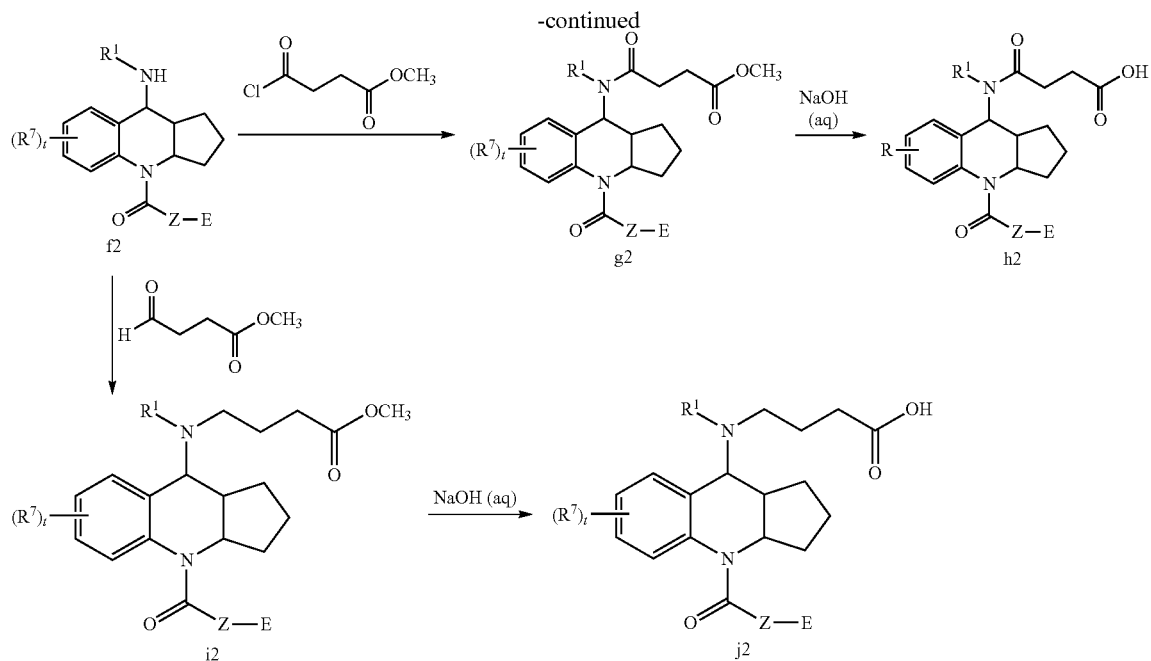

The starting materials and reagents used in preparing compounds described below are either available from commercial suppliers such as Aldrich Chemical Co. (Wisconsin, USA) and Acros Organics Co. (New Jersey, USA) or were prepared by literature methods known to those skilled in the art.

Where the stereodesignations of the specifically exemplified compounds in the tables below specify "racemic, cis,cis", this description means that the compound is racemic and has a structure wherein the bonds joining the tetrahydroquinoline ring in the core to the cycloalkyl ring have a cis configuration, and that the bond joining the —N(R$^1$)(R$^2$) group to the tetrahydroquinoline ring and the adjacent bond also has a cis configuration. By way of example, where an example indicates that the isolated compound has the structure:

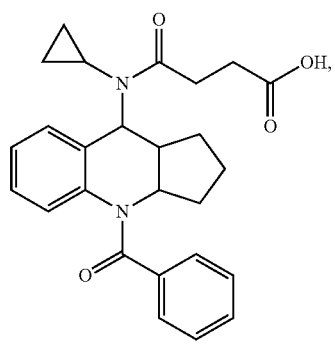 [SMILES: O=C(O)CCC(=O)N(C1CC1)C1c2ccccc2N(C(=O)c2ccccc2)C2CCCC21]

and has a stereodesignation indicated as "racemic, cis,cis", this designation means that the isolated compound is a racemic mixture of the following enantiomers:

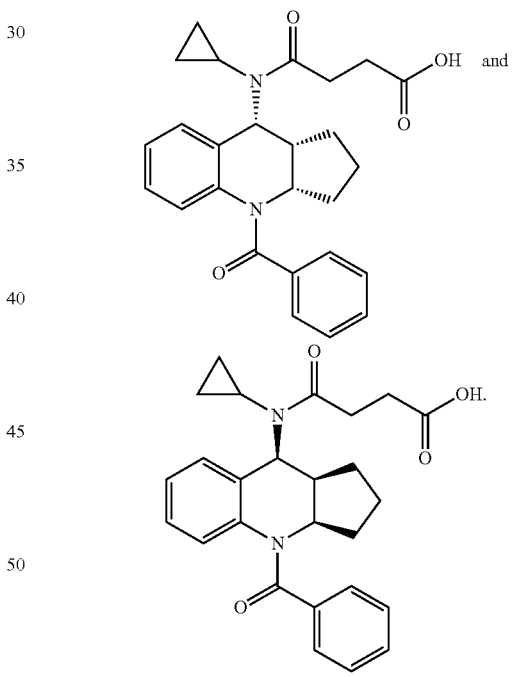

Where the stereodesignations of the specifically exemplified compounds in the tables below specify "cis,cis, single enantiomer" or "cis,cis, enantiopure," this designation means that the isolated compound is a single enantiomer or is enriched in a single enantiomer as compared to the other enantiomer. Furthermore, this description means that the compound has a structure wherein the bonds joining the tetrahydroquinoline ring in the core to the cycloalkyl ring have a cis configuration, and that the bond joining the —N(R$^1$)(R$^2$) group to the tetrahydroquinoline ring and the adjacent bond also has a cis configuration.

These examples are being provided to further illustrate the present invention. They are for illustrative purposes only; the scope of the invention is not to be considered limited in any way thereby.

EXAMPLES

Example 1

Preparation of Racemic Benzyl cis,cis-9-(cyclopropylamino)-1,2,3,3a,9,9a-hexahydro-4H-cyclopenta[b]quinoline-4-carboxylate (1E)

Step 1: Benzyl 2-allyl-4-oxo-3,4-dihydroquinoline-1(2H)-carboxylate

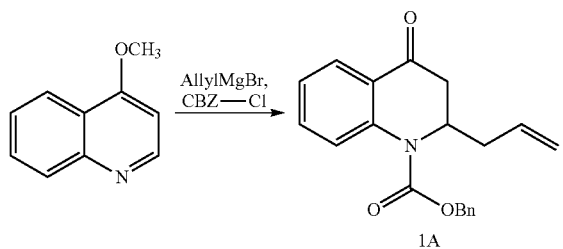

A solution of allylmagnesium bromide (1.00 M in tetrahydrofuran, 101 mL, 101 mmol, 2.00 equiv) was added to a solution of 4-methoxyquinoline (8.00 g, 50.3 mmol, 1 equiv) in tetrahydrofuran (335 mL) at −78° C. The reaction mixture was stirred at −78° C. for 1 h, then benzyl chloroformate (14.35 mL, 101.0 mmol, 2.00 equiv) was added via syringe over 5 min. The reaction mixture was stirred for an additional 15 minutes at −78° C., then the cooling bath was removed and the reaction mixture was allowed to warm to 23° C. After 1 h, added methanol (40 mL). After stirring for 5 min, aqueous hydrochloric acid solution (2 N, 20 mL) was added and the mixture was stirred for 10 min. The mixture was then concentrated by rotary evaporation to remove most of the tetrahydrofuran and methanol, and the residue was partitioned between ethyl acetate and water. The organic phase was washed with brine, and the washed solution was dried over sodium sulfate. The dried solution was filtered, and the filtrate was concentrated. The residue was purified by flash-column chromatography (5% ethyl acetate-hexanes, grading to 20% ethyl acetate-hexanes) to afford 1A as a colorless oil. [M+H]⁺: 322.2.

Step 2: Benzyl 2-(3-hydroxypropyl)-4-oxo-3,4-dihydroquinoline-1(2H)-carboxylate

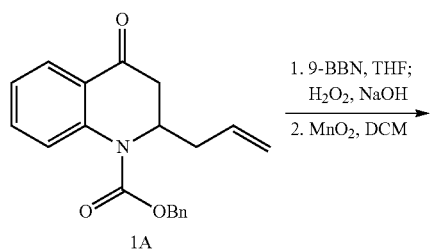

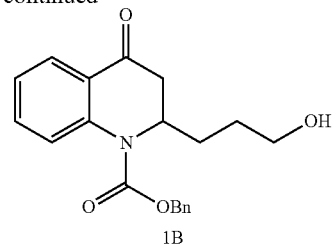

A solution of 9-borabicyclo[3.3.1]nonane (0.4 M in hexanes, 224 mL, 90 mmol, 2 equiv) was added to a solution of benzyl 2-allyl-4-oxo-3,4-dihydroquinoline-1(2H)-carboxylate (13.7 g, 42.6 mmol, 1 equiv) in tetrahydrofuran (213 mL) at 0° C. After the addition was complete, the cooling bath was removed and the reaction mixture was stirred for 15 h. The reaction mixture was then cooled to 0° C., and aqueous sodium hydroxide solution (5 M, 85 mL, equiv) was added by addition funnel over 10 minutes. After the addition was complete, aqueous hydrogen peroxide solution (30% by weight, 174 mL, 40 equiv) was added by addition funnel over 10 minutes. After the addition was complete, the cooling bath was removed and the biphasic reaction mixture was stirred for 45 minutes. The mixture was then partitioned between ethyl acetate and saturated aqueous sodium chloride solution. The layers were separated, and the organic phase was washed with an additional portion of saturated aqueous sodium chloride solution. The washed solution was dried over sodium sulfate, and the dried solution was then filtered. The filtrate was concentrated, and the residue was dissolved in 1,2-dichloroethane (213 mL). Manganese dioxide (18.5 g, 213 mmol, 5.00 equiv) was added, and the reaction mixture was heated to 80° C. After stirring for 2 h at 80° C., the reaction mixture was cooled to 23° C. and filtered through Celite®. The filtrate was concentrated, and the residue was purified by flash-column chromatography (50% ethyl acetate-hexanes, grading to ethyl acetate) to afford 1B as a colorless oil. [M+H]⁺: 340.2.

Step 3: Benzyl 2-(3-iodopropyl)-4-oxo-3,4-dihydroquinoline-1(2H)-carboxylate

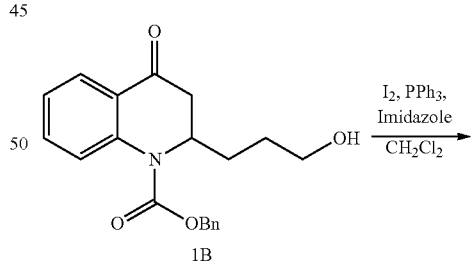

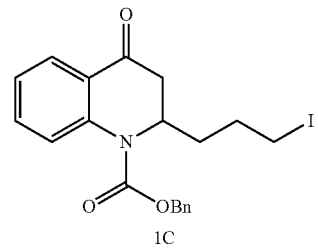

Iodine (12.5 g, 49.4 mmol, 1.30 equiv) was added to a solution of benzyl 2-(3-hydroxypropyl)-4-oxo-3,4-dihydroquinoline-1(2H)-carboxylate (12.9 g, 38.0 mmol, 1 equiv), triphenylphosphine (13.0 g, 49.4 mmol, 1.30 equiv), and imidazole (6.47 g, 95.0 mmol, 1 equiv) in dichloromethane (380 mL) at 23° C. After stirring for 15 minutes, the reaction mixture was partitioned between dichloromethane and water. The organic phase was dried over sodium sulfate, and the dried solution was filtered. The filtrate was concentrated, and the residue was purified by flash-column chromatography (hexanes, grading to 30% ethyl acetate-hexanes) to afford 1C as a colorless oil. [M+H]$^+$: 450.1.

Step 4: Racemic Benzyl cis-9-oxo-1,2,3,3a,9,9a-hexahydro-4H-cyclopenta[b]quinoline-4-carboxylate

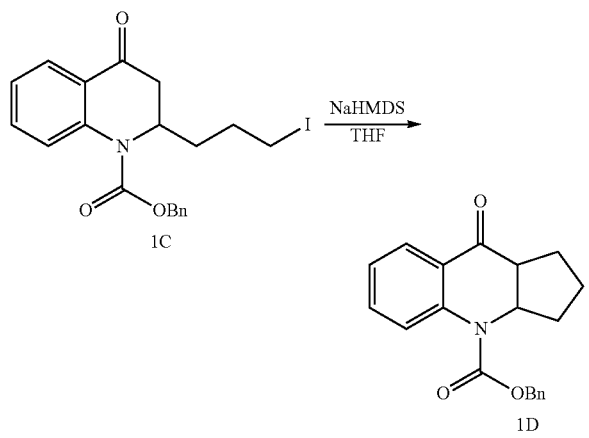

A solution of sodium bis(trimethylsilyl)amide in tetrahydrofuran (1.0 M, 39.4 mL, 39.4 mmol, 1.10 equiv) was added to a solution of benzyl 2-(3-iodopropyl)-4-oxo-3,4-dihydroquinoline-1(2H)-carboxylate (16.1 g, 35.8 mmol, 1 equiv) in tetrahydrofuran (716 mL) at −78° C. The reaction mixture was stirred at −78° C. for 1 h, then the cooling bath was removed and the reaction mixture was allowed to warm. After stirring for 40 min, water was added (300 mL), and the reaction mixture was concentrated by rotary evaporation to remove most of the tetrahydrofuran. The residue was partitioned between ethyl acetate and water. The organic phase was washed with saturated aqueous sodium chloride solution, and the washed solution was dried over sodium sulfate. The dried solution was filtered, and the filtrate was concentrated. The residue was purified by flash-column chromatography (hexanes, grading to 40% ethyl acetate-hexanes) to afford 1D as a colorless oil. [M+H]$^+$: 322.2.

Step 5: Racemic Benzyl cis,cis-9-(cyclopropylamino)-1,2,3,3a,9,9a-hexahydro-4H-cyclopenta[b]quinoline-4-carboxylate

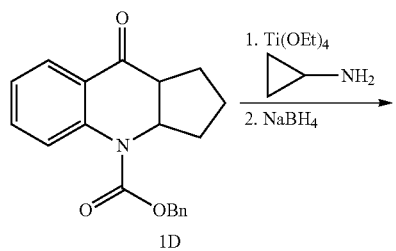

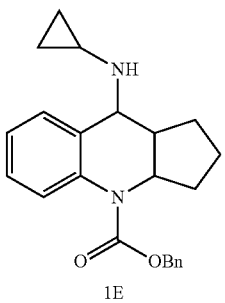

Titanium (IV) ethoxide (4.84 mL, 23.3 mmol, 2.50 equiv) was added to a solution of benzyl cis-9-oxo-1,2,3,3a,9,9a-hexahydro-4H-cyclopenta[b]quinoline-4-carboxylate (3.00 g, 9.34 mmol, 1 equiv) and cyclopropylamine (1.83 mL, 23.3 mmol, 2.50 equiv) in tetrahydrofuran. The reaction vessel was sealed and heated to 60° C. After stirring for 16 h, the reaction mixture was cooled to 23° C. and poured over saturated aqueous sodium chloride solution (50 mL). The biphasic mixture was stirred for 5 min, then filtered through Celite® with the aid of ethyl acetate. The filtrate was partitioned between ethyl acetate and brine, and the organic phase was then dried over sodium sulfate. The dried solution was filtered, and the filtrate was concentrated. The residue was dissolved in methanol (30 mL) and tetrahydrofuran (60 mL), and the solution was cooled to 0° C. Sodium borohydride (855 mg, 22.6 mmol, 2.50 equiv) was added to the cooled solution. After stirring for 15 min at 0° C., the cooling bath was removed, and the reaction mixture was partitioned between ethyl acetate and saturated aqueous sodium bicarbonate solution. The organic layer was washed with saturated aqueous sodium chloride solution, and the washed solution was dried over sodium sulfate. The dried solution was filtered, and the filtrate was concentrated to afford 1E. [M+H]$^+$: 363.3.

Example 2

Preparation of Racemic Benzyl cis,cis-9-amino-1,2,3,3a,9,9a-hexahydro-4H-cyclopenta[b]quinoline-4-carboxylate (2)

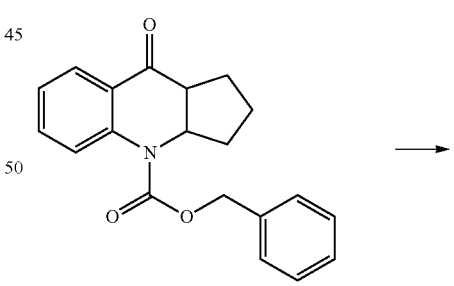

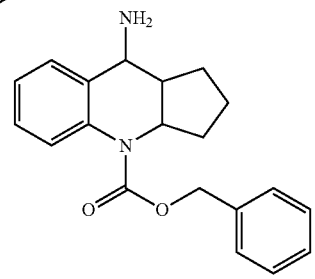

Sodium cyanoborohydride (78 mg, 1.2 mmol, 2.0 equiv) was added to a mixture of benzyl cis-9-oxo-1,2,3,3a,9,9a-hexahydro-4H-cyclopenta[b]quinoline-4-carboxylate (200 mg, 0.622 mmol, 1 equiv) and ammonium acetate (480 mg, 6.22 mmol, 10 equiv) in methanol (6.2 mL). The reaction vessel was sealed and heated to 70° C. After stirring at 70° C. for 90 min, the reaction mixture was cooled to 23° C. and partitioned between ethyl acetate and saturated aqueous sodium bicarbonate solution. The organic layer was washed with saturated aqueous sodium chloride solution, and the washed solution was dried over sodium sulfate. The dried solution was filtered, and the filtrate was concentrated. The residue was purified by flash-column chromatography (50% ethyl acetate-hexanes, grading to ethyl acetate, then flushing with 10% methanol-dichloromethane) to afford 2.

Example 3

Preparation of Racemic Benzyl cis,cis-9-(acetylamino)-1,2,3,3a,9,9a-hexahydro-4H-cyclopenta[b]quinoline-4-carboxylate (3)

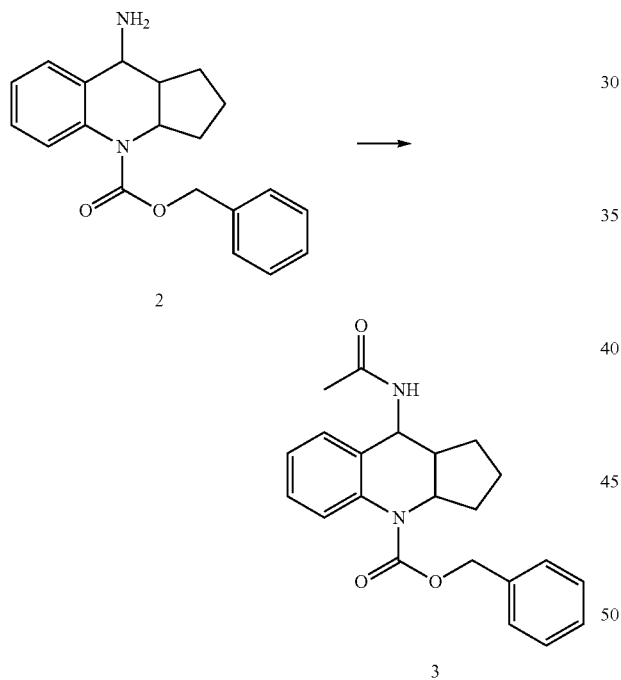

Acetic anhydride (0.250 mL, 2.65 mmol, 5.00 equiv) was added to a solution of benzyl cis,cis-9-amino-1,2,3,3a,9,9a-hexahydro-4H-cyclopenta[b]quinoline-4-carboxylate 2 (171 mg, 0.530 mmol, 1 equiv) and N,N-diisopropylethylamine (0.278 mL, 1.59 mmol, 3.00 equiv) in dioxane (5.3 mL) at 23° C. The reaction mixture was stirred for 10 min, and then was partitioned between ethyl acetate and aqueous hydrochloric acid solution (1N). The organic layer was washed with saturated aqueous sodium chloride solution, and the washed solution was dried over sodium sulfate. The dried solution was filtered, and the filtrate was concentrated to afford 3. [M+H]$^+$: 365.2.

Example 4

Preparation of Racemic Benzyl cis,cis-9-(cyclobutylamino)-1,2,3,3a,9,9a-hexahydro-4H-cyclopenta[b]quinoline-4-carboxylate (4A)

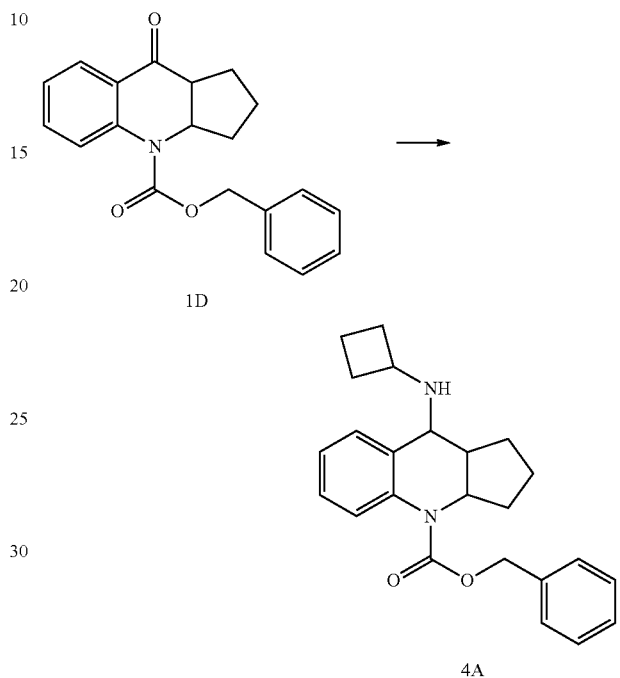

Benzyl cis,cis-9-(cyclobutylamino)-1,2,3,3a,9,9a-hexahydro-4H-cyclopenta[b]quinoline-4-carboxylate 4A was prepared from benzyl cis-9-oxo-1,2,3,3a,9,9a-hexahydro-4H-cyclopenta[b]quinoline-4-carboxylate using a procedure similar to that used for Example 1, Step 5, substituting cyclobutylamine and acetic acid for ammonium acetate. [M+H]$^+$: 377.3.

Example 5

Preparation of Racemic Benzyl cis,cis-9-(isopropylamino)-1,2,3,3a,9,9a-hexahydro-4H-cyclopenta[b]quinoline-4-carboxylate

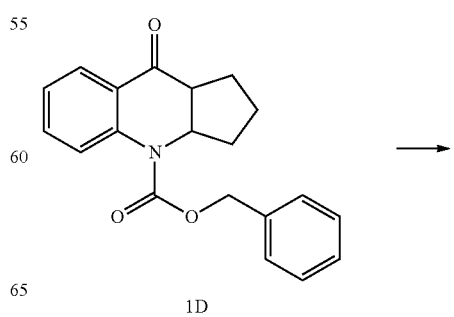

-continued

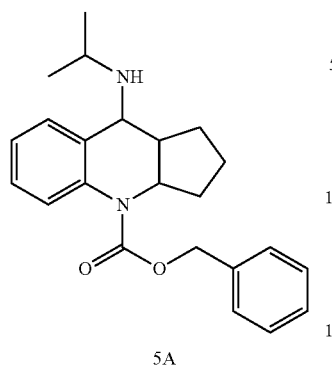

5A

Benzyl cis,cis-9-(isopropylamino)-1,2,3,3a,9,9a-hexahydro-4H-cyclopenta[b]quinoline-4-carboxylate 5A was prepared from racemic benzyl cis-9-oxo-1,2,3,3a,9,9a-hexahydro-4H-cyclopenta[b]quinoline-4-carboxylate using a procedure similar to that used in Example 1, Step 5. [M+H]$^+$: 365.3.

Example 6

Preparation of Racemic Benzyl cis,cis-9-(cyclopropylamino)-6-fluoro-1,2,3,3a,9,9a-hexahydro-4H-cyclopenta[b]quinoline-4-carboxylate (6D)

Step 1: 2-[(3-Fluorophenyl)amino]cyclopentanecarboxylic acid (6A)

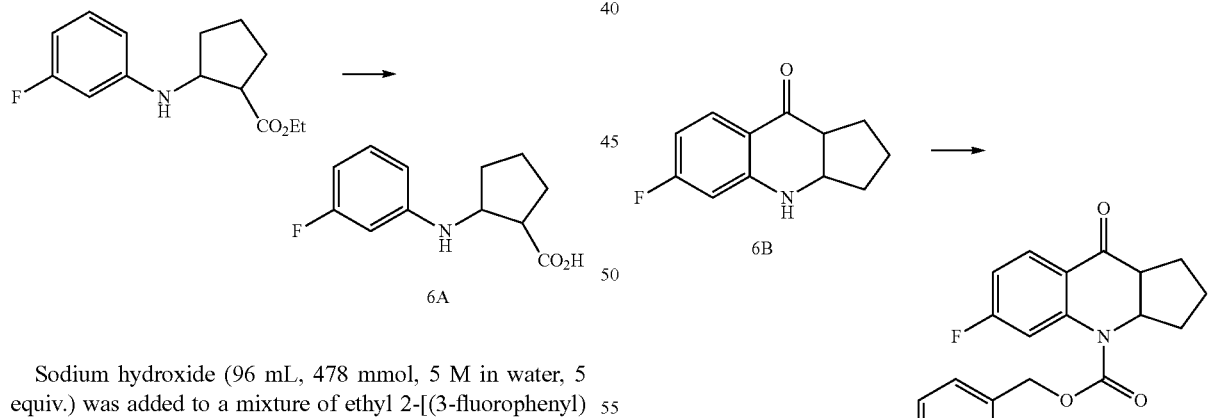

Sodium hydroxide (96 mL, 478 mmol, 5 M in water, 5 equiv.) was added to a mixture of ethyl 2-[(3-fluorophenyl)amino]cyclopentanecarboxylate (reported by Micovic et al., *Synthesis*, 1991, 1043-1045) (24.0 g, 96 mmol, 1 equiv) in dioxane (95 mL). The reaction was heated to 100° C. and stirred for one hour. The reaction mixture was then cooled to 23° C. and acidified to pH=3 with 2N HCl. The reaction mixture was then partitioned between ethyl acetate and water. The organic layer was washed with saturated aqueous sodium chloride solution, and the washed solution was dried over sodium sulfate. The dried solution was filtered, and the filtrate was concentrated to afford 6A as a mixture of cis and trans isomers. [M+H]$^+$: 224.1.

Step 2: Racemic cis-6-Fluoro-1,2,3,3a,4,9a-hexahydro-9H-cyclopenta[b]quinolin-9-one (6B)

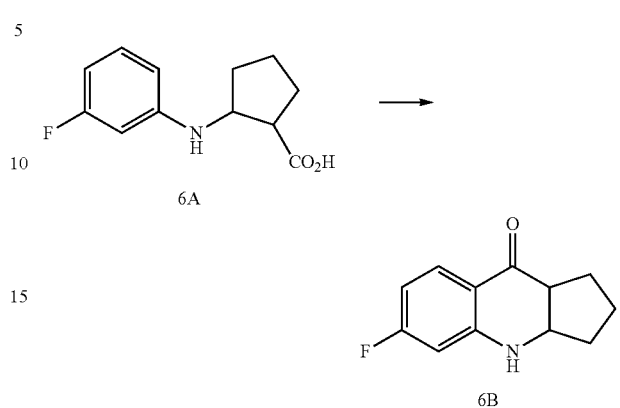

Eaton's reagent (100 mL, 630 mmol, 6.6 equiv.) was added to 2-[(3-fluorophenyl)amino]cyclopentanecarboxylic acid 6A (21.3 g, 95 mmol, 1 equiv). The mixture was heated to 70° C. and stirred for one hour. The reaction mixture was then cooled to 23° C. and quenched with the addition of wet ice. The mixture was then neutralized to pH=10 with the portionwise addition of solid sodium hydroxide pellets. The reaction mixture was then partitioned between ethyl acetate and water. The organic layer was washed with saturated aqueous sodium chloride solution, and the washed solution was dried over sodium sulfate. The dried solution was filtered, and the filtrate was concentrated. The filtrate was purified by flash-column chromatography (hexanes, grading to 50% ethyl acetate-hexanes) to afford 6B. [M+H]$^+$: 206.2.

Step 3: Racemic Benzyl cis-6-fluoro-9-oxo-1,2,3,3a,9,9a-hexahydro-4H-cyclopenta[b]quinoline-4-carboxylate (6C)

Phosgene (20% in toluene, 1.0 g, 2.2 mmol, 1.5 equiv) was added to a solution of cis-6-fluoro-1,2,3,3a,4,9a-hexahydro-9H-cyclopenta[b]quinolin-9-one 6B (300 mg, 1.5 mmol, 1 equiv) and diisopropyl ethylamine (380 uL, 2.2 mmol, 1.5 equiv) in THF (14.6 mL). After stirring at 23° C. for two hours the solution was treated with benzyl alcohol (450 µL, 4.4 mmol, 3 equiv) and sodium hydride (60% in mineral oil, 230 mg, 5.9 mmol, 4 equiv). After stirring at 23° C. for 12 hours the reaction was neutralized to pH=7 with 1N HCl. The reaction mixture was then partitioned between ethyl acetate and water. The organic layer was washed with saturated aqueous sodium chloride solution, and the washed solution was dried over sodium sulfate. The dried solution was filtered, and the filtrate was concentrated. The filtrate was purified by flash-column chromatography (hexanes, grading to 50% ethyl acetate-hexanes) to afford 6C. [M+H]$^+$: 340.2.

Step 4: Racemic Benzyl cis,cis-9-(cyclopropylamino)-6-fluoro-1,2,3,3a,9,9a-hexahydro-4H-cyclopenta[b]quinoline-4-carboxylate (6D)

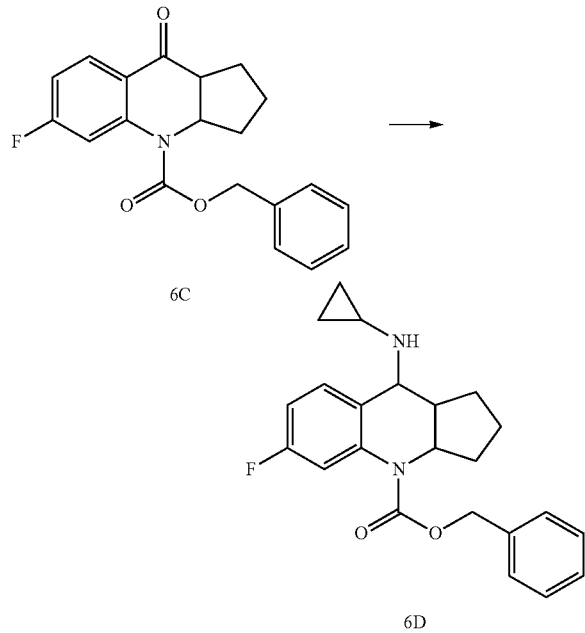

Benzyl cis,cis-9-(cyclopropylamino)-6-fluoro-1,2,3,3a,9,9a-hexahydro-4H-cyclopenta[b]quinoline-4-carboxylate 6D was prepared from benzyl cis-6-fluoro-9-oxo-1,2,3,3a,9,9a-hexahydro-4H-cyclopenta[b]quinoline-4-carboxylate using a procedure similar to that used in Example 1, Step 5. [M+H]$^+$: 381.2.

Example 7

Preparation of Racemic 4-[{cis,cis-4-[(Benzyloxy)carbonyl]-2,3,3a,4,9,9a-hexahydro-1H-cyclopenta[b]quinolin-9-yl}(cyclopropyl)amino]-4-oxobutanoic acid (7)

Step 1: Racemic Benzyl cis,cis-9-[cyclopropyl(4-methoxy-4-oxobutanoyl)amino]-1,2,3,3a,9,9a-hexahydro-4H-cyclopenta[b]quinoline-4-carboxylate (7A)

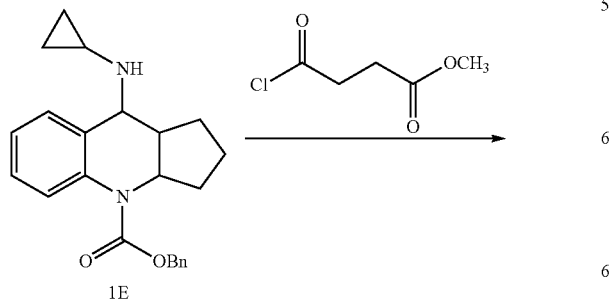

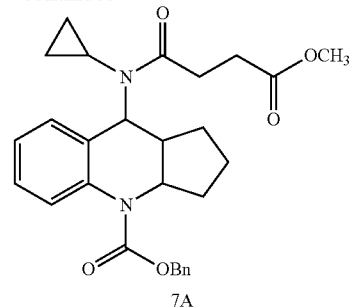

Methyl 4-chloro-4-oxobutanoate (1.54 mL, 12.3 mmol, 2.50 equiv) was added to a solution of benzyl cis,cis-9-(cyclopropylamino)-1,2,3,3a,9,9a-hexahydro-4H-cyclopenta[b]quinoline-4-carboxylate (1E) (1.78 g, 4.91 mmol, 1 equiv) and N,N-diisopropylethylamine (2.57 mL, 14.7 mmol, 3.00 equiv) in dioxane (33 mL) at 23° C. (used a 23° C. water bath to control the exotherm that was observed during the addition). The reaction mixture was stirred for 1 h, and then it was partitioned between ethyl acetate and aqueous hydrochloric acid solution (1 N). The organic layer was washed sequentially with aqueous sodium hydroxide solution (1 N) and saturated aqueous sodium chloride solution, and the washed organic layer was dried over sodium sulfate. The dried solution was filtered, and the filtrate was concentrated. The residue was purified by flash-column chromatography (20% ethyl acetate-hexanes, grading to ethyl acetate) to afford 7A. [M+H]$^+$: 477.2.

Step 2: Racemic 4-[{cis,cis-4-[(Benzyloxy)carbonyl]-2,3,3a,4,9,9a-hexahydro-1H-cyclopenta[b]quinolin-9-yl}(cyclopropyl)amino]-4-oxobutanoic acid (7)

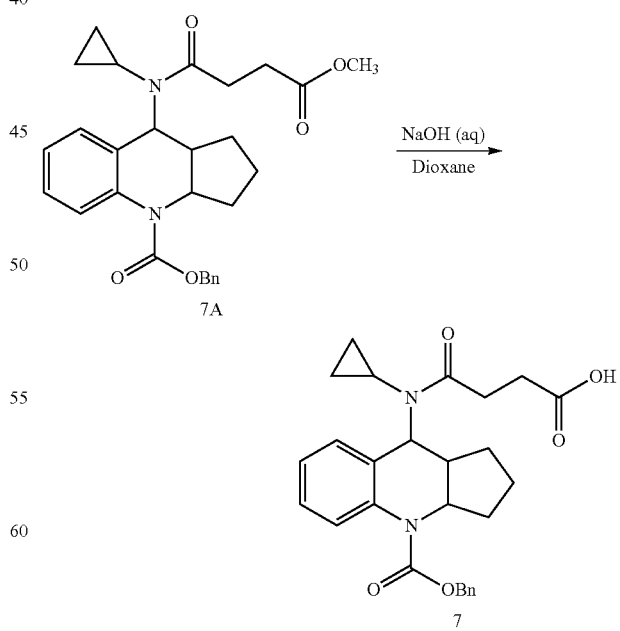

Aqueous sodium hydroxide solution (1 N, 0.168 mL, 0.168 mmol, 4.0 equiv) was added to a solution of benzyl cis,cis-9-

[cyclopropyl(4-methoxy-4-oxobutanoyl)amino]-1,2,3,3a,9,9a-hexahydro-4H-cyclopenta[b]quinoline-4-carboxylate 7A (20 mg, 0.42 mmol, 1 equiv) in dioxane (0.42 mL). The reaction vessel was sealed and heated to 80° C. After stirring for 1 h at 80° C., the reaction mixture was cooled to 23° C. and partitioned between ethyl acetate and aqueous hydrochloric acid solution. The organic layer was washed with saturated aqueous sodium chloride solution, and the washed solution was dried over sodium sulfate. The dried solution was filtered, and the filtrate was concentrated to afford 7 as a white solid. [M+H]⁺: 463.3.

Example 8

Preparation of Enantiomerically Pure 1,2,3,3a,4,9a-hexahydro-9H-cyclopenta[b]quinolin-9-one (8)

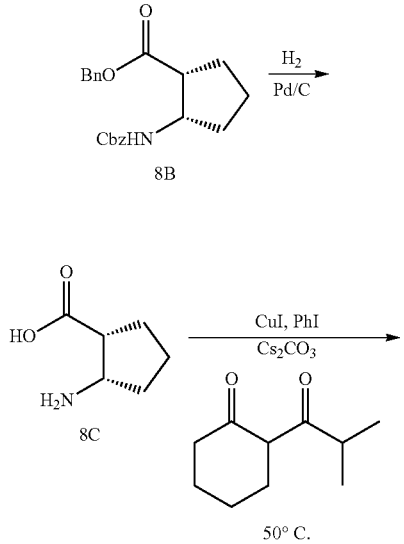

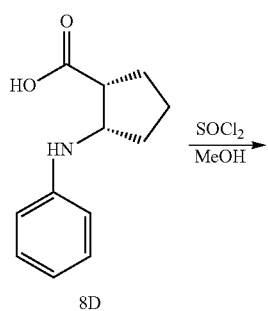

Step 1

Isobutyl chloroformate (1.5 mL, 11.5 mmol) was added to a solution of i-Pr$_2$NEt (2.3 mL, 13 mmol) and (1S,2R)-2-(benzyloxycarbonyl)-cyclopentane-carboxylic acid 8A, (Small Molecules, Inc., Hoboken, N.J.) (2.15 g, 8.70 mmol) in acetone (35 mL) at 0° C. The resulting solution was stirred at 0° C. for 1 h. A solution of NaN$_3$ (1.40 g, 21.0 mmol) in 14 mL of water was added. The resulting mixture was stirred at room temperature for another hour. DCM was added to the reaction mixture. The aqueous layer was separated and extracted with DCM. The organic extracts were combined and washed with brine, dried (MgSO$_4$), filtered and concentrated in vacuo. The residue was dissolved in toluene (50 mL), and benzyl alcohol (1.5 mL, 14.5 mmol) and Et$_3$N (2.4 mL, 17.1 mmol) were added. The resulting mixture was heated at 130° C. for 1 h. The reaction mixture was cooled to room temperature, diluted with EtOAc, and washed with 1 N HCl. The aqueous layer was separated, and extracted with EtOAc. The organic extracts were combined and washed with brine, dried (MgSO$_4$), filtered and concentrated in vacuo. The residue was purified over a silica gel column (80 g), eluting with 10% EtOAc in hexanes, followed by 15% EtOAc in hexanes to give 3.14 g of product 8B as a white solid (95%).

Step 2

10% Pd on carbon (3 g) was added to a solution of compound 8B (3.14 g, 10.2 mmol) in MeOH (45 mL). The resulting mixture was placed under 1 atm of hydrogen and stirred at room temperature overnight. The mixture was filtered through a pad of Celite®, and the filtrate was concentrated in vacuo to give 1.4 g of the desired product 8C as a white solid (100%).

Step 3

Compound 8C (1.0 g, 7.8 mmol), iodobenzene (1.76 g, 8.7 mmol), CuI (148 mg, 0.78 mmol), Cs$_2$CO$_3$ (7.64 g, 23.4 mmol) were mixed in DMF (12 mL) in a sealed tube. The content was evacuated and refilled with nitrogen three times. 2-Isobutyrylcyclohexanone (0.26 mL, 1.6 mmol) was added to the mixture with a syringe via a septum. The septum was replaced with a screwed cap, and the sealed tube was heated at 50° C. overnight. The reaction mixture was cooled to room temperature and checked with TLC. EtOAc and water were added to the mixture. The aqueous layer was separated and washed with EtOAc. The EtOAc layers were combined and extracted with 1 N NaOH three times to make sure that the desired product is retained in the basic water layer. The aqueous layer was treated with 1 N HCl carefully to adjust the pH to between 4 and 5. The resulting aqueous layer was then extracted with EtOAc. The combined organic extracts were washed with brine, dried (MgSO$_4$), filtered and concentrated in vacuo to give 1.24 g (77%) desired product 8D as a brown oil.

Step 4

Thionyl chloride (0.56 mL, 3.0 mmol) was added dropwise to compound 8D (0.85 g, 2.57 mmol) in MeOH (12 mL) at 0° C. The resulting solution was stirred at 0° C. for 30 min and then at room temperature for 4 h. The mixture was concentrated under vacuum. The residue was dissolved in DCM and washed with 1N NaOH. The organic layer was washed with brine, dried (MgSO$_4$) and concentrated in vacuo. The residue was purified over a 40 g silica gel column, eluting with 5% EtOAc in hexanes, followed by 10% EtOAc in hexanes to give 0.68 g desired product 8E as an off-white solid (78%).

Step 5

LHMDS (0.4 mL, 1M in THF, 0.40 mmol) was added to compound 8E; (35 mg, 0.16 mmol) in THF (2 mL) at 0° C. The mixture was stirred at room temperature overnight. The reaction was monitored by TLC and LCMS. EtOAc and water were added to the mixture. The aqueous layer was separated and extracted with EtOAc. The organic extracts were combined, washed with brine, dried (MgSO$_4$), filtered and concentrated. The residue was purified by silica gel thin-layer-chromatography, eluting with 1:5 EtOAc-hexanes, to give 20 mg of desired product 8F.

Step 6

Triflic acid (20 μL, 0.23 mmol) was added to a solution of compound 8F (20 mg, 0.11 mmol) in DCE (1 mL) at 0° C. The reaction was followed by LCMS until done. The reaction mixture was diluted with EtOAc and washed with 1N NaOH. The aqueous layer was separated and extracted with EtOAc. The combined organic extracts was washed with brine, dried (MgSO$_4$), filtered and concentrated in vacuo. The residue was purified by thin-layer-chromatography, eluting with EtOAc-hexanes, to give 15 mg desired compound 8 (75%). The enantiomeric purity of compound 8, predominantly in (3aS, 9aR) configuration, was determined by HPLC analysis to be 92%.

Example 9

Preparation of Compounds 9, 9A, and 9B

The compounds in the following table were prepared from corresponding unsubstituted tricyclic ketone or N-Cbz substituted tricyclic ketone in a similar manner to the process shown in Example 1, step 5, and Example 7, steps 1 and 2. The corresponding unsubstituted ketone or N-Cbz substituted ketones were resolved with chiral HPLC to provide enantiomerically pure ketone intermediates which were converted to final products.

| # | Structure | Stereo designation | Name | [M + H]$^+$ |
|---|---|---|---|---|
| 9 | 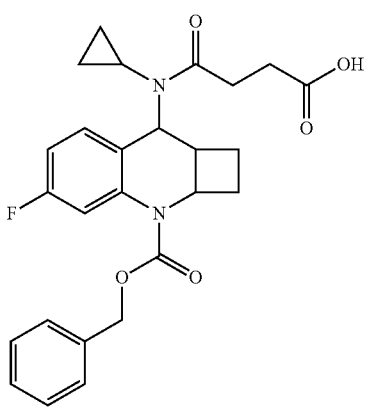 [SMILES: O=C(O)CCC(=O)N(C1CC1)C1c2ccc(F)cc2N(C(=O)OCc2ccccc2)C2CCC21] | cis, cis, single enantiomer | 3-(phenylmethyl) cis,cis-8-[(3-carboxy-1-oxopropyl)cyclopropylamino]-5-fluoro-2,2a,8,8a-tetrahydrocyclobuta[b]quinoline-3(1H)-carboxylate | 489 [M + Na]$^+$ |

| # | Structure | Stereo designation | Name | [M + H]+ |
|---|---|---|---|---|
| 9A | 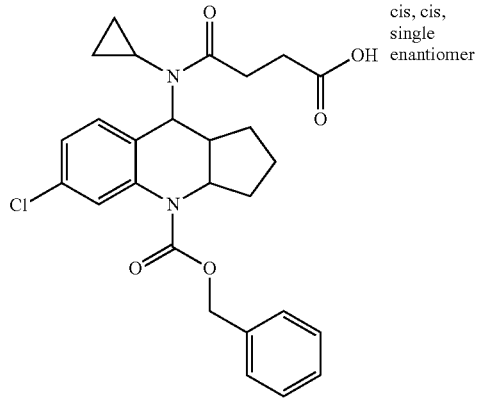 | cis, cis, single enantiomer | 4-(phenylmethyl) cis,cis-[(3-carboxy-1-oxopropyl)cyclopropylamino]-6-chloro-1,2,3,3a,9,9a-hexahydro-4H-cyclopenta[b]quinoline-4-carboxylate | 519.0 [M + Na]+ |
| 9B | 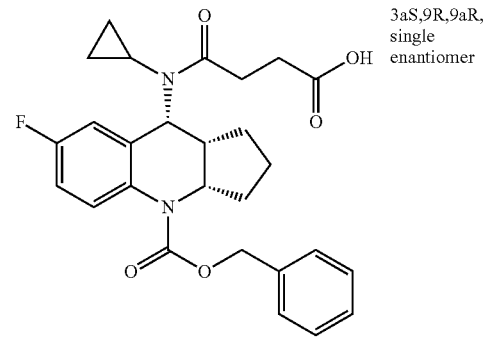 | 3aS,9R,9aR, single enantiomer | 4-(((3aS,9R,9aR)-4-((benzyloxy)carbonyl)-7-fluoro-2,3,3a,4,9,9a-hexahydro-1H-cyclopenta[b]quinolin-9-yl)(cyclopropyl)amino)-4-oxobutanoic acid | 481.2 |

Example 10

Preparation of Racemic 4-[{cis,cis-4-[(Benzyloxy)carbonyl]-2,3,3a,4,9,9a-hexahydro-1H-cyclopenta[b]quinolin-9-yl}(cyclopropyl)amino]-2-methyl-4-oxobutanoic acid (10)

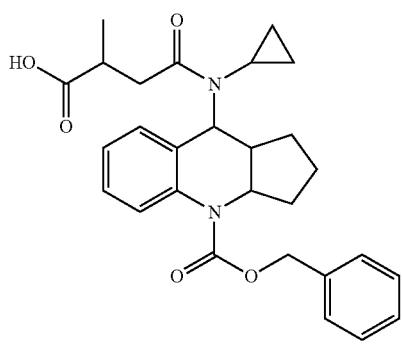

A solution of racemic benzyl cis,cis-9-(cyclopropylamino)-1,2,3,3a,9,9a-hexahydro-4H-cyclopenta[b]quinoline-4-carboxylate (1E) (25 mg, 0.069 mmol, 1 equiv) and 3-methyldihydrofuran-2,5-dione (0.15 mL, 1.6 mmol, 23 equiv) in dioxane (0.35 mL) was heated to 110° C. in a sealed tube. After heating for 1 h, the oil bath temperature was increased to 130° C. for 1 h. The reaction mixture was then cooled to 23° C. and partitioned between ethyl acetate and aqueous hydrochloric acid solution. The organic layer was washed with saturated aqueous sodium chloride solution, and the washed solution was dried over sodium sulfate. The dried solution was filtered, and the filtrate was concentrated. The residue was purified by flash-column chromatography (dichloromethane, grading to 10% methanol-dichloromethane). The residue was then dissolved in DMSO (1 mL), and purified by reverse-phase HPLC (40% acetonitrile-water, grading to 80% acetonitrile-water, with 0.1% trifluoroacetic acid in both the acetonitrile and water) to afford 10. [M+H]+: 477.2.

Example 11

Preparation of N1-cyclopropyl-N1-((3aS,9R,9aR)-7-fluoro-4-(4-(trifluoromethoxy)benzoyl)-2,3,3a,4,9,9a-hexahydro-1H-cyclopenta[b]quinolin-9-yl)-N4-(methylsulfonyl)succinamide

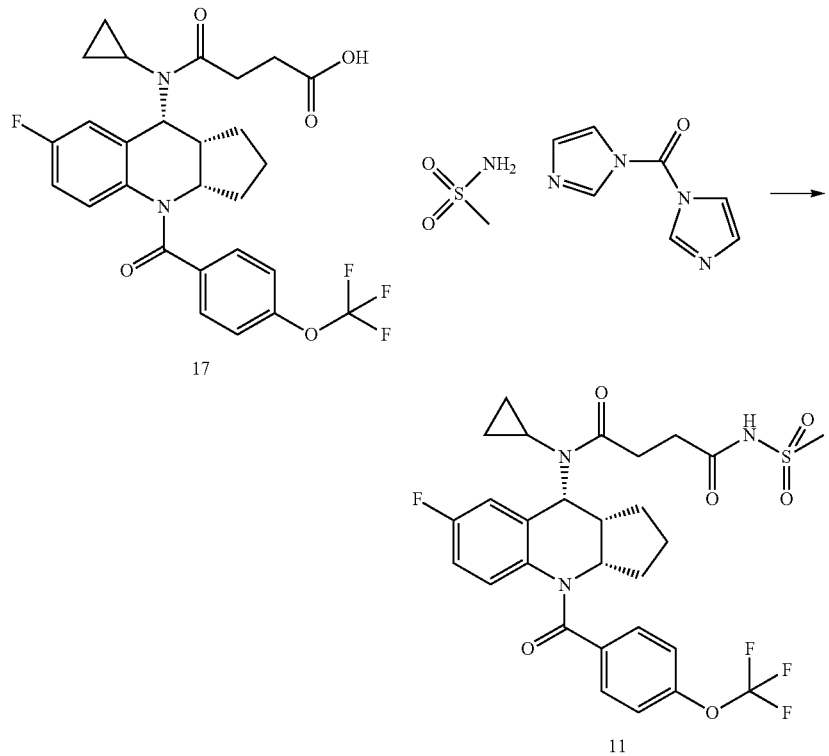

Carbonyldiimidazole (13.65 mg, 0.084 mmol) was added to a stirred mixture of compound 17 (30 mg, 0.056 mmol) (see Example 17 below) in tetrahydrofuran (2 mL) at room temperature. The mixture was stirred at 70° C. for 2 h before it was cooled to room temperature and DBU (0.017 mL, 0.112 mmol) and methanesulfonamide (8.01 mg, 0.084 mmol) were added. The reaction mixture was stirred at room temperature for overnight before it was concentrated under reduced pressure. The residue was purified via preparative TLC, eluting with $CH_2Cl_2$/MeOH=10:1 to give enantiopure 11 (26.3 mg, 0.043 mmol, 77% yield) as a white solid. $[M+H]^+$: 611.8.

Compound 11A, 11B, and 11C were prepared using a similar procedure as is described above. Compound 11A was prepared from compound 17. Compounds 11B and 11C were prepared from compound 83 (see below).

| # | Structure | Stereo designation | Name | $[M + H]^+$ |
|---|-----------|--------------------|------|-------------|
| 11A | 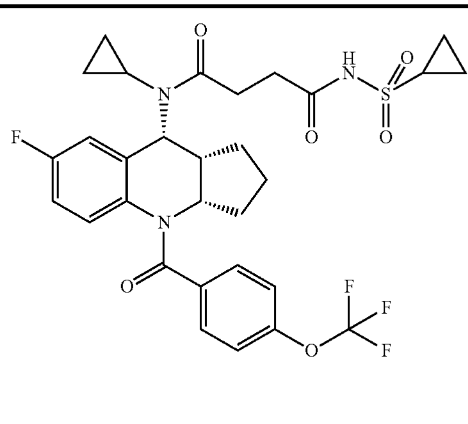 | 3aS,9R,9aR, single enantiomer | N1-cyclopropyl-N4-(cyclopropylsulfonyl)-N1-((3aS,9R,9aR)-7-fluoro-4-(4-(trifluoromethoxy)benzoyl)-2,3,3a,4,9,9a-hexahydro-1H-cyclopenta[b]quinolin-9-yl)succinamide | 637.7 |

-continued

| # | Structure | Stereo designation | Name | [M + H]+ |
|---|---|---|---|---|
| 11B | 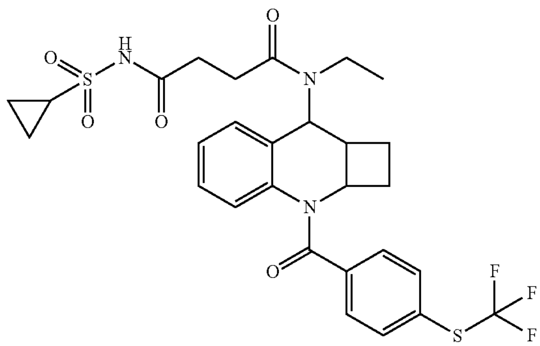 [SMILES: CCN(C(=O)CCC(=O)NS(=O)(=O)C1CC1)C1c2ccccc2N(C(=O)c2ccc(SC(F)(F)F)cc2)C2CCC12] | cis, cis, single enantiomer | N1-(cyclopropylsulfonyl)-N4-ethyl-N4-(cis,cis-3-(4-(trifluoromethylthio)benzoyl)-1,2,2a,3,8,8a-hexahydrocyclobuta[b]quinolin-8-yl)succinamide | 610.1 |
| 11C | 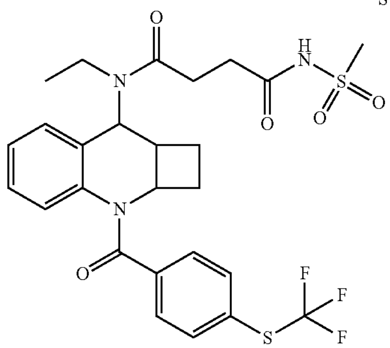 | cis, cis, single enantiomer | N1-ethyl-N4-(methylsulfonyl)-N1-(cis,cis-3-(4-(trifluoromethylthio)benzoyl)-1,2,2a,3,8,8a-hexahydrocyclobuta[b]quinolin-8-yl)succinamide | 584.1 |

Example 12

Preparation of Racemic Benzyl cis,cis-9-[(4-methoxy-4-oxobutanoyl)(phenyl)amino]-1,2,3,3a,9,9a-hexahydro-4H-cyclopenta[b]quinoline-4-carboxylate (12)

Step 1: Racemic Benzyl cis,cis-9-anilino-1,2,3,3a,9,9a-hexahydro-4H-cyclopenta[b]quinoline-4-carboxylate (12A)

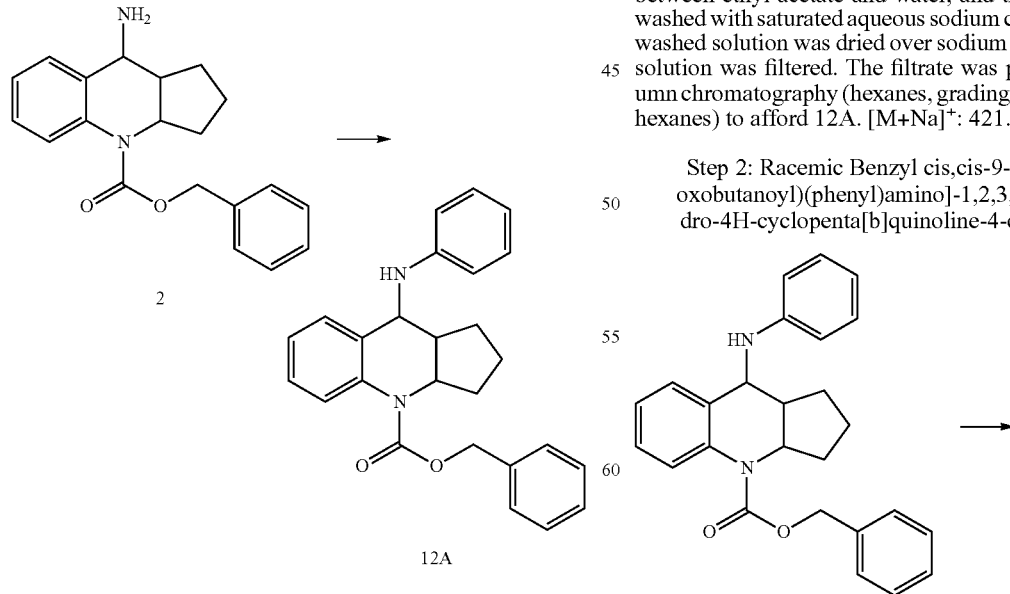

Tris(dibenzylideneacetone)dipalladium (89 mg, 0.098 mmol, 0.15 equiv), 2-dicyclohexylphosphino-2'-(N,N-dimethylamino)biphenyl (115 mg, 0.293 mmol, 0.45 equiv), and benzyl cis,cis-9-amino-1,2,3,3a,9,9a-hexahydro-4H-cyclopenta[b]quinoline-4-carboxylate 2 (210 mg, 0.651 mmol, 1 equiv) were charged in a reaction vial and tetrahydrofuran (6.5 mL) was added. Nitrogen gas was bubbled through the solution for 5 min to remove excess oxygen, and then iodobenzene (0.145 mL, 1.30 mmol, 2.0 equiv) and lithium bis(trimethylsilyl)amide in tetrahydrofuran (1.0 M, 0.977 mL, 0.977 mmol, 1.50 equiv) were added sequentially. The reaction vial was sealed and heated to 55° C. for 16 h. After cooling to 23° C., the reaction mixture was partitioned between ethyl acetate and water, and the organic layer was washed with saturated aqueous sodium chloride solution. The washed solution was dried over sodium sulfate, and the dried solution was filtered. The filtrate was purified by flash-column chromatography (hexanes, grading to 30% ethyl acetate-hexanes) to afford 12A. [M+Na]+: 421.2.

Step 2: Racemic Benzyl cis,cis-9-[(4-methoxy-4-oxobutanoyl)(phenyl)amino]-1,2,3,3a,9,9a-hexahydro-4H-cyclopenta[b]quinoline-4-carboxylate (12)

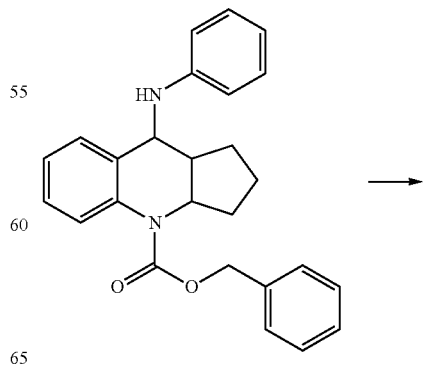

12A

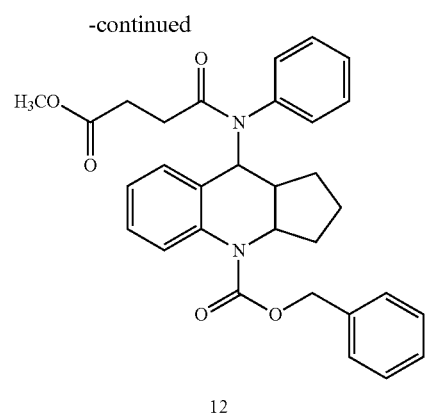

12

Sodium hydride (60% dispersion in oil, 58.2 mg, 1.46 mmol, 4.0 equiv) was added to a solution of methyl 4-chloro-4-oxobutanoate (0.183 mL, 1.46 mmol, 4.0 equiv) and 12A (145 mg, 0.364 mmol, 1 equiv) in dioxane (2.4 mL) at 23° C. The reaction vessel was sealed, and the reaction mixture was heated to 75° C. After stirring for 2.5 h, the temperature was increased to 85° C. After stirring at 85° C. for 2.5 h, the reaction mixture was cooled to 23° C., and saturated aqueous ammonium chloride solution was added slowly (vigorous gas evolution). The quenched reaction mixture was partitioned between ethyl acetate and water, and the organic layer was washed with saturated aqueous sodium chloride solution. The washed solution was dried over sodium sulfate, and the dried solution was filtered. The filtrate was purified by flash-column chromatography (hexanes, grading to 60% ethyl acetate-hexanes) to afford compound 17. [M+H]$^+$: 513.3.

The following compounds were prepared from racemic benzyl cis,cis-9-[(4-methoxy-4-oxobutanoyl)(phenyl)amino]-1,2,3,3a,9,9a-hexahydro-4H-cyclopenta[b]quinoline-4-carboxylate 12A, using procedures similar to those described in Example 14 below.

| # | Structure | Stereo designation | Name | [M + H]$^+$ |
|---|---|---|---|---|
| 12B | 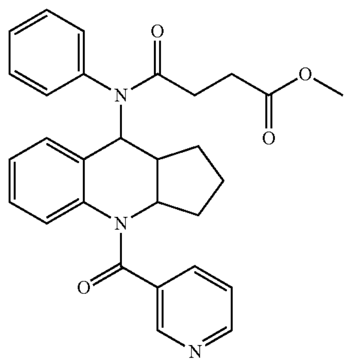 [SMILES: COC(=O)CCC(=O)N(c1ccccc1)C1c2ccccc2N(C(=O)c2cccnc2)C2CCCC21] | racemic, cis, cis | methyl 4-oxo-4-{phenyl[cis,cis-4-(pyridin-3-ylcarbonyl)-2,3,3a,4,9,9a-hexahydro-1H-cyclopenta[b]quinolin-9-yl]amino}butanoate | 484.2 |
| 12C | 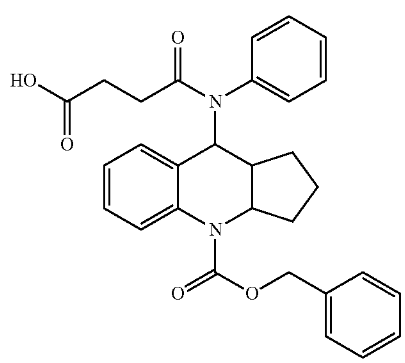 [SMILES: O=C(O)CCC(=O)N(c1ccccc1)C1c2ccccc2N(C(=O)OCc2ccccc2)C2CCCC21] | racemic, cis, cis | 4-[{cis,cis-4-[(benzyloxy)carbonyl]-2,3,3a,4,9,9a-hexahydro-1H-cyclopenta[b]quinolin-9-yl}(phenyl)amino]-4-oxobutanoic acid | 499.2 |
| 12D | 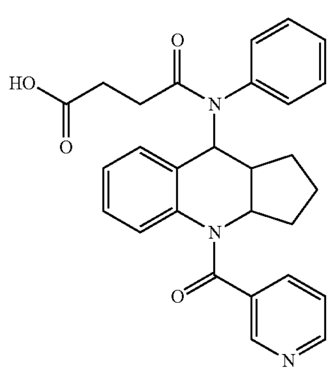 [SMILES: O=C(O)CCC(=O)N(c1ccccc1)C1c2ccccc2N(C(=O)c2cccnc2)C2CCCC21] | racemic, cis, cis | 4-oxo-4-{phenyl[cis,cis-4-(pyridin-3-ylcarbonyl)-2,3,3a,4,9,9a-hexahydro-1H-cyclopenta[b]quinolin-9-yl]amino}butanoic acid | 470.2 |

-continued

| # | Structure | Stereo designation | Name | [M + H]+ |
|---|-----------|--------------------|------|----------|
| 12E | 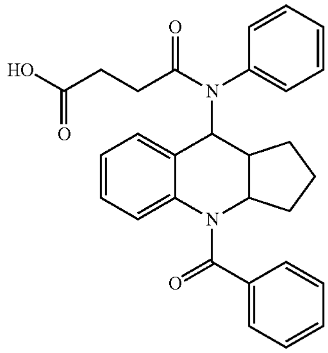 [SMILES: O=C(O)CCC(=O)N(c1ccccc1)C1c2ccccc2N(C(=O)c2ccccc2)C2CCCC21] | racemic, cis, cis | 4-oxo-4-{phenyl[cis,cis-4-(phenylcarbonyl)-2,3,3a,4,9,9a-hexahydro-1H-cyclopenta[b]quinolin-9-yl]amino}butanoic acid | 469.2 |

Example 13

Preparation of Racemic 4-[{cis,cis-4-[(Benzyloxy)carbonyl]-2,3,3a,4,9,9a-hexahydro-1H-cyclopenta[b]quinolin-9-yl}(ethyl)amino]-4-oxobutanoic acid (13)

Step 1: Racemic benzyl cis,cis-9-(ethylamino)-1,2,3,3a,9,9a-hexahydro-4H-cyclopenta[b]quinoline-4-carboxylate (13)

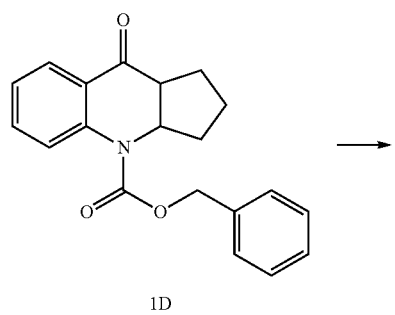

A was prepared from benzyl cis-9-oxo-1,2,3,3a,9,9a-hexahydro-4H-cyclopenta[b]quinoline-4-carboxylate 1D using a procedure similar to that used in Example 1, Step 5. [M+H]+: 351.2.

Step 2: Racemic 4-[{cis,cis-4-[(Benzyloxy)carbonyl]-2,3,3a,4,9,9a-hexahydro-1H-cyclopenta[b]quinolin-9-yl}(ethyl)amino]-4-oxobutanoic acid (13)

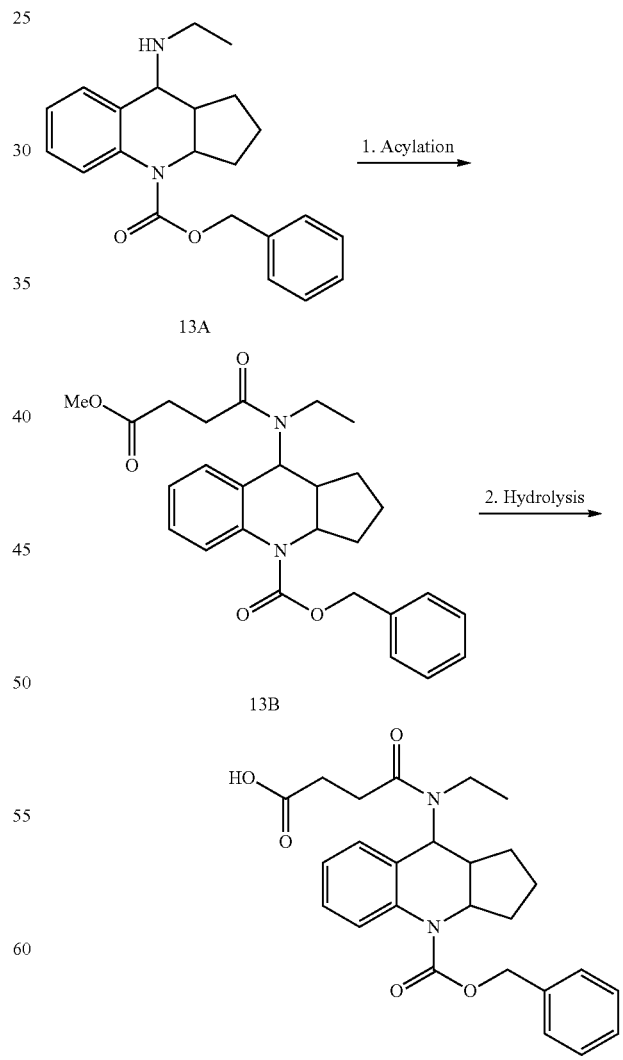

4-[{Cis,cis-4-[(Benzyloxy)carbonyl]-2,3,3a,4,9,9a-hexahydro-1H-cyclopenta[b]quinolin-9-yl}(ethyl)amino]-4-oxobutanoic acid ([M+H]+: 451.2) was prepared from 13B using a sequence similar to that used for Example 7, step 2. Compound 13B was prepared from 13A following a similar procedure as Example 7, step 1.

The following examples were prepared from racemic benzyl cis,cis-9-[ethyl(4-methoxy-4-oxobutanoyl)amino]-1,2,3,3a,9,9a-hexahydro-4H-cyclopenta[b]quinoline-4-carboxylate (13B) using procedures similar to those used in Example 14.

| # | Structure | Stereo designation | Name | [M + H]+ |
|---|---|---|---|---|
| 13C | 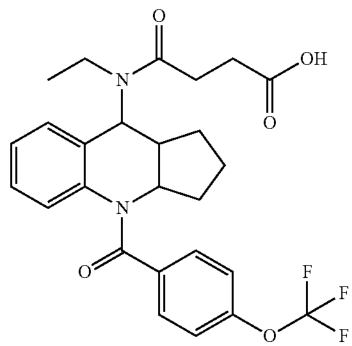 [SMILES: CCN(C(=O)CCC(=O)O)C1c2ccccc2N(C(=O)c2ccc(OC(F)(F)F)cc2)C2CCCC12] | racemic, cis, cis | 4-{ethyl [cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid | 505.1 |
| 13D | 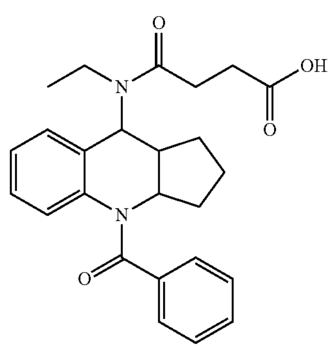 [SMILES: CCN(C(=O)CCC(=O)O)C1c2ccccc2N(C(=O)c2ccccc2)C2CCCC12] | racemic, cis, cis | 4-{ethyl[cis,cis-4-(phenylcarbonyl)-2,3,3a,4,9,9a-hexahydro-1H-cyclopenta[b]quinolin-9-yl]amino}-4-oxobutanoic acid | 421.2 |
| 13E | 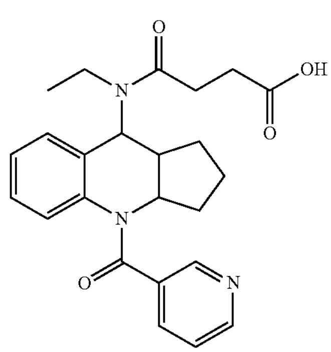 [SMILES: CCN(C(=O)CCC(=O)O)C1c2ccccc2N(C(=O)c2cccnc2)C2CCCC12] | racemic, cis, cis | 4-{ethyl[cis,cis-4-(pyridin-3-ylcarbonyl)-2,3,3a,4,9,9a-hexahydro-1H-cyclopenta[b]quinolin-9-yl]amino}-4-oxobutanoic acid | 422.2 |

Example 14

Preparation of Racemic 4-{Cyclopropyl[cis,cis-4-(phenylcarbonyl)-2,3,3a,4,9,9a-hexahydro-1H-cyclopenta[b]quinolin-9-yl]amino}-4-oxobutanoic acid (14)

Step 1: Methyl 4-{cyclopropyl[cis,cis-2,3,3a,4,9,9a-hexahydro-1H-cyclopenta[b]quinolin-9-yl]amino}-4-oxobutanoate (14A)

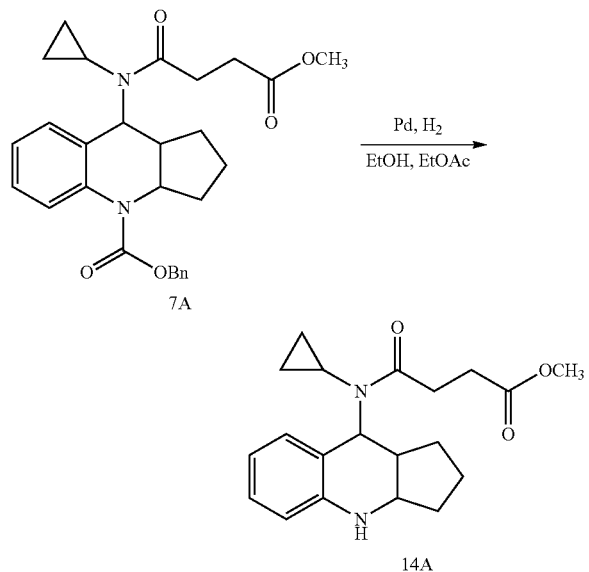

Palladium (10% on carbon, 103 mg, 0.050 equiv) was added to a solution of benzyl cis,cis-9-[cyclopropyl(4-methoxy-4-oxobutanoyl)amino]-1,2,3,3a,9,9a-hexahydro-4H-cyclopenta[b]quinoline-4-carboxylate 7A (922 mg, 1.93 mmol, 1 equiv) in ethanol (14.5 mL) and ethyl acetate (4.84 mL). A three-way stopcock connected to a hydrogen balloon and a vacuum line was fitted to the top of the flask, and the flask was subjected to alternating vacuum purging and hydrogen filling cycles (4×). The reaction mixture was then stirred under hydrogen for 90 min at 23° C., and then was filtered through cotton. The filtrate was concentrated to afford 14A, which was used without further purification. [M+H]⁺: 343.2.

Step 2: Methyl 4-[[cis,cis-4-benzoyl-2,3,3a,4,9,9a-hexahydro-1H-cyclopenta[b]quinolin-9-yl](cyclopropyl)amino]-4-oxobutanoate (14B)

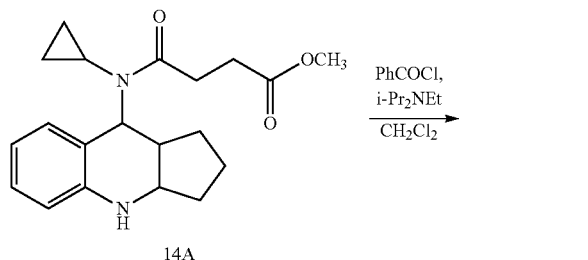

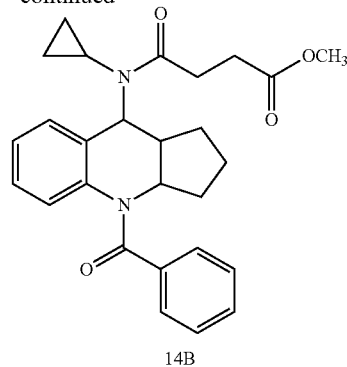

Benzoyl chloride (0.028 mL, 0.24 mmol, 1.5 equiv) was added to a solution of methyl 4-{cyclopropyl[cis,cis-2,3,3a,4,9,9a-hexahydro-1H-cyclopenta[b]quinolin-9-yl]amino}-4-oxobutanoate 14A (55 mg, 0.16 mmol, 1 equiv) and N,N-diisopropylethylamine (0.084 mL, 0.48 mmol, 3.0 equiv) in dichloromethane (1.60 mL) at 23° C. The reaction mixture was stirred at 23° C. for 30 min, and then was partitioned between ethyl acetate and aqueous hydrochloric acid solution (1N). The organic layer was washed with saturated aqueous sodium chloride solution, and the washed solution was dried over sodium sulfate. The dried solution was filtered, and the filtrate was concentrated. The residue was purified by flash-column chromatography (40% ethyl acetate-hexanes, grading to ethyl acetate) to afford 14B. [M+H]⁺: 447.2.

Step 3: 4-[[cis,cis-4-Benzoyl-2,3,3a,4,9,9a-hexahydro-1H-cyclopenta[b]quinolin-9-yl](cyclopropyl)amino]-4-oxobutanoic acid (14)

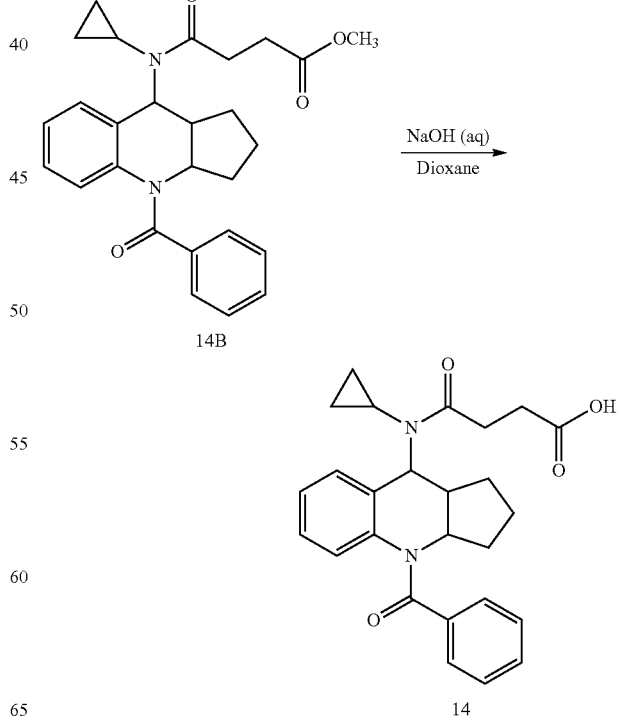

Compound 14 was prepared from methyl 4-[[cis,cis-4-benzoyl-2,3,3a,4,9,9a-hexahydro-1H-cyclopenta[b]quinolin-9-yl](cyclopropyl)amino]-4-oxobutanoate 14B using a procedure similar to that used in Example 2, Step 2. [M+H]+: 433.2

The following compounds were made from racemic methyl 4-{cyclopropyl[cis,cis-2,3,3a,4,9,9a-hexahydro-1H-cyclopenta[b]quinolin-9-yl]amino}-4-oxobutanoate (14A) using procedures similar to those used in Example 14, Steps 2 and 3:

| # | Structure | Stereo designation | Name | [M + H]+ |
|---|---|---|---|---|
| 14C | 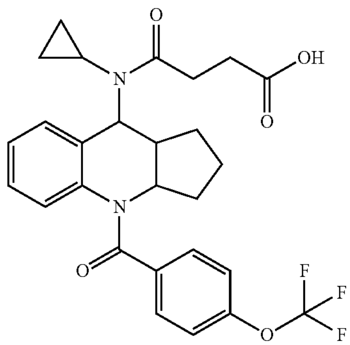 [SMILES: O=C(O)CCC(=O)N(C1CC1)C1c2ccccc2N(C(=O)c2ccc(OC(F)(F)F)cc2)C2CCCC21] | racemic, cis, cis | 4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid | 517.2 |
| 14D | 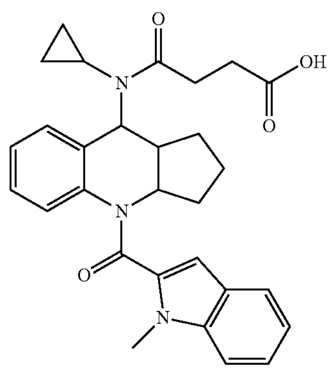 [SMILES: Cn1c(C(=O)N2c3ccccc3C(N(C(=O)CCC(=O)O)C3CC3)C3CCCC32)cc2ccccc21] | racemic, cis, cis | 4-(cyclopropyl{cis,cis-4-[(1-methyl-1H-indol-2-yl)carbonyl]-2,3,3a,4,9,9a-hexahydro-1H-cyclopenta[b]quinolin-9-yl}amino)-4-oxobutanoic acid | 486.2 |
| 14E | 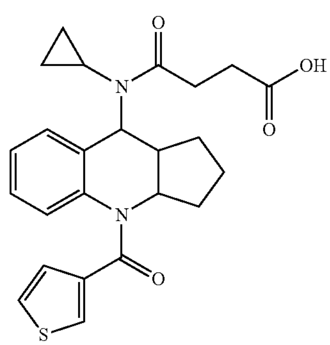 [SMILES: O=C(O)CCC(=O)N(C1CC1)C1c2ccccc2N(C(=O)c2ccsc2)C2CCCC21] | racemic, cis, cis | 4-{cyclopropyl[cis,cis-4-(thiophen-3-ylcarbonyl)-2,3,3a,4,9,9a-hexahydro-1H-cyclopenta[b]quinolin-9-yl]amino}-4-oxobutanoic acid | 439.0 |
| 14F | 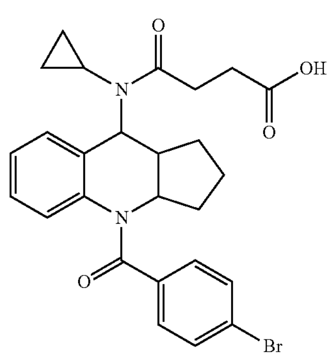 [SMILES: O=C(O)CCC(=O)N(C1CC1)C1c2ccccc2N(C(=O)c2ccc(Br)cc2)C2CCCC21] | racemic, cis, cis | 4-[{cis,cis-4-[(4-bromophenyl)carbonyl]-2,3,3a,4,9,9a-hexahydro-1H-cyclopenta[b]quinolin-9-yl}(cyclopropyl)amino]-4-oxobutanoic acid | 511.1 |

| # | Structure | Stereo designation | Name | [M + H]+ |
|---|---|---|---|---|
| 14G | 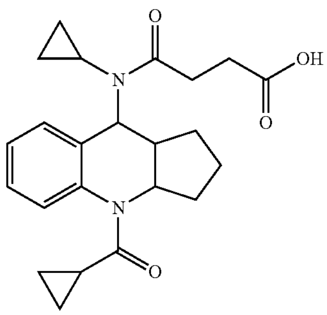 [SMILES: O=C(O)CCC(=O)N(C1CC1)C1c2ccccc2N(C(=O)C2CC2)C2CCCC21] | racemic, cis, cis | 4-{cyclopropyl[cis,cis-4-(cyclopropylcarbonyl)-2,3,3a,4,9,9a-hexahydro-1H-cyclopenta[b]quinolin-9-yl]amino}-4-oxobutanoic acid | 397.0 |
| 14H | 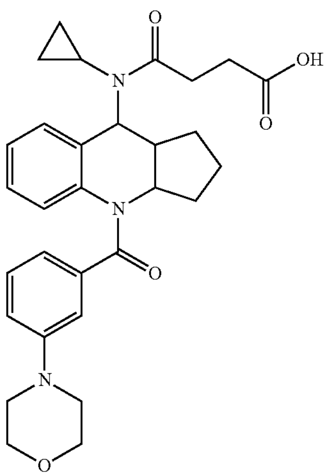 [SMILES: O=C(O)CCC(=O)N(C1CC1)C1c2ccccc2N(C(=O)c2cccc(N3CCOCC3)c2)C2CCCC21] | racemic, cis, cis | 4-(cyclopropyl{cis,cis-4-[(3-morpholin-4-ylphenyl)carbonyl]-2,3,3a,4,9,9a-hexahydro-1H-cyclopenta[b]quinolin-9-yl}amino)-4-oxobutanoic acid | 518.2 |
| 14i | 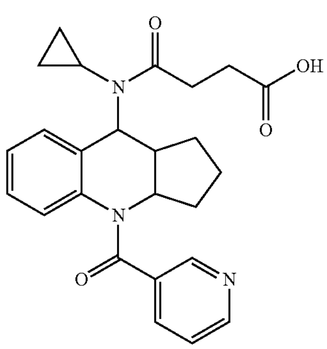 [SMILES: O=C(O)CCC(=O)N(C1CC1)C1c2ccccc2N(C(=O)c2cccnc2)C2CCCC21] | racemic, cis, cis | 4-{cyclopropyl[cis,cis-4-(pyridin-3-ylcarbonyl)-2,3,3a,4,9,9a-hexahydro-1H-cyclopenta[b]quinolin-9-yl]amino}-4-oxobutanoic acid | 434.2 |
| 14K | 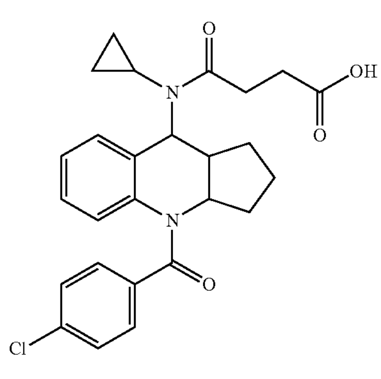 [SMILES: O=C(O)CCC(=O)N(C1CC1)C1c2ccccc2N(C(=O)c2ccc(Cl)cc2)C2CCCC21] | racemic, cis, cis | 4-[{cis,cis-4-[(4-chlorophenyl)carbonyl]-2,3,3a,4,9,9a-hexahydro-1H-cyclopenta[b]quinolin-9-yl}(cyclopropyl)amino]-4-oxobutanoic acid | 467.1 |

| # | Structure | Stereo designation | Name | [M + H]+ |
|---|---|---|---|---|
| 14L | 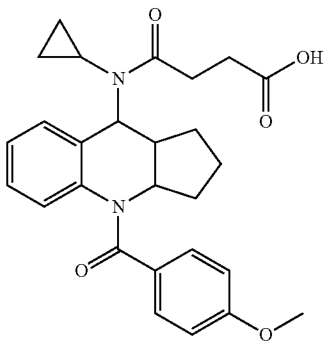 [SMILES: COc1ccc(C(=O)N2c3ccccc3C(N(C(=O)CCC(=O)O)C3CC3)C3CCCC32)cc1] | racemic, cis, cis | 4-(cyclopropyl{cis,cis-4-[(4-methoxyphenyl)carbonyl]-2,3,3a,4,9,9a-hexahydro-1H-cyclopenta[b]quinolin-9-yl}amino)-4-oxobutanoic acid | 463.2 |
| 14N | 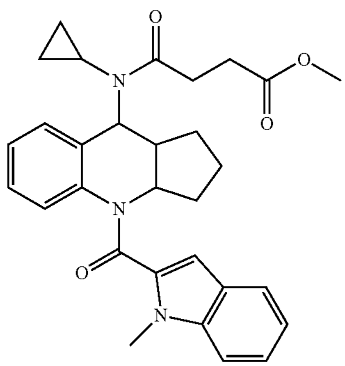 [SMILES: COC(=O)CCC(=O)N(C1CC1)C1c2ccccc2N(C(=O)c2cc3ccccc3n2C)C2CCCC21] | racemic, cis, cis | methyl 4-(cyclopropyl{cis,cis-4-[(1-methyl-1H-indol-2-yl)carbonyl]-2,3,3a,4,9,9a-hexahydro-1H-cyclopenta[b]quinolin-9-yl}amino)-4-oxobutanoate | 500.2 |
| 14o | 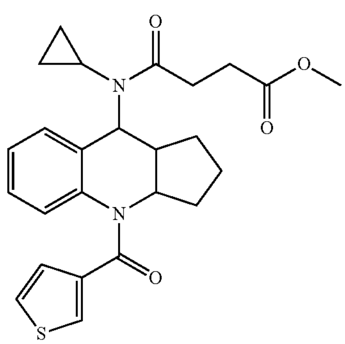 [SMILES: COC(=O)CCC(=O)N(C1CC1)C1c2ccccc2N(C(=O)c2ccsc2)C2CCCC21] | racemic, cis, cis | methyl 4-{cyclopropyl[cis,cis-4-(thiophen-3-ylcarbonyl)-2,3,3a,4,9,9a-hexahydro-1H-cyclopenta[b]quinolin-9-yl]amino}-4-oxobutanoate | 453.2 |
| 14P | 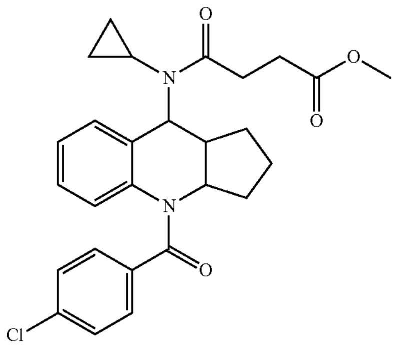 [SMILES: COC(=O)CCC(=O)N(C1CC1)C1c2ccccc2N(C(=O)c2ccc(Cl)cc2)C2CCCC21] | racemic, cis, cis | methyl 4-[{cis,cis-4-[(4-chlorophenyl)carbonyl]-2,3,3a,4,9,9a-hexahydro-1H-cyclopenta[b]quinolin-9-yl}(cyclopropyl)amino]-4-oxobutanoate | 481.2 |

Example 15

Preparation of Racemic Benzyl cis,cis-9-[cyclopropyl(4-methoxy-4-oxobutanoyl)amino]-6-fluoro-1,2,3,3a,9,9a-hexahydro-4H-cyclopenta[b]quinoline-4-carboxylate (15)

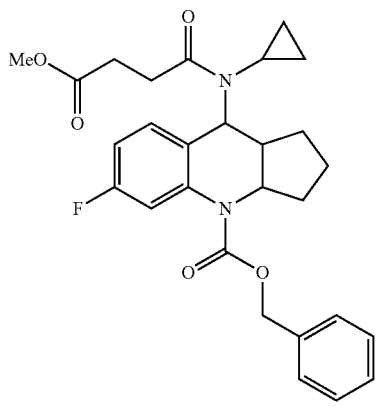

15 was prepared from benzyl cis,cis-9-(cyclopropylamino)-6-fluoro-1,2,3,3a,9,9a-hexahydro-4H-cyclopenta[b]quinoline-4-carboxylate (6D) using a procedure similar to that used for Example 7, Step 1. [M+H]$^+$: 495.2.

Example 16

4-[{cis,cis-4-[(Benzyloxy)carbonyl]-6-fluoro-2,3,3a,4,9,9a-hexahydro-1H-cyclopenta[b]quinolin-9-yl}(cyclopropyl)amino]-4-oxobutanoic acid (16)

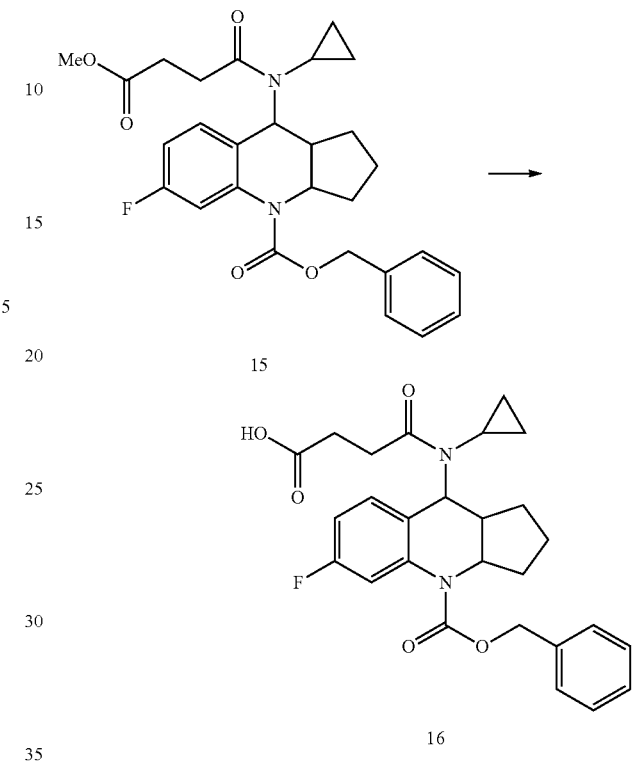

16 was prepared from benzyl cis,cis-9-[cyclopropyl(4-methoxy-4-oxobutanoyl)amino]-6-fluoro-1,2,3,3a,9,9a-hexahydro-4H-cyclopenta[b]quinoline-4-carboxylate (15) using a procedure similar to that used in Example 7, Step 2. [M+H]$^+$: 481.2.

The following examples were prepared from racemic benzyl cis,cis-9-[cyclopropyl(4-methoxy-4-oxobutanoyl)amino]-6-fluoro-1,2,3,3a,9,9a-hexahydro-4H-cyclopenta[b]quinoline-4-carboxylate (15) using procedures similar to that used in Example 14, Steps 1 and 2 (for the esters in the table) and Example 14, Steps 1-3 (for the carboxylic acids in the table).

| # | Structure | Stereo Designation | Name | [M + H]$^+$ |
|---|---|---|---|---|
| 16A | 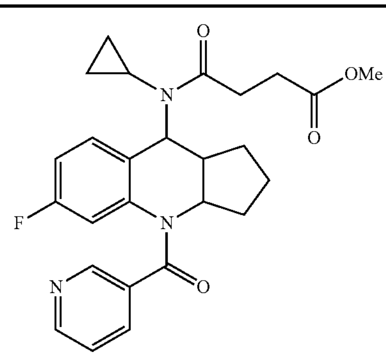 | racemic, cis, cis | Methyl 4-{cyclopropyl[cis,cis-6-fluoro-4-(pyridin-3-ylcarbonyl)-2,3,3a,4,9,9a-hexahydro-1H-cyclopenta[b]quinolin-9-yl]amino}-4-oxobutanoate | 466.2 |

| # | Structure | Stereo Designation | Name | [M + H]+ |
|---|---|---|---|---|
| 16B | 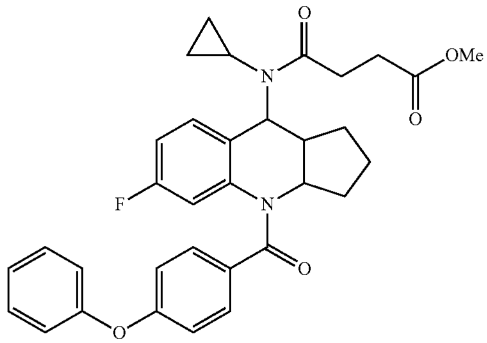 [SMILES: COC(=O)CCC(=O)N(C1CC1)C1c2ccc(F)cc2N(C(=O)c2ccc(Oc3ccccc3)cc2)C2CCCC21] | racemic, cis, cis | Methyl 4-{cyclopropyl[cis,cis-6-fluoro-4-[(4-phenoxyphenyl)carbonyl]-2,3,3a,4,9,9a-hexahydro-1H-cyclopenta[b]quinolin-9-yl}amino)-4-oxobutanoate | 557.2 |
| 16C | 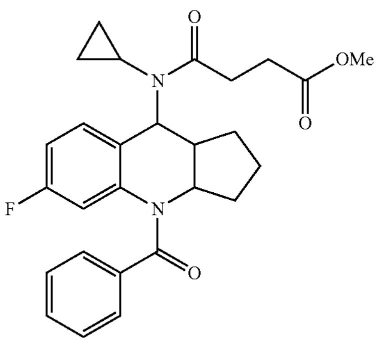 [SMILES: COC(=O)CCC(=O)N(C1CC1)C1c2ccc(F)cc2N(C(=O)c2ccccc2)C2CCCC21] | racemic, cis, cis | Methyl 4-{cyclopropyl[cis,cis-6-fluoro-4-(phenylcarbonyl)-2,3,3a,4,9,9a-hexahydro-1H-cyclopenta[b]quinolin-9-yl]amino}-4-oxobutanoate | 465.2 |
| 16D | 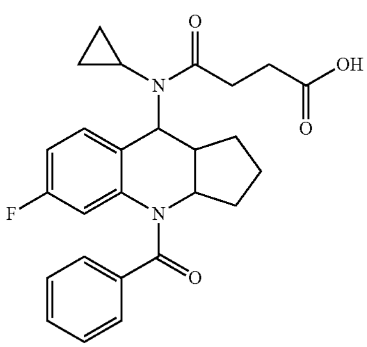 [SMILES: O=C(O)CCC(=O)N(C1CC1)C1c2ccc(F)cc2N(C(=O)c2ccccc2)C2CCCC21] | racemic, cis, cis | 4-{cyclopropyl[cis,cis-6-fluoro-4-(phenylcarbonyl)-2,3,3a,4,9,9a-hexahydro-1H-cyclopenta[b]quinolin-9-yl]amino}-4-oxobutanoic acid | 461.1 |
| 16E | 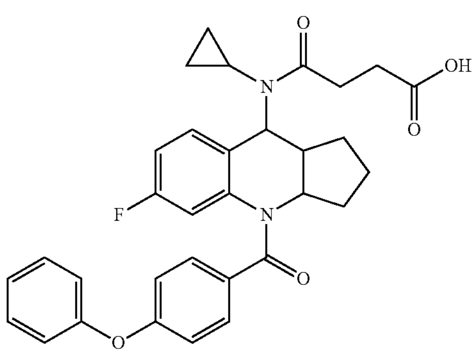 [SMILES: O=C(O)CCC(=O)N(C1CC1)C1c2ccc(F)cc2N(C(=O)c2ccc(Oc3ccccc3)cc2)C2CCCC21] | racemic, cis, cis | 4-{cyclopropyl[cis,cis-6-fluoro-4-[(4-phenoxyphenyl)carbonyl]-2,3,3a,4,9,9a-hexahydro-1H-cyclopenta[b]quinolin-9-yl}amino)-4-oxobutanoic acid | 543.2 |

Example 17

Preparation of Enantiopure 4-(Cyclopropyl((3aS,9R, 9aR)-7-fluoro-4-(4-(trifluoromethoxy)benzoyl)-2,3, 3a,4,9,9a-hexahydro-1H-cyclopenta[b]quinolin-9-yl) amino)-4-oxobutanoic acid (17)

Step 1

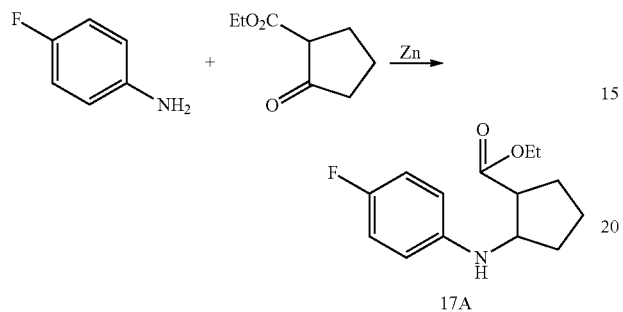

In a 500 mL round bottom flask was added acetic acid (81 mL), water (8.05 mL, 447 mmol), 4-fluoroaniline (10 mL, 97 mmol), ethyl 2-oxocyclopentanecarboxylate (13.13 mL, 97 mmol) followed by zinc (25.4 g, 388 mmol). The reaction was warmed to 80° C., during which time gas evolution was noted. After 2 h, the bubbling had stopped and the reaction was cooled to rt. The slurry was then diluted with MeOH and the zinc solids were removed by filtering through a fritted funnel. The collected filtrate was then concentrated on the rotovap and then diluted with DCM and wet ice. The solution was neutralized with NH$_4$OH to pH=10. The mixture was then poured into a separation funnel containing DCM and water. The mixture was extracted 3× with DCM. The combined fractions were washed with brine, dried over Na$_2$SO$_4$ and concentrated in vacuo. The resulting oil 17A was used without further purification.

Step 2

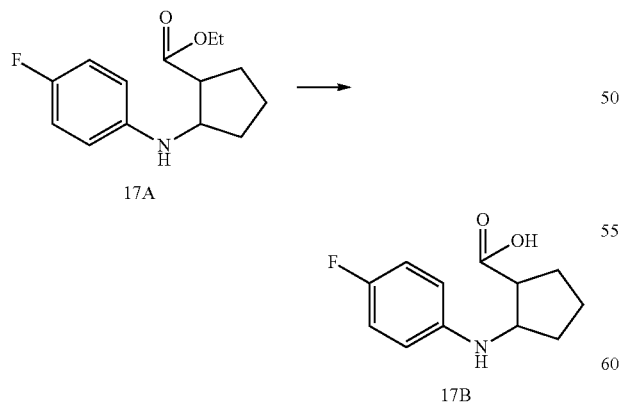

The above obtained ester 17A (24.0 g, 96 mmol) was dissolved in Dioxane (95 mL) and treated with NaOH (96 mL, 478 mmol). The reaction stirred at 100 C for one hour. The reaction was then cooled to rt and acidified with 2 N HCl to pH=3. The reaction mixture was then poured into a separation funnel containing EtOAc and water. The mixture was extracted 3× with EtOAc. The combined fractions were washed with brine, dried over Na$_2$SO$_4$ and concentrated in vacuo. The resulting oil was used without further purification.

Step 3

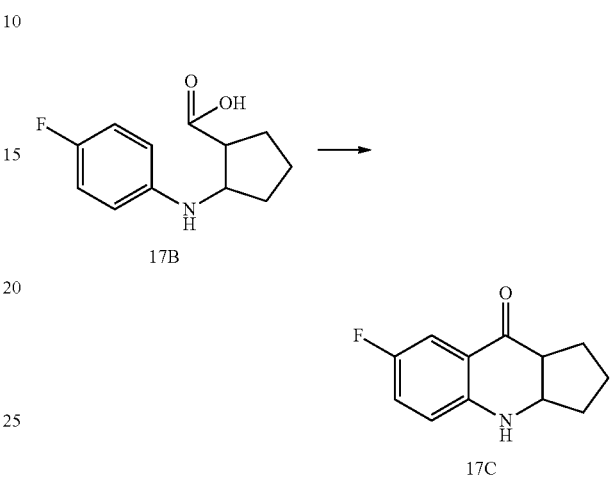

Acid 17B (21.3 g, 95 mmol) was treated with Eaton's reagent (100 mL, 630 mmol) and warmed to 70° C. The reaction stirred for one hour. As the reaction stirred it turned deep red/brown. LCMS shows that the SM has been consumed. The reaction is cooled to rt and then quenched by the portionwise addition of wet ice. The mixture was then treated with solid NaOH pellets until the pH was 10. The reaction mixture was then poured into a separation funnel containing EtOAc and water. The mixture was extracted 3× with EtOAc. The combined fractions were washed with brine, dried over Na$_2$SO$_4$ and concentrated in vacuo. The residue was purified by column chromatography (Biotage, 340 g, 0-50% EtOAc/heptane) which afforded 17C (10 g).

Step 4

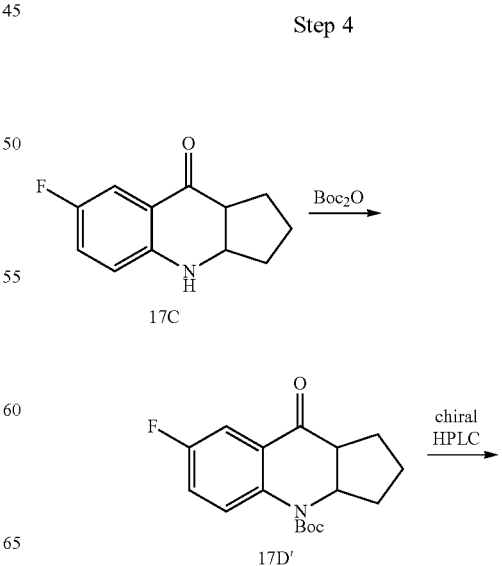

-continued

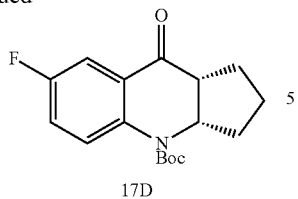
17D

Boc₂O (9.50 g, 41.7 mmol) was added to the solution of 7-fluoro-2,3,3a,4-tetrahydro-1H-cyclopenta[b]quinolin-9(9aH)-one 17C (13.9 mmol), Et₃N (5.80 mL, 41.7 mmol) and DMAP (1.70 g, 13.9 mmol) in 1,4-dioxane (100 mL), the resultant mixture was kept stirring at rt overnight. The mixture was diluted with EtOAc (100 mL), washed with H₂O (100 mL), and brine (100 mL), the organic was dried over MgSO₄ and concentrated. The residue was purified via silica gel column chromatography (EtOAc/Hexane=1:10), to obtain the racemic, Boc protected ketone amine 17D' as a light yellow syrup, 4.0 g. The racemic ketone 17D' was resolved with chiral HPLC to give enantiomerically pure 17D using an OJ-H, 4.6×250 mm column eluting with an isocratic system of 15% w/IPA in supercritical CO₂ at a flow rate of 3 mL/min. The configuration of 17D was determined to have the 3aS, 9aR configuration by inference from the configuration of the subsequently prepared product 17 below.

Step 5

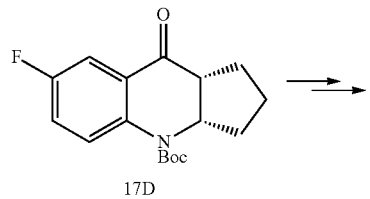

The ketone 17D was converted to the desired enantiopure amide 17E following steps similar to those described in Example 1 and Example 7.

Step 6

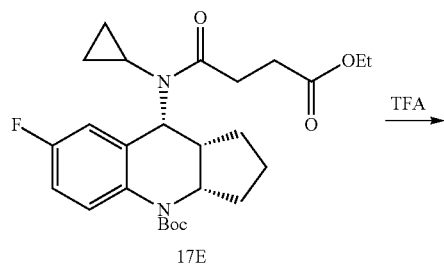

-continued

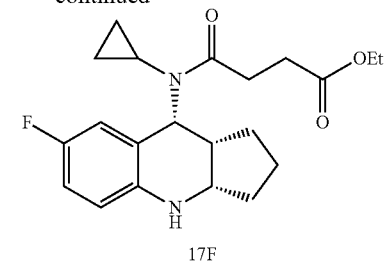
17F

TFA (1 mL) was added to the solution of Boc amide 17E (0.723 mmol) in CH₂Cl₂ (2 mL), the resultant mixture was kept stirring at rt for 2 hrs. The solution was concentrated to dryness, the residue was taken up in CH₂Cl₂ (10 mL), washed with NaHCO₃ (1N, 5 mL), the organic layer was dried over MgSO₄ and concentrated. The residue was purified via silica gel column chromatography (EtOAc/Hexane=1:3), obtained enantiopure free amine 17F as a light yellow solid 200 mg; [M+H]⁺=357.

Step 7

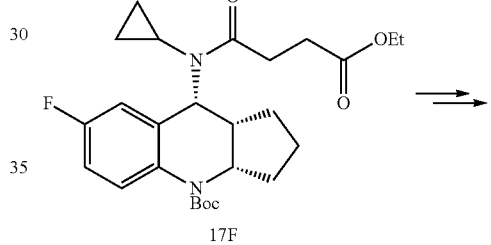

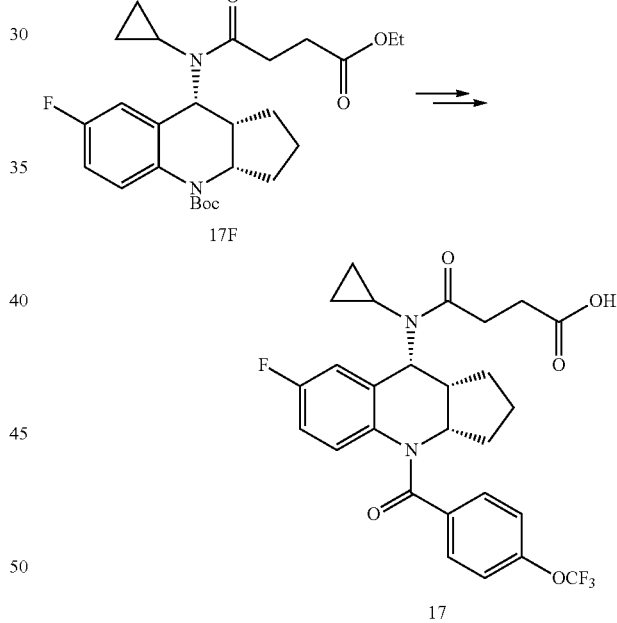

The amine 17F was converted the final enantiopure amide product 17 by following steps similar to those described in Example 14, steps 2 and 3. ¹H NMR (500 MHz, CDCl₃) δ ppm: 7.29 (d, 2H); 7.08 (d, 2H); 6.60 (m, 2H); 6.38 (m, 1H); 5.168 (m, 1H); 3.09 (m, 3H); 2.82 (m, 3H); 2.42 (m, 1H); 2.03 (m, 1H); 1.57 (m, 2H); 1.40 (m, 2H); 1.22~1.00 (m, 5H). [M+H]⁺=534.8.

The structure of product 17, C₂₇H₂₆F4N₂O₅, C₇H₈, was determined by single-crystal X-ray crystallography on a crystal isolated from material crystallized from toluene (10 mg anhydrous compound dissolved in 200 µL toluene and evaporated overnight). The crystal selected was representative of the bulk sample. Crystal data at 100 K:

| | | |
|---|---|---|
| a = 11.1083(13) Å | α = 90.00° | V = 1528.4(3) Å³ |
| b = 8.7372(10) | β = 100.730(6) | Space group = P2₁, #4 |
| c = 16.028(2) | γ = 90.00 | Z = 2 |

Data were collected on a Bruker CCD diffractometer using copper Kα radiation and integrated to a resolution of 0.84 Å$^{-1}$ which yielded 4840 unique reflections from 34030 measured reflections.

The structure was solved using direct methods. The refined model has all non-H atoms refined anisotropically, and H atoms at their calculated positions, with agreement statistics of: $R_1$=3.4%, for 407 variables and 4629 reflections and $wR_2$=9.4% using all 4840 reflections. The compound crystallized as a monotoluene solvate. There were no unusual bond distances or angles. The absolute stereochemistry was determined unambiguously using resonant scattering effects as R,S,R at C1, C8 and C12, respectively. A perspective view of 17 calculated from the crystallographic coordinates is presented in FIG. 1.

The compounds in the following table were prepared by a similar synthetic process as illustrated in Examples 1, 14 and 17. The enantiomerically pure final products are either obtained through chiral resolution of final racemic compounds (17BN, 17BX, 17BY, 17BZ, 17CA, 17CJ) or prepared from enantiomerically pure tetraquinoline amides (prepared from a Boc-protected, CBz-protected, or unprotected chiral tetrahydroquinolin-9(9aH)-one) (17AE, 17AF, 17AG, 17BM, 17BO, 17BP, 17BQ, 17BR, 17BS, 17BT, 17BU, 17BV, 17BW, 17CC, 17CD, 17CE, 17CF, 17CG, 17CH, 17CI, 17CK, and 17CL-17DL). Chiral HPLC separation of racemic tetrahydroquinolin-9(9aH)-ones such as 17D' (Boc-protected), 1D (CBz-protected), and 17C (unprotected) affords enantiomerically pure chiral tetrahydroquinolin-9(9aH)-ones.

| # | structure | stereo designation | chemical name | [M + H]⁺ |
|---|---|---|---|---|
| 17G | 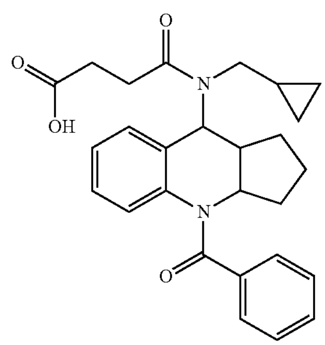 [SMILES: O=C(O)CCC(=O)N(CC1CC1)C1c2ccccc2N(C(=O)c2ccccc2)C2CCCC12] | racemic, cis, cis | 4-[[cis,cis-4-benzoyl-2,3,3a,4,9,9a-hexahydro-1H-cyclopenta[b]quinolin-9-yl](cyclopropylmethyl)amino]-4-oxobutanoic acid | 447.2 |
| 17H | 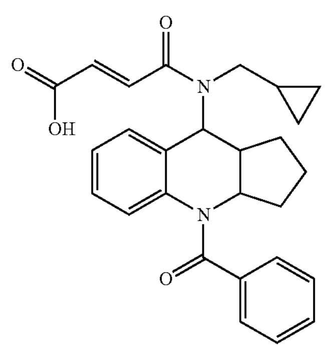 [SMILES: O=C(O)/C=C/C(=O)N(CC1CC1)C1c2ccccc2N(C(=O)c2ccccc2)C2CCCC12] | racemic, E, cis, cis | (2E)-4-[[cis,cis-4-benzoyl-2,3,3a,4,9,9a-hexahydro-1H-cyclopenta[b]quinolin-9-yl](cyclopropylmethyl)amino]-4-oxo-2-butenoic acid | 445.2 |
| 17i | 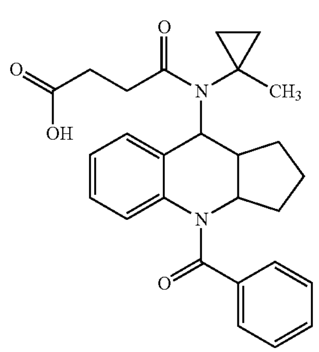 [SMILES: CC1(N(C(=O)CCC(=O)O)C2c3ccccc3N(C(=O)c3ccccc3)C3CCCC32)CC1] | racemic, cis, cis | 4-[[cis,cis-4-benzoyl-2,3,3a,4,9,9a-hexahydro-1H-cyclopenta[b]quinolin-9-yl](1-methylcyclopropyl)amino]-4-oxobutanoic acid | 447.2 |

-continued

| # | structure | stereo designation | chemical name | [M + H]+ |
|---|---|---|---|---|
| 17J | 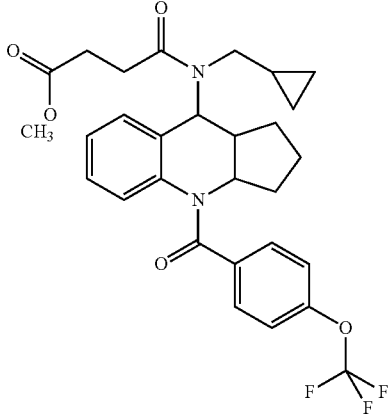 | racemic, cis, cis | methyl 4-[(cyclopropylmethyl)[cis,cis-2,3,3a,4,9,9a-hexahydro-4-[4-(trifluoromethoxy)benzoyl]-1H-cyclopenta[b]quinolin-9-yl]amino]-4-oxobutanoate | 545.3 |
| 17K | 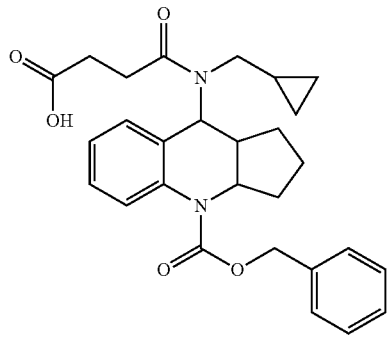 [SMILES: O=C(O)CCC(=O)N(CC1CC1)C1c2ccccc2N(C(=O)OCc2ccccc2)C2CCCC12] | racemic, cis, cis | 4-(phenylmethyl) cis,cis-9-[(3-carboxy-1-oxopropyl)(cyclopropylmethyl)amino]-1,2,3,3a,9,9a-hexahydro-4H-cyclopenta[b]quinoline-4-carboxylate | 477.3 |
| 17L | 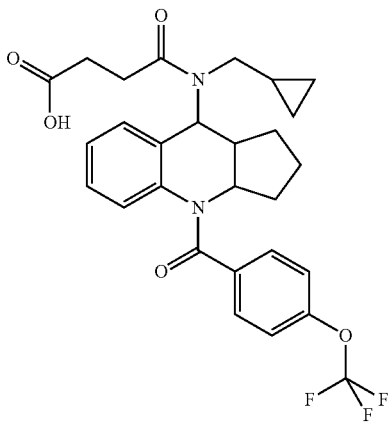 [SMILES: O=C(O)CCC(=O)N(CC1CC1)C1c2ccccc2N(C(=O)c2ccc(OC(F)(F)F)cc2)C2CCCC12] | racemic, cis, cis | 4-[(cyclopropylmethyl)[cis,cis-2,3,3a,4,9,9a-hexahydro-4-[4-(trifluoromethoxy)benzoyl]-1H-cyclopenta[b]quinolin-9-yl]amino]-4-oxobutanoic acid | 531.3 |
| 17M | 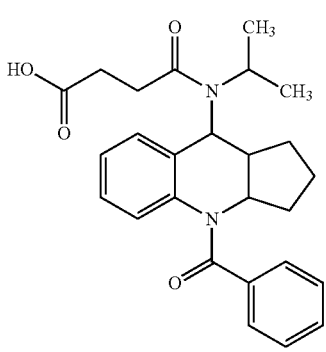 [SMILES: CC(C)N(C(=O)CCC(=O)O)C1c2ccccc2N(C(=O)c2ccccc2)C2CCCC21] | racemic, cis, cis | 4-[[cis,cis-4-benzoyl-2,3,3a,4,9,9a-hexahydro-1H-cyclopenta[b]quinolin-9-yl](1-methylethyl)amino]-4-oxobutanoic acid | 435.2 |

| # | structure | stereo designation | chemical name | [M + H]+ |
|---|---|---|---|---|
| 17N | 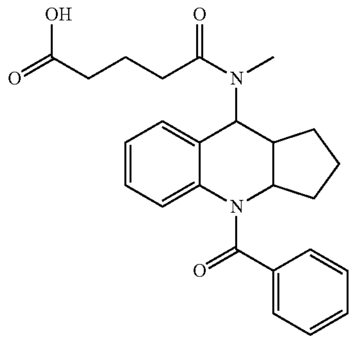 [SMILES: CN(C(=O)CCCC(=O)O)C1c2ccccc2N(C(=O)c2ccccc2)C2CCCC12] | racemic, cis, cis | 5-[[cis,cis-4-benzoyl-2,3,3a,4,9,9a-hexahydro-1H-cyclopenta[b]quinolin-9-yl]methylamino]-5-oxopentanoic acid | 421.2 |
| 17o | 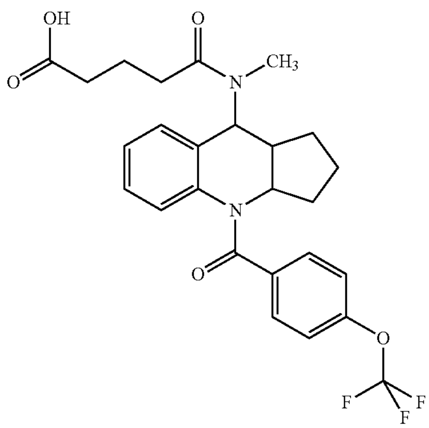 [SMILES: CN(C(=O)CCCC(=O)O)C1c2ccccc2N(C(=O)c2ccc(OC(F)(F)F)cc2)C2CCCC12] | racemic, cis, cis | 5-[[cis,cis-2,3,3a,4,9,9a-hexahydro-4-[4-(trifluoromethoxy)benzoyl]-1H-cyclopenta[b]quinolin-9-yl]methylamino]-5-oxopentanoic acid | 505.3 |
| 17P | 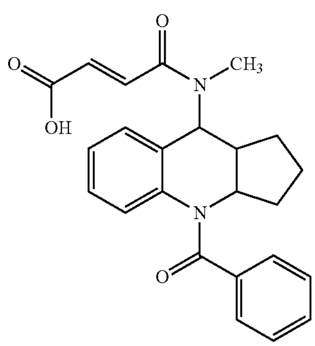 [SMILES: CN(C(=O)/C=C/C(=O)O)C1c2ccccc2N(C(=O)c2ccccc2)C2CCCC12] | racemic, cis, cis | (2E)-4-[[cis,cis-4-benzoyl-2,3,3a,4,9,9a-hexahydro-1H-cyclopenta[b]quinolin-9-yl]methylamino]-4-oxo-2-butenoic acid | 405.2 |
| 17Q | 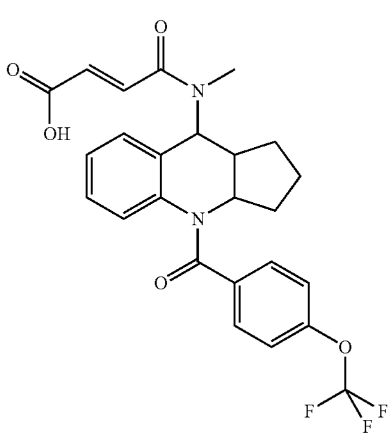 [SMILES: CN(C(=O)/C=C/C(=O)O)C1c2ccccc2N(C(=O)c2ccc(OC(F)(F)F)cc2)C2CCCC12] | racemic, cis, cis | (2E)-4-[[cis,cis-2,3,3a,4,9,9a-hexahydro-4-[4-(trifluoromethoxy)benzoyl]-1H-cyclopenta[b]quinolin-9-yl]methylamino]-4-oxo-2-butenoic acid | 489.3 |

| # | structure | stereo designation | chemical name | [M + H]+ |
|---|---|---|---|---|
| 17R | 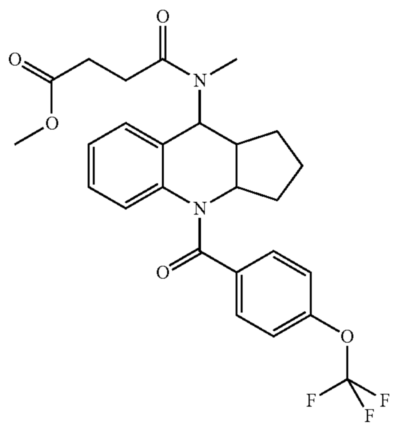 [SMILES: COC(=O)CCC(=O)N(C)C1c2ccccc2N(C(=O)c2ccc(OC(F)(F)F)cc2)C2CCCC12] | racemic, cis, cis | methyl 4-[[cis,cis-2,3,3a,4,9,9a-hexahydro-4-[4-(trifluoromethoxy)benzoyl]-1H-cyclopenta[b]quinolin-9-yl]methylamino]-4-oxobutanoate | 505.3 |
| 17S | 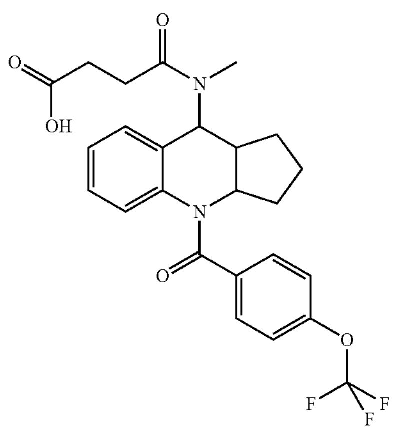 [SMILES: CN(C(=O)CCC(=O)O)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl]methylamino]-4-oxobutanoic acid | 491.3 |
| 17T | 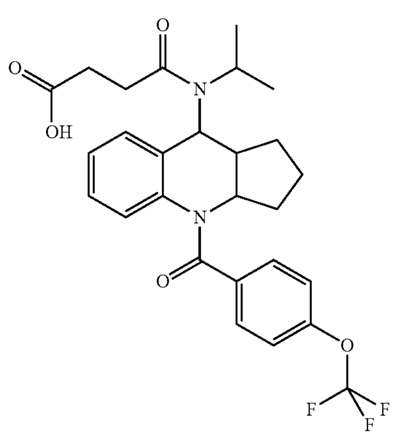 [SMILES: CC(C)N(C(=O)CCC(=O)O)C1c2ccccc2N(C(=O)c2ccc(OC(F)(F)F)cc2)C2CCCC21] | racemic, cis, cis | 4-[[cis,cis-2,3,3a,4,9,9a-hexahydro-4-[4-(trifluoromethoxy)benzoyl]-1H-cyclopenta[b]quinolin-9-yl](1-methylethyl)amino]-4-oxobutanoic acid | 519.3 |

| # | structure | stereo designation | chemical name | [M + H]+ |
|---|---|---|---|---|
| 17U | 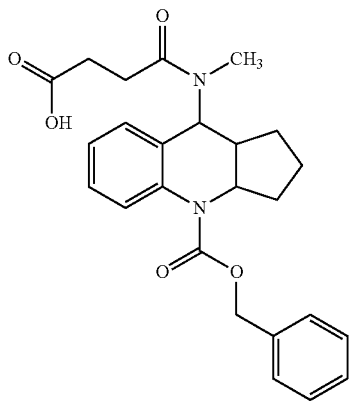 [SMILES: CN(C(=O)CCC(=O)O)C1c2ccccc2N(C(=O)OCc2ccccc2)C2CCCC12] | racemic, cis, cis | 4-(phenylmethyl) cis,cis-9-[(3-carboxy-1-oxopropyl)methylamino]-1,2,3,3a,9,9a-hexahydro-4H-cyclopenta[b]quinoline-4-carboxylate | 437.2 |
| 17V | 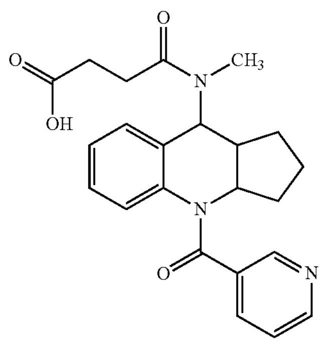 [SMILES: CN(C(=O)CCC(=O)O)C1c2ccccc2N(C(=O)c2cccnc2)C2CCCC12] | racemic, cis, cis | 4-[[cis,cis-2,3,3a,4,9,9a-hexahydro-4-(3-pyridinylcarbonyl)-1H-cyclopenta[b]quinolin-9-yl]methylamino]-4-oxobutanoic acid | 408.2 |
| 17W | 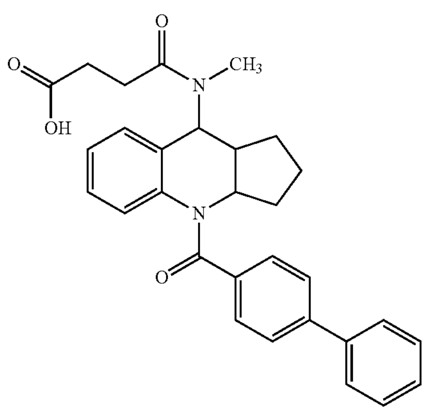 [SMILES: CN(C(=O)CCC(=O)O)C1c2ccccc2N(C(=O)c2ccc(-c3ccccc3)cc2)C2CCCC12] | racemic, cis, cis | 4-[[cis,cis-4-([1,1'-biphenyl]-4-ylcarbonyl)-2,3,3a,4,9,9a-hexahydro-1H-cyclopenta[b]quinolin-9-yl]methylamino]-4-oxobutanoic acid | 483.3 |
| 17X | 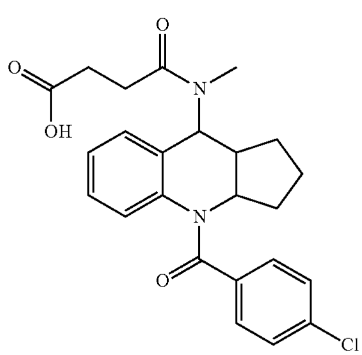 [SMILES: CN(C(=O)CCC(=O)O)C1c2ccccc2N(C(=O)c2ccc(Cl)cc2)C2CCCC12] | racemic, cis, cis | 4-[[cis,cis-4-(4-chlorobenzoyl)-2,3,3a,4,9,9a-hexahydro-1H-cyclopenta[b]quinolin-9-yl]methylamino]-4-oxobutanoic acid | 441.2 |

-continued

| # | structure | stereo designation | chemical name | [M + H]+ |
|---|---|---|---|---|
| 17Y | 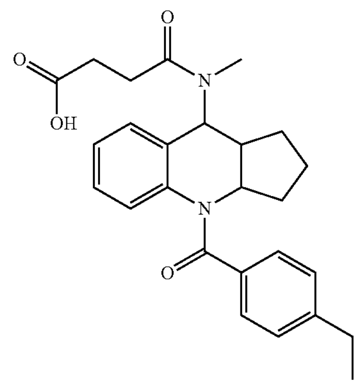 [SMILES: CCc1ccc(C(=O)N2c3ccccc3C(N(C)C(=O)CCC(=O)O)C3CCCC32)cc1] | racemic, cis, cis | 4-[[cis,cis-4-(4-ethylbenzoyl)-2,3,3a,4,9,9a-hexahydro-1H-cyclopenta[b]quinolin-9-yl]methylamino]-4-oxobutanoic acid | 435.2 |
| 17Z | 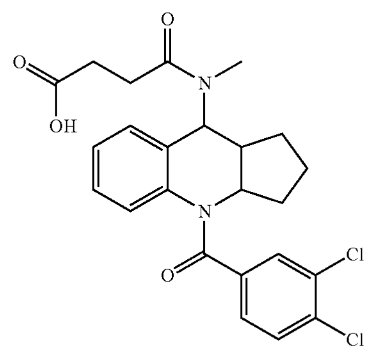 [SMILES: CN(C(=O)CCC(=O)O)C1c2ccccc2N(C(=O)c2ccc(Cl)c(Cl)c2)C2CCCC12] | racemic, cis, cis | 4-[[cis,cis-4-(3,4-dichlorobenzoyl)-2,3,3a,4,9,9a-hexahydro-1H-cyclopenta[b]quinolin-9-yl]methylamino]-4-oxobutanoic acid | 475.3 |
| 17AA | 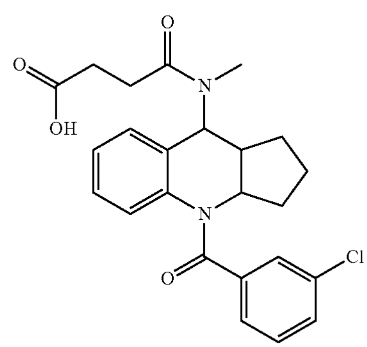 [SMILES: CN(C(=O)CCC(=O)O)C1c2ccccc2N(C(=O)c2cccc(Cl)c2)C2CCCC12] | racemic, cis, cis | 4-[[cis,cis-4-(3-chlorobenzoyl)-2,3,3a,4,9,9a-hexahydro-1H-cyclopenta[b]quinolin-9-yl]methylamino]-4-oxobutanoic acid | 441.2 |
| 17AB | 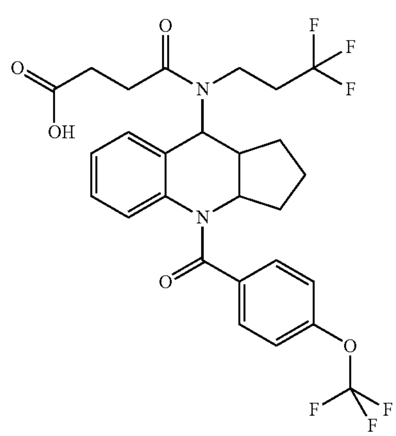 [SMILES: O=C(O)CCC(=O)N(CCC(F)(F)F)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl](3,3,3-trifluoropropyl)amino]-4-oxobutanoic acid | 573.3 |

-continued

| # | structure | stereo designation | chemical name | [M + H]+ |
|---|---|---|---|---|
| 17AC | 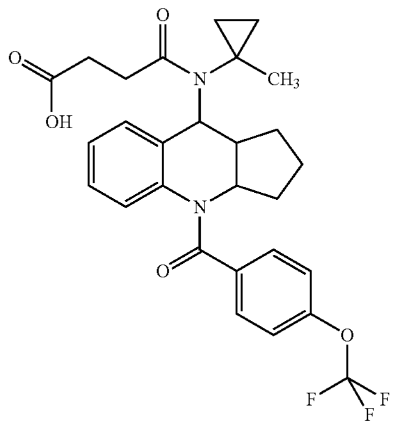 [SMILES: CC1(N(C(=O)CCC(=O)O)C2c3ccccc3N(C(=O)c3ccc(OC(F)(F)F)cc3)C3CCCC32)CC1] | racemic, cis, cis | 4-[[cis,cis-2,3,3a,4,9,9a-hexahydro-4-[4-(trifluoromethoxy)benzoyl]-1H-cyclopenta[b]quinolin-9-yl](1-methylcyclopropyl)amino]-4-oxobutanoic acid | 531.3 |
| 17AD | 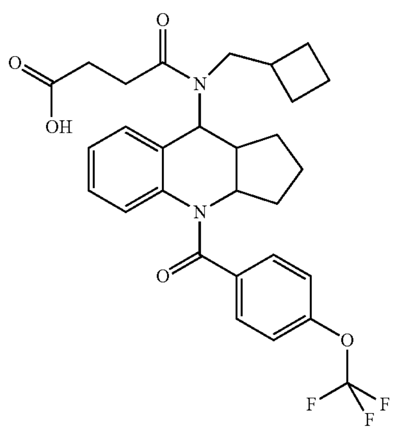 [SMILES: O=C(O)CCC(=O)N(CC1CCC1)C1c2ccccc2N(C(=O)c2ccc(OC(F)(F)F)cc2)C2CCCC12] | racemic, cis, cis | 4-[(cyclobutylmethyl)[cis,cis-2,3,3a,4,9,9a-hexahydro-4-[4-(trifluoromethoxy)benzoyl]-1H-cyclopenta[b]quinolin-9-yl]amino]-4-oxobutanoic acid | 545.3 |
| 17AE | 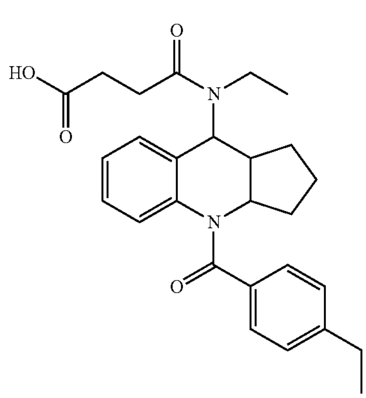 [SMILES: CCc1ccc(C(=O)N2c3ccccc3C(N(CC)C(=O)CCC(=O)O)C3CCCC32)cc1] | cis, cis single enantiomer | 4-[ethyl[cis,cis-4-(4-ethylbenzoyl)-2,3,3a,4,9,9a-hexahydro-1H-cyclopenta[b]quinolin-9-yl]amino]-4-oxobutanoic acid | 449.2 |

-continued

| # | structure | stereo designation | chemical name | [M + H]+ |
|---|---|---|---|---|
| 17AF | 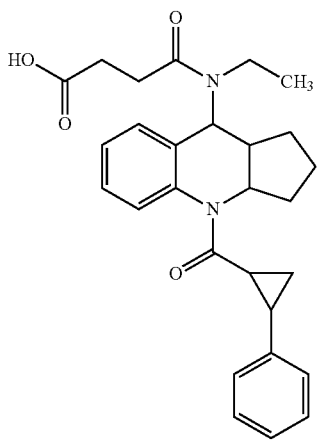 [SMILES: CCN(C(=O)CCC(=O)O)C1c2ccccc2N(C(=O)C2CC2c2ccccc2)C2CCCC12] | (cis, cis); Cyclopropyl ring trans (racemic). | 4-[ethyl[cis,cis-2,3,3a,4,9,9a-hexahydro-4-[(2-phenyl-1-cyclopropyl)carbonyl]-1H-cyclopenta[b]quinolin-9-yl]amino]-4-oxobutanoic acid | 461.3 |
| 17AG | 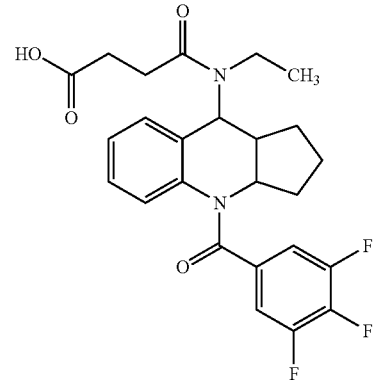 [SMILES: CCN(C(=O)CCC(=O)O)C1c2ccccc2N(C(=O)c2cc(F)c(F)c(F)c2)C2CCCC12] | cis, cis single enantiomer | 4-[ethyl[cis,cis-2,3,3a,4,9,9a-hexahydro-4-(3,4,5-trifluorobenzoyl)-1H-cyclopenta[b]quinolin-9-yl]amino]-4-oxobutanoic acid | 475.3 |
| 17AH | 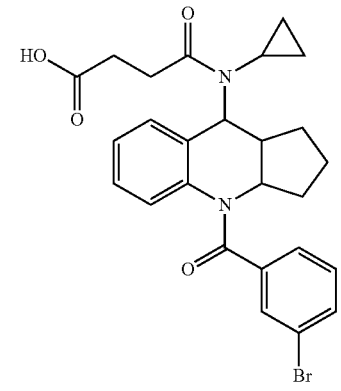 [SMILES: O=C(O)CCC(=O)N(C1CC1)C1c2ccccc2N(C(=O)c2cccc(Br)c2)C2CCCC21] | racemic, cis, cis | 4-[[cis,cis-4-(3-bromobenzoyl)-2,3,3a,4,9,9a-hexahydro-1H-cyclopenta[b]quinolin-9-yl]cyclopropylamino]-4-oxobutanoic acid | 511.3 |

| # | structure | stereo designation | chemical name | [M + H]+ |
|---|---|---|---|---|
| 17Ai | 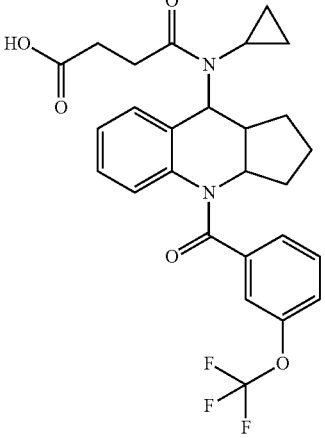 | racemic, cis, cis | 4-[cyclopropyl[cis,cis-2,3,3a,4,9,9a-hexahydro-4-[3-(trifluoromethoxy)benzoyl]-1H-cyclopenta[b]quinolin-9-yl]amino]-4-oxobutanoic acid | 517.3 |
| 17AJ | 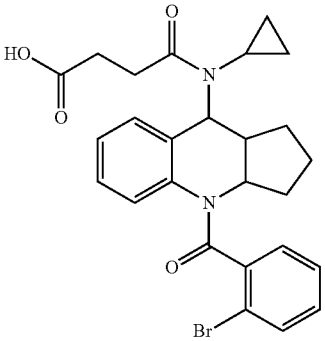 [SMILES: O=C(O)CCC(=O)N(C1CC1)C1c2ccccc2N(C(=O)c2ccccc2Br)C2CCCC21] | racemic, cis, cis | 4-[[cis,cis-4-(2-bromobenzoyl)-2,3,3a,4,9,9a-hexahydro-1H-cyclopenta[b]quinolin-9-yl]cyclopropylamino]-4-oxobutanoic acid | 511.3 |
| 17AK | 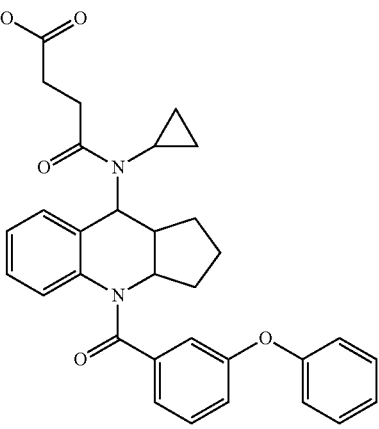 | racemic, cis, cis | 4-[cyclopropyl[cis,cis-2,3,3a,4,9,9a-hexahydro-4-(3-phenoxybenzoyl)-1H-cyclopenta[b]quinolin-9-yl]amino]-4-oxo-butanoic acid | 525.3 |

| # | structure | stereo designation | chemical name | [M + H]⁺ |
|---|---|---|---|---|
| 17AL | 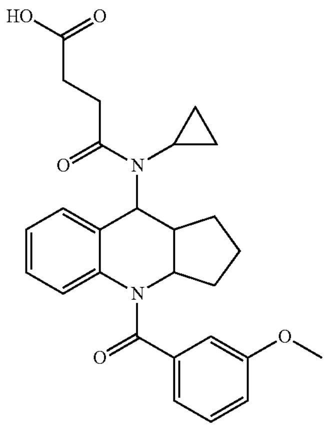 [SMILES: COc1cccc(C(=O)N2c3ccccc3C(N(C(=O)CCC(=O)O)C3CC3)C3CCCC32)c1] | racemic, cis, cis | 4-[cyclopropyl[cis,cis-2,3,3a,4,9,9a-hexahydro-4-(3-methoxybenzoyl)-1H-cyclopenta[b]quinolin-9-yl]amino]-4-oxobutanoic acid | 463.3 |
| 17AM | 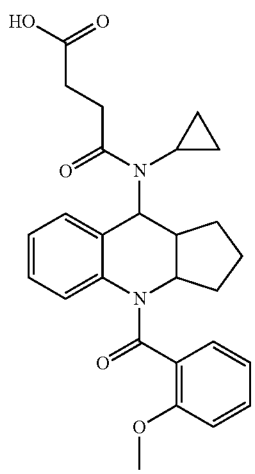 [SMILES: COc1ccccc1C(=O)N1c2ccccc2C(N(C(=O)CCC(=O)O)C2CC2)C2CCCC21] | racemic, cis, cis | 4-[cyclopropyl[cis,cis-2,3,3a,4,9,9a-hexahydro-4-(2-methoxybenzoyl)-1H-cyclopenta[b]quinolin-9-yl]amino]-4-oxobutanoic acid | 463.3 |
| 17AN | 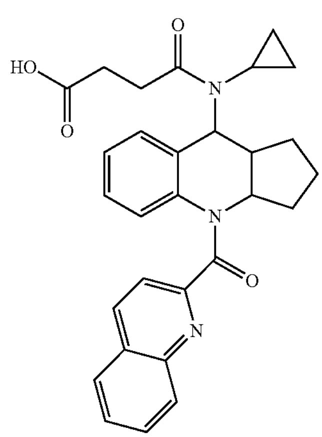 [SMILES: O=C(O)CCC(=O)N(C1CC1)C1c2ccccc2N(C(=O)c2ccc3ccccc3n2)C2CCCC21] | racemic, cis, cis | 4-[cyclopropyl[cis,cis-2,3,3a,4,9,9a-hexahydro-4-(2-quinolinylcarbonyl)-1H-cyclopenta[b]quinolin-9-yl]amino]-4-oxobutanoic acid | 484.3 |

| # | structure | stereo designation | chemical name | [M + H]+ |
|---|---|---|---|---|
| 17Ao | 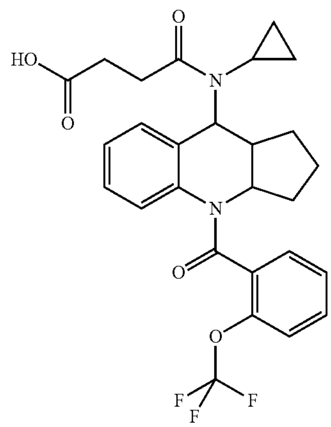 [SMILES: O=C(O)CCC(=O)N(C1CC1)C1c2ccccc2N(C(=O)c2ccccc2OC(F)(F)F)C2CCCC21] | racemic, cis, cis | 4-[cyclopropyl[cis,cis-2,3,3a,4,9,9a-hexahydro-4-[2-(trifluoromethoxy)benzoyl]-1H-cyclopenta[b]quinolin-9-yl]amino]-4-oxobutanoic acid | 517.3 |
| 17AP | 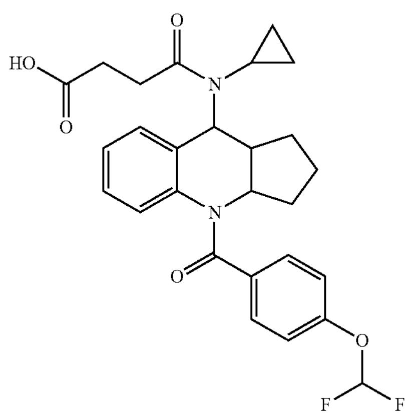 [SMILES: O=C(O)CCC(=O)N(C1CC1)C1c2ccccc2N(C(=O)c2ccc(OC(F)F)cc2)C2CCCC21] | racemic, cis, cis | 4-[cyclopropyl[cis,cis-4-[4-(difluoromethoxy)benzoyl]-2,3,3a,4,9,9a-hexahydro-1H-cyclopenta[b]quinolin-9-yl]amino]-4-oxobutanoic acid | 499.3 |
| 17AQ | 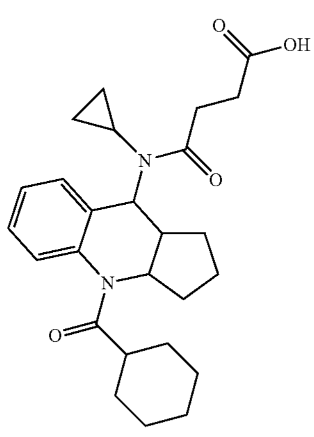 [SMILES: O=C(O)CCC(=O)N(C1CC1)C1c2ccccc2N(C(=O)C2CCCCC2)C2CCCC21] | racemic, cis, cis | 4-((cis,cis-4-(cyclohexanecarbonyl)-2,3,3a,4,9,9a-hexahydro-1H-cyclopenta[b]quinolin-9-yl)(cyclopropyl)amino)-4-oxobutanoic acid | 439.2 |

| # | structure | stereo designation | chemical name | [M + H]+ |
|---|---|---|---|---|
| 17AR | 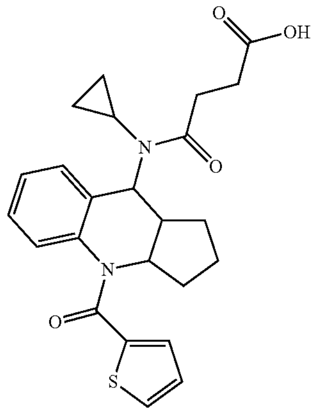 [SMILES: O=C(O)CCC(=O)N(C1CC1)C1c2ccccc2N(C(=O)c2cccs2)C2CCCC21] | racemic, cis, cis | 4-(cyclopropyl(cis,cis-4-(thiophene-2-carbonyl)-2,3,3a,4,9,9a-hexahydro-1H-cyclopenta[b]quinolin-9-yl)amino)-4-oxobutanoic acid | 439.2 |
| 17AS | 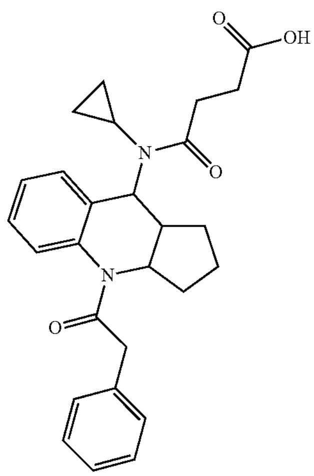 [SMILES: O=C(O)CCC(=O)N(C1CC1)C1c2ccccc2N(C(=O)Cc2ccccc2)C2CCCC21] | racemic, cis, cis | 4-(cyclopropyl(cis,cis-4-(2-phenylacetyl)-2,3,3a,4,9,9a-hexahydro-1H-cyclopenta[b]quinolin-9-yl)amino)-4-oxobutanoic acid | 447.2 |
| 17AT | 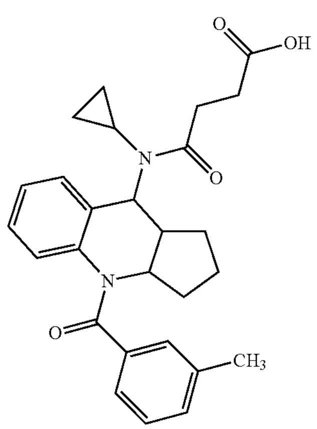 [SMILES: Cc1cccc(C(=O)N2c3ccccc3C(N(C(=O)CCC(=O)O)C3CC3)C3CCCC32)c1] | racemic, cis, cis | 4-(cyclopropyl(cis,cis-4-(3-methylbenzoyl)-2,3,3a,4,9,9a-hexahydro-1H-cyclopenta[b]quinolin-9-yl)amino)-4-oxobutanoic acid | 447.2 |

-continued

| # | structure | stereo designation | chemical name | [M + H]+ |
|---|---|---|---|---|
| 17AU | 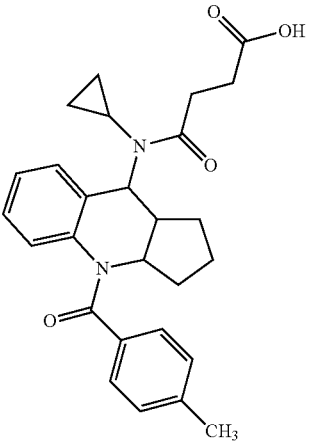 [SMILES: Cc1ccc(C(=O)N2c3ccccc3C(N(C(=O)CCC(=O)O)C3CC3)C3CCCC32)cc1] | racemic, cis, cis | 4-(cyclopropyl(cis,cis-4-(4-methylbenzoyl)-2,3,3a,4,9,9a-hexahydro-1H-cyclopenta[b]quinolin-9-yl)amino)-4-oxobutanoic acid | 447.2 |
| 17AV | 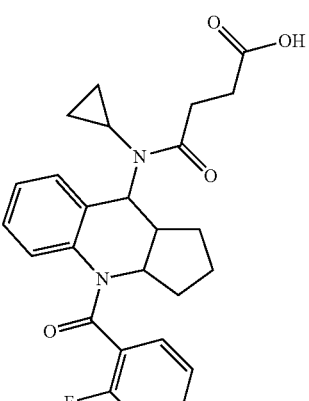 | racemic, cis, cis | 4-(cyclopropyl(cis,cis-4-(2-fluorobenzoyl)-2,3,3a,4,9,9a-hexahydro-1H-cyclopenta[b]quinolin-9-yl)amino)-4-oxobutanoic acid | 451.2 |
| 17AW | 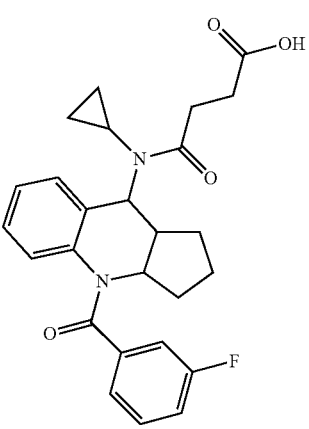 [SMILES: O=C(O)CCC(=O)N(C1CC1)C1c2ccccc2N(C(=O)c2cccc(F)c2)C2CCCC21] | racemic, cis, cis | 4-(cyclopropyl(cis,cis-4-(3-fluorobenzoyl)-2,3,3a,4,9,9a-hexahydro-1H-cyclopenta[b]quinolin-9-yl)amino)-4-oxobutanoic acid | 451.2 |

| # | structure | stereo designation | chemical name | [M + H]+ |
|---|---|---|---|---|
| 17AX | 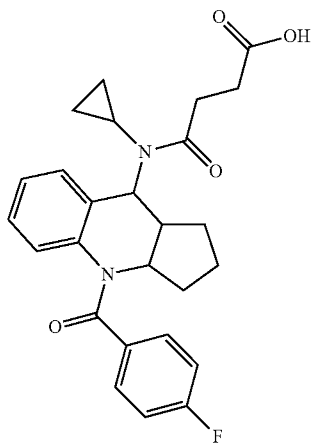 [SMILES: O=C(O)CCC(=O)N(C1CC1)C1c2ccccc2N(C(=O)c2ccc(F)cc2)C2CCCC21] | racemic, cis, cis | 4-(cyclopropyl(cis,cis-4-(4-fluorobenzoyl)-2,3,3a,4,9,9a-hexahydro-1H-cyclopenta[b]quinolin-9-yl)amino)-4-oxobutanoic acid | 451.2 |
| 17AY | 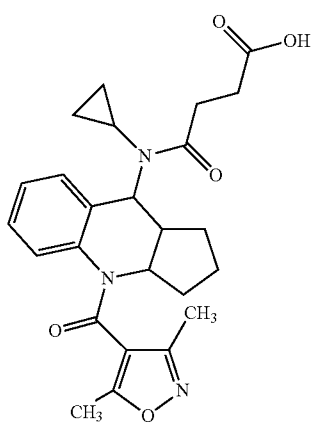 [SMILES: Cc1noc(C)c1C(=O)N1c2ccccc2C(N(C(=O)CCC(=O)O)C2CC2)C2CCCC21] | racemic, cis, cis | 4-(cyclopropyl(cis,cis-4-(3,5-dimethylisoxazole-4-carbonyl)-2,3,3a,4,9,9a-hexahydro-1H-cyclopenta[b]quinolin-9-yl)amino)-4-oxobutanoic acid | 452.2 |
| 17AZ | 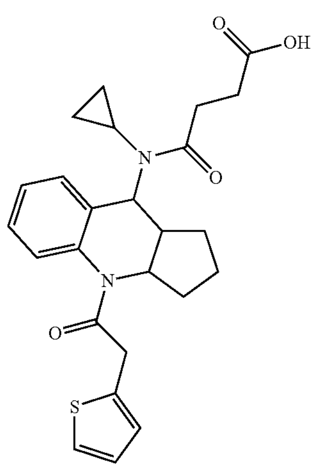 [SMILES: O=C(O)CCC(=O)N(C1CC1)C1c2ccccc2N(C(=O)Cc2cccs2)C2CCCC21] | racemic, cis, cis | 4-(cyclopropyl(cis,cis-4-(2-(thiophen-2-yl)acetyl)-2,3,3a,4,9,9a-hexahydro-1H-cyclopenta[b]quinolin-9-yl)amino)-4-oxobutanoic acid | 453.2 |

| # | structure | stereo designation | chemical name | [M + H]+ |
|---|---|---|---|---|
| 17BA | 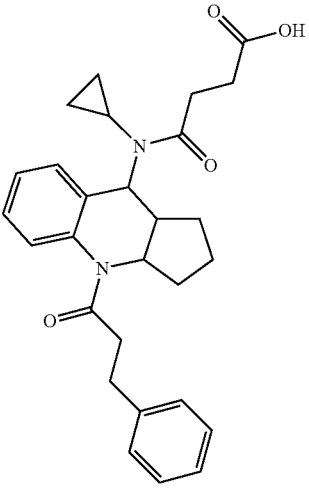 | racemic, cis, cis | 4-(cyclopropyl(cis,cis-4-(3-phenylpropanoyl)-2,3,3a,4,9,9a-hexahydro-1H-cyclopenta[b]quinolin-9-yl)amino)-4-oxobutanoic acid | 461.3 |
| 17BB | 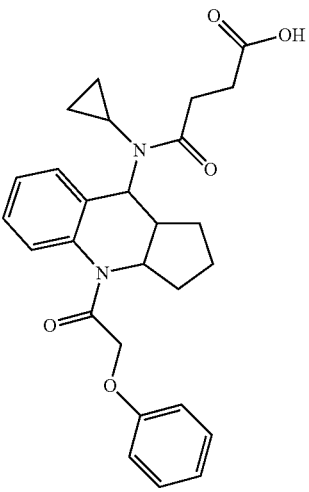 [SMILES: O=C(O)CCC(=O)N(C1CC1)C1c2ccccc2N(C(=O)CCc2ccccc2)C2CCCC21] | racemic, cis, cis | 4-(cyclopropyl(cis,cis-4-(2-phenoxyacetyl)-2,3,3a,4,9,9a-hexahydro-1H-cyclopenta[b]quinolin-9-yl)amino)-4-oxobutanoic acid | 463.3 |
| 17BC | 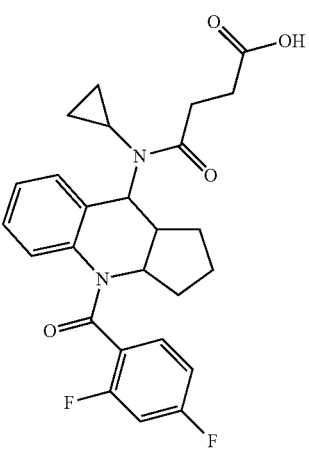 [SMILES: O=C(O)CCC(=O)N(C1CC1)C1c2ccccc2N(C(=O)c2ccc(F)cc2F)C2CCCC21] | racemic, cis, cis | 4-(cyclopropyl(cis,cis-4-(2,4-difluorobenzoyl)-2,3,3a,4,9,9a-hexahydro-1H-cyclopenta[b]quinolin-9-yl)amino)-4-oxobutanoic acid | 469.3 |

| # | structure | stereo designation | chemical name | [M + H]+ |
|---|---|---|---|---|
| 17BD | 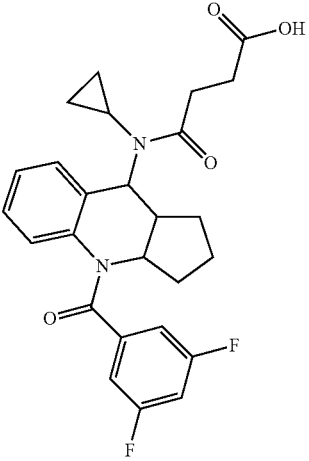 [SMILES: O=C(O)CCC(=O)N(C1CC1)C1c2ccccc2N(C(=O)c2cc(F)cc(F)c2)C2CCCC21] | racemic, cis, cis | 4-(cyclopropyl((cis,cis-4-(3,5-difluorobenzoyl)-2,3,3a,4,9,9a-hexahydro-1H-cyclopenta[b]quinolin-9-yl)amino)-4-oxobutanoic acid | 469.3 |
| 17BE | 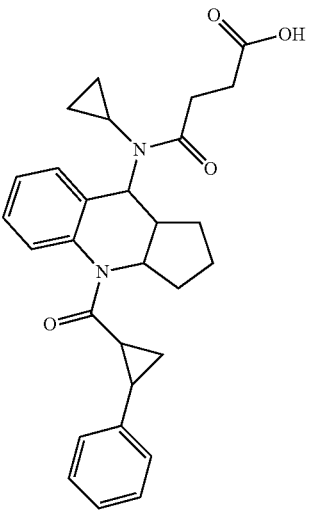 [SMILES: O=C(O)CCC(=O)N(C1CC1)C1c2ccccc2N(C(=O)C2CC2c2ccccc2)C2CCCC21] | racemic, cis, cis, (cyclopropyl ring is trans substituted) | 4-(cyclopropyl(cis,cis-4-trans-2-phenylcyclopropanecarbonyl)-2,3,3a,4,9,9a-hexahydro-1H-cyclopenta[b]quinolin-9-yl)amino)-4-oxobutanoic acid | 473.3 |
| 17BF | 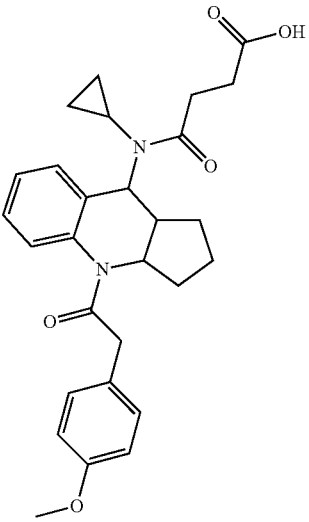 [SMILES: COc1ccc(CC(=O)N2c3ccccc3C(N(C(=O)CCC(=O)O)C3CC3)C3CCCC32)cc1] | racemic, cis, cis | 4-(cyclopropyl(cis,cis-4-(2-(4-methoxyphenyl)acetyl)-2,3,3a,4,9,9a-hexahydro-1H-cyclopenta[b]quinolin-9-yl)amino)-4-oxobutanoic acid | 477.3 |

-continued

| # | structure | stereo designation | chemical name | [M + H]+ |
|---|---|---|---|---|
| 17BG | 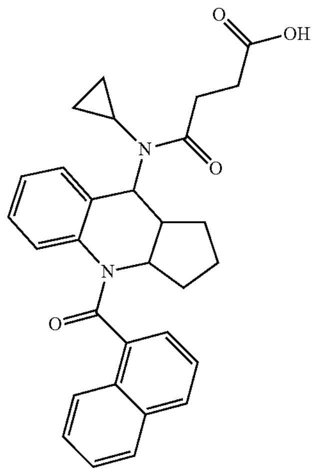 [SMILES: O=C(O)CCC(=O)N(C1CC1)C1c2ccccc2N(C(=O)c2cccc3ccccc23)C2CCCC21] | racemic, cis, cis | 4-((cis,cis-4-(1-naphthoyl)-2,3,3a,4,9,9a-hexahydro-1H-cyclopenta[b]quinolin-9-yl)(cyclopropyl)amino)-4-oxobutanoic acid | 483.3 |
| 17BH | 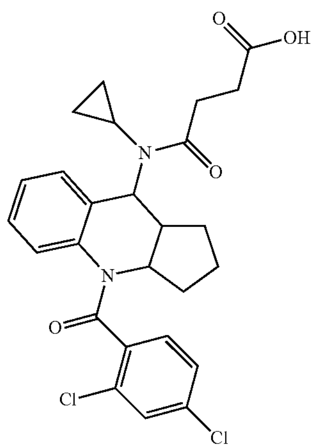 [SMILES: O=C(O)CCC(=O)N(C1CC1)C1c2ccccc2N(C(=O)c2ccc(Cl)cc2Cl)C2CCCC21] | racemic, cis, cis | 4-(cyclopropyl(cis,cis-4-(2,4-dichlorobenzoyl)-2,3,3a,4,9,9a-hexahydro-1H-cyclopenta[b]quinolin-9-yl)amino)-4-oxobutanoic acid | 501.3 |
| 17Bi | 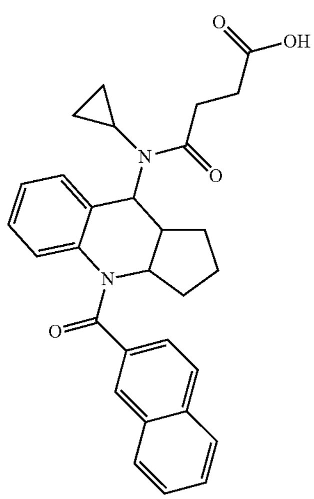 [SMILES: O=C(O)CCC(=O)N(C1CC1)C1c2ccccc2N(C(=O)c2ccc3ccccc3c2)C2CCCC21] | racemic, cis, cis | 4-((cis,cis-4-(2-naphthoyl)-2,3,3a,4,9,9a-hexahydro-1H-cyclopenta[b]quinolin-9-yl)(cyclopropyl)amino)-4-oxobutanoic acid | 483.3 |

| # | structure | stereo designation | chemical name | [M + H]+ |
|---|---|---|---|---|
| 17BJ | 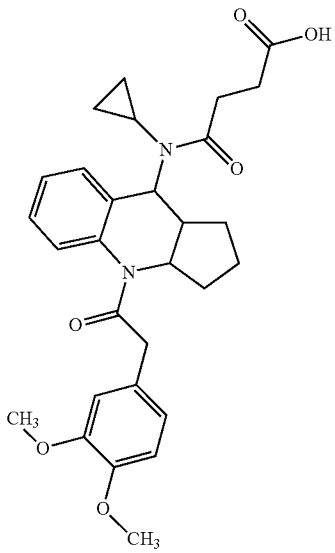 [SMILES: COc1ccc(CC(=O)N2c3ccccc3C(N(C(=O)CCC(=O)O)C3CC3)C3CCCC32)cc1OC] | racemic, cis, cis | 4-(cyclopropyl(cis,cis-4-(2-(3,4-dimethoxyphenyl)acetyl)-2,3,3a,4,9,9a-hexahydro-1H-cyclopenta[b]quinolin-9-yl)amino)-4-oxobutanoic acid | 507.3 |
| 17BK | 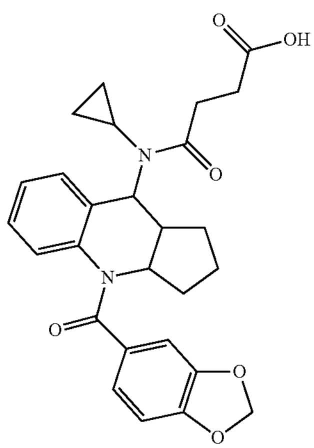 [SMILES: O=C(O)CCC(=O)N(C1CC1)C1c2ccccc2N(C(=O)c2ccc3c(c2)OCO3)C2CCCC21] | racemic, cis, cis | 4-(((cis,cis)-4-(benzo[d][1,3]dioxole-5-carbonyl)-2,3,3a,4,9,9a-hexahydro-1H-cyclopenta[b]quinolin-9-yl)(cyclopropyl)amino)-4-oxobutanoic acid | 477.3 |
| 17BL | 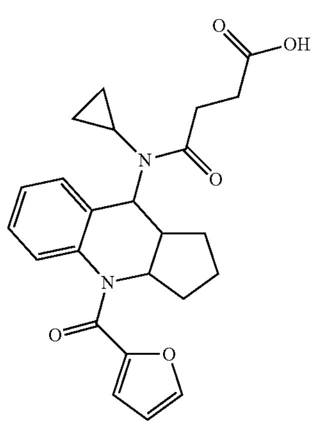 [SMILES: O=C(O)CCC(=O)N(C1CC1)C1c2ccccc2N(C(=O)c2ccco2)C2CCCC21] | racemic, cis, cis | 4-(cyclopropyl(cis,cis-4-(furan-2-carbonyl)-2,3,3a,4,9,9a-hexahydro-1H-cyclopenta[b]quinolin-9-yl)amino)-4-oxobutanoic acid | 423.2 |

-continued

| # | structure | stereo designation | chemical name | [M + H]+ |
|---|---|---|---|---|
| 17BM | 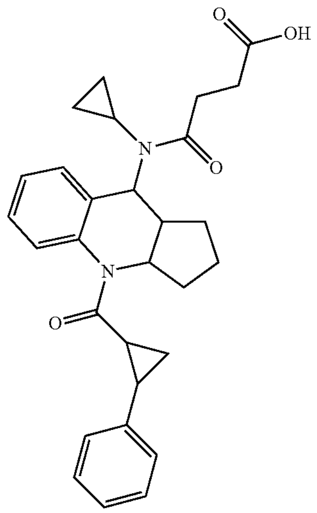 [SMILES: O=C(O)CCC(=O)N(C1CC1)C1c2ccccc2N(C(=O)C2CC2c2ccccc2)C2CCCC21] | cis, cis at fused ring enantiopure; (racemic cyclopropyl ring is trans substituted) | 4-[cyclopropyl[cis,cis-2,3,3a,4,9,9a-hexahydro-4-[(trans-2-phenylcyclopropyl)carbonyl]-1H-cyclopenta[b]quinolin-9-yl]amino]-4-oxobutanoic acid | 473.3 |
| 17BN | 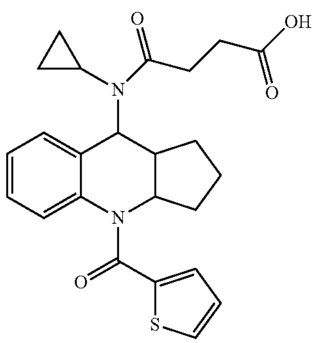 [SMILES: O=C(O)CCC(=O)N(C1CC1)C1c2ccccc2N(C(=O)c2cccs2)C2CCCC21] | cis, cis, single enantiomer | 4-[cyclopropyl[cis,cis-2,3,3a,4,9,9a-hexahydro-4-(2-thienylcarbonyl)-1H-cyclopenta[b]quinolin-9-yl]amino]-4-oxobutanoic acid | 439.2 |
| 17Bo | 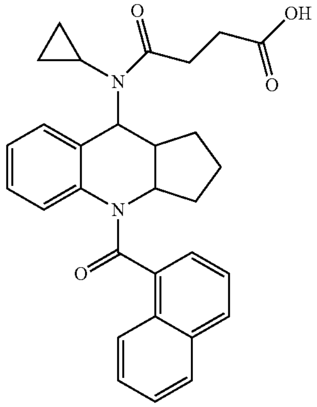 [SMILES: O=C(O)CCC(=O)N(C1CC1)C1c2ccccc2N(C(=O)c2cccc3ccccc23)C2CCCC21] | cis, cis, single enantiomer | 4-[cyclopropyl[cis,cis-2,3,3a,4,9,9a-hexahydro-4-(1-naphthalenylcarbonyl)-1H-cyclopenta[b]quinolin-9-yl]amino]-4-oxobutanoic acid | 483.3 |

| # | structure | stereo designation | chemical name | [M + H]+ |
|---|---|---|---|---|
| 17BP | 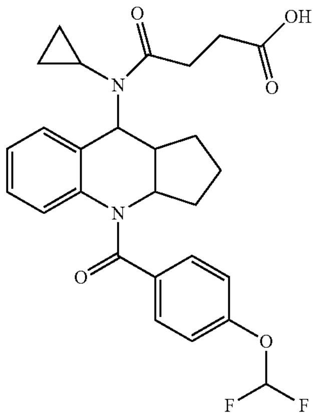 [SMILES: O=C(O)CCC(=O)N(C1CC1)C1c2ccccc2N(C(=O)c2ccc(OC(F)F)cc2)C2CCCC21] | cis, cis, single enantiomer | 4-[cyclopropyl[cis,cis-4-[4-(difluoromethoxy)benzoyl]-2,3,3a,4,9,9a-hexahydro-1H-cyclopenta[b]quinolin-9-yl]amino]-4-oxobutanoic acid | 499.3 |
| 17BQ | 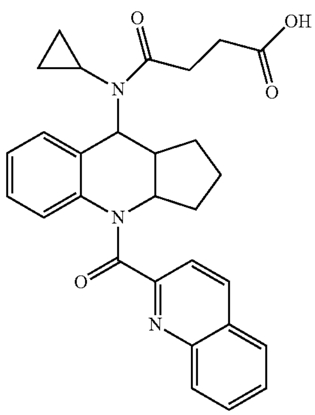 [SMILES: O=C(O)CCC(=O)N(C1CC1)C1c2ccccc2N(C(=O)c2ccc3ccccc3n2)C2CCCC21] | cis, cis, single enantiomer | 4-[cyclopropyl[cis,cis-2,3,3a,4,9,9a-hexahydro-4-(2-quinolinylcarbonyl)-1H-cyclopenta[b]quinolin-9-yl]amino]-4-oxobutanoic acid | 484.3 |
| 17BR | 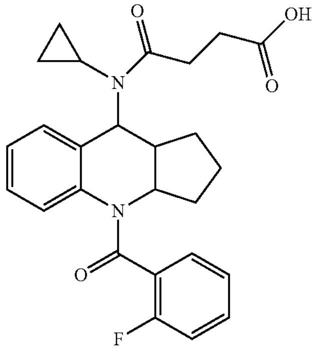 [SMILES: O=C(O)CCC(=O)N(C1CC1)C1c2ccccc2N(C(=O)c2ccccc2F)C2CCCC21] | cis, cis, single enantiomer | 4-[cyclopropyl[cis,cis-4-(2-fluorobenzoyl)-2,3,3a,4,9,9a-hexahydro-1H-cyclopenta[b]quinolin-9-yl]amino]-4-oxobutanoic acid | 451.2 |

-continued

| # | structure | stereo designation | chemical name | [M + H]+ |
|---|---|---|---|---|
| 17BS | 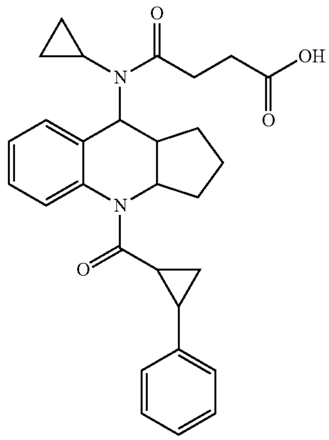 [SMILES: O=C(O)CCC(=O)N(C1CC1)C1c2ccccc2N(C(=O)C2CC2c2ccccc2)C2CCCC21] | cis, cis at fused ring (enantiopure), trans-substitution at cyclopropyl, single diastereomer 1 | 4-[cyclopropyl[cis,cis-2,3,3a,4,9,9a-hexahydro-4-[(trans-2-phenylcyclopropyl)carbonyl]-1H-cyclopenta[b]quinolin-9-yl]amino]-4-oxobutanoic acid | 473.3 |
| 17BT | 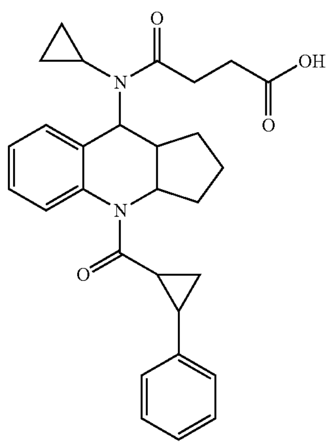 [SMILES: O=C(O)CCC(=O)N(C1CC1)C1c2ccccc2N(C(=O)C2CC2c2ccccc2)C2CCCC21] | cis, cis fused ring (enantiopure), trans-substitution at cyclopropyl,, single diastereomer 2 | 4-[cyclopropyl[cis,cis-2,3,3a,4,9,9a-hexahydro-4-[(trans-2-phenylcyclopropyl)carbonyl]-1H-cyclopenta[b]quinolin-9-yl]amino]-4-oxobutanoic acid | 473.3 |
| 17BU | 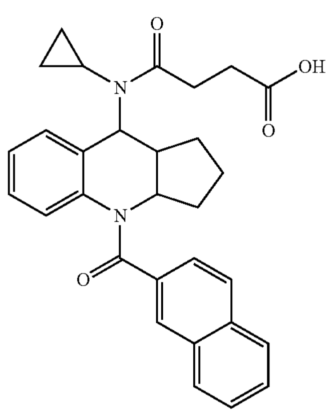 [SMILES: O=C(O)CCC(=O)N(C1CC1)C1c2ccccc2N(C(=O)c2ccc3ccccc3c2)C2CCCC21] | cis, cis,, single enantiomer | 4-[cyclopropyl[cis,cis-2,3,3a,4,9,9a-hexahydro-4-(2-naphthalenylcarbonyl)-1H-cyclopenta[b]quinolin-9-yl]amino]-4-oxobutanoic acid | 483.3 |

| # | structure | stereo designation | chemical name | [M + H]+ |
|---|---|---|---|---|
| 17BV | 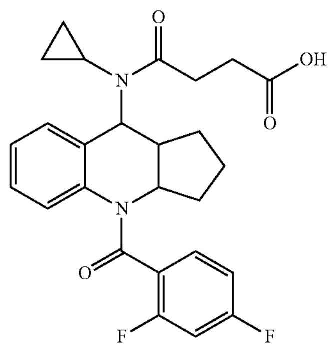 [SMILES: O=C(O)CCC(=O)N(C1CC1)C1c2ccccc2N(C(=O)c2ccc(F)cc2F)C2CCCC21] | cis, cis, single enantiomer | 4-[cyclopropyl[cis,cis-4-(2,4-difluorobenzoyl)-2,3,3a,4,9,9a-hexahydro-1H-cyclopenta[b]quinolin-9-yl]amino]-4-oxobutanoic acid | 469.3 |
| 17BW | 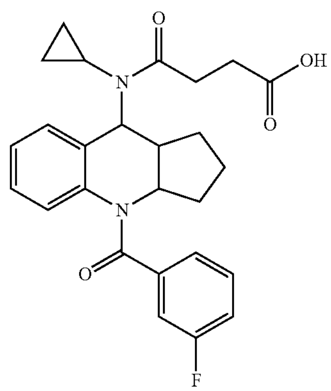 [SMILES: O=C(O)CCC(=O)N(C1CC1)C1c2ccccc2N(C(=O)c2cccc(F)c2)C2CCCC21] | cis, cis, single enantiomer | 4-[cyclopropyl[cis,cis-4-(3-fluorobenzoyl)-2,3,3a,4,9,9a-hexahydro-1H-cyclopenta[b]quinolin-9-yl]amino]-4-oxobutanoic acid | 451.2 |
| 17BX | 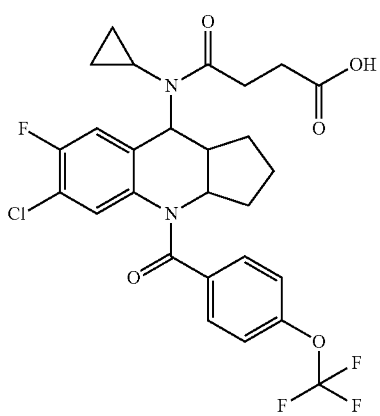 [SMILES: O=C(O)CCC(=O)N(C1CC1)C1c2cc(F)c(Cl)cc2N(C(=O)c2ccc(OC(F)(F)F)cc2)C2CCCC21] | cis, cis, single enantiomer, peak 1 | 4-[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]-4-oxobutanoic acid | 568.8 |
| 17BY | 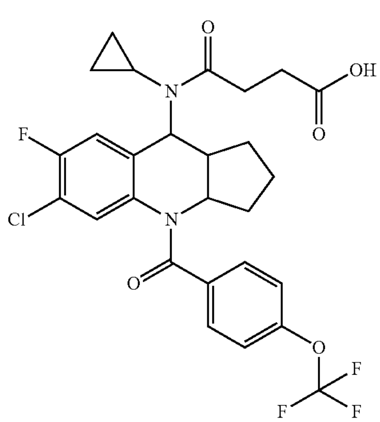 [SMILES: O=C(O)CCC(=O)N(C1CC1)C1c2cc(F)c(Cl)cc2N(C(=O)c2ccc(OC(F)(F)F)cc2)C2CCCC21] | cis, cis, single enantiomer, peak 2 | 4-[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]-4-oxobutanoic acid | 590.8 [M + Na]+ |

| # | structure | stereo designation | chemical name | [M + H]+ |
|---|---|---|---|---|
| 17BZ | 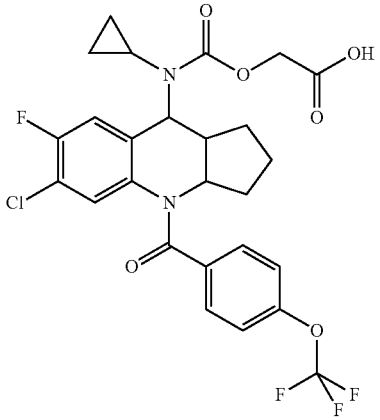 [SMILES: O=C(O)COC(=O)N(C1CC1)C1c2cc(F)c(Cl)cc2N(C(=O)c2ccc(OC(F)(F)F)cc2)C2CCCC21] | cis, cis, single enantiomer, peak 1 | [[[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]carbonyl]oxy]acetic acid | 571 |
| 17CA | 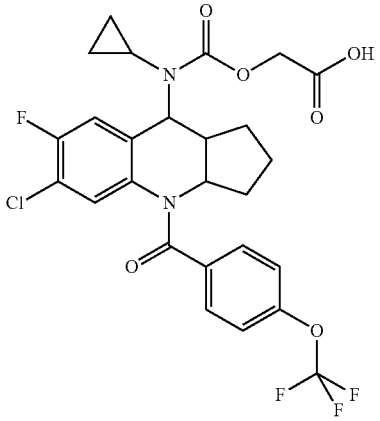 [SMILES: O=C(O)COC(=O)N(C1CC1)C1c2cc(F)c(Cl)cc2N(C(=O)c2ccc(OC(F)(F)F)cc2)C2CCCC21] | cis, cis, single enantiomer, peak 2 | [[[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]carbonyl]oxy]acetic acid | 571 |
| 17CB | 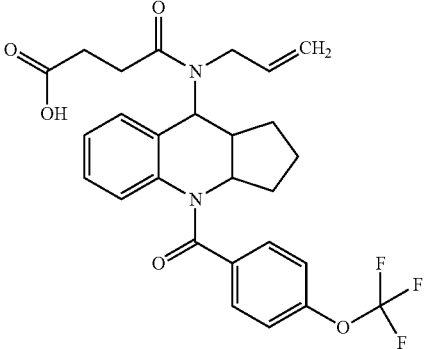 [SMILES: C=CCN(C(=O)CCC(=O)O)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl](2-propenyl)amino]-4-oxobutanoic acid | 517 |
| 17CC | 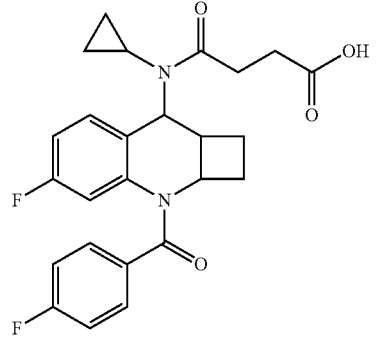 | cis, cis, single enantiomer | 4-[cyclopropyl[cis,cis-5-fluoro-3-(4-fluorobenzoyl)-1,2,2a,3,8,8a-hexahydrocyclobuta[b]quinolin-8-yl]amino]-4-oxobutanoic acid | 455 |

-continued

| # | structure | stereo designation | chemical name | [M + H]+ |
|---|---|---|---|---|
| 17CD | 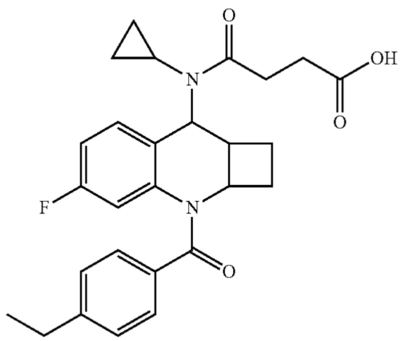 [SMILES: CCc1ccc(C(=O)N2c3cc(F)ccc3C(N(C(=O)CCC(=O)O)C3CC3)C3CCC32)cc1] | cis, cis, single enantiomer | 4-[cyclopropyl[cis,cis-3-(4-ethylbenzoyl)-5-fluoro-1,2,2a,3,8,8a-hexahydrocyclobuta[b]quinolin-8-yl]amino]-4-oxobutanoic acid | 465 |
| 17CE | 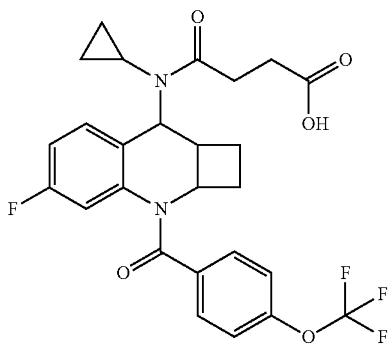 [SMILES: O=C(O)CCC(=O)N(C1CC1)C1c2ccc(F)cc2N(C(=O)c2ccc(OC(F)(F)F)cc2)C2CCC21] | cis, cis, single enantiomer | 4-[cyclopropyl[cis,cis-5-fluoro-1,2,2a,3,8,8a-hexahydro-3-[4-(trifluoromethoxy)benzoyl]cyclobuta[b]quinolin-8-yl]amino]-4-oxobutanoic acid | 543 [M + Na]+ |
| 17CF | 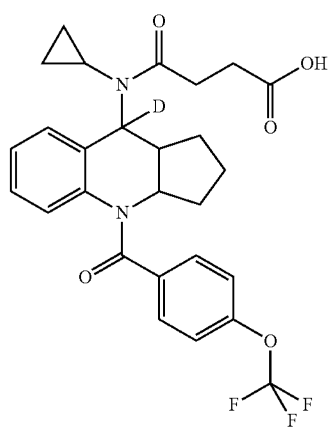 [SMILES: [2H]C1(N(C(=O)CCC(=O)O)C2CC2)c2ccccc2N(C(=O)c2ccc(OC(F)(F)F)cc2)C2CCCC21] | cis, cis, single enantiomer | deuterated-4-[cyclopropyl[cis,cis-2,3,3a,4,9,9a-hexahydro-4-[4-(trifluoromethoxy)benzoyl]-1H-cyclopenta[b]quinolin-9(R)-yl-(d)]amino]-4-oxobutanoic acid | 518.2 |
| 17CG | 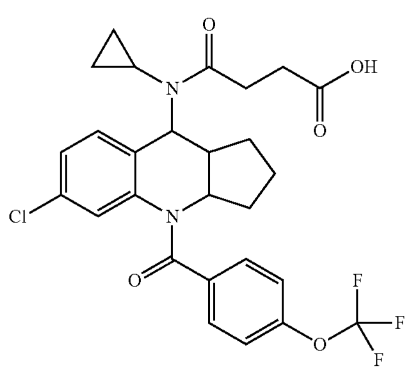 [SMILES: O=C(O)CCC(=O)N(C1CC1)C1c2ccc(Cl)cc2N(C(=O)c2ccc(OC(F)(F)F)cc2)C2CCCC21] | racemic, cis, cis | 4-[[cis-6-chloro-2,3,3a,4,9,9a-hexahydro-4-[4-(trifluoromethoxy)benzoyl]-1H-cyclopenta[b]quinolin-9-yl]cyclopropylamino]-4-oxobutanoic acid | 550.5 |

| # | structure | stereo designation | chemical name | [M + H]+ |
|---|---|---|---|---|
| 17CH | 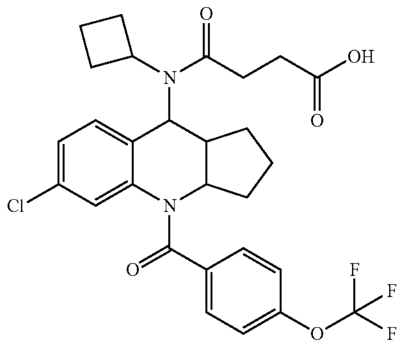 [SMILES: O=C(O)CCC(=O)N(C1CCC1)C1c2ccc(Cl)cc2N(C(=O)c2ccc(OC(F)(F)F)cc2)C2CCCC21] | racemic, cis, cis | 4-[[cis,cis-6-chloro-2,3,3a,4,9,9a-hexahydro-4-[4-(trifluoromethoxy)benzoyl]-1H-cyclopenta[b]quinolin-9-yl]cyclobutylamino]-4-oxobutanoic acid | 564.5 |
| 17Ci | 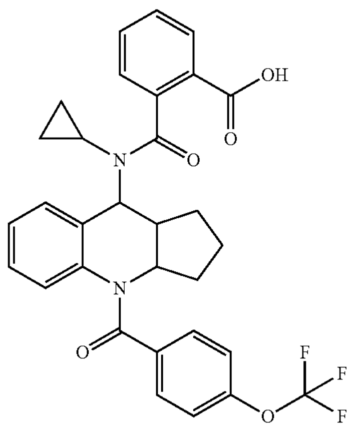 [SMILES: O=C(O)c1ccccc1C(=O)N(C1CC1)C1c2ccccc2N(C(=O)c2ccc(OC(F)(F)F)cc2)C2CCCC21] | racemic, cis, cis | 2-[[cyclopropyl[cis,cis-2,3,3a,4,9,9a-hexahydro-4-[4-(trifluoromethoxy)benzoyl]-1H-cyclopenta[b]quinolin-9-yl]amino]carbonyl]benzoic acid | 564.6 |
| 17CJ | 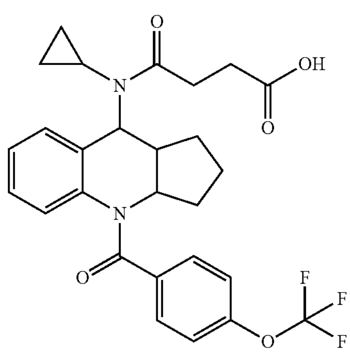 [SMILES: O=C(O)CCC(=O)N(C1CC1)C1c2ccccc2N(C(=O)c2ccc(OC(F)(F)F)cc2)C2CCCC21] | cis, cis, single enantiomer | 4-[cyclopropyl[cis,cis-2,3,3a,4,9,9a-hexahydro-4-[4-(trifluoromethoxy)benzoyl]-1H-cyclopenta[b]quinolin-9-yl]amino]-4-oxobutanoic acid | 516.7 |
| 17CK | 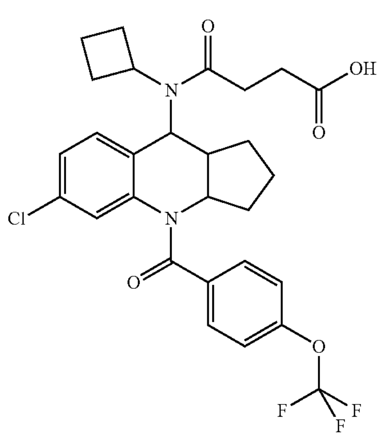 [SMILES: O=C(O)CCC(=O)N(C1CCC1)C1c2ccc(Cl)cc2N(C(=O)c2ccc(OC(F)(F)F)cc2)C2CCCC21] | cis, cis, single enantiomer | 4-[[cis,cis-6-chloro-2,3,3a,4,9,9a-hexahydro-4-[4-(trifluoromethoxy)benzoyl]-1H-cyclopenta[b]quinolin-9-yl]cyclobutylamino]-4-oxobutanoic acid | 565.3 |

| # | structure | stereo designation | chemical name | [M + H]+ |
|---|---|---|---|---|
| 17CL | 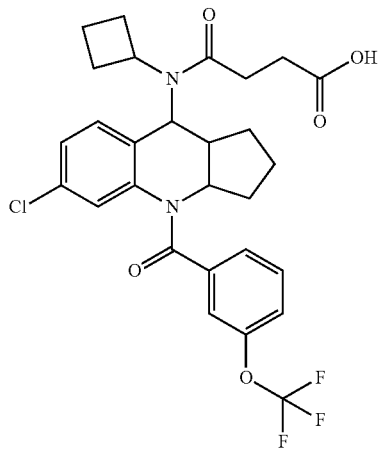 [SMILES: O=C(O)CCC(=O)N(C1CCC1)C1c2ccc(Cl)cc2N(C(=O)c2cccc(OC(F)(F)F)c2)C2CCCC21] | cis, cis, single enantiomer | 4-[[cis,cis-6-chloro-2,3,3a,4,9,9a-hexahydro-4-[3-(trifluoromethoxy)benzoyl]-1H-cyclopenta[b]quinolin-9-yl]cyclobutylamino]-4-oxobutanoic acid | 565.3 |
| 17CM | 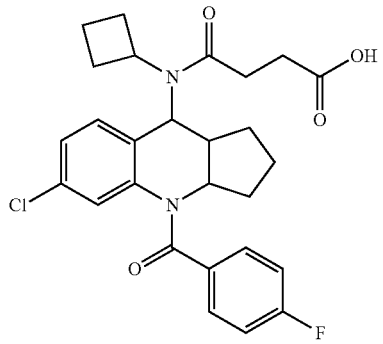 [SMILES: O=C(O)CCC(=O)N(C1CCC1)C1c2ccc(Cl)cc2N(C(=O)c2ccc(F)cc2)C2CCCC21] | cis, cis, single enantiomer | 4-[[cis,cis-6-chloro-4-(4-fluorobenzoyl)-2,3,3a,4,9,9a-hexahydro-1H-cyclopenta[b]quinolin-9-yl]cyclobutylamino]-4-oxobutanoic acid | 499.3 |
| 17CN | 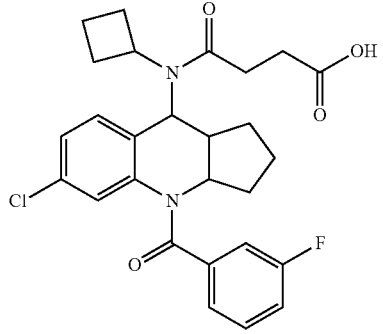 [SMILES: O=C(O)CCC(=O)N(C1CCC1)C1c2ccc(Cl)cc2N(C(=O)c2cccc(F)c2)C2CCCC21] | cis, cis, single enantiomer | 4-[[cis,cis-6-chloro-4-(3-fluorobenzoyl)-2,3,3a,4,9,9a-hexahydro-1H-cyclopenta[b]quinolin-9-yl]cyclobutylamino]-4-oxobutanoic acid | 499.3 |
| 17Co | 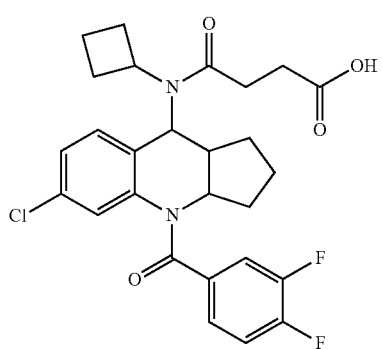 [SMILES: O=C(O)CCC(=O)N(C1CCC1)C1c2ccc(Cl)cc2N(C(=O)c2ccc(F)c(F)c2)C2CCCC21] | cis, cis, single enantiomer | 4-[[cis,cis-6-chloro-4-(3,4-difluorobenzoyl)-2,3,3a,4,9,9a-hexahydro-1H-cyclopenta[b]quinolin-9-yl]cyclobutylamino]-4-oxobutanoic acid | 517.3 |

-continued

| # | structure | stereo designation | chemical name | [M + H]+ |
|---|---|---|---|---|
| 17CP | 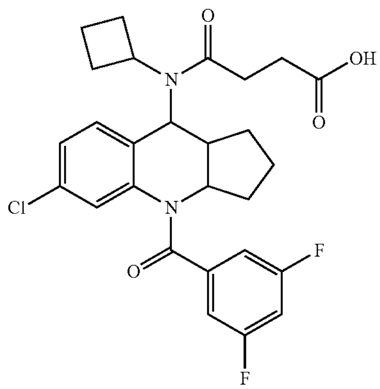 [SMILES: O=C(O)CCC(=O)N(C1CCC1)C1c2ccc(Cl)cc2N(C(=O)c2cc(F)cc(F)c2)C2CCCC21] | cis, cis, single enantiomer | 4-[[cis,cis-6-chloro-4-(3,5-difluorobenzoyl)-2,3,3a,4,9,9a-hexahydro-1H-cyclopenta[b]quinolin-9-yl]cyclobutylamino]-4-oxobutanoic acid | 538.5 [M + Na]+ |
| 17CQ | 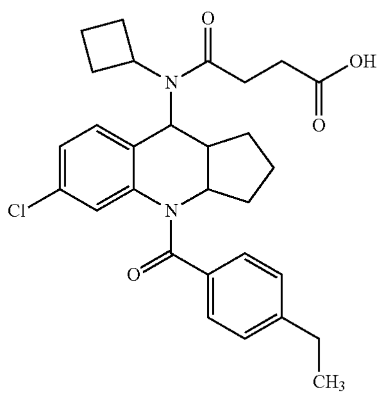 [SMILES: CCc1ccc(C(=O)N2c3cc(Cl)ccc3C(N(C(=O)CCC(=O)O)C3CCC3)C3CCCC32)cc1] | cis, cis, single enantiomer | 4-[[cis,cis-6-chloro-4-(4-ethylbenzoyl)-2,3,3a,4,9,9a-hexahydro-1H-cyclopenta[b]quinolin-9-yl]cyclobutylamino]-4-oxobutanoic acid | 509.3 |
| 17CR | 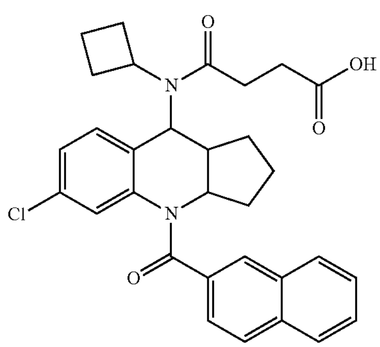 [SMILES: O=C(O)CCC(=O)N(C1CCC1)C1c2ccc(Cl)cc2N(C(=O)c2ccc3ccccc3c2)C2CCCC21] | cis, cis, single enantiomer | 4-[[cis,cis-6-chloro-2,3,3a,4,9,9a-hexahydro-4-(2-naphthalenylcarbonyl)-1H-cyclopenta[b]quinolin-9-yl]cyclobutylamino]-4-oxobutanoic acid | 531.3 |
| 17CS | 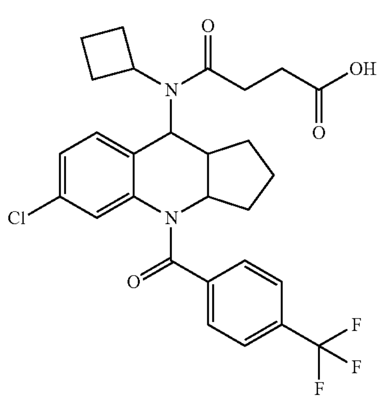 [SMILES: O=C(O)CCC(=O)N(C1CCC1)C1c2ccc(Cl)cc2N(C(=O)c2ccc(C(F)(F)F)cc2)C2CCCC21] | cis, cis, single enantiomer | 4-[[cis,cis-6-chloro-2,3,3a,4,9,9a-hexahydro-4-[4-(trifluoromethyl)benzoyl]-1H-cyclopenta[b]quinolin-9-yl]cyclobutylamino]-4-oxobutanoic acid | 549.3 |

| # | structure | stereo designation | chemical name | [M + H]+ |
|---|---|---|---|---|
| 17CT | 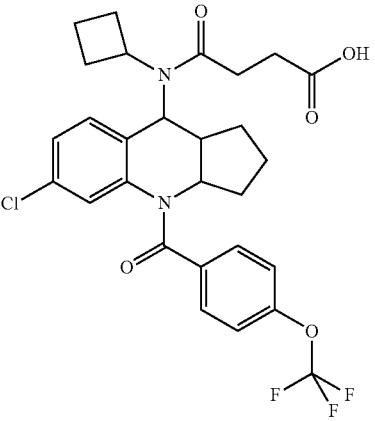 [SMILES: O=C(O)CCC(=O)N(C1CCC1)C1c2ccc(Cl)cc2N(C(=O)c2ccc(OC(F)(F)F)cc2)C2CCCC21] | cis, cis, single enantiomer | 4-[[cis,cis-6-chloro-2,3,3a,4,9,9a-hexahydro-4-[4-(trifluoromethoxy)benzoyl]-1H-cyclopenta[b]quinolin-9-yl]cyclopropylamino]-4-oxobutanoic acid | 551 |
| 17CU | 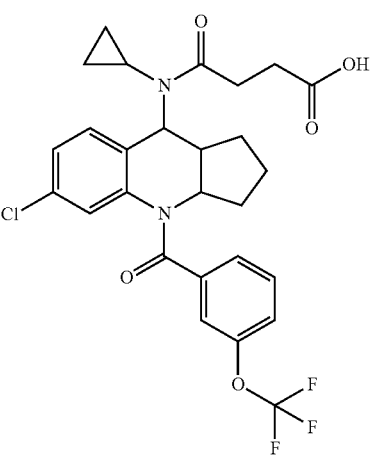 [SMILES: O=C(O)CCC(=O)N(C1CC1)C1c2ccc(Cl)cc2N(C(=O)c2cccc(OC(F)(F)F)c2)C2CCCC21] | cis, cis, single enantiomer | 4-[[cis,cis-6-chloro-2,3,3a,4,9,9a-hexahydro-4-[3-(trifluoromethoxy)benzoyl]-1H-cyclopenta[b]quinolin-9-yl]cyclopropylamino]-4-oxobutanoic acid | 551 |
| 17CV | 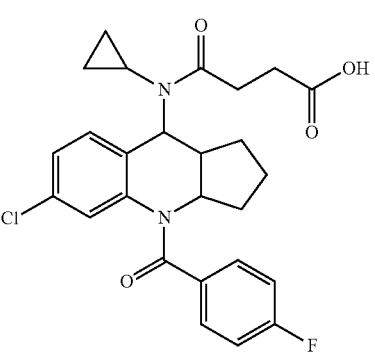 [SMILES: O=C(O)CCC(=O)N(C1CC1)C1c2ccc(Cl)cc2N(C(=O)c2ccc(F)cc2)C2CCCC21] | cis, cis, single enantiomer | 4-[[cis,cis-6-chloro-4-(4-fluorobenzoyl)-2,3,3a,4,9,9a-hexahydro-1H-cyclopenta[b]quinolin-9-yl]cyclopropylamino]-4-oxobutanoic acid | 485.6 |

| # | structure | stereo designation | chemical name | [M + H]+ |
|---|---|---|---|---|
| 17CW | 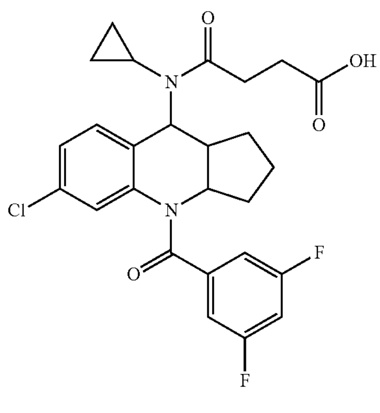 [SMILES: O=C(O)CCC(=O)N(C1CC1)C1c2ccc(Cl)cc2N(C(=O)c2cc(F)cc(F)c2)C2CCCC21] | cis, cis, single enantiomer | 4-[[cis,cis-6-chloro-4-(3,5-difluorobenzoyl)-2,3,3a,4,9,9a-hexahydro-1H-cyclopenta[b]quinolin-9-yl]cyclopropylamino]-4-oxobutanoic acid | 503.6 |
| 17CX | 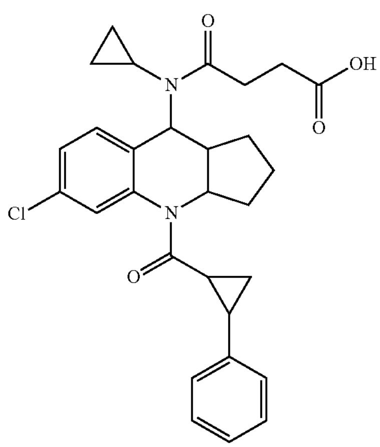 [SMILES: O=C(O)CCC(=O)N(C1CC1)C1c2ccc(Cl)cc2N(C(=O)C2CC2c2ccccc2)C2CCCC21] | cis, cis at fused ring (enantiopure) trans substitution at cyclopropyl ring (enantiopure), single diastereomer, (less polar one) | 4-[[cis,cis-6-chloro-2,3,3a,4,9,9a-hexahydro-4-[(trans-2-phenylcyclopropyl)carbonyl]-1H-cyclopenta[b]quinolin-9-yl]cyclopropylamino]-4-oxobutanoic acid | 506.7 |
| 17CY | 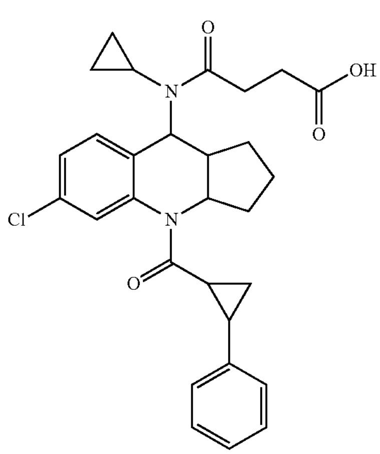 [SMILES: O=C(O)CCC(=O)N(C1CC1)C1c2ccc(Cl)cc2N(C(=O)C2CC2c2ccccc2)C2CCCC21] | cis, cis at fused ring (enantiopure), trans substitution at the cyclopropyl ring (enantiopure) single diastereomer, (more polar one) | 4-[[cis,cis-6-chloro-2,3,3a,4,9,9a-hexahydro-4-[(trans-2-phenylcyclopropyl)carbonyl]-1H-cyclopenta[b]quinolin-9-yl]cyclopropylamino]-4-oxobutanoic acid | 506.6 |

-continued

| # | structure | stereo designation | chemical name | [M + H]+ |
|---|---|---|---|---|
| 17CZ | 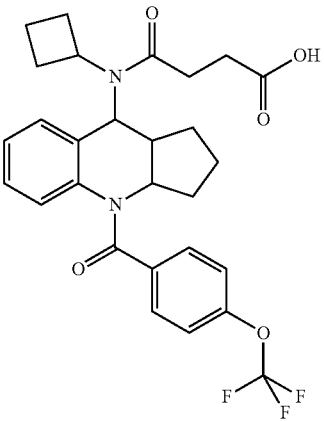 [SMILES: O=C(O)CCC(=O)N(C1CCC1)C1c2ccccc2N(C(=O)c2ccc(OC(F)(F)F)cc2)C2CCCC21] | cis, cis, single enantiomer | 4-[cyclobutyl[cis,cis-2,3,3a,4,9,9a-hexahydro-4-[4-(trifluoromethoxy)benzoyl]-1H-cyclopenta[b]quinolin-9-yl]amino]-4-oxobutanoic acid | 552.5 [M + Na]+ |
| 17DA | 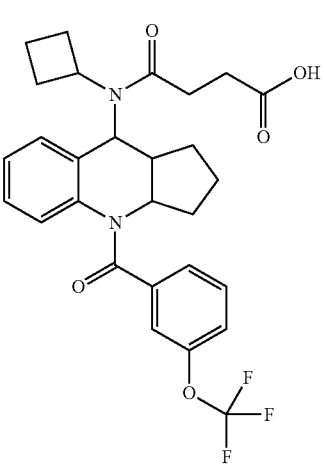 [SMILES: O=C(O)CCC(=O)N(C1CCC1)C1c2ccccc2N(C(=O)c2cccc(OC(F)(F)F)c2)C2CCCC21] | cis, cis, single enantiomer | 4-[cyclobutyl[cis,cis-2,3,3a,4,9,9a-hexahydro-4-[3-(trifluoromethoxy)benzoyl]-1H-cyclopenta[b]quinolin-9-yl]amino]-4-oxobutanoic acid | 552.5 [M + Na]+ |
| 17DB | 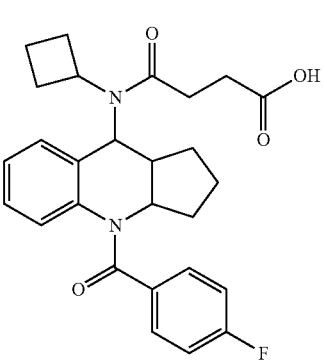 [SMILES: O=C(O)CCC(=O)N(C1CCC1)C1c2ccccc2N(C(=O)c2ccc(F)cc2)C2CCCC21] | cis, cis, single enantiomer | 4-[cyclobutyl[cis,cis-4-(4-fluorobenzoyl)-2,3,3a,4,9,9a-hexahydro-1H-cyclopenta[b]quinolin-9-yl]amino]-4-oxobutanoic acid | 486.7 [M + Na]+ |

| # | structure | stereo designation | chemical name | [M + H]+ |
|---|---|---|---|---|
| 17DC | 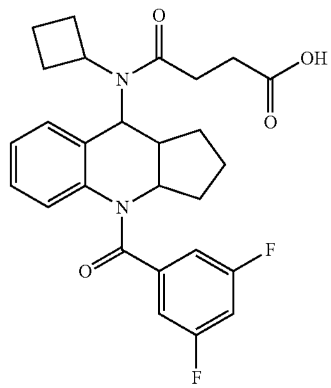 [SMILES: O=C(O)CCC(=O)N(C1CCC1)C1c2ccccc2N(C(=O)c2cc(F)cc(F)c2)C2CCCC21] | cis, cis, single enantiomer | 4-[cyclobutyl[cis,cis-4-(3,5-difluorobenzoyl)-2,3,3a,4,9,9a-hexahydro-1H-cyclopenta[b]quinolin-9-yl]amino]-4-oxobutanoic acid | 504.6 [M + Na]+ |
| 17DD | 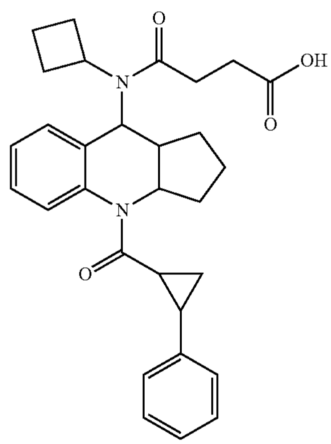 [SMILES: O=C(O)CCC(=O)N(C1CCC1)C1c2ccccc2N(C(=O)C2CC2c2ccccc2)C2CCCC21] | cis, cis at fused ring (enantiopure), trans substitution at cyclopropyl ring (enantiopure), single diastereomer, (less polar one) | 4-[cyclobutyl[cis,cis-2,3,3a,4,9,9a-hexahydro-4-[(trans-2-phenylcyclopropyl)carbonyl]-1H-cyclopenta[b]quinolin-9-yl]amino]-4-oxobutanoic acid | 508.6 [M + Na]+ |
| 17DE | 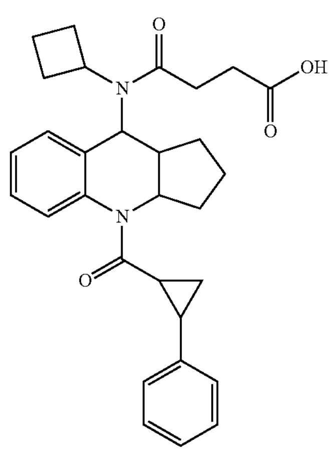 [SMILES: O=C(O)CCC(=O)N(C1CCC1)C1c2ccccc2N(C(=O)C2CC2c2ccccc2)C2CCCC21] | cis, cis at fused ring (enantiopure), trans substitution at cyclopropyl ring (enantiopure), single diastereomer, (more polar one) | 4-[cyclobutyl[cis,cis-2,3,3a,4,9,9a-hexahydro-4-[(trans-2-phenylcyclopropyl)carbonyl]-1H-cyclopenta[b]quinolin-9-yl]amino]-4-oxobutanoic acid | 486.7 |

-continued

| # | structure | stereo designation | chemical name | [M + H]+ |
|---|---|---|---|---|
| 17DF | 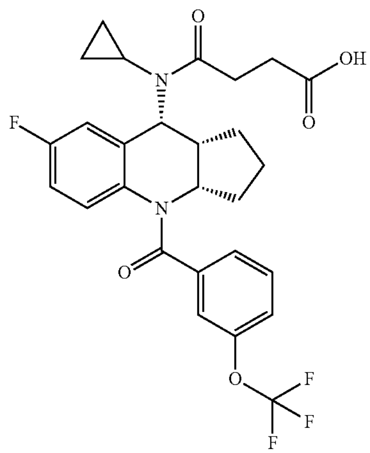 [SMILES: O=C(O)CCC(=O)N(C1CC1)[C@H]1c2cc(F)ccc2N(C(=O)c2cccc(OC(F)(F)F)c2)[C@H]2CCC[C@H]21] | 3aS,9R,9aR single enantiomer | 4-[cyclopropyl[(3aS,9R,9aR)-7-fluoro-2,3,3a,4,9,9a-hexahydro-4-[3-(trifluoromethoxy)benzoyl]-1H-cyclopenta[b]quinolin-9-yl]amino]-4-oxobutanoic acid | 534.6 |
| 17DG | 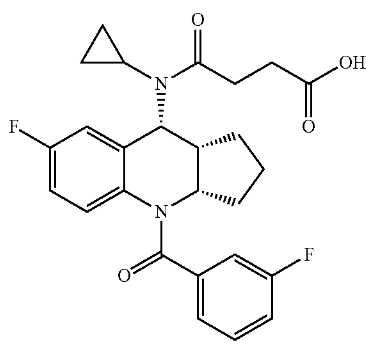 [SMILES: O=C(O)CCC(=O)N(C1CC1)[C@H]1c2cc(F)ccc2N(C(=O)c2cccc(F)c2)[C@H]2CCC[C@H]21] | 3aS,9R,9aR single enantiomer | 4-[cyclopropyl[(3aS,9R,9aR)-7-fluoro-4-(3-fluorobenzoyl)-2,3,3a,4,9,9a-hexahydro-1H-cyclopenta[b]quinolin-9-yl]amino]-4-oxobutanoic acid | 468.7 |
| 17DH | 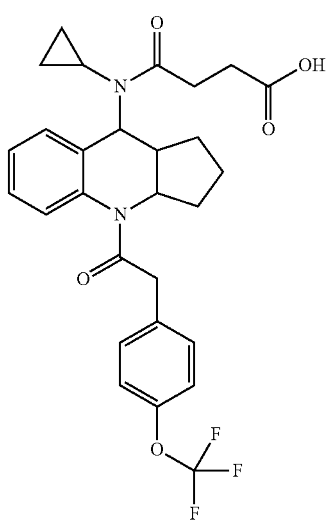 [SMILES: O=C(O)CCC(=O)N(C1CC1)C1c2ccccc2N(C(=O)Cc2ccc(OC(F)(F)F)cc2)C2CCCC21] | cis, cis, single enantiomer | 4-[cyclopropyl[cis,cis-2,3,3a,4,9,9a-hexahydro-4-[[4-(trifluoromethoxy)phenyl]acetyl]-1H-cyclopenta[b]quinolin-9-yl]amino]-4-oxobutanoic acid | 530.7 |

| # | structure | stereo designation | chemical name | [M + H]+ |
|---|---|---|---|---|
| 17Di | 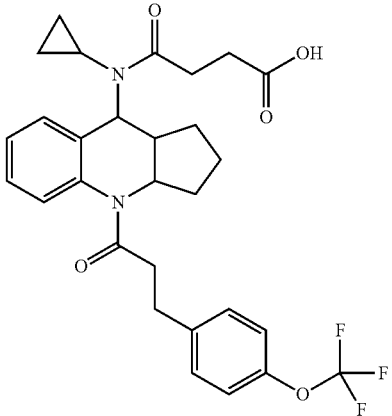 [SMILES: O=C(O)CCC(=O)N(C1CC1)C1c2ccccc2N(C(=O)CCc2ccc(OC(F)(F)F)cc2)C2CCCC21] | cis, cis, single enantiomer | 4-[cyclopropyl[cis,cis-2,3,3a,4,9,9a-hexahydro-4-[1-oxo-3-[4-(trifluoromethoxy)phenyl]propyl]-1H-cyclopenta[b]quinolin-9-yl]amino]-4-oxobutanoic acid | 544.7 |
| 17DJ | 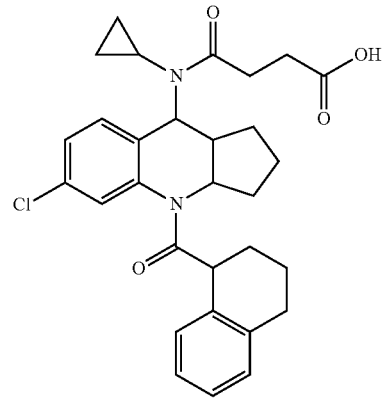 [SMILES: O=C(O)CCC(=O)N(C1CC1)C1c2ccc(Cl)cc2N(C(=O)C2CCCc3ccccc32)C2CCCC21] | Cis, cis at fused ring (enantiopure); R and S diastereomers at 1 napthalenyl atom | 4-[[cis,cis-6-chloro-2,3,3a,4,9,9a-hexahydro-4-[(1,2,3,4-tetrahydro-1-naphthalenyl)carbonyl]-1H-cyclopenta[b]quinolin-9-yl]cyclopropylamino]-4-oxobutanoic acid | 520.6 |
| 17DK | 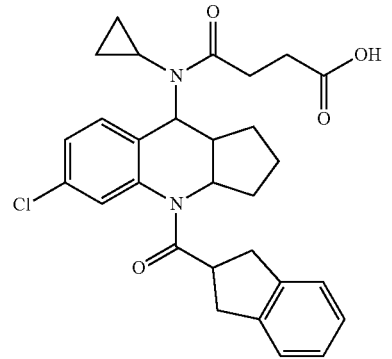 [SMILES: O=C(O)CCC(=O)N(C1CC1)C1c2ccc(Cl)cc2N(C(=O)C2Cc3ccccc3C2)C2CCCC21] | cis, cis, single enantiomer | 4-[[cis,cis-6-chloro-4-[(2,3-dihydro-1H-inden-2-yl)carbonyl]-2,3,3a,4,9,9a-hexahydro-1H-cyclopenta[b]quinolin-9-yl]cyclopropylamino]-4-oxobutanoic acid | 506.6 |
| 17DL | 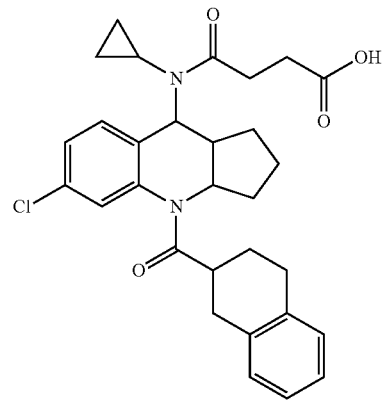 [SMILES: O=C(O)CCC(=O)N(C1CC1)C1c2ccc(Cl)cc2N(C(=O)C2CCc3ccccc3C2)C2CCCC21] | cis, cis (enantiopure), R and S diastereomers at 1 napthalenyl atom | 4-[[cis,cis-6-chloro-2,3,3a,4,9,9a-hexahydro-4-[(1,2,3,4-tetrahydro-2-naphthalenyl)carbonyl]-1H-cyclopenta[b]quinolin-9-yl]cyclopropylamino]-4-oxobutanoic acid | 521.2 |

| # | structure | stereo designation | chemical name | [M + H]+ |
|---|---|---|---|---|
| 17DN | 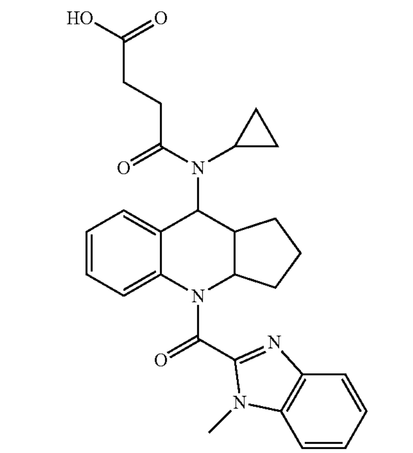 [SMILES: Cn1c(C(=O)N2c3ccccc3C(N(C(=O)CCC(=O)O)C3CC3)C3CCCC32)nc2ccccc21] | racemic, cis, cis | 4-[cyclopropyl[cis,cis-2,3,3a,4,9,9a-hexahydro-4-[(1-methyl-1H-benzimidazol-2-yl)carbonyl]-1H-cyclopenta[b]quinolin-9-yl]amino]-4-oxobutanoic acid | 487.3 |
| 17Do | 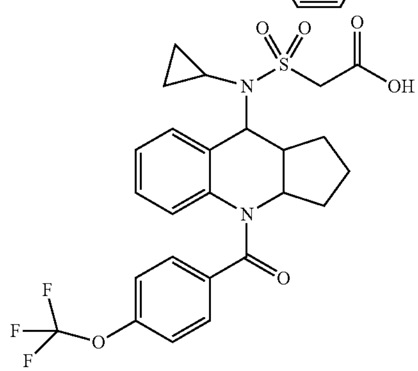 | racemic, cis, cis | [[cyclopropyl[cis,cis-2,3,3a,4,9,9a-hexahydro-4-[4-(trifluoromethoxy)benzoyl]-1H-cyclopenta[b]quinolin-9-yl]amino]sulfonyl]acetic acid | 539 |

Alternative Preparation of the Intermediate (3aS, 9aR)-tert-butyl 7-fluoro-9-oxo-3,3a,9,9a-tetrahydro-1H-cyclopenta[b]quinoline-4(2H)-carboxylate (17D)

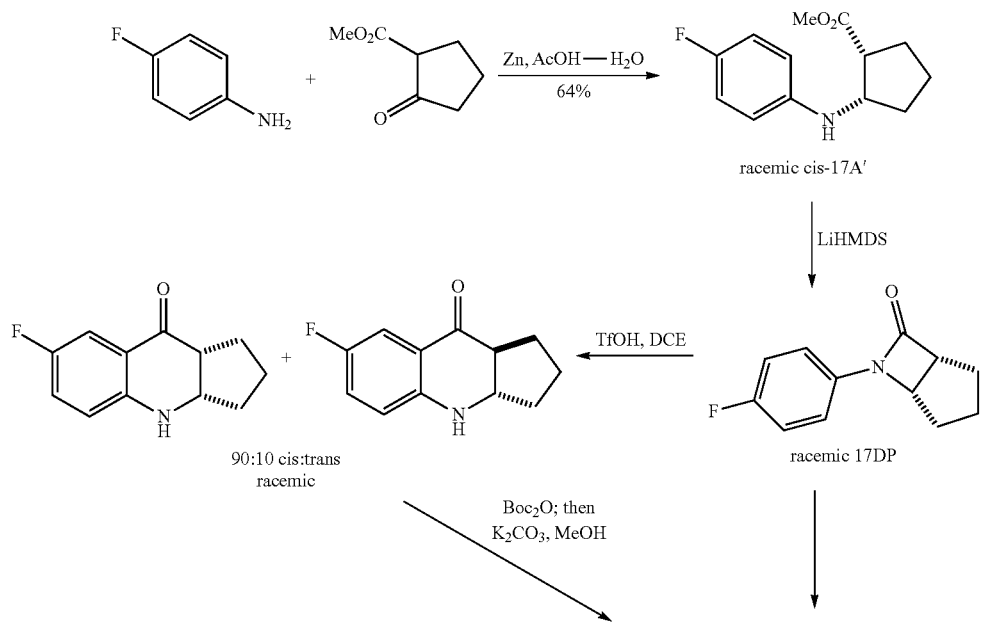

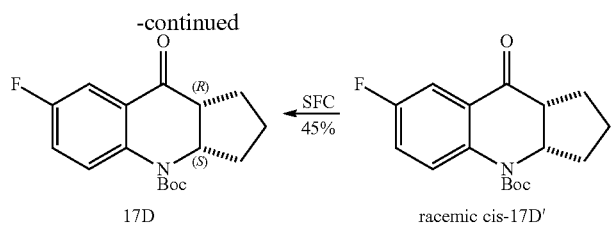

Step 1

Cis-methyl 2-((4-fluorophenyl)amino)cyclopentanecarboxylate (racemic cis-17A')

A 1-L, three-necked, round-bottomed flask was charged with 4-fluoroaniline (50 mL, 528 mmol), methyl 2-oxocyclopentane-1-carboxylate (78.0 g, 528 mmol), 600 mL of AcOH, and 60 mL of water. Zn dust (<10 micron, 103.6 g, 1584 mmol) was added portionwise over 10 minutes and then, the mixture was stirred at 70° C. for 3 h. The reaction mixture was cooled to room temperature, filtered through Celite® with the aid of MeOH, and concentrated. Dichloromethane (500 mL) was added in one portion and the pH was carefully adjusted with ammonium hydroxide to 10. The resulting organic layer was separated, washed with brine, and concentrated to give 130 g of an orange solid. Recrystallization from hexanes afforded 80 g (64%) of cis-methyl 2-((4-fluorophenyl)amino) cyclopentanecarboxylate (racemic cis-17A') as off-white crystals.

Step 2

Cis-6-(4-fluorophenyl)-6-azabicyclo[3.2.0]heptan-7-one (racemic 17DP)

A 500-mL, three-necked, round-bottomed flask was charged with cis-methyl 2-((4-fluorophenyl)amino)cyclopentanecarboxylate (racemic cis-17A') (15.77 g, 66.5 mmol) and 75 mL of THF. The reaction mixture was cooled at 5° C. while a 1M solution of LiHMDS (73.1 mL, 73.1 mmol) was added dropwise via syringe over 10 min. The resulting reaction mixture was stirred at 5° C. to 15° C. for 1.5 h. The reaction mixture was then quenched into 200 mL of aqueous ammonium chloride and 250 mL of ethyl acetate. The organic layer was separated, washed with brine, dried over magnesium sulfate, filtered, and concentrated to give 14 g of cis-6-(4-fluorophenyl)-6-azabicyclo[3.2.0]heptan-7-one (racemic 17DP) as an orange oil.

Step 3

7-Fluoro-2,3,3a,4-tetrahydro-1H-cyclopenta[b]quinolin-9(9aH)-one

A 500-mL, three-necked, round-bottomed flask was charged with cis-6-(4-fluorophenyl)-6-azabicyclo[3.2.0] heptan-7-one (racemic 17DP) (26.5 g, 129 mmol) and 250 mL of dichloroethane. The reaction mixture was cooled at 5° C. while triflic acid was added via syringe over 10 min. The reaction mixture was stirred at 50° C. for 4 h. The reaction mixture was cooled to room temperature with an ice-water bath and then quenched with saturated sodium bicarbonate to adjust the pH to 10. The organic layer was separated, washed with brine, dried over MgSO$_4$, filtered, and concentrated to give 26.5 g of a 90:10 mixture of the title compound as a brown semi-solid.

Step 4

Cis-tert-butyl 7-fluoro-9-oxo-3,3a,9,9a-tetrahydro-1H-cyclopenta[b]quinoline-4(2H)-carboxylate (racemic cis-17D')

A 500-mL, three-necked, round-bottomed flask was charged with the tricyclic aniline (90:10) (26.5 g, 129 mmol), triethylamine (45.0 mL, 323 mmol), DMAP (1.57 g, 12.9 mmol), and 200 mL of dioxane. Boc$_2$O (59.2 g, 271 mmol) was added in one portion and the reaction mixture was stirred at room temperature for 17 h. The reaction mixture was then diluted with EtOAc and water. The organic layer was separated, washed with a 0.5 M solution of HCl, washed with saturated sodium bicarbonate, washed with brine, dried over MgSO$_4$, filtered, and concentrated to give a brown oil. This material was diluted with 200 mL of MeOH and charged with potassium carbonate. The reaction mixture was stirred at room temperature for 2 h. Purification by column chromatography afforded 30 g (76% 3-step yield from the starting tricyclic aniline) of cis-tert-butyl 7-fluoro-9-oxo-3,3a,9,9a-tetrahydro-1H-cyclopenta[b]quinoline-4(2H)-carboxylate (racemic cis-17D') as a thick, yellow oil.

Step 5

(3aS,9aR)-tert-butyl 7-fluoro-9-oxo-3,3a,9,9a-tetrahydro-1H-cyclopenta[b]quinoline-4(2H)-carboxylate (17D)

Racemic cis-17D' (30 g) was separated by supercritical fluid chromatography using the conditions described below to give 13.5 g of (3aS,9aR)-tert-butyl 7-fluoro-9-oxo-3,3a,9,9a-tetrahydro-1H-cyclopenta[b]quinoline-4(2H)-carboxylate (17D) (45% yield, >99% ee). 17D was the first eluting enantiomer under these conditions.

SFC Separation Conditions:

Flow rate: 260 g/min

Modifier percentage: 5%

Back Pressure: 150 bar

Column: AD-H, 50×250 mm

Inj: 0.7 mL

Modifier: IPA

UV: 227 nm

Concentration: 50 mg/mL in MeOH

Example 18

Preparation of Racemic 4-[Cyclopropyl[cis,cis-2,3,3a,4,9,9a-hexahydro-4-[4-(2-pyrimidinyl)benzoyl]-1H-cyclopenta[b]quinolin-9-yl]amino]-4-oxobutanoic acid

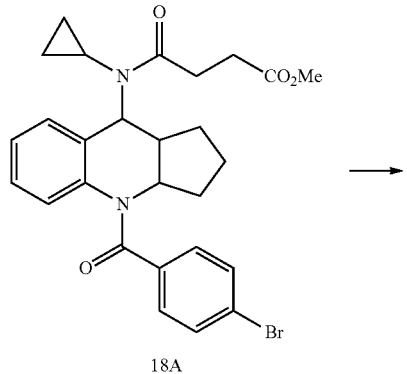

18A

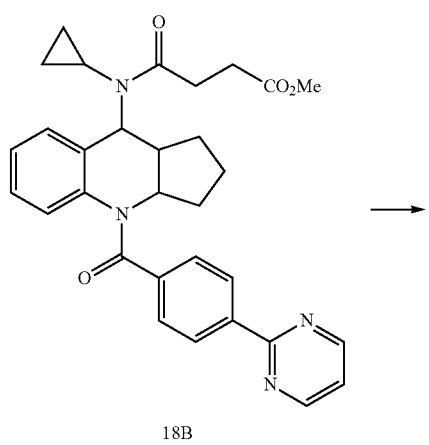

18B

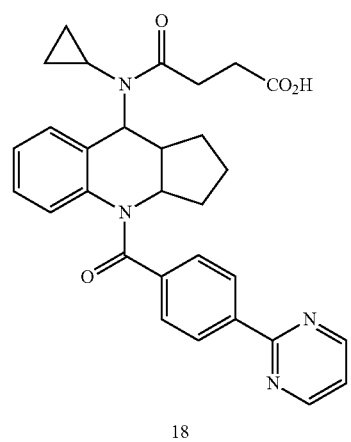

18

Bromide (18A, 60 mg, 0.11 mmol.) which was prepared from 14A following a similar procedure as described in Example 14, step 2 with 4-bromobenzoylchloride, 2-(tributylstannyl)pyrimidine (126 mg, 0.34 mmol) and tetrakis(triphenylphosphine)palladium(0) (26 mg, 0.023 mmol) were mixed in DMF (1 mL). The reaction mixture was degassed and heated in a sealed vial at 80° C. overnight. The reaction mixture was cooled to room temperature, filtered through Celite®. The filtrate was diluted with ethyl acetate and washed with water. The organic extracts were combined, washed with brine, dried ($MgSO_4$), filtered and concentrated. The residue was purified by preparative TLC (eluted with 50% ethyl actetate-hexane) to afford the desired compound (20 mg, 0.038 mmol). Ester 18B was hydrolyzed to give compound 18 following the same procedure as described in Example 14, step 3. $[M+H]^+$=511.3.

The compounds in the following table were prepared in a similar fashion to the process illustrated in Example 18, starting from the appropriate bromides using coupling reactions.

| # | Structure | Stereo Designation | Name | $[M + H]^+$ |
|---|---|---|---|---|
| 18C | 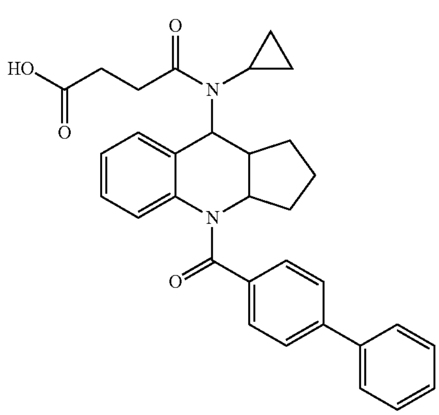 [SMILES: O=C(O)CCC(=O)N(C1CC1)C1c2ccccc2N(C(=O)c2ccc(-c3ccccc3)cc2)C2CCCC21] | racemic, cis, cis | 4-[[cis,cis-4-([1,1'-biphenyl]-4-ylcarbonyl)-2,3,3a,4,9,9a-hexahydro-1H-cyclopenta[b]quinolin-9-yl]cyclopropylamino]-4-oxobutanoic acid | 509.3 |

-continued

| # | Structure | Stereo Designation | Name | [M + H]+ |
|---|---|---|---|---|
| 18D | 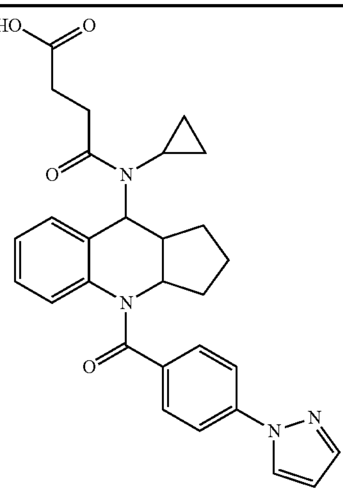 | racemic, cis, cis | 4-[cyclopropyl[cis,cis-2,3,3a,4,9,9a-hexahydro-4-[4-(1H-pyrazol-1-yl)benzoyl]-1H-cyclopenta[b]quinolin-9-yl]amino]-4-oxobutanoic acid | 499.3 |
| 18E | 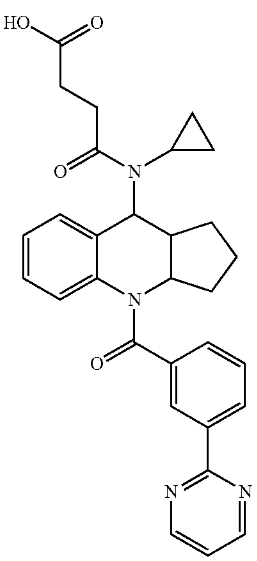 [SMILES: O=C(O)CCC(=O)N(C1CC1)C1c2ccccc2N(C(=O)c2cccc(-c3ncccn3)c2)C2CCCC21] | racemic, cis, cis | 4-[cyclopropyl[cis,cis-2,3,3a,4,9,9a-hexahydro-4-[3-(2-pyrimidinyl)benzoyl]-1H-cyclopenta[b]quinolin-9-yl]amino]-4-oxobutanoic acid | 511.3 |
| 18F | 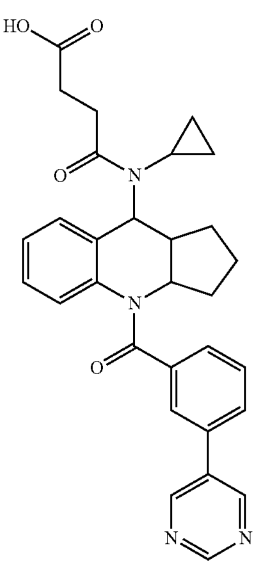 [SMILES: O=C(O)CCC(=O)N(C1CC1)C1c2ccccc2N(C(=O)c2cccc(-c3cncnc3)c2)C2CCCC21] | racemic, cis, cis | 4-[cyclopropyl[cis,cis-2,3,3a,4,9,9a-hexahydro-4-[3-(5-pyrimidinyl)benzoyl]-1H-cyclopenta[b]quinolin-9-yl]amino]-4-oxobutanoic acid | 511.3 |

-continued

| # | Structure | Stereo Designation | Name | [M + H]+ |
|---|---|---|---|---|
| 18G | 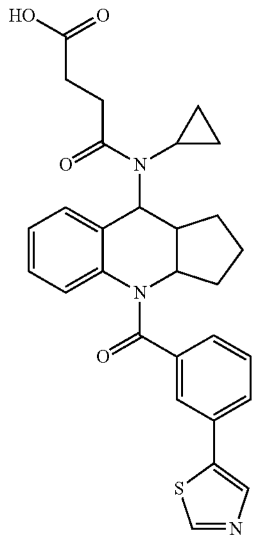 [SMILES: O=C(O)CCC(=O)N(C1CC1)C1c2ccccc2N(C(=O)c2cccc(-c3cncs3)c2)C2CCCC21] | racemic, cis, cis | 4-[cyclopropyl[cis,cis-2,3,3a,4,9,9a-hexahydro-4-[3-(5-thiazolyl)benzoyl]-1H-cyclopenta[b]quinolm-9-yl]amino]-4-oxobutanoic acid | 516.3 |
| 18H | 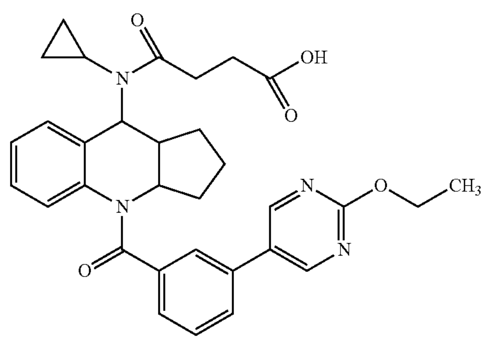 [SMILES: CCOc1ncc(-c2cccc(C(=O)N3c4ccccc4C(N(C(=O)CCC(=O)O)C4CC4)C4CCCC43)c2)cn1] | racemic, cis, cis | 4-[cyclopropyl[cis,cis-4-[3-(2-ethoxy-5-pyrimidinyl)benzoyl]-2,3,3a,4,9,9a-hexahydro-1H-cyclopenta[b]quinolin-9-yl]amino]-4-oxobutanoic acid | 555.3 |
| 18i | 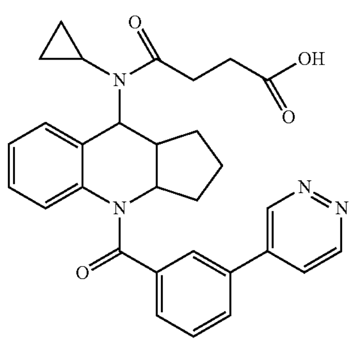 [SMILES: O=C(O)CCC(=O)N(C1CC1)C1c2ccccc2N(C(=O)c2cccc(-c3ccnnc3)c2)C2CCCC21] | racemic, cis, cis | 4-[cyclopropyl[cis,cis-2,3,3a,4,9,9a-hexahydro-4-[3-(4-pyridazinyl)benzoyl]-1H-cyclopenta[b]quinolin-9-yl]amino]-4-oxobutanoic acid | 511.3 |
| 18J | 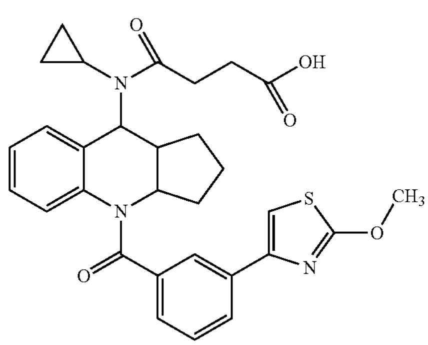 [SMILES: COc1nc(-c2cccc(C(=O)N3c4ccccc4C(N(C(=O)CCC(=O)O)C4CC4)C4CCCC43)c2)cs1] | racemic, cis, cis | 4-[cyclopropyl[cis,cis-2,3,3a,4,9,9a-hexahydro-4-[3-(2-methoxy-4-thiazolyl)benzoyl]-1H-cyclopenta[b]quinolin-9-yl]amino]-4-oxobutanoic acid | 546.3 |

-continued

| # | Structure | Stereo Designation | Name | [M + H]+ |
|---|---|---|---|---|
| 18K | 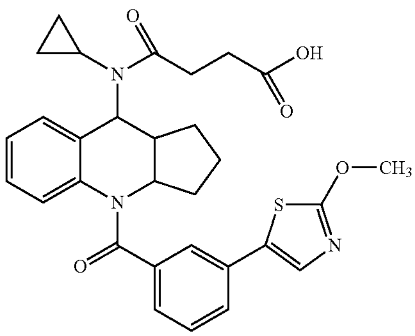 [SMILES: COc1ncc(-c2cccc(C(=O)N3c4ccccc4C(N(C(=O)CCC(=O)O)C4CC4)C4CCCC43)c2)s1] | racemic, cis, cis | 4-[cyclopropyl[cis,cis-2,3,3a,4,9,9a-hexahydro-4-[3-(2-methoxy-5-thiazolyl)benzoyl]-1H-cyclopenta[b]quinolin-9-yl]amino]-4-oxobutanoic acid | 546.3 |
| 18L | 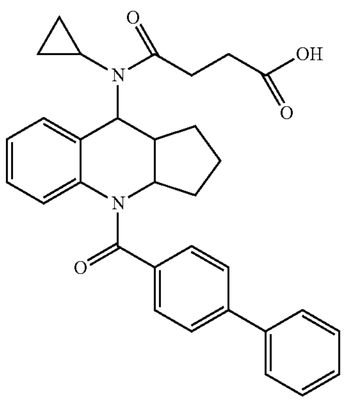 [SMILES: O=C(O)CCC(=O)N(C1CC1)C1c2ccccc2N(C(=O)c2ccc(-c3ccccc3)cc2)C2CCCC21] | cis, cis, single enantiomer | 4-[[cis, cis-4-([1,1'-biphenyl]-4-ylcarbonyl)-2,3,3a,4,9,9a-hexahydro-1H-cyclopenta[b]quinolin-9-yl]cyclopropylamino]-4-oxobutanoic acid | 509.3 |
| 18M | 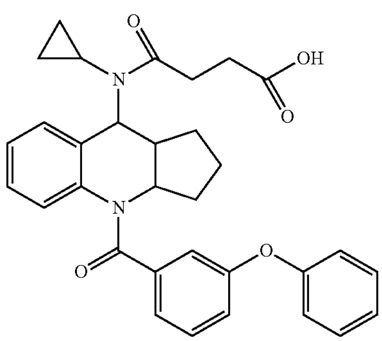 [SMILES: O=C(O)CCC(=O)N(C1CC1)C1c2ccccc2N(C(=O)c2cccc(Oc3ccccc3)c2)C2CCCC21] | cis, cis, single enantiomer | 4-[cyclopropyl[cis, cis-2,3,3a,4,9,9a-hexahydro-4-(3-phenoxybenzoyl)-1H-cyclopenta[b]quinolin-9-yl]amino]-4-oxobutanoic acid | 525.3 |
| 18N | 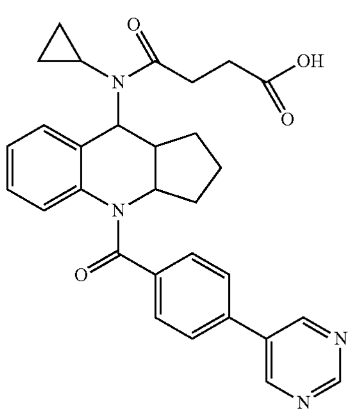 [SMILES: O=C(O)CCC(=O)N(C1CC1)C1c2ccccc2N(C(=O)c2ccc(-c3cncnc3)cc2)C2CCCC21] | racemic, cis, cis | 4-[cyclopropyl[cis,cis-2,3,3a,4,9,9a-hexahydro-4-[4-(5-pyrimidinyl)benzoyl]-1H-cyclopenta[b]quinolin-9-yl]amino]-4-oxobutanoic acid | 511.3 |

-continued

| # | Structure | Stereo Designation | Name | [M + H]⁺ |
|---|---|---|---|---|
| 18o | 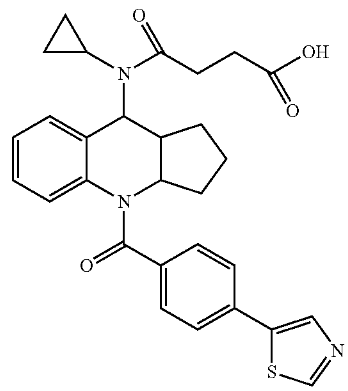 [SMILES: O=C(O)CCC(=O)N(C1CC1)C1c2ccccc2N(C(=O)c2ccc(-c3cncs3)cc2)C2CCCC21] | racemic, cis, cis | 4-[cyclopropyl[cis,cis-2,3,3a,4,9,9a-hexahydro-4-[4-(5-thiazolyl)benzoyl]-1H-cyclopenta[b]quinolin-9-yl]amino]-4-oxobutanoic acid | 516.3 |
| 18P | 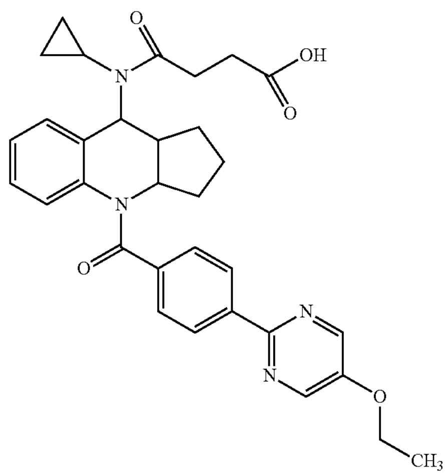 [SMILES: CCOc1cnc(-c2ccc(C(=O)N3c4ccccc4C(N(C(=O)CCC(=O)O)C4CC4)C4CCCC43)cc2)nc1] | racemic, cis, cis | 4-[cyclopropyl[cis,cis-4-[4-(5-ethoxy-2-pyrimidinyl)benzoyl]-2,3,3a,4,9,9a-hexahydro-1H-cyclopenta[b]quinolin-9-yl]amino]-4-oxobutanoic acid | 555.3 |
| 18Q | 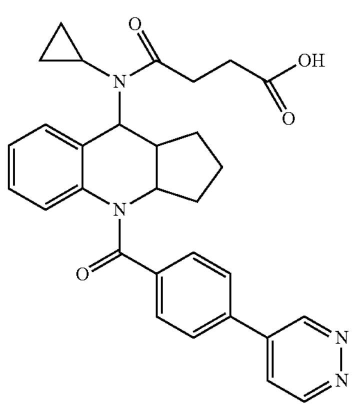 [SMILES: O=C(O)CCC(=O)N(C1CC1)C1c2ccccc2N(C(=O)c2ccc(-c3ccnnc3)cc2)C2CCCC21] | racemic, cis, cis | 4-[cyclopropyl[cis,cis-2,3,3a,4,9,9a-hexahydro-4-[4-(4-pyridazinyl)benzoyl]-1H-cyclopenta[b]quinolin-9-yl]amino]-4-oxobutanoic acid | 511.3 |

| # | Structure | Stereo Designation | Name | [M + H]+ |
|---|---|---|---|---|
| 18R | 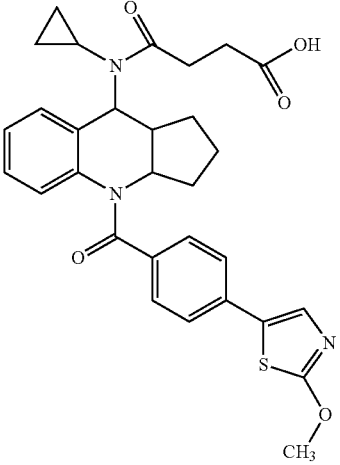 [SMILES: COc1ncc(-c2ccc(C(=O)N3c4ccccc4C(N(C(=O)CCC(=O)O)C4CC4)C4CCCC43)cc2)s1] | racemic, cis, cis | 4-[cyclopropyl[cis,cis-2,3,3a,4,9,9a-hexahydro-4-[4-(2-methoxy-5-thiazolyl)benzoyl]-1H-cyclopenta[b]quinolin-9-yl]amino]-4-oxobutanoic acid | 546.3 |
| 18S | 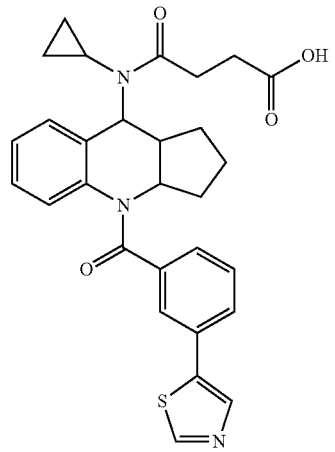 [SMILES: O=C(O)CCC(=O)N(C1CC1)C1c2ccccc2N(C(=O)c2cccc(-c3cncs3)c2)C2CCCC21] | Cis, cis, single enantiomer | 4-[cyclopropyl[cis, cis-2,3,3a,4,9,9a-hexahydro-4-[3-(5-thiazolyl)benzoyl]-1H-cyclopenta[b]quinolin-9-yl]amino]-4-oxobutanoic acid | 516.3 |
| 18T | 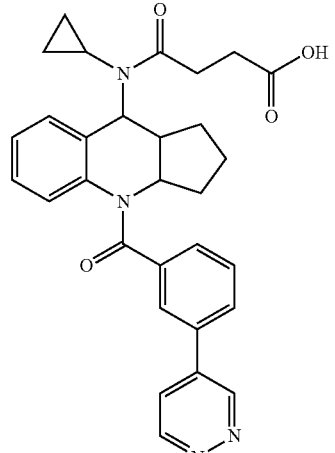 | cis, cis,, single enantiomer | 4-[cyclopropyl[cis, cis-2,3,3a,4,9,9a-hexahydro-4-[3-(4-pyridazinyl)benzoyl]-1H-cyclopenta[b]quinolin-9-yl]amino]-4-oxobutanoic acid | 511.3 |

Example 19

Preparation of Racemic 4-(Phenylmethyl)cis,cis-9-[(3-carboxy-1-oxopropyl)cyclopropylamino]-1,2,3,3a,9,9a-hexahydro-2,2-dimethyl-4H-cyclopenta[b]quinoline-4-carboxylate (19)

Step 1

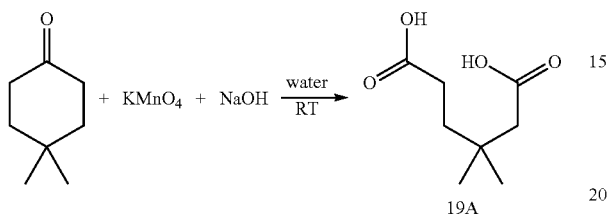

4,4-Dimethylcyclohexanone (9.0 g, 71.31 mmol) and potassium permanganate (22.53 g, 142.63 mmol) were taken up in 450 mL of water. To this, an aqueous solution of NaOH (1.02 g, 25.67 mmol) in 9 mL water was added at room temperature. The mixture was stirred for 48 hours. Aqueous sodium bisulfite was then added until the purple color disappeared. A brown solid was filtered off, and the clear filtrate was brought to pH 1 with concentrated HCl. The solution was extracted with ether (100 mL) three times. The combined ether layers were then dried over anhydrous sodium sulfate. The filtrate was concentrated in vacuo to afford the product diacid 19A (9.01 g) in 73% yield.

Step 2

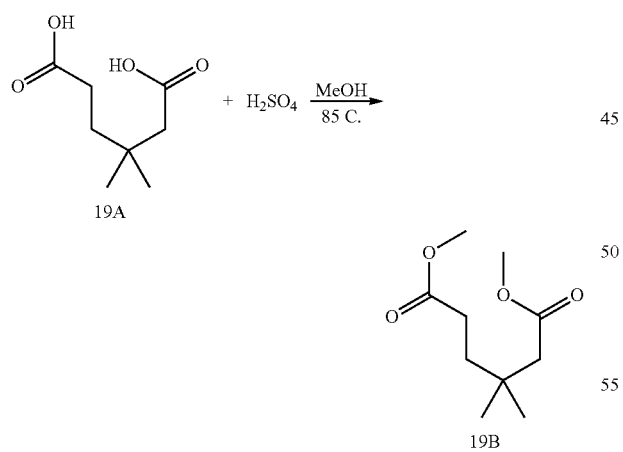

The diacid 19A (4.0 g, 22.96 mmol) was dissolved in 10 mL methanol, and to this solution, concentrated sulfuric acid (0.7 mL) was added dropwise. The solution was heated to 85° C. for 2 hours. The methanol was removed by concentration. Water was added and the pH of the mixture was adjusted to pH 7 by slow addition of saturated sodium bicarbonate. The solution was extracted with ether three times. The combined ether layers were then dried over anhydrous sodium sulfate. The filtrate was concentrated in vacuo to afford the product diester 19B (3.86 g) in 83% yield.

Step 3

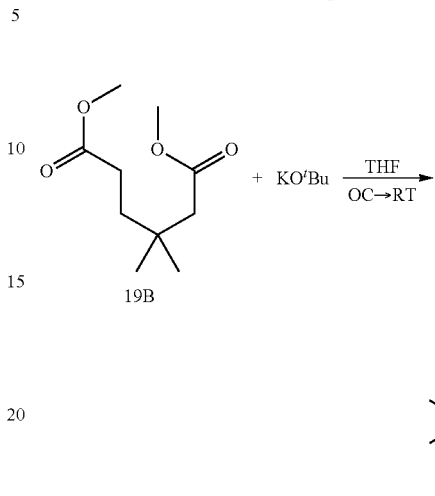

Potassium tert-butoxide (5.3 g, 47.31 mmol) was taken up in 45 mL THF and cooled to 0° C. To this, the diester 19B (6.38 g, 31.54 mmol) was added, and the solution was stirred at room temperature for 24 hours. Glacial acetic acid (2.5 mL) was added resulting in an orange solution containing a white precipitate. A solution of $Na_2HPO_4$ (7.2 g) in 50 mL water was added causing the suspension to become homogeneous. The solution was extracted with dichloromethane (25 mL) three times. The combined organic layers were then washed with brine and dried over anhydrous sodium sulfate. The filtrate was concentrated in vacuo and the residue was purified by flash chromatography on silica gel eluting with 0 to 20% ethyl acetate in hexane to afford the product ketoester 19C (5.36 g) in 100% yield.

Step 4

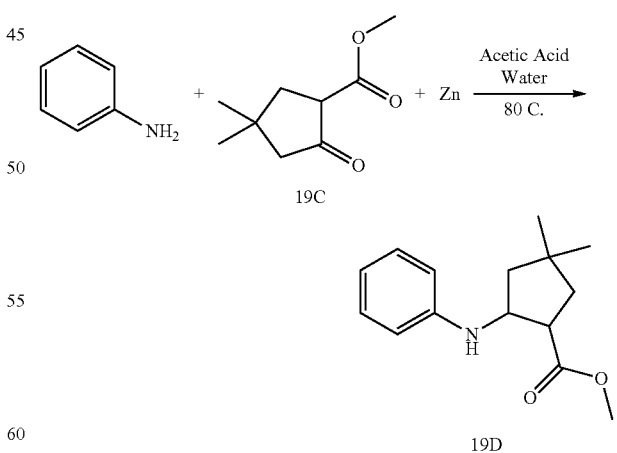

In a 1 L flask, was added glacial acetic acid (20 mL), water (2.5 mL), aniline (2.15 mL, 23.62 mmol), keto-ester 19C (4.0 g, 23.62 mmol), and zinc (6.17 g, 94.48 mmol) and heated to 80° C. for 1 hour and 15 minutes. Zinc salts were filtered off, and the solution was diluted with methanol. The filtrate was concentrated followed by dilution with dichloromethane and ice water. The pH was adjusted to pH 10 with ammonium hydroxide, and the mixture was extracted with dichloromethane three times. The combined organic layers were then washed with brine and dried over anhydrous sodium sulfate. The filtrate was concentrated in vacuo to afford the product aniline ester 19D (7.72 g) in >100% yield (crude).

Step 5

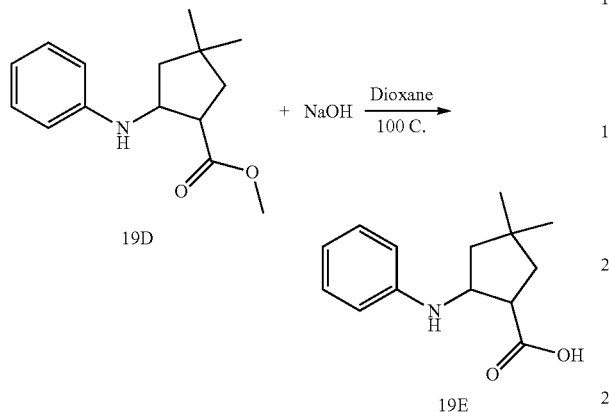

Aniline ester 19D (5.84 g, 23.61 mmol) was dissolved in dioxane (25 mL) and 5M NaOH (23.61 mL, 118.05 mmol) added and heated to 100° C. for 1 hour. The reaction mixture was cooled to room temperature and brought to pH 3 with 2 N concentrated HCl. The solution was extracted with dichloromethane three times. The combined organic layers were then washed with brine and dried over anhydrous sodium sulfate. The filtrate was concentrated in vacuo to afford the product aniline acid 19E (6.3 g) in >100% yield (crude).

Step 6

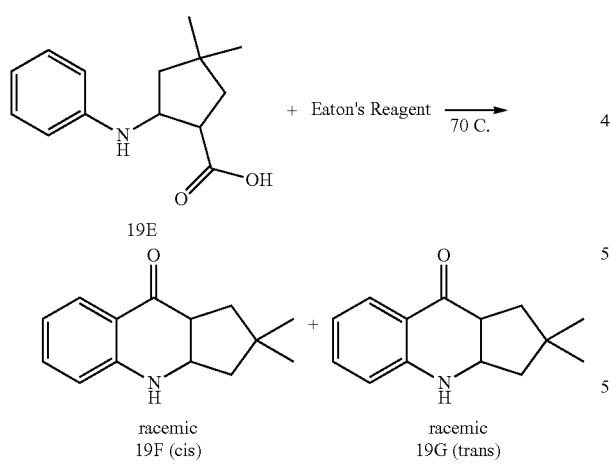

Aniline acid 19E (5.5 g, 23.57 mmol) was taken up in Eaton's Reagent (24.69 mL, 155.58 mmol) and heated to 70° C. for 3 hours. The mixture was cooled to 0° C. and quenched portion-wise with ice water. NaOH pellets were added until pH 10 was reached. The mixture extracted with ethyl acetate three times. The combined organic layers were then washed with brine and dried over anhydrous sodium sulfate. The filtrate was concentrated in vacuo and the residue purified by flash chromatography on silica gel eluting with 0 to 50% ethyl acetate in hexane to afford the product cis-ketone amine 19F (0.550 g) in 11% yield.

Step 7

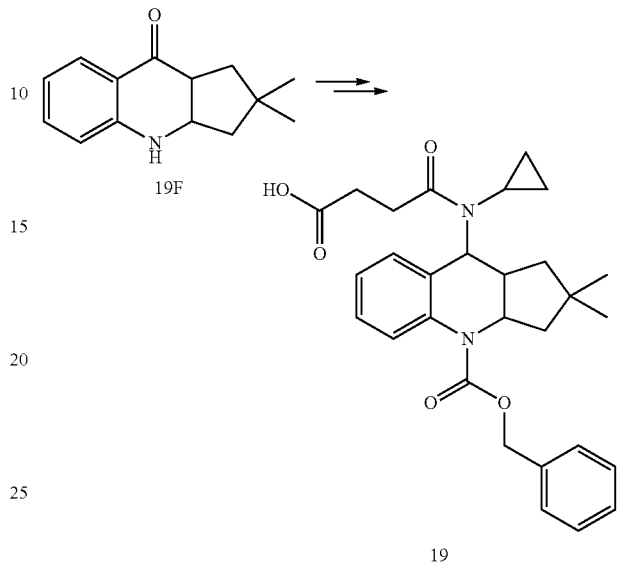

Compound 19 (racemic, cis,cis) was obtained from the cis-ketone amine 19F following steps similar to those described in Examples 6, step 3 and 4, and Example 7, steps 1 and 2. [M+H]$^+$=491.3.

Example 20

Preparation of 4-[Cyclopropyl[cis,cis-2,3,3a,4,9,9a-hexahydro-2,2-dimethyl-4-[4-(trifluoromethoxy)benzoyl]-1H-cyclopenta[b]quinolin-9-yl]amino]-4-oxobutanoic acid (20)

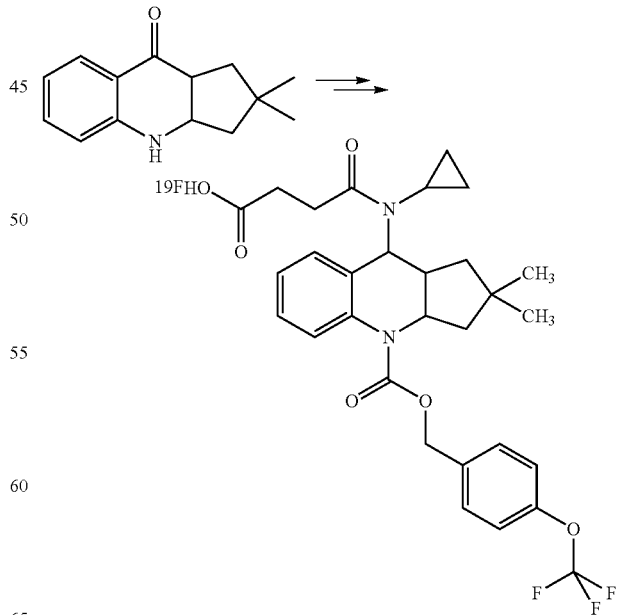

Compound 20 was prepared from the ketone amine 19F following similar procedures as those described in Examples 14, step 2 (to introduce 4-trifluoromethoxy benzoylamide), and Example 6, step 4, and then Example 7, steps 1 and 2. [M+H]⁺=545.3.

Example 21

Preparation of Racemic 4-(Cyclopropyl{cis,cis-4-[(1-methylethoxy)carbonyl]-2,3,3a,4,9,9a-hexahydro-1H-cyclopenta[b]quinolin-9-yl}amino)-4-oxobutanoic acid (21)

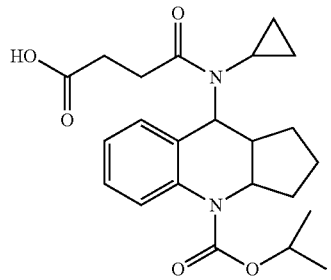

A solution of methyl 4-[[cis,cis-4-(chlorocarbonyl)-2,3,3a,4,9,9a-hexahydro-1H-cyclopenta[b]quinolin-9-yl](cyclopropyl)amino]-4-oxobutanoate (prepared as in Example 22, mixture A) (36 mg, 0.089 mmol) in tetrahydrofuran (356 µl) was added to isopropanol (13.6 µl, 0.178 mmol) in a Bohdan tube. Sodium bis(trimethylsilyl)amide (133 µl, 0.133 mmol) was added to the reaction mixture. The tube was capped and left to shake at rt overnight. In the morning, the reaction mixture was transferred to a microwave vial and lithium hydroxide (1.0 M in water, 540 µl, 54 mmol) was added. The vial was capped, and the reaction mixture was heated thermally at 65° C. for 1 h. The reaction mixture was allowed to cool to rt, dried in vacuo, and diluted with DMSO (1 mL). Analytically pure material was obtained by purification by preparative HPLC reverse phase (C-18), eluting with acetonitrile/water+0.05% formic acid. Lyophilizing afforded 21 as the formate salt. [M+H]⁺: 415.1.

The following compounds were prepared from racemic methyl 4-[[cis,cis-4-(chlorocarbonyl)-2,3,3a,4,9,9a-hexahydro-1H-cyclopenta[b]quinolin-9-yl](cyclopropyl)amino]-4-oxobutanoate with a procedure similar to that used for example 21, varying the alcohol used in the first step:

| # | Structure | Stereo designation | Name | [M + H]⁺ |
|---|---|---|---|---|
| 21A | 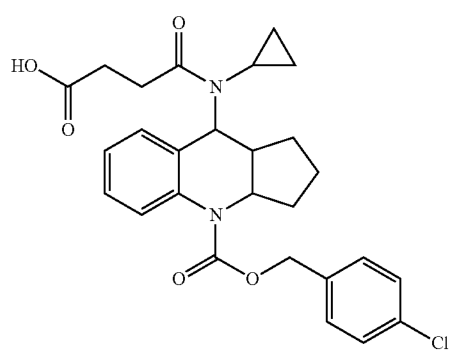 [SMILES: O=C(O)CCC(=O)N(C1CC1)C1c2ccccc2N(C(=O)OCc2ccc(Cl)cc2)C2CCCC21] | racemic, cis, cis | 4-{[cis, cis-4-{[(4-chlorobenzyl)oxy]carbonyl}-2,3,3a,4,9,9a-hexahydro-1H-cyclopenta[b]quinolin-9-yl](cyclopropyl)amino}-4-oxobutanoic acid | 497.2 |
| 21B | 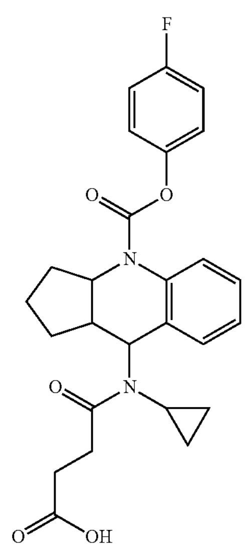 [SMILES: O=C(O)CCC(=O)N(C1CC1)C1c2ccccc2N(C(=O)Oc2ccc(F)cc2)C2CCCC21] | racemic, cis, cis | 4-(cyclopropyl{cis, cis-4-[(4-fluorophenoxy)carbonyl]-2,3,3a,4,9,9a-hexahydro-1H-cyclopenta[b]quinolin-9-yl}amino)-4-oxobutanoic acid | 467.1 |

-continued

| # | Structure | Stereo designation | Name | [M + H]⁺ |
|---|---|---|---|---|
| 21C | 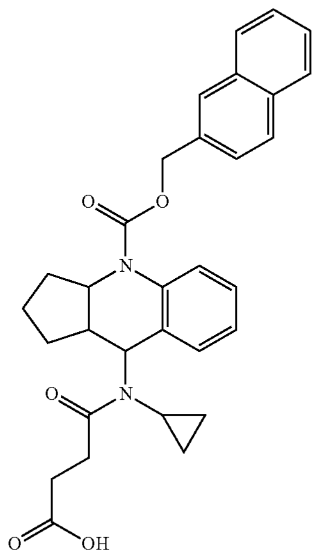 [SMILES: O=C(O)CCC(=O)N(C1CC1)C1c2ccccc2N(C(=O)OCc2ccc3ccccc3c2)C2CCCC21] | racemic, cis, cis | 4-(cyclopropyl{cis, cis-4-[(naphthalen-2-ylmethoxy)carbonyl]-2,3,3a,4,9,9a-hexahydro-1H-cyclopenta[b]quinolin-9-yl}amino)-4-oxobutanoic acid | 513.2 |
| 21D | 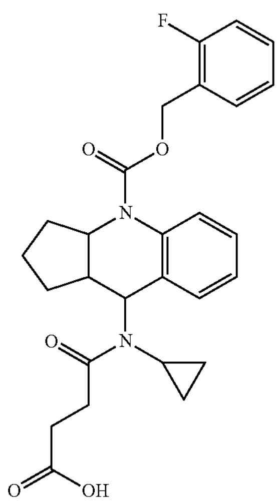 [SMILES: O=C(O)CCC(=O)N(C1CC1)C1c2ccccc2N(C(=O)OCc2ccccc2F)C2CCCC21] | racemic, cis, cis | 4-{cyclopropyl[cis, cis-4-{[(2-fluorobenzyl)oxy]carbonyl}-2,3,3a,4,9,9a-hexahydro-1H-cyclopenta[b]quinolin-9-yl]amino}-4-oxobutanoic acid | 481.1 |
| 21E | 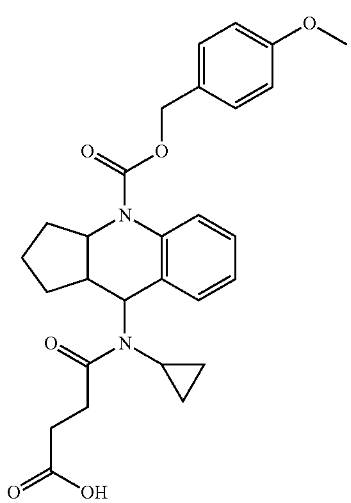 [SMILES: COc1ccc(COC(=O)N2c3ccccc3C(N(C(=O)CCC(=O)O)C3CC3)C3CCCC32)cc1] | racemic, cis, cis | 4-{cyclopropyl[cis, cis-4-{[(4-methoxybenzyl)oxy]carbonyl}-2,3,3a,4,9,9a-hexahydro-1H-cyclopenta[b]quinolin-9-yl]amino}-4-oxobutanoic acid | 493.2 |

-continued

| # | Structure | Stereo designation | Name | [M + H]+ |
|---|---|---|---|---|
| 21F | 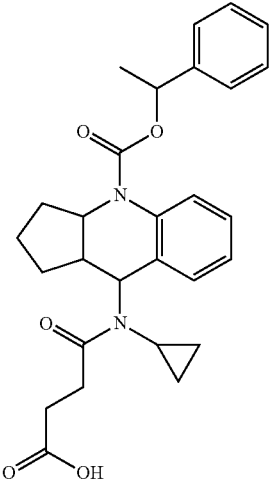 [SMILES: CC(OC(=O)N1c2ccccc2C(N(C(=O)CCC(=O)O)C2CC2)C2CCCC21)c1ccccc1] | racemic, cis, cis | 4-(cyclopropyl{cis, cis-4-[(1-phenylethoxy)carbonyl]-2,3,3a,4,9,9a-hexahydro-1H-cyclopenta[b]quinolin-9-yl}amino)-4-oxobutanoic acid | 477.1 |
| 21G | 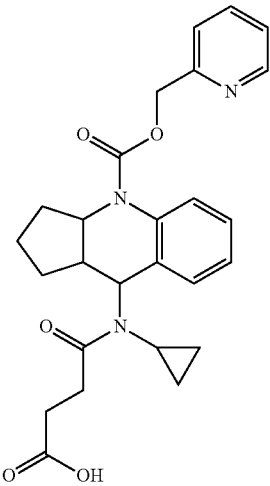 [SMILES: O=C(O)CCC(=O)N(C1CC1)C1c2ccccc2N(C(=O)OCc2ccccn2)C2CCCC21] | racemic, cis, cis | 4-(cyclopropyl{cis, cis-4-[(pyridin-2-ylmethoxy)carbonyl]-2,3,3a,4,9,9a-hexahydro-1H-cyclopenta[b]quinolin-9-yl}amino)-4-oxobutanoic acid | 464.1 |
| 21H | 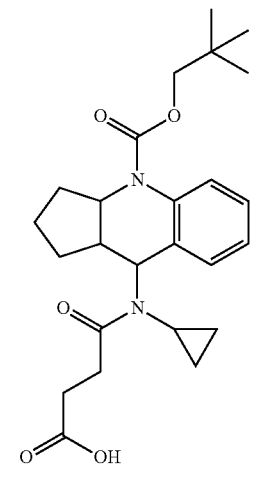 [SMILES: CC(C)(C)COC(=O)N1c2ccccc2C(N(C(=O)CCC(=O)O)C2CC2)C2CCCC21] | racemic, cis, cis | 4-(cyclopropyl{cis, cis-4-[(2,2-dimethylpropoxy)carbonyl]-2,3,3a,4,9,9a-hexahydro-1H-cyclopenta[b]quinolin-9-yl}amino)-4-oxobutanoic acid | 443.2 |

| # | Structure | Stereo designation | Name | [M + H]+ |
|---|---|---|---|---|
| 21i | 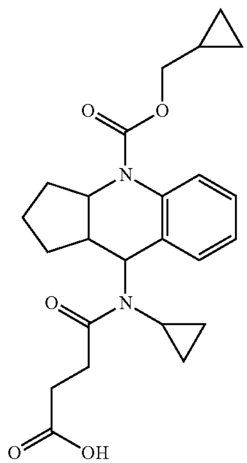 [SMILES: O=C(O)CCC(=O)N(C1CC1)C1c2ccccc2N(C(=O)OCC2CC2)C2CCCC21] | racemic, cis, cis | 4-(cyclopropyl{cis, cis-4-[(cyclopropylmethoxy)carbonyl]-2,3,3a,4,9,9a-hexahydro-1H-cyclopenta[b]quinolin-9-yl}amino)-4-oxobutanoic acid | 427.1 |
| 21J | 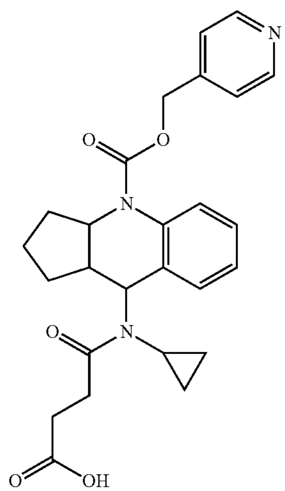 [SMILES: O=C(O)CCC(=O)N(C1CC1)C1c2ccccc2N(C(=O)OCc2ccncc2)C2CCCC21] | racemic, cis, cis | 4-(cyclopropyl{cis, cis-4-[(pyridin-4-ylmethoxy)carbonyl]-2,3,3a,4,9,9a-hexahydro-1H-cyclopenta[b]quinolin-9-yl}amino)-4-oxobutanoic acid | 464.2 |
| 21K | 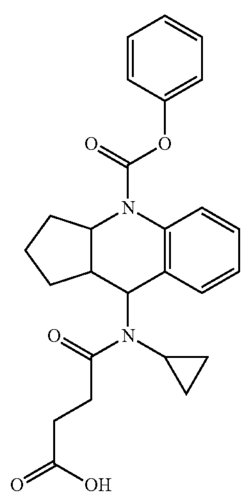 [SMILES: O=C(O)CCC(=O)N(C1CC1)C1c2ccccc2N(C(=O)Oc2ccccc2)C2CCCC21] | racemic, cis, cis | 4-{cyclopropyl[cis, cis-4-(phenoxycarbonyl)-2,3,3a,4,9,9a-hexahydro-1H-cyclopenta[b]quinolin-9-yl]amino}-4-oxobutanoic acid | 449.1 |

| # | Structure | Stereo designation | Name | [M + H]+ |
|---|---|---|---|---|
| 21L | 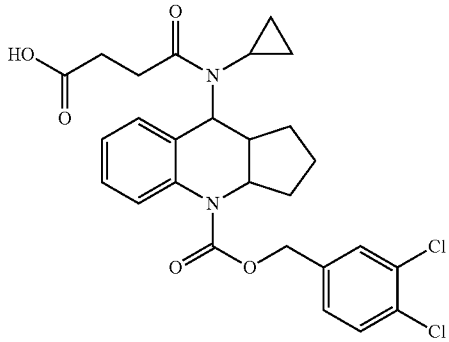 [SMILES: O=C(O)CCC(=O)N(C1CC1)C1c2ccccc2N(C(=O)OCc2ccc(Cl)c(Cl)c2)C2CCCC21] | racemic, cis, cis | 4-{cyclopropyl[cis, cis-4-{[(3,4-dichlorobenzyl)oxy]carbonyl}-2,3,3a,4,9,9a-hexahydro-1H-cyclopenta[b]quinolin-9-yl]amino}-4-oxobutanoic acid | 531.1 |

Example 22

Preparation of Enantiopure 4-[(4-Fluorophenyl)methyl]cis,cis-[(3-carboxy-1-oxopropyl)cyclopropylamino]-1,2,3,3a,9,9a-hexahydro-4H-cyclopenta[b]quinoline-4-carboxylate (22)

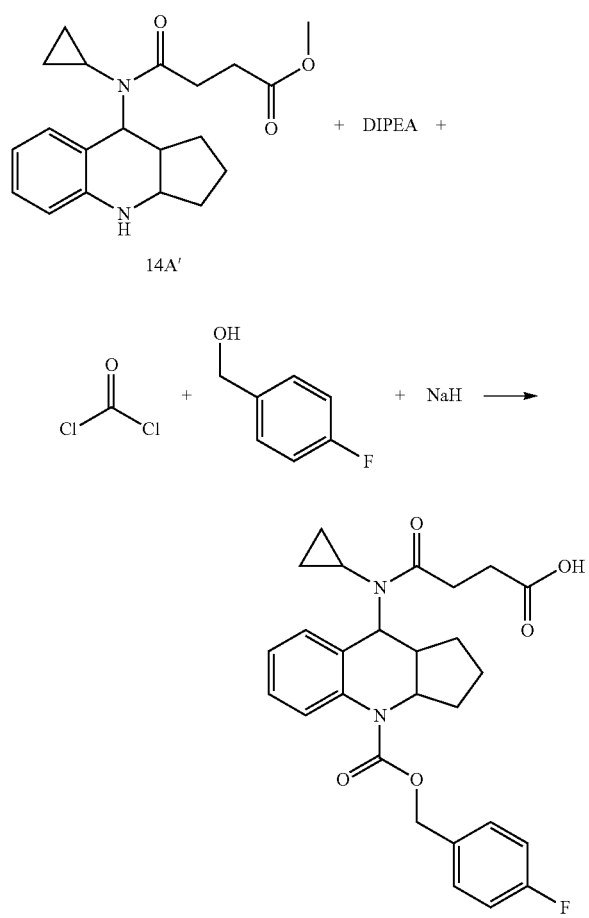

The solution of starting enantiopure ester 14A' (50 mg, 0.146 mmol, prepared from enantiomer of 1D after chiral HPLC separation following similar sequences in Example 1, step 5; Example 7, step 1 and Example 14, step 1.) and DIPEA (80 μL, 0.438 mmol) in CH$_2$Cl$_2$ (1 mL) was cooled in an ice-H$_2$O bath, phosgene (20% solution in toluene) (170 μL, 0.292 mmol) was added, the resultant mixture was kept stirring at 0° C. for 2 hrs, then rt for 15 mins. The mixture was concentrated to dryness; the residue was taken up in THF (1 mL) and cooled in an ice-H$_2$O bath as mixture A.

To the solution of the benzyl alcohol (0.876 mmol) in THF (1 mL) was added NaH (72 mg, 1.75 mmol). The resultant mixture was kept stirring at rt for 30 min, and then cooled in an ice-H$_2$O bath as mixture B.

The mixture A was added to the mixture B in an ice-H$_2$O bath via a syringe, the resultant mixture was kept stirring at 0° C. for 1 hrs, then rt for 16 h. The mass spectrum indicated the disappearance of the starting material ester and intermediate. MeOH (2 mL) and H$_2$O (2 mL) were added, the mixture was kept stirring at rt for 1 h. The mass spectrum indicated completion of the hydrolysis of the ester. Et$_2$O (3 mL) and H$_2$O (1 mL) were added, the aqueous layer was separated, acidified with 1 N HCl to pH ~2, extracted with Et$_2$O (2×3 mL), the combined organic layer was dried over MgSO$_4$ and concentrated. The residue was purified by reverse phase HPLC, to obtain a white solid, 40 mg as the desired enantiopure product 22. [M+H]$^+$=480.8. $^1$H NMR (500 MHz, CDCl$_3$) δ ppm: 7.37 (m, 3H); 7.19 (t, 1H); 7.06 (m, 3H); 6.75 (m, 1H); 5.24 (d, J=11 Hz, 1H); 5.13 (d, J=11 Hz, 1H); 4.86 (m, 1H); 3.09~2.75 (m, 6H); 2.15 (m, 1H); 1.91 (m, 1H); 1.53 (m, 2H); 1.40 (m, 1H); 1.20~0.9 (m, 6H).

The compounds in the following table were prepared in a similar manner as described in Example 22 from the appropriate starting material tetraquinoline amide esters. The enantiomerically pure final products were either obtained through chiral resolution of final racemic product (22J, 22K) or were prepared from enantiomerically pure tetraquinoline amides (prepared from chiral tetrahydroquinolin-9(9aH)-one) (22A, 22D-22I, 22L-22Y). Some final acids were obtained from hydrolysis of esters with NaOH (1 N).

| # | Structure | stereo designation | Name | [M + H]+ |
|---|---|---|---|---|
| 22A | 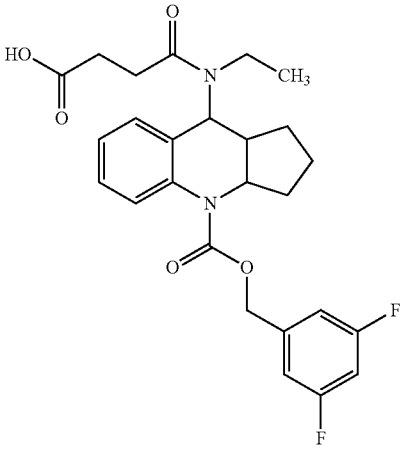 [SMILES: CCN(C(=O)CCC(=O)O)C1c2ccccc2N(C(=O)OCc2cc(F)cc(F)c2)C2CCCC12] | cis, cis,, single enantiomer | 4-[(3,5-difluorophenyl)methyl] cis, cis-[(3-carboxy-1-oxopropyl)ethylamino]-1,2,3,3a,9,9a-hexahydro-4H-cyclopenta[b]quinoline-4-carboxylate | 487.3 |
| 22D | 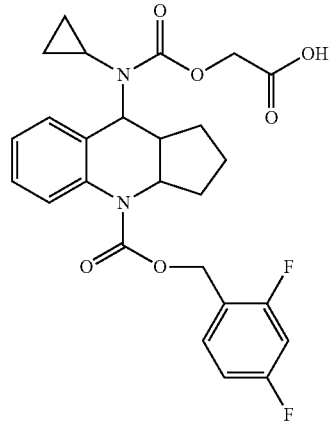 [SMILES: O=C(O)COC(=O)N(C1CC1)C1c2ccccc2N(C(=O)OCc2ccc(F)cc2F)C2CCCC21] | cis, cis, single enantiomer | 4-[(2,4-difluorophenyl)methyl] cis, cis-[[(carboxymethoxy)carbonyl] cyclopropylamino]-1,2,3,3a,9,9a-hexahydro-4H-cyclopenta[b]quinoline-4-carboxylate | 523 [M + Na]+ |
| 22E | 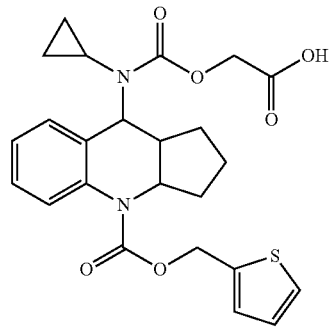 [SMILES: O=C(O)COC(=O)N(C1CC1)C1c2ccccc2N(C(=O)OCc2cccs2)C2CCCC21] | cis, cis, single enantiomer | 4-(2-thienylmethyl) cis, cis-[[(carboxymethoxy)carbonyl] cyclopropylamino]-1,2,3,3a,9,9a-hexahydro-4H-cyclopenta[b]quinoline-4-carboxylate | 493 [M + Na]+ |
| 22F | 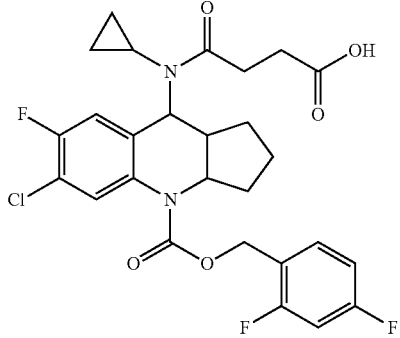 [SMILES: O=C(O)CCC(=O)N(C1CC1)C1c2cc(F)c(Cl)cc2N(C(=O)OCc2ccc(F)cc2F)C2CCCC21] | cis, cis, single enantiomer | 4-[(2,4-difluorophenyl)methyl] cis, cis-[(3-carboxy-1-oxopropyl)cyclopropylamino]-6-chloro-7-fluoro-1,2,3,3a,9,9a-hexahydro-4H-cyclopenta[b]quinoline-4-carboxylate | 551.3 |

| # | Structure | stereo designation | Name | [M + H]+ |
|---|---|---|---|---|
| 22G | 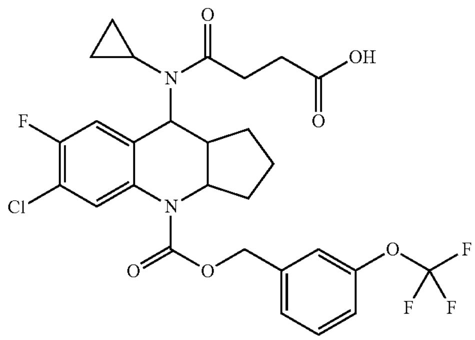 [SMILES: O=C(O)CCC(=O)N(C1CC1)C1c2cc(F)c(Cl)cc2N(C(=O)OCc2cccc(OC(F)(F)F)c2)C2CCCC21] | cis, cis, single enantiomer | 4-[[3-(trifluoromethoxy)phenyl]methyl] cis, cis-[(3-carboxy-1-oxopropyl)cyclopropylamino]-6-chloro-7-fluoro-1,2,3,3a,9,9a-hexahydro-4H-cyclopenta[b]quinoline-4-carboxylate | 599.3 |
| 22H | 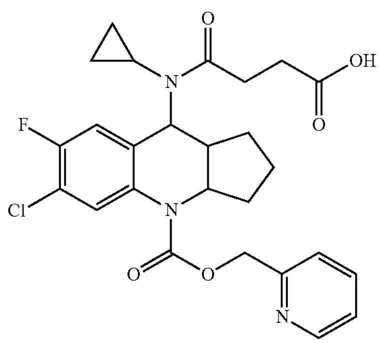 [SMILES: O=C(O)CCC(=O)N(C1CC1)C1c2cc(F)c(Cl)cc2N(C(=O)OCc2ccccn2)C2CCCC21] | cis, cis, single enantiomer | 4-(2-pyridinylmethyl) cis, cis-[(3-carboxy-1-oxopropyl)cyclopropylamino]-6-chloro-7-fluoro-1,2,3,3a,9,9a-hexahydro-4H-cyclopenta[b]quinoline-4-carboxylate | 516.3 |
| 22i | 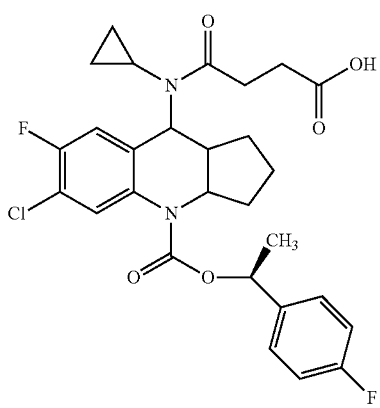 [SMILES: C[C@H](OC(=O)N1c2cc(Cl)c(F)cc2C(N(C(=O)CCC(=O)O)C2CC2)C2CCCC21)c1ccc(F)cc1] | cis, cis (enantiopure), (S configuration at benzylic carbon atom) | 4-[1(S)-(4-fluorophenyl)ethyl] cis, cis-[(3-carboxy-1-oxopropyl)cyclopropylamino]-6-chloro-7-fluoro-1,2,3,3a,9,9a-hexahydro-4H-cyclopenta[b]quinoline-4-carboxylate | 547.3 |
| 22J | 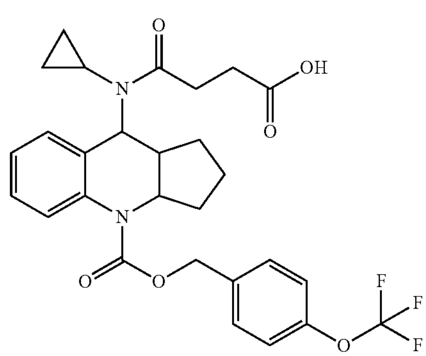 [SMILES: O=C(O)CCC(=O)N(C1CC1)C1c2ccccc2N(C(=O)OCc2ccc(OC(F)(F)F)cc2)C2CCCC21] | Single enantiomer, derived from Peak I off SFC separation | 4-[[4-(trifluoromethoxy)phenyl]methyl] cis, cis-[(3-carboxy-1-oxopropyl)cyclopropylamino]-1,2,3,3a,9,9a-hexahydro-4H-cyclopenta[b]quinoline-4-carboxylate | 546.7 |

| # | Structure | stereo designation | Name | [M + H]+ |
|---|---|---|---|---|
| 22K | 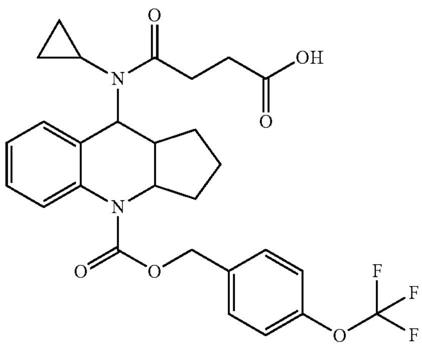 [SMILES: O=C(O)CCC(=O)N(C1CC1)C1c2ccccc2N(C(=O)OCc2ccc(OC(F)(F)F)cc2)C2CCCC21] | Single enantiomer, derived from Peak II off SFC separation | 4-[[4-(trifluoromethoxy)phenyl] methyl] cis, cis-[(3-carboxy-1-oxopropyl)cyclopropylamino]-1,2,3,3a,9,9a-hexahydro-4H-cyclopenta[b]quinoline-4-carboxylate | 546.7 |
| 22L | 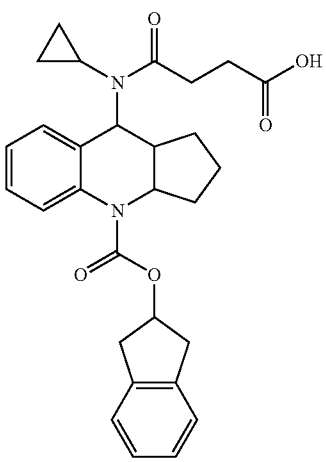 [SMILES: O=C(O)CCC(=O)N(C1CC1)C1c2ccccc2N(C(=O)OC2Cc3ccccc3C2)C2CCCC21] | cis, cis, single enantiomer | 4-(2,3-dihydro-1H-inden-2-yl) cis, cis-[(3-carboxy-1-oxopropyl)cyclopropylamino]-1,2,3,3a,9,9a-hexahydro-4H-cyclopenta[b]quinoline-4-carboxylate | 510.8 [M + Na]+ |
| 22M | 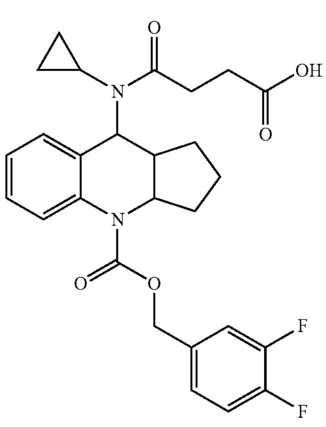 [SMILES: O=C(O)CCC(=O)N(C1CC1)C1c2ccccc2N(C(=O)OCc2ccc(F)c(F)c2)C2CCCC21] | cis, cis, single enantiomer | 4-[(3,4-difluorophenyl)methyl] cis, cis-[(3-earboxy-1-oxopropyl)cyclopropylamino]-1,2,3,3a,9,9a-hexahydro-4H-cyclopenta[b]quinoline-4-carboxylate | 498.7 |

-continued

| # | Structure | stereo designation | Name | [M + H]+ |
|---|---|---|---|---|
| 22N | 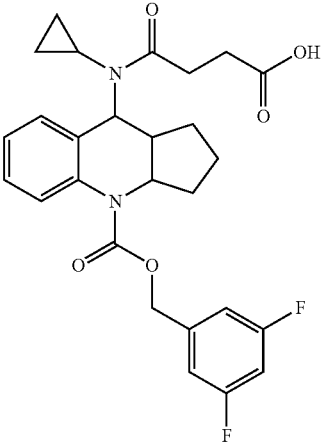 [SMILES: O=C(O)CCC(=O)N(C1CC1)C1c2ccccc2N(C(=O)OCc2cc(F)cc(F)c2)C2CCCC21] | cis, cis, single enantiomer | 4-[(3,5-difluorophenyl)methyl] cis, cis-[(3-carboxy-1-oxopropyl)cyclopropylamino]-1,2,3,3a,9,9a-hexahydro-4H-cyclopenta[b]quinoline-4-carboxylate | 498.7 |
| 22o | 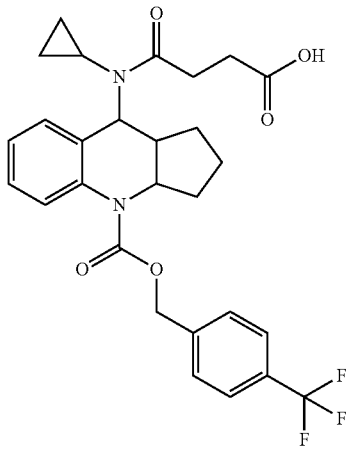 [SMILES: O=C(O)CCC(=O)N(C1CC1)C1c2ccccc2N(C(=O)OCc2ccc(C(F)(F)F)cc2)C2CCCC21] | cis, cis, single enantiomer | 4-[[4-(trifluoromethyl)phenyl] methyl] cis, cis-[(3-carboxy-1-oxopropyl)cyclopropylamino]-1,2,3,3a,9,9a-hexahydro-4H-cyclopenta[b]quinoline-4-carboxylate | 530.7 |
| 22P | 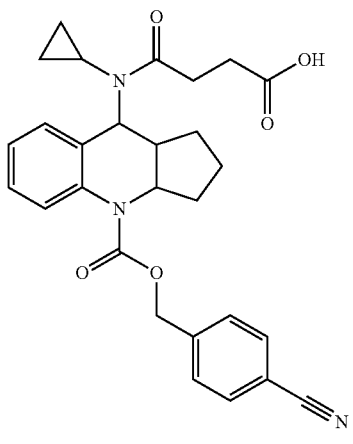 [SMILES: N#Cc1ccc(COC(=O)N2c3ccccc3C(N(C(=O)CCC(=O)O)C3CC3)C3CCCC32)cc1] | cis, cis, single enantiomer | 4-[(4-cyanophenyl)methyl] cis, cis-[(3-carboxy-1-oxopropyl)cyclopropylamino]-1,2,3,3a,9,9a-hexahydro-4H-cyclopenta[b]quinoline-4-carboxylate | 487.7 |

| # | Structure | stereo designation | Name | [M + H]+ |
|---|---|---|---|---|
| 22Q | 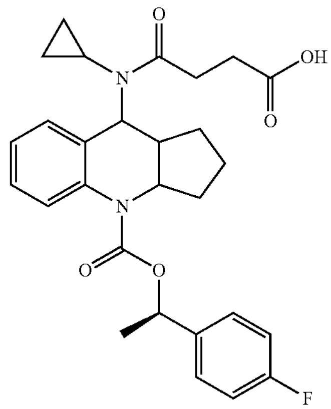 [SMILES: C[C@@H](OC(=O)N1c2ccccc2C(N(C(=O)CCC(=O)O)C2CC2)C2CCCC21)c1ccc(F)cc1] | cis, cis (enantiopure), (R-configuration at fluorobenzylic carbon) single enantiomer | 4-[1(R)-(4-fluorophenyl)ethyl] cis, cis-[(3-carboxy-1-oxopropyl)cyclopropylamino]-1,2,3,3a,9,9a-hexahydro-4H-cyclopenta[b]quinoline-4-carboxylate | 516.7 [M + Na]+ |
| 22R | 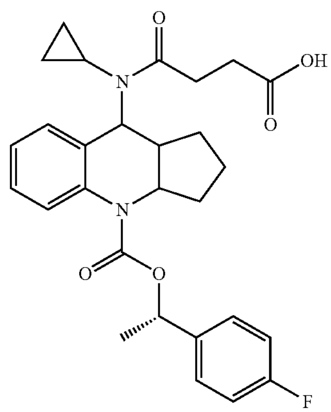 [SMILES: C[C@H](OC(=O)N1c2ccccc2C(N(C(=O)CCC(=O)O)C2CC2)C2CCCC21)c1ccc(F)cc1] | cis, cis (enantiopure), (S-configuration at fluorobenzylic carbon) single enantiomer | 4-[1(S)-(4-fluorophenyl)ethyl] cis, cis-[(3-carboxy-1-oxopropyl)cyclopropylamino]-1,2,3,3a,9,9a-hexahydro-4H-cyclopenta[b]quinoline-4-carboxylate | 516.7 [M + Na]+ |
| 22S | 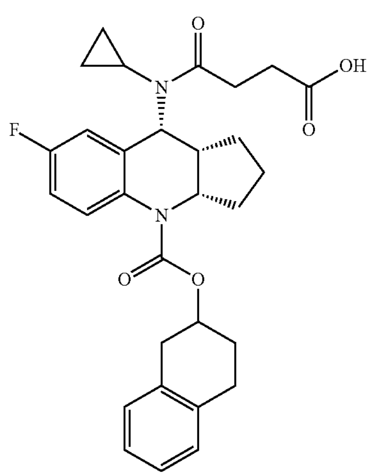 [SMILES: O=C(O)CCC(=O)N(C1CC1)[C@H]1c2cc(F)ccc2N(C(=O)OC2CCc3ccccc3C2)[C@H]2CCC[C@H]21] | 3aS,9R,9aR, (racemic at 2-tetralene carbon atom) | 4-(1,2,3,4-tetrahydro-2(RS)-naphthalenyl) (3aS,9R,9aR)-[(3-carboxy-1-oxopropyl)cyclopropylamino]-7-fluoro-1,2,3,3a,9,9a-hexahydro-4H-cyclopenta[b]quinoline-4-carboxylate | 520.8 |

-continued

| # | Structure | stereo designation | Name | [M + H]+ |
|---|---|---|---|---|
| 22T | 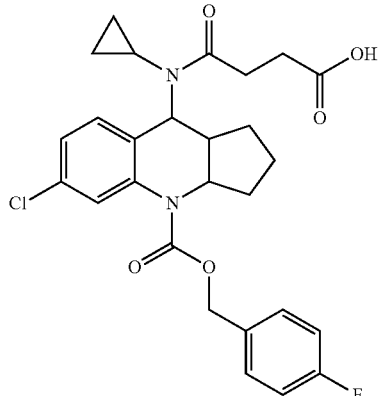 | cis, cis, single enantiomer | 4-[(4-fluorophenyl)methyl] cis, cis-[(3-carboxy-1-oxopropyl)cyclopropylamino]-6-chloro-1,2,3,3a,9,9a-hexahydro-4H-cyclopenta[b]quinoline-4-carboxylate | 514.8 |
| 22U | 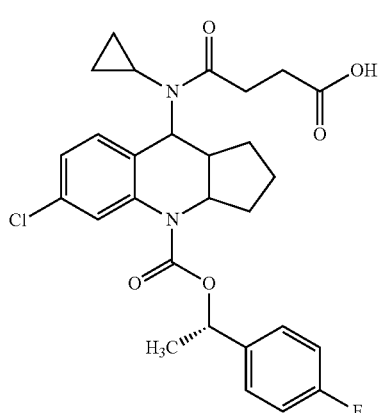 | cis, cis, single enantiomer | 4-[1(S)-(4-fluorophenyl)ethyl] cis, cis-[(3-carboxy-1-oxopropyl)cyclopropylamino]-6-chloro-1,2,3,3a,9,9a-hexahydro-4H-cyclopenta[b]quinoline-4-carboxylate | 551.7 [M + Na]+ |
| 22V | 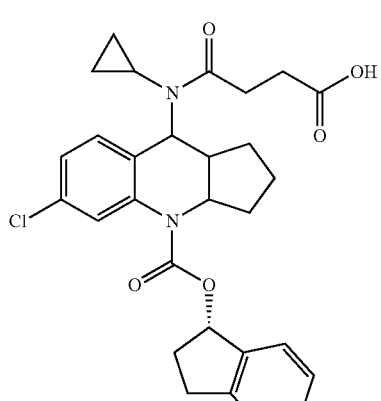 | cis, cis (enantiopure), S(S configuration at 1-indane carbon atom) single enantiomer | 4-(2,3-dihydro-1H-inden-1(S)-yl) cis, cis-[(3-carboxy-1-oxopropyl)cyclopropylamino]-6-chloro-1,2,3,3a,9,9a-hexahydro-4H-cyclopenta[b]quinoline-4-carboxylate | 545.3 [M + Na]+ |

| # | Structure | stereo designation | Name | [M + H]+ |
|---|---|---|---|---|
| 22W | 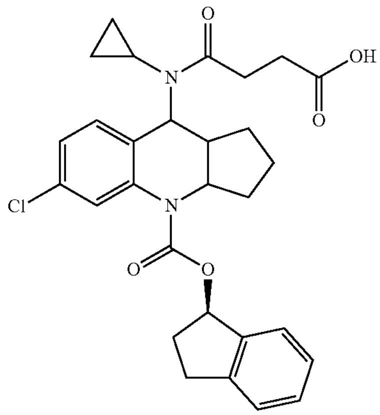 [SMILES: O=C(O)CCC(=O)N(C1CC1)C1c2ccc(Cl)cc2N(C(=O)O[C@@H]2CCc3ccccc32)C2CCCC21] | cis, cis (enantiopure), (R configuration at 1-indane carbon atom) single enantiomer | 4-(2,3-dihydro-1H-inden-1(R)-yl) cis, cis-[(3-carboxy-1-oxopropyl)cyclopropylamino]-6-chloro-1,2,3,3a,9,9a-hexahydro-4H-cyclopenta[b]quinoline-4-carboxylate | 545.2 [M + Na]+ |
| 22X | 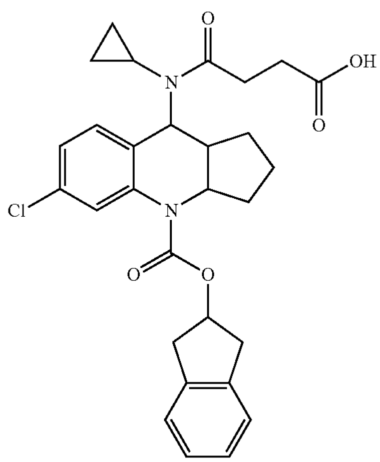 [SMILES: O=C(O)CCC(=O)N(C1CC1)C1c2ccc(Cl)cc2N(C(=O)OC2Cc3ccccc3C2)C2CCCC21] | cis, cis, single enantiomer | 4-(2,3-dihydro-1H-inden-2-yl) cis, cis-[(3-carboxy-1-oxopropyl)cyclopropylamino]-6-chloro-1,2,3,3a,9,9a-hexahydro-4H-cyclopenta[b]quinoline-4-carboxylate | 545.8 [M + Na]+ |
| 22Y | 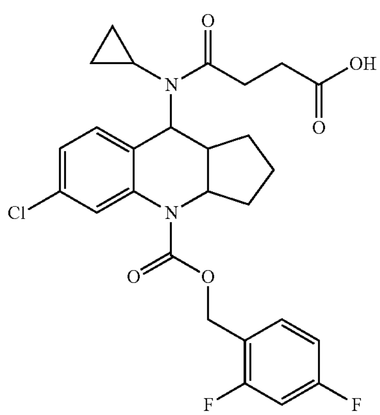 [SMILES: O=C(O)CCC(=O)N(C1CC1)C1c2ccc(Cl)cc2N(C(=O)OCc2ccc(F)cc2F)C2CCCC21] | cis, cis, single enantiomer | 4-[(2,4-difluorophenyl)methyl] cis, cis-[(3-carboxy-1-oxopropyl)cyclopropylamino]-6-chloro-1,2,3,3a,9,9a-hexahydro-4H-cyclopenta[b]quinoline-4-carboxylate | 555.8 [M + Na]+ |

Example 23

Preparation of Racemic 4-{Cyclopropyl[cis,cis-4-(2,3-dihydro-1H-indol-1-ylcarbonyl)-2,3,3a,4,9,9a-hexahydro-1H-cyclopenta[b]quinolin-9-yl]amino}-4-oxobutanoic acid (23)

Step 1: Methyl 4-{cyclopropyl[cis,cis-4-(2,3-dihydro-1H-indol-1-ylcarbonyl)-2,3,3a,4,9,9a-hexahydro-1H-cyclopenta[b]quinolin-9-yl]amino}-4-oxobutanoate (23A)

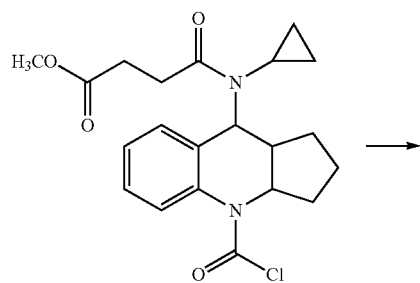

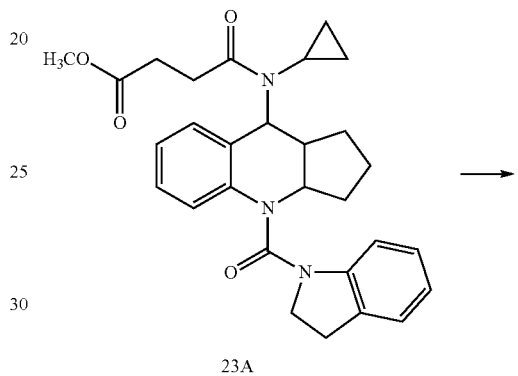

23A

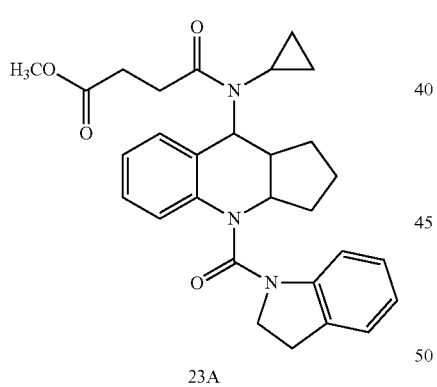

23A

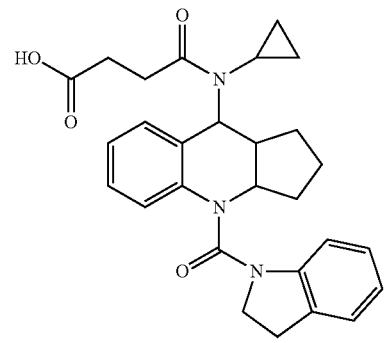

23

Indoline (36.8 mg, 0.309 mmol, 2.5 equiv) was added to a solution of methyl 4-[[(cis,cis,)-4-(chlorocarbonyl)-2,3,3a,4,9,9a-hexahydro-1H-cyclopenta[b]quinolin-9-yl](cyclopropyl)amino]-4-oxobutanoate (50 mg, 0.123 mmol, 1 equiv, prepared from Example 22 mixture A where the crude reaction mixture was worked up by diluting with ethyl acetate and water, and the organic phase was washed with brine and dried (MgSO$_4$) followed by removal of solvent) in dichloromethane at 23° C. The reaction mixture was heated at 60° C. in a sealed tube for 16 h, and then was cooled to 23° C. The cooled reaction mixture was partitioned between dichloromethane and aqueous potassium bisulfate. The organic layer was washed with water, and concentrated to afford 23A, which was used in the subsequent step without further purification. [M+H]$^+$: 488.2.

Step 2: 4-{Cyclopropyl[cis,cis-4-(2,3-dihydro-1H-indol-1-ylcarbonyl)-2,3,3a,4,9,9a-hexahydro-1H-cyclopenta[b]quinolin-9-yl]amino}-4-oxobutanoic acid (23)

23 was prepared from methyl 4-{cyclopropyl[cis,cis-4-(2,3-dihydro-1H-indol-1-ylcarbonyl)-2,3,3a,4,9,9a-hexahydro-1H-cyclopenta[b]quinolin-9-yl]amino}-4-oxobutanoate 23A using a procedure similar to that used in Example 14, Step 3. [M+H]$^+$: 474.2.

The following examples were prepared from racemic methyl 4-[[cis,cis-4-(chlorocarbonyl)-2,3,3a,4,9,9a-hexahydro-1H-cyclopenta[b]quinolin-9-yl](cyclopropyl)amino]-4-oxobutanoate using a procedure similar to that used in Example 23, Steps 1 and 2.

| # | Structure | Stereo designation | Name | [M + H]+ |
|---|---|---|---|---|
| 23B | 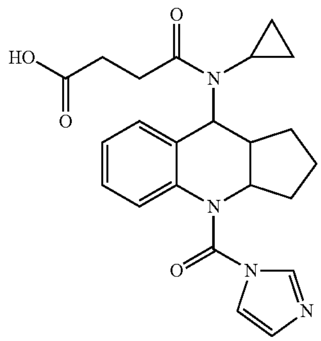 [SMILES: O=C(O)CCC(=O)N(C1CC1)C1c2ccccc2N(C(=O)n2ccnc2)C2CCCC21] | racemic, cis, cis | 4-{cyclopropyl[cis, cis-4-(1H-imidazol-1-ylcarbonyl)-2,3,3a,4,9,9a-hexahydro-1H-cyclopenta[b]quinolin-9-yl]amino}-4-oxobutanoic acid | 423.2 |
| 23C | 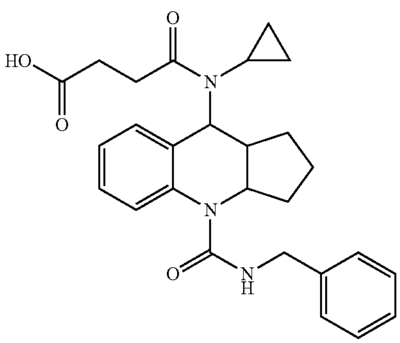 [SMILES: O=C(O)CCC(=O)N(C1CC1)C1c2ccccc2N(C(=O)NCc2ccccc2)C2CCCC21] | racemic, cis, cis | 4-{[cis, cis-4-(benzylcarbamoyl)-2,3,3a,4,9,9a-hexahydro-1H-cyclopenta[b]quinolin-9-yl](cyclopropyl)amino}-4-oxobutanoic acid | 462.2 |
| 23D | 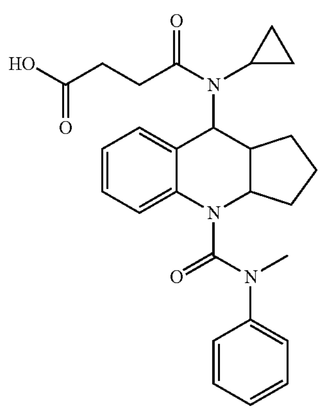 [SMILES: CN(C(=O)N1c2ccccc2C(N(C(=O)CCC(=O)O)C2CC2)C2CCCC21)c1ccccc1] | racemic, cis, cis | 4-(cyclopropyl{cis, cis-4-[methyl(phenyl)carbamoyl]-2,3,3a,4,9,9a-hexahydro-1H-cyclopenta[b]quinolin-9-yl}amino)-4-oxobutanoic acid | 462.2 |
| 23E | 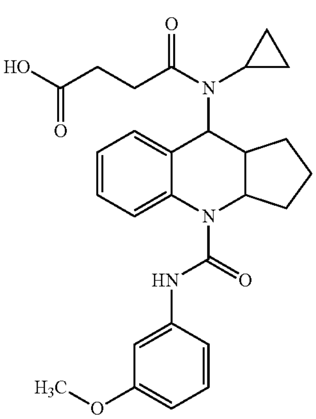 [SMILES: COc1cccc(NC(=O)N2c3ccccc3C(N(C(=O)CCC(=O)O)C3CC3)C3CCCC32)c1] | racemic, cis, cis | 4-[cyclopropyl[cis,cis-2,3,3a,4,9,9a-hexahydro-4-[[(3-methoxyphenyl)amino]carbonyl]-1H-cyclopenta[b]quinolin-9-yl]amino]-4-oxobutanoic acid | 478.3 |

| # | Structure | Stereo designation | Name | [M + H]+ |
|---|---|---|---|---|
| 23F | 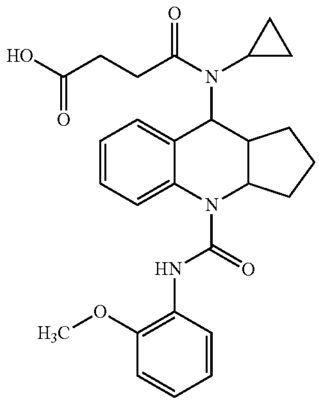 [SMILES: COc1ccccc1NC(=O)N1c2ccccc2C(N(C(=O)CCC(=O)O)C2CC2)C2CCCC21] | racemic, cis, cis | 4-[cyclopropyl[cis,cis-2,3,3a,4,9,9a-hexahydro-4-[[(2-methoxyphenyl)amino]carbonyl]-1H-cyclopenta[b]quinolin-9-yl]amino]-4-oxobutanoic acid | 478.3 |
| 23G | 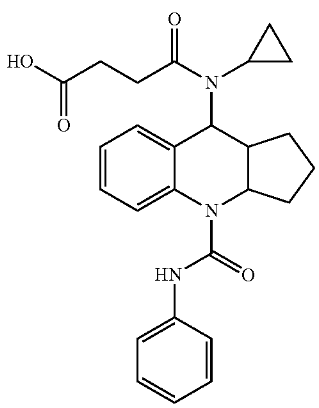 [SMILES: O=C(O)CCC(=O)N(C1CC1)C1c2ccccc2N(C(=O)Nc2ccccc2)C2CCCC21] | racemic, cis, cis | 4-[cyclopropyl[cis,cis-2,3,3a,4,9,9a-hexahydro-4-[(phenylamino)carbonyl]-1H-cyclopenta[b]quinolin-9-yl]amino]-4-oxobutanoic acid | 448.2 |
| 23H | 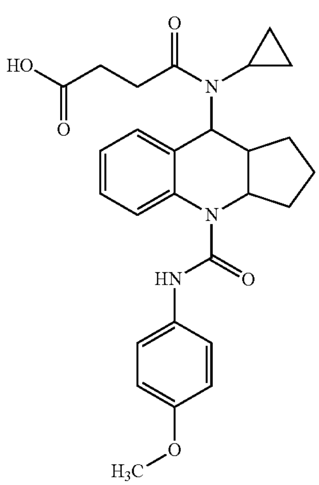 [SMILES: COc1ccc(NC(=O)N2c3ccccc3C(N(C(=O)CCC(=O)O)C3CC3)C3CCCC32)cc1] | racemic, cis, cis | 4-[cyclopropyl[cis,cis-2,3,3a,4,9,9a-hexahydro-4-[[(4-methoxyphenyl)amino]carbonyl]-1H-cyclopenta[b]quinolin-9-yl]amino]-4-oxobutanoic acid | 478.3 |

| # | Structure | Stereo designation | Name | [M + H]+ |
|---|---|---|---|---|
| 23i | 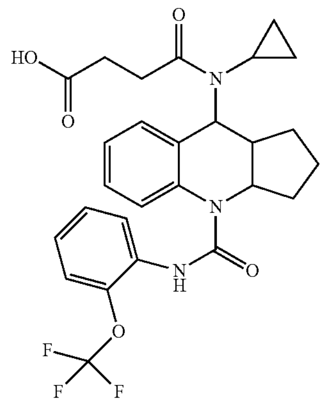 [SMILES: O=C(O)CCC(=O)N(C1CC1)C1c2ccccc2N(C(=O)Nc2ccccc2OC(F)(F)F)C2CCCC21] | racemic, cis, cis | 4-[cyclopropyl[cis,cis-2,3,3a,4,9,9a-hexahydro-4-[[[2-(trifluoromethoxy)phenyl]amino]carbonyl]-1H-cyclopenta[b]quinolin-9-yl]amino]-4-oxobutanoic acid | 532.3 |

Example 24

Preparation of Racemic 4-[Cyclopropyl[cis,cis-2,3,3a,4,9,9a-hexahydro-4-(phenylsulfonyl)-1H-cyclopenta[b]quinolin-9-yl]amino]-4-oxobutanoic acid (24)

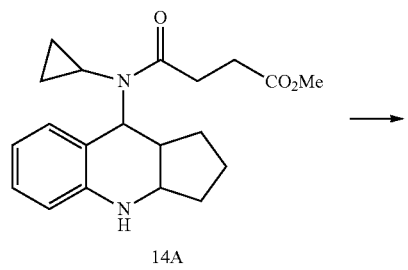

14A

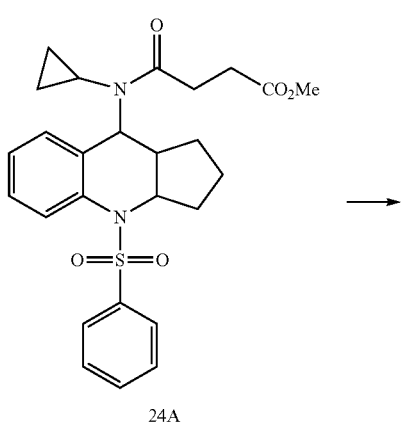

24A

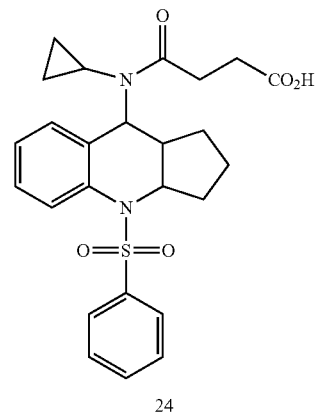

24

Methyl 4-(cyclopropyl(2,3,3a,4,9,9a-hexahydro-1H-cyclopenta[b]quinolin-9-yl)amino)-4-oxobutanoate 14A (30 mg, 0.088 mmol) and benzenesulfonyl chloride (23 mg, 0.13 mmol) were mixed in pyridine (0.3 mL). The reaction mixture was heated at 70° C. overnight and cooled to room temperature. 1 N HCl (aq.) was added. The aqueous layer was separated and extracted with DCM. The organic extracts were combined, washed with brine, dried (MgSO$_4$), filtered and concentrated. The residue was purified by preparative TLC (eluted with 50% ethyl acetate-hexane) to afford sulfonamide methyl 4-(cyclopropyl(4-(phenylsulfonyl)-2,3,3a,4,9,9a-hexahydro-1H-cyclopenta[b]quinolin-9-yl)amino)-4-oxobutanoate 24A (20 mg, 0.042 mmol) which was hydrolyzed to compound 24 with a similar procedure as Example 7, step 2. [M+H]+=469.3.

The compounds in the following table were prepared in a similar fashion to Example 24.

| # | Structure | Stereo designation | Name | [M + H]+ |
|---|-----------|--------------------|------|----------|
| 24B | 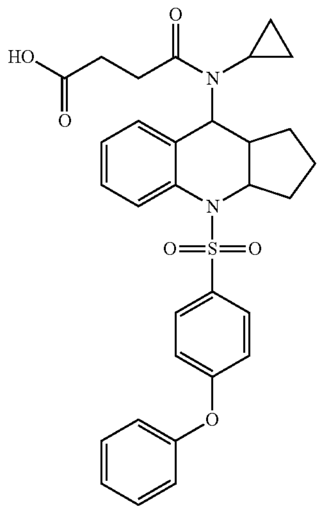 [SMILES: O=C(O)CCC(=O)N(C1CC1)C1c2ccccc2N(S(=O)(=O)c2ccc(Oc3ccccc3)cc2)C2CCCC12] | racemic, cis, cis | 4-[cyclopropyl[cis,cis-2,3,3a,4,9,9a-hexahydro-4-[(4-phenoxyphenyl)sulfonyl]-1H-cyclopenta[b]quinolin-9-yl]amino]-4-oxobutanoic acid | 561.3 |
| 24C | 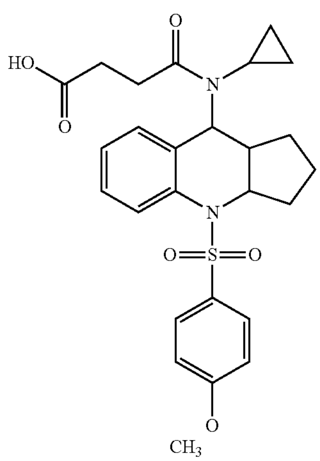 | racemic, cis, cis | 4-[cyclopropyl[cis,cis-2,3,3a,4,9,9a-hexahydro-4-[(4-methoxyphenyl)sulfonyl]-1H-cyclopenta[b]quinolin-9-yl]amino]-4-oxobutanoic acid | 499.3 |
| 24D | 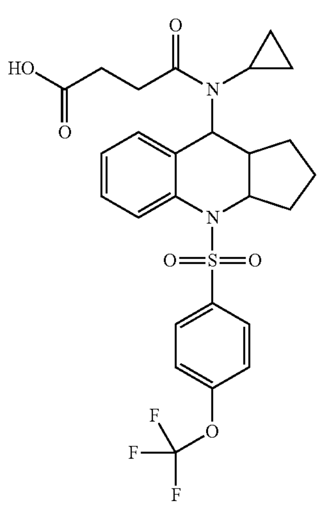 [SMILES: O=C(O)CCC(=O)N(C1CC1)C1c2ccccc2N(S(=O)(=O)c2ccc(OC(F)(F)F)cc2)C2CCCC12] | racemic, cis, cis | 4-[cyclopropyl[cis,cis-2,3,3a,4,9,9a-hexahydro-4-[[4-(trifluoromethoxy)phenyl]sulfonyl]-1H-cyclopenta[b]quinolin-9-yl]amino]-4-oxobutanoic acid | 553.3 |

Example 25

Preparation of Racemic 4-[{cis,cis-3-[(Benzyloxy)carbonyl]-1,2,2a,3,8,8a-hexahydrocyclobuta[b]quinolin-8-yl}(cyclopropyl)amino]-4-oxobutanoic acid (25)

Step 1: Benzyl 4-oxo-2-(2-oxoethyl)-3,4-dihydroquinoline-1(2H)-carboxylate (25A)

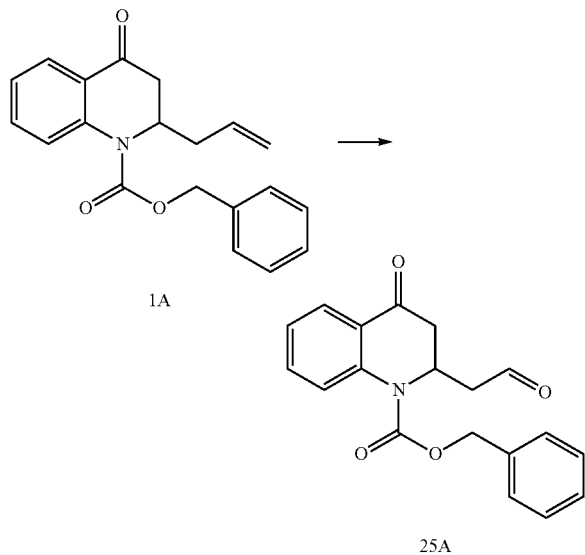

Osmium tetroxide (5% in water, 2.0 mL, 0.33 mmol, 0.025 equiv) was added to a biphasic mixture of benzyl 2-allyl-4-oxo-3,4-dihydroquinoline-1(2H)-carboxylate (1A) (4.20 g, 13.1 mmol, 1 equiv), sodium periodate (11.2 g, 52.3 mmol, 4.00 equiv) and 2,6-lutidine (3.04 mL, 26.1 mmol, 2.0 equiv) in water (33 mL) and dioxane (98 mL) at 23° C. The reaction mixture was stirred at 23° C. for 3 h, and then it was partitioned between water and dichloromethane. The aqueous layer was further extracted with dichloromethane (1×), and the combined organic layers were dried over sodium sulfate. The dried solution was filtered, and the filtrate was concentrated. The residue was purified by flash-column chromatography (15% ethyl acetate-hexanes, grading to 70% ethyl acetate-hexanes) to afford 25A. [M+H]⁺: 324.1

Step 2: Benzyl 2-(2-hydroxyethyl)-4-oxo-3,4-dihydroquinoline-1(2H)-carboxylate (25B)

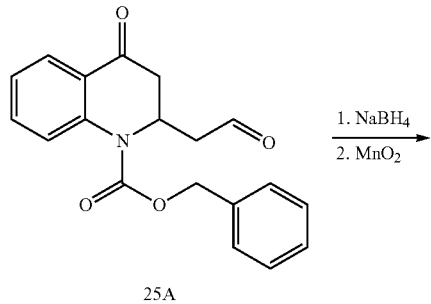

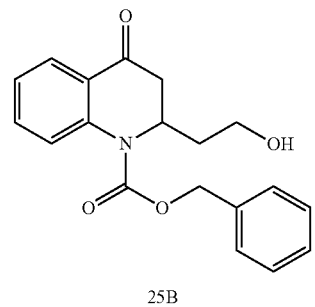

Sodium borohydride (1.27 g, 33.5 mmol, 3.0 equiv) was added to a solution of 25A (3.61 g, 11.2 mmol, 1 equiv) in methanol (112 mL) at 0° C. After stirring at 0° C. for 25 min, the reaction mixture was partitioned between ethyl acetate and water. The organic layer was washed with saturated aqueous sodium chloride solution, and the washed solution was dried over sodium sulfate. The dried solution was filtered, and the filtrate was concentrated.

The residue was dissolved in 1,2-dichloroethane (50 mL), and manganese dioxide (4.41 g, 50.7 mmol, 5 equiv) was added. The reaction mixture was heated to 65° C. for 2.5 h, and then the heating bath was removed. The cooled reaction mixture was filtered through Celite®, and the filtrate was concentrated to afford 25B, which was used in subsequent steps without further purification. [M+H]⁺: 326.2.

Step 3: Benzyl cis-8-oxo-2,2a,8,8a-tetrahydrocyclobuta[b]quinoline-3(1H)-carboxylate (25C)

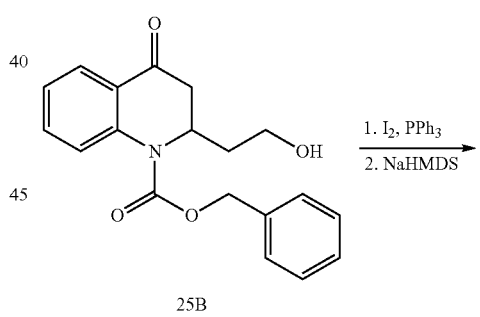

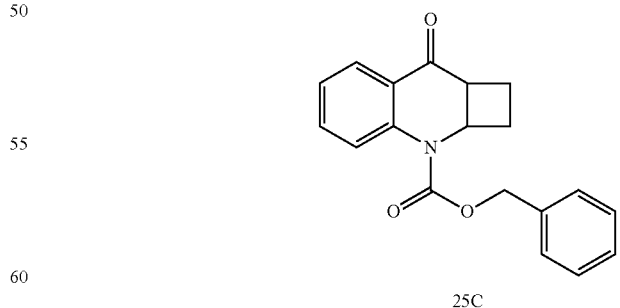

25C was prepared from benzyl 2-(2-hydroxyethyl)-4-oxo-3,4-dihydroquinoline-1(2H)-carboxylate (25B) using procedure similar to those used in Example 1, Steps 3 and 4. [M+H]⁺: 308.2.

Step 4: Benzyl cis,cis-8-[cyclopropyl(4-methoxy-4-oxobutanoyl)amino]-2,2a,8,8a-tetrahydrocyclobuta[b]quinoline-3(1H)-carboxylate (25D)

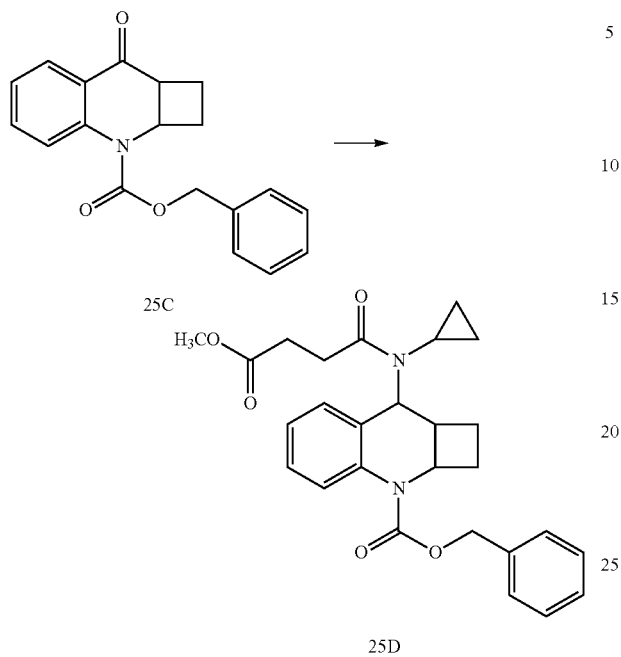

25D was prepared from benzyl cis-8-oxo-2,2a,8,8a-tetrahydrocyclobuta[b]quinoline-3(1H)-carboxylate 25C using a procedure similar to that used for Example 1, Step 5 and Example 7, Step 1. [M+H]$^+$: 463.2.

Step 5: Racemic 4-[{cis,cis-3-[(Benzyloxy)carbonyl]-1,2,2a,3,8,8a-hexahydrocyclobuta[b]quinolin-8-yl}(cyclopropyl)amino]-4-oxobutanoic acid (25)

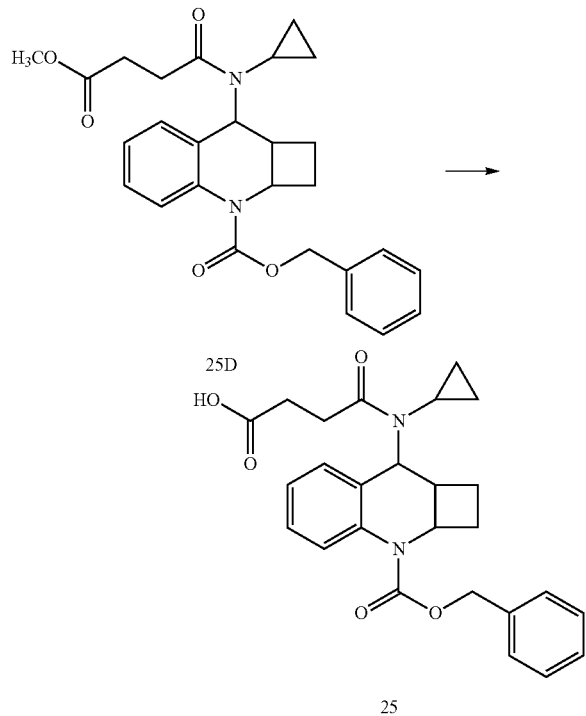

Compound 25 was prepared from benzyl cis,cis-8-[cyclopropyl(4-methoxy-4-oxobutanoyl)amino]-2,2a,8,8a-tetrahydrocyclobuta[b]quinoline-3(1H)-carboxylate 25D using a procedure similar to that used for Example 7, Step 2. [M+H]$^+$: 449.2.

Example 26

Preparation of Racemic Methyl 4-{cyclopropyl[cis,cis-3-{[4-(trifluoromethoxy)phenyl]carbonyl}-1,2,2a,3,8,8a-hexahydrocyclobuta[b]quinolin-8-yl]amino}-4-oxobutanoate (26)

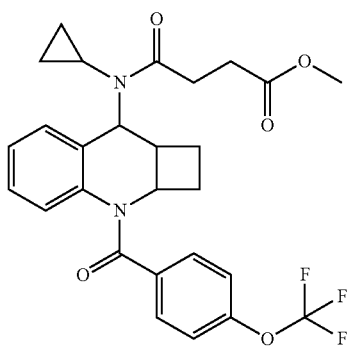

Compound 26 was prepared from benzyl cis,cis-8-[cyclopropyl(4-methoxy-4-oxobutanoyl)amino]-2,2a,8,8a-tetrahydrocyclobuta[b]quinoline-3(1H)-carboxylate (25D) using a procedure similar to that used in Example 14, Steps 1 and 2. [M+H]$^+$: 517.2.

Example 27

Preparation of Racemic 4-{Cyclopropyl[cis,cis-3-{[4-(trifluoromethoxy)phenyl]carbonyl}-1,2,2a,3,8,8a-hexahydrocyclobuta[b]quinolin-8-yl]amino}-4-oxobutanoic acid (27)

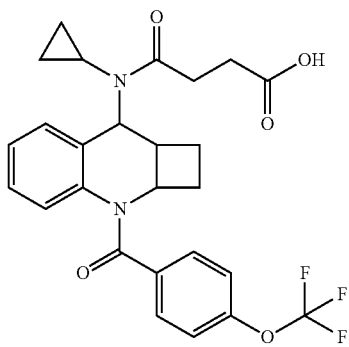

Compound 27 was prepared from methyl 4-{cyclopropyl[cis,cis-3-{[4-(trifluoromethoxy)phenyl]carbonyl}-1,2,2a,3,8,8a-hexahydrocyclobuta[b]quinolin-8-yl]amino}-4-oxobutanoate 26 using a procedure similar to that used in Example 14, Step 3. [M+H]$^+$: 503.2.

The compounds in the following table were prepared by a similar synthetic process as illustrated in Examples 25-27, and 14. The enantiomerically pure final products were prepared from enantiomerically pure tetraquinoline amides (prepared from chiral tetrahydroquinolin-9(9aH)-one).

| # | Structure | Stereo designation | Name | [M + H]+ |
|---|---|---|---|---|
| 27A | 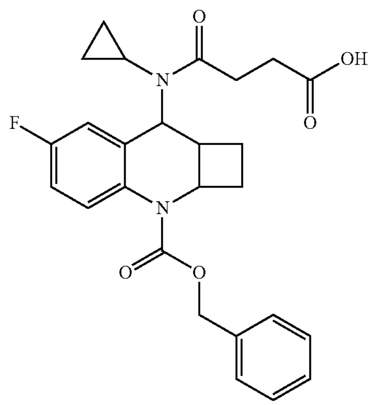 [SMILES: O=C(O)CCC(=O)N(C1CC1)C1c2cc(F)ccc2N(C(=O)OCc2ccccc2)C2CCC21] | cis, cis, single enantiomer | 3-(phenylmethyl) cis, cis-[(3-carboxy-1-oxopropyl)cyclopropylamino]-6-fluoro-2,2a,8,8a-tetrahydrocyclobuta[b]quinoline-3(1H)-carboxylate | 467 |
| 27B | 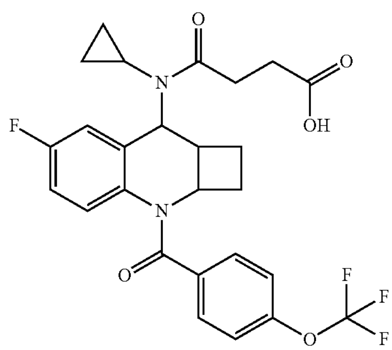 [SMILES: O=C(O)CCC(=O)N(C1CC1)C1c2cc(F)ccc2N(C(=O)c2ccc(OC(F)(F)F)cc2)C2CCC21] | cis, cis, single enantiomer | 4-[cyclopropyl[cis, cis-6-fluoro-1,2,2a,3,8,8a-hexahydro-3-[4-(trifluoromethoxy)benzoyl]cyclobuta[b]quinolin-8-yl]amino]-4-oxobutanoic acid | 521 |
| 27C | 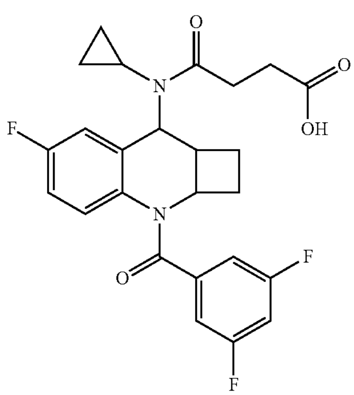 [SMILES: O=C(O)CCC(=O)N(C1CC1)C1c2cc(F)ccc2N(C(=O)c2cc(F)cc(F)c2)C2CCC21] | cis, cis, single enantiomer | 4-[cyclopropyl[cis, cis-3-(3,5-difluorobenzoyl)-6-fluoro-1,2,2a,3,8,8a-hexahydrocyclobuta[b]quinolin-8-yl]amino]-4-oxobutanoic acid | 473 |
| 27D | 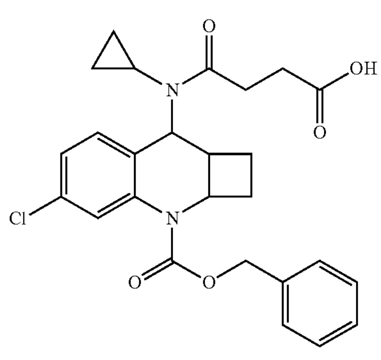 [SMILES: O=C(O)CCC(=O)N(C1CC1)C1c2ccc(Cl)cc2N(C(=O)OCc2ccccc2)C2CCC21] | cis, cis single enantiomer | 3-(phenylmethyl) cis, cis-[(3-carboxy-1-oxopropyl)cyclopropylamino]-5-chloro-2,2a,8,8a-tetrahydrocyclobuta[b]quinoline-3(1H)-carboxylate | 483 |

-continued

| # | Structure | Stereo designation | Name | [M + H]+ |
|---|---|---|---|---|
| 27E | 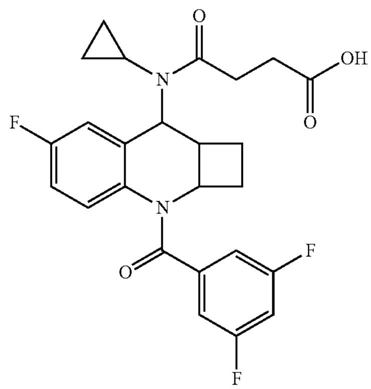 [SMILES: O=C(O)CCC(=O)N(C1CC1)C1c2cc(F)ccc2N(C(=O)c2cc(F)cc(F)c2)C2CCC21] | cis, cis single enantiomer | 4-[cyclopropyl[cis, cis-3-(3,5-difluorobenzoyl)-6-fluoro-1,2,2a,3,8,8a-hexahydrocyclobuta[b]quinolin-8-yl]amino]-4-oxobutanoic acid | 472 |
| 27F | 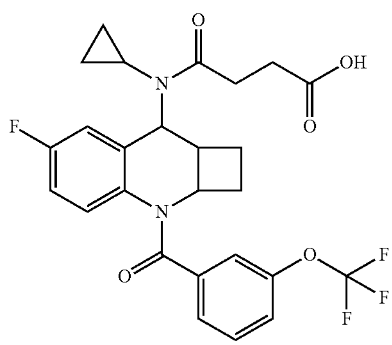 [SMILES: O=C(O)CCC(=O)N(C1CC1)C1c2cc(F)ccc2N(C(=O)c2cccc(OC(F)(F)F)c2)C2CCC21] | cis, cis single enantiomer | 4-[cyclopropyl[cis, cis-6-fluoro-1,2,2a,3,8,8a-hexahydro-3-[3-(trifluoromethoxy)benzoyl]cyclobuta[b]quinolin-8-yl]amino]-4-oxobutanoic acid | 520 |
| 27G | 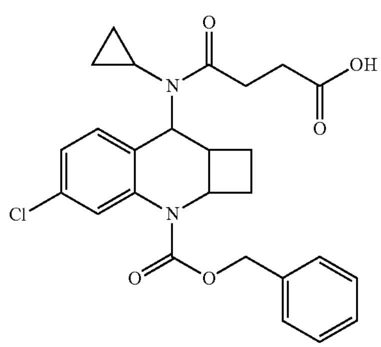 [SMILES: O=C(O)CCC(=O)N(C1CC1)C1c2ccc(Cl)cc2N(C(=O)OCc2ccccc2)C2CCC21] | cis, cis, single enantiomer | 3-(phenylmethyl) cis, cis-[(3-carboxyl-1-oxopropyl)cyclopropylamino]-5-chloro-2,2a,8,8a-tetrahydrocyclobuta[b]quinoline-3(1H)-carboxylate | 483 |
| 27H | 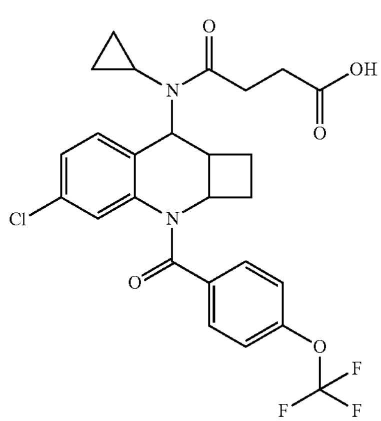 [SMILES: O=C(O)CCC(=O)N(C1CC1)C1c2ccc(Cl)cc2N(C(=O)c2ccc(OC(F)(F)F)cc2)C2CCC21] | cis, cis single enantiomer | 4-[[cis, cis-5-chloro-1,2,2a,3,8,8a-hexahydro-3-[4-(trifluoromethoxy)benzoyl]cyclobuta[b]quinolin-8-yl]cyclopropylamino]-4-oxobutanoic acid | 537 |

| # | Structure | Stereo designation | Name | [M + H]⁺ |
|---|---|---|---|---|
| 27i | 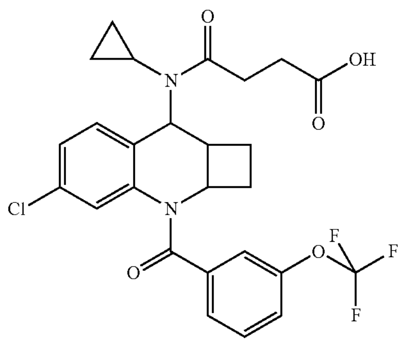 [SMILES: O=C(O)CCC(=O)N(C1CC1)C1c2ccc(Cl)cc2N(C(=O)c2cccc(OC(F)(F)F)c2)C2CCC21] | cis, cis single enantiomer | 4-[[cis, cis-5-chloro-1,2,2a,3,8,8a-hexahydro-3-[3-(trifluoromethoxy)benzoyl]cyclobuta[b]quinolin-8-yl]cyclopropylamino]-4-oxobutanoic acid | 537 |
| 27J | 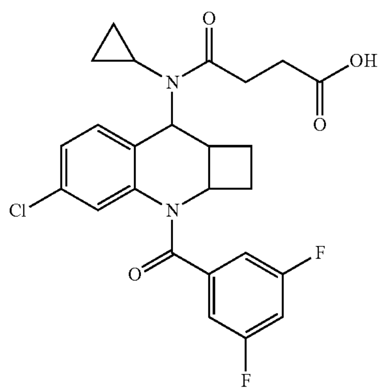 [SMILES: O=C(O)CCC(=O)N(C1CC1)C1c2ccc(Cl)cc2N(C(=O)c2cc(F)cc(F)c2)C2CCC21] | cis, cis single enantiomer | 4-[[cis, cis-5-chloro-3-(3,5-difluorobenzoyl)-1,2,2a,3,8,8a-hexahydrocyclobuta[b]quinolin-8-yl]cyclopropylamino]-4-oxobutanoic acid | 489 |
| 27K | 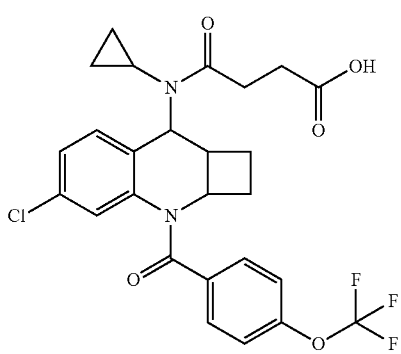 [SMILES: O=C(O)CCC(=O)N(C1CC1)C1c2ccc(Cl)cc2N(C(=O)c2ccc(OC(F)(F)F)cc2)C2CCC21] | cis, cis, single enantiomer | 4-[[cis, cis-5-chloro-1,2,2a,3,8,8a-hexahydro-3-[4-(trifluoromethoxy)benzoyl]cyclobuta[b]quinolin-8-yl]cyclopropylamino]-4-oxobutanoic acid | 537 |
| 27L | 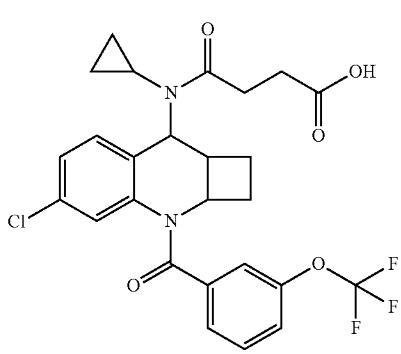 [SMILES: O=C(O)CCC(=O)N(C1CC1)C1c2ccc(Cl)cc2N(C(=O)c2cccc(OC(F)(F)F)c2)C2CCC21] | cis, cis, single enantiomer | 4-[[cis, cis-5-chloro-1,2,2a,3,8,8a-hexahydro-3-[3-(trifluoromethoxy)benzoyl]cyclobuta[b]quinolin-8-yl]cyclopropylamino]-4-oxobutanoic acid | 537 |

| # | Structure | Stereo designation | Name | [M + H]⁺ |
|---|---|---|---|---|
| 27M | 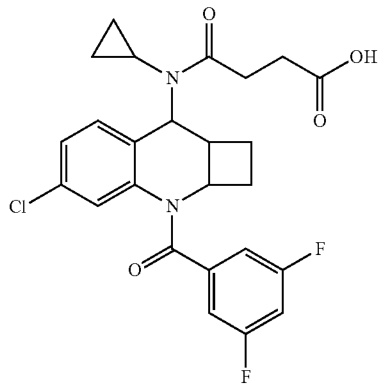 [SMILES: O=C(O)CCC(=O)N(C1CC1)C1c2ccc(Cl)cc2N(C(=O)c2cc(F)cc(F)c2)C2CCC21] | cis, cis, single enantiomer | 4-[[cis, cis-5-chloro-3-(3,5-difluorobenzoyl)-1,2,2a,3,8,8a-hexahydrocyclobuta[b]quinolin-8-yl]cyclopropylamino]-4-oxobutanoic acid | 489 |
| 27N | 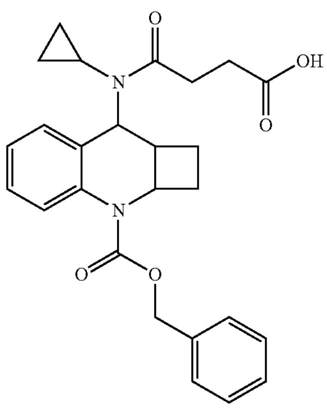 [SMILES: O=C(O)CCC(=O)N(C1CC1)C1c2ccccc2N(C(=O)OCc2ccccc2)C2CCC21] | cis, cis, single enantiomer | 3-(phenylmethyl) cis, cis-[(3-carboxy-1-oxopropyl)cyclopropylamino]-2,2a,8,8a-tetrahydrocyclobuta[b]quinoline-3(1H)-carboxylate | 449 |
| 27O | 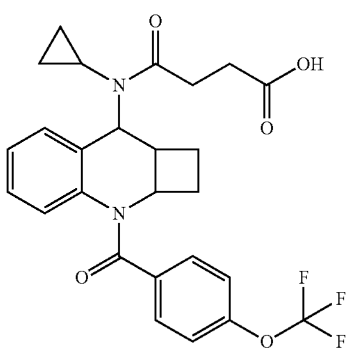 [SMILES: O=C(O)CCC(=O)N(C1CC1)C1c2ccccc2N(C(=O)c2ccc(OC(F)(F)F)cc2)C2CCC21] | cis, cis, single enantiomer | 4-[cyclopropyl[cis, cis-1,2,2a,3,8,8a-hexahydro-3-[4-(trifluoromethoxy)benzoyl]cyclobuta[b]quinolin-8-yl]amino]-4-oxobutanoic acid | 503 |
| 27Q | 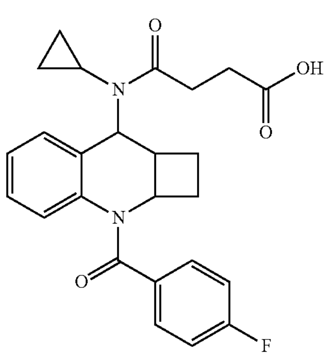 [SMILES: O=C(O)CCC(=O)N(C1CC1)C1c2ccccc2N(C(=O)c2ccc(F)cc2)C2CCC21] | cis, cis, single enantiomer | 4-[cyclopropyl[cis, cis-3-(4-fluorobenzoyl)-1,2,2a,3,8,8a-hexahydrocyclobuta[b]quinolin-8-yl]amino]-4-oxobutanoic acid | 437 |

| # | Structure | Stereo designation | Name | [M + H]⁺ |
|---|---|---|---|---|
| 27R | 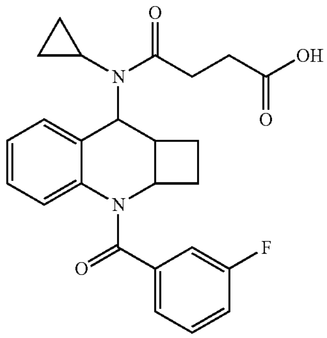 [SMILES: O=C(O)CCC(=O)N(C1CC1)C1c2ccccc2N(C(=O)c2cccc(F)c2)C2CCC21] | cis, cis, single enantiomer | 4-[cyclopropyl[cis, cis-3-(3-fluorobenzoyl)-1,2,2a,3,8,8a-hexahydrocyclobuta[b]quinolin-8-yl]amino]-4-oxobutanoic acid | 437 |
| 27S | 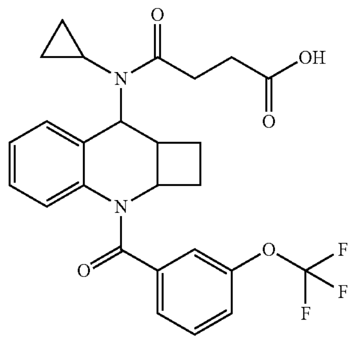 [SMILES: O=C(O)CCC(=O)N(C1CC1)C1c2ccccc2N(C(=O)c2cccc(OC(F)(F)F)c2)C2CCC21] | cis, cis, single enantiomer | 4-[cyclopropyl[cis,cis-1,2,2a,3,8,8a-hexahydro-3-[3-(trifluoromethoxy)benzoyl]cyclobuta[b]quinolin-8-yl]amino]-4-oxobutanoic acid | 503 |

Example 28

Racemic 4-[{cis,cis-10-[(Benzyloxy)carbonyl]-1,2,3,4,4a,9,9a,10-octahydroacridin-9-yl}(cyclopropyl)amino]-4-oxobutanoic acid (28)

Step 1: Benzyl 2-but-3-en-1-yl-4-oxo-3,4-dihydroquinoline-1(2H)-carboxylate (28A)

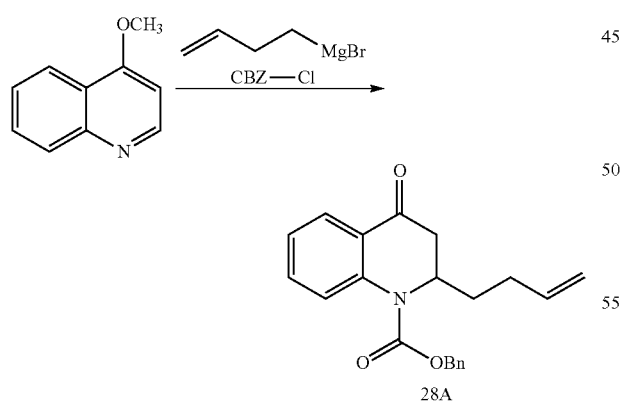

3-Butenylmagnesium bromide (0.5 M in THF, 100 mL, 50.0 mmol, 1.7 equiv) was added was added to a solution of 4-methoxyquinoline (4.65 g, 29.2 mmol, 1 equiv) in tetrahydrofuran (195 mL) at −78° C. The reaction mixture was stirred at −78° C. for 1 h, then benzyl chloroformate (8.34 mL, 58.4 mmol, 2.00 equiv) was added via syringe over 5 min. Stirred for an additional 15 minutes at −78° C., then the cooling bath was removed and the reaction mixture was allowed to warm to 23° C. After 1 h, methanol was added (20 mL). After stirring for 5 min, aqueous hydrochloric acid solution (2 N, 20 mL) was added and the mixture was stirred for 10 min. The mixture was then concentrated by rotary evaporation to remove most of the tetrahydrofuran and methanol, and the residue was partitioned between ethyl acetate and water. The organic phase was washed with brine, and the washed solution was dried over sodium sulfate. The dried solution was filtered, and the filtrate was concentrated. The residue was purified by flash-column chromatography (5% ethyl acetate-hexanes, grading to 20% ethyl acetate-hexanes) to afford 28A as a colorless oil. [M+H]⁺: 336.2.

Step 2: 4-[{cis,cis-10-[(Benzyloxy)carbonyl]-1,2,3,4,4a,9,9a,10-octahydroacridin-9-yl}(cyclopropyl)amino]-4-oxobutanoic acid was prepared from benzyl 2-but-3-en-1-yl-4-oxo-3,4-dihydroquinoline-1(2H)-carboxylate (28)

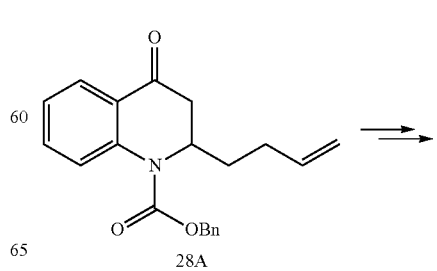

28A

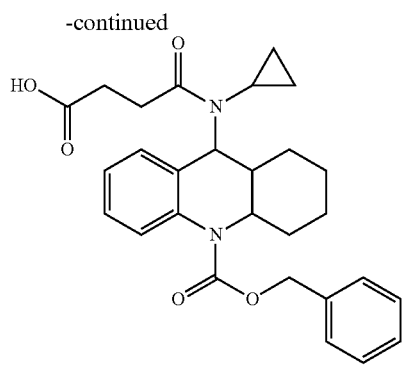

28

28 was prepared from benzyl 2-but-3-en-1-yl-4-oxo-3,4-dihydroquinoline-1(2H)-carboxylate (28A) using a sequence with procedures similar to those used for Example 1, Steps 2-5, and Example 7. [M+H]⁺: 477.2.

Example 29

Racemic 2-Hydroxyethyl cyclopropyl[cis,cis-4-(phenylcarbonyl)-2,3,3a,4,9,9a-hexahydro-1H-cyclopenta[b]quinolin-9-yl]carbamate (29)

Step 1: Benzyl cis,cis-9-[{[2-(benzyloxy)ethoxy]carbonyl}(cyclopropyl)amino]-1,2,3,3a,9,9a-hexahydro-4H-cyclopenta[b]quinoline-4-carboxylate (29A)

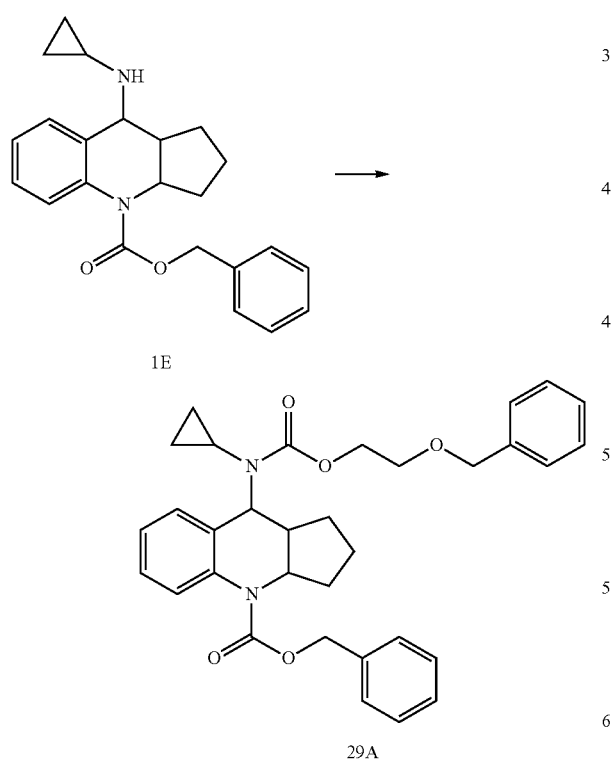

1E

29A 2-(Benzyloxy)ethyl chloridocarbonate (0.080 mL, 0.44 mmol, 2.0 equiv) was added to a solution of benzyl cis,cis-9-(cyclopropylamino)-1,2,3,3a,9,9a-hexahydro-4H-cyclopenta[b]quinoline-4-carboxylate 1E (80 mg, 0.22 mmol, 1 equiv) and N,N-diisopropylethylamine (0.154 mL, 0.883 mmol, 4.0 equiv) in dioxane (1.5 mL). The reaction mixture was heated at 40° C. for 16 h, and then cooled to 23° C. The cooled reaction mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (15% ethyl acetate-hexanes, grading to 65% ethyl acetate-hexanes) to afford 29A. [M+H]⁺: 541.2.

Step 2: 2-(Benzyloxy)ethyl cyclopropyl[cis,cis-2,3,3a,4,9,9a-hexahydro-1H-cyclopenta[b]quinolin-9-yl]carbamate (29B)

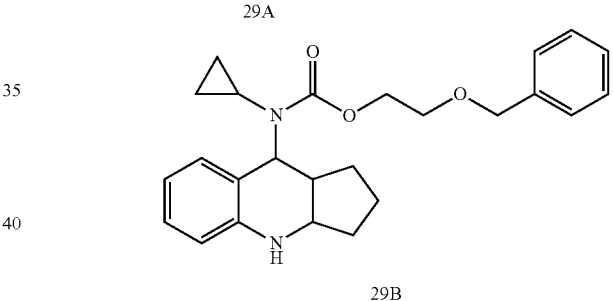

29A

29B 29B was prepared from benzyl cis,cis-9-[{[2-(benzyloxy)ethoxy]carbonyl}(cyclopropyl)amino]-1,2,3,3a,9,9a-hexahydro-4H-cyclopenta[b]quinoline-4-carboxylate using a procedure similar to that used in Example 14, Step 1. [M+H]⁺: 407.2.

Step 3: 2-(Benzyloxy)ethyl[cis,cis-4-benzoyl-2,3,3a,4,9,9a-hexahydro-1H-cyclopenta[b]quinolin-9-yl]cyclopropylcarbamate (29C)

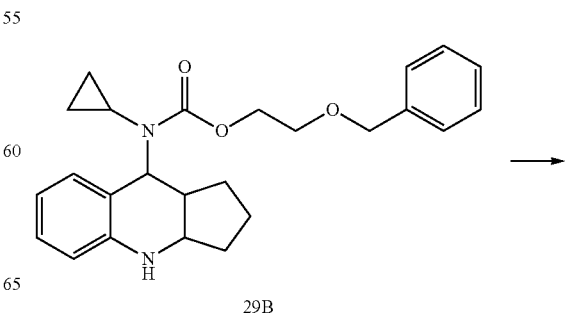

29B

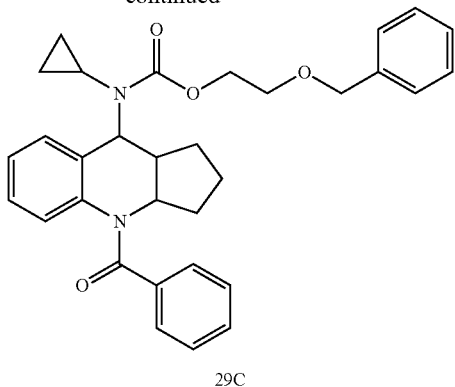

29C 29C was prepared from 2-(benzyloxy)ethyl cyclopropyl[cis,cis-2,3,3a,4,9,9a-hexahydro-1H-cyclopenta[b]quinolin-9-yl]carbamate 29B using a procedure similar to that used for Example 14, Step 2. [M+H]⁺: 511.2.

Step 4: 2-Hydroxyethyl cyclopropyl[cis,cis-4-(phenylcarbonyl)-2,3,3a,4,9,9a-hexahydro-1H-cyclopenta[b]quinolin-9-yl]carbamate (29)

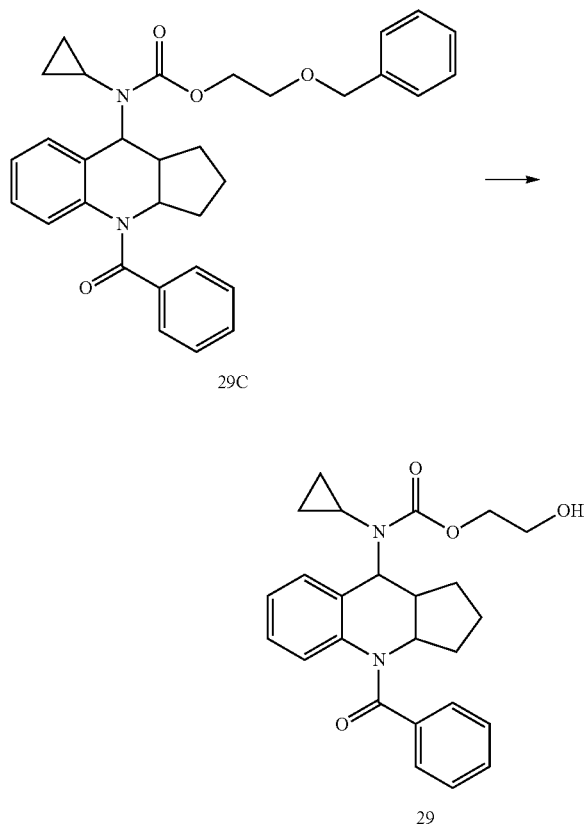

Palladium (10% on carbon, 12.3 mg, 0.012 mmol, 0.10 equiv) was added to a solution of 2-(benzyloxy)ethyl[cis,cis-4-benzoyl-2,3,3a,4,9,9a-hexahydro-1H-cyclopenta[b]quinolin-9-yl]cyclopropylcarbamate 29C (62 mg, 0.12 mmol, 1 equiv) in tetrahydrofuran (2.4 mL). A three-way stopcock connected to a hydrogen balloon and a vacuum line was fitted to the top of the flask, and the flask was subjected to alternating vacuum purging and hydrogen filling cycles (4×). The reaction mixture was then stirred under hydrogen for 18 h at 23° C., and then was filtered through cotton. The filtrate was concentrated, and the residue was purified by flash-column chromatography (50% ethyl acetate-hexanes, grading to ethyl acetate) to afford 29. [M+H]⁺: 421.2.

Example 30

Preparation of Racemic ({Cyclopropyl[cis,cis-4-(phenylcarbonyl)-2,3,3a,4,9,9a-hexahydro-1H-cyclopenta[b]quinolin-9-yl]carbamoyl}oxy)acetic acid (30)

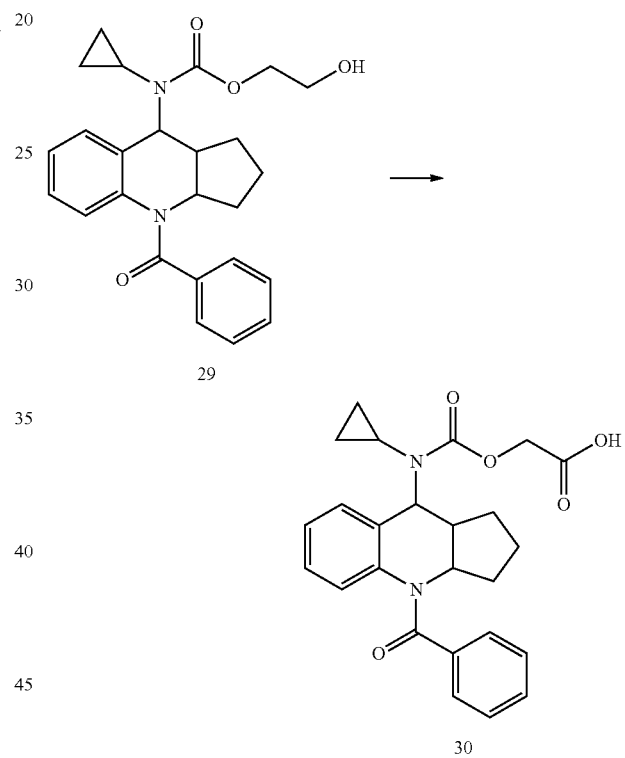

Jones Reagent (0.200 mL) was added to a solution of 2-hydroxyethyl cyclopropyl[cis,cis-4-(phenylcarbonyl)-2,3,3a,4,9,9a-hexahydro-1H-cyclopenta[b]quinolin-9-yl]carbamate 29 (46 mg, 0.11 mmol) in acetone (2.2 mL) at 23° C. After stirring for 30 min, an additional portion of Jones Reagent (0.200 mL) was added, and the reaction mixture was stirred at 23° C. for a further 20 min. The reaction mixture was then partitioned between ethyl acetate and aqueous hydrogen chloride solution (1 N). The organic layer was washed with saturated aqueous sodium chloride solution, and the washed solution was dried over sodium sulfate. The dried solution was filtered, and the filtrate was concentrated. The residue was then dissolved in DMSO (2 mL), and purified by reverse-phase HPLC (40% acetonitrile-water, grading to 80% acetonitrile-water, with 0.1% trifluoroacetic acid in both the acetonitrile and water) to afford 30. [M+H]⁺: 435.2.

Example 31

Preparation of ({Cyclopropyl[cis,cis-4-{[4-(trifluoromethoxy)phenyl]carbonyl}-2,3,3a,4,9,9a-hexahydro-1H-cyclopenta[b]quinolin-9-yl]carbamoyl}oxy) acetic acid (31)

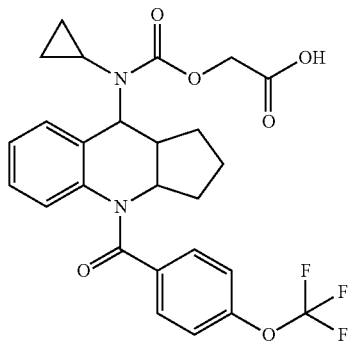

Compound 31 was prepared from 2-(benzyloxy)ethyl cyclopropyl[cis,cis-2,3,3a,4,9,9a-hexahydro-1H-cyclopenta[b]quinolin-9-yl]carbamate 29B, using procedures similar to those used in Example 29, Steps 3-4, and Example 30. [M+H]$^+$: 519.1.

Example 32

Preparation of Enantiopure 4-(Phenylmethyl)cis,cis-[[(1(S)-carboxyethoxy)carbonyl]cyclopropylamino]-1,2,3,3a,9,9a-hexahydro-4H-cyclopenta[b]quinoline-4-carboxylate (32)

Step 1: Enantiopure cis,cis-Benzyl 9-(chlorocarbonyl(cyclopropyl)amino)-3,3a,9,9a-tetrahydro-1H-cyclopenta[b]quinoline-4(2H)-carboxylate (32A)

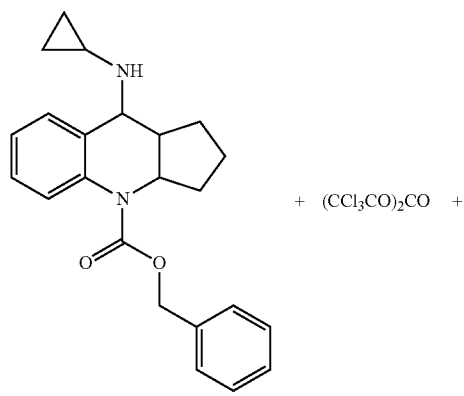

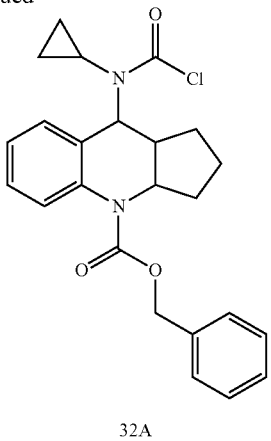

Triphosgene (1.2 g, 4.14 mmol) was added to a solution of enantiopure cis,cis-benzyl 9-(cyclopropylamino)-3,3a,9,9a-tetrahydro-1H-cyclopenta[b]quinoline-4(2H)-carboxylate (1.0 g, 2.76 mmol) and DIPEA (720 µL, 4.14 mmol) in THF (2 0 mL). After stirring at rt for 2 h, EtOAc (20 mL) and H$_2$O (20 mL) were added. The aqueous layer was extracted once more with EtOAc (15 mL). The combined organic was washed with brine (10 mL), dried over MgSO$_4$ and concentrated. The residue 32A was used directly in the next step.

Step 2: Enantiopure(cis,cis,)-Benzyl 9-(cyclopropyl(((S)-1-methoxy-1-oxopropan-2-yloxy)carbonyl)amino)-3,3a,9,9a-tetrahydro-1H-cyclopenta[b]quinoline-4(2H)-carboxylate (32B)

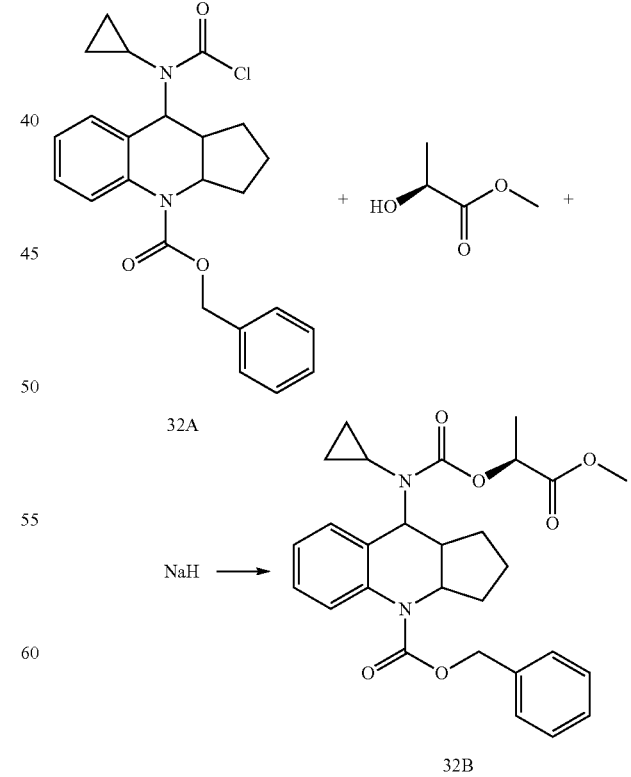

A solution of enantiopure cis,cis-benzyl 9-(chlorocarbonyl(cyclopropyl)amino)-3,3a,9,9a-tetrahydro-1H-cyclopenta

[b]quinoline-4(2H)-carboxylate 32A (25 μL, 0.240 mmol) in 1,4-dioxane (2 mL) was stirred at rt, and NaH (16 mg, 0.4 mmol) was added. After stirring at rt for 30 mins, (S)-methyl 2-hydroxypropanoate (85 mg, 0.2 mmol) in 1,4-dioxane (1 mL) was added, and the resultant mixture was kept stirring at rt for 2 hours. EtOAc (10 mL) was added, followed by the icy-H$_2$O (5 mL), and the organic was dried over MgSO$_4$ and concentrated. The residue was purified via silica gel column chromatography (EtOAc/Hexane=1:3), to obtain 32B as a yellow foam, 36 mg; [M+H]$^+$=493.

Step 3: Enantiopure (cis,cis,)-Benzyl 9-(cyclopropyl (((S)-1-methoxy-1-oxopropan-2-yloxy)carbonyl) amino)-3,3a,9,9a-tetrahydro-1H-cyclopenta[b]quinoline-4(2H)-carboxylate (32)

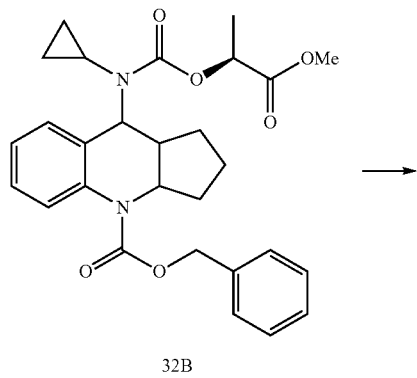

32B

→

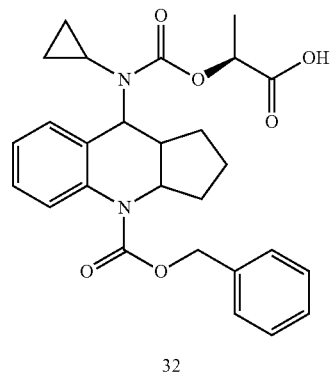

32

32B was converted to the desired enantiopure acid 32 by hydrolysis with NaOH (1 N), [M+Na]$^+$=500.7. $^1$H NMR (500 MHz, CDCl$_3$) δ ppm: 7.42 (m, 6H); 7.25 (m, 1H); 7.24 (m 1H); 7.17 (m, 1H); 7.04 (m, 1H); 5.32 (d, J=13 Hz, 1H); 5.22 (d, J=13 Hz, 1H); 5.11 (q, J=7 Hz, 1H); 3.01 (m, 1H); 2.71 (m 1H); 2.15 (m, 1H); 1.94 (m, 1H); 1.59 (m, 3H); 1.45 (m, 2H); 1.32 (m, 1H); 1.22~1.14 (m, 2H); 1.11~0.80 (m, 4H).

The compounds in the following table were prepared by a similar synthetic process as described above in Example 32. The enantiomerically pure final products were prepared from enantiomerically pure tetraquinoline amides (prepared from chiral tetrahydroquinolin-9(9aH)-one).

| # | Structure | Stereo designation | Name | [M + H]$^+$ |
|---|---|---|---|---|
| 32C | 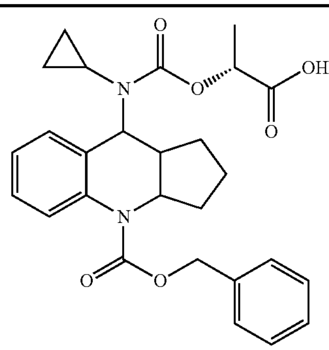 | cis, cis (enantiopure), R single enantiomer | 4-(phenylmethyl) cis, cis-[[(1R)-carboxyethoxy)carbonyl] cyclopropylamino]-1,2,3,3a-9,9a-hexahydro-4H-cyclopenta[b]quinoline-4-carboxylate | 500.6 [M + Na]$^+$ |
| 32D | 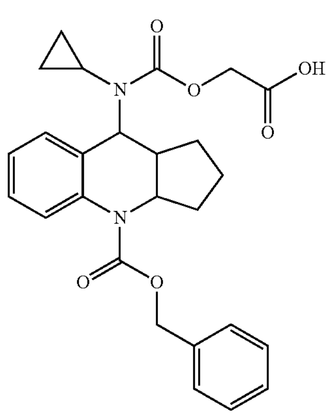 [SMILES: O=C(O)COC(=O)N(C1CC1)C1c2ccccc2N(C(=O)OCc2ccccc2)C2CCCC21] | cis, cis single enantiomer | 4-(phenylmethyl) cis, cis-[[(carboxymethoxy)carbonyl] cyclopropylamino]-1,2,3,3a,9,9a-hexahydro-4H-cyclopenta[b]quinoline-4-carboxylate | 464.7 |

| # | Structure | Stereo designation | Name | [M + H]+ |
|---|---|---|---|---|
| 32E | 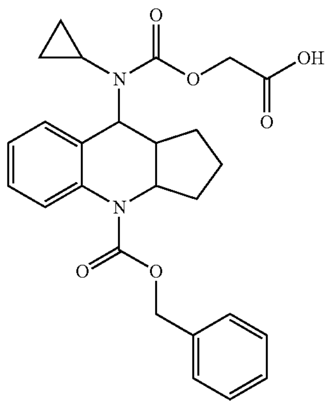 [SMILES: O=C(O)COC(=O)N(C1CC1)C1c2ccccc2N(C(=O)OCc2ccccc2)C2CCCC21] | cis, cis, single enantiomer | 4-(phenylmethyl) cis, cis-[[(carboxymethoxy)carbonyl] cyclopropylamino]-1,2,3,3a, 9,9a-hexahydro-4H-cyclopenta[b]quinoline-4-carboxylate | 464.7 |
| 32F | 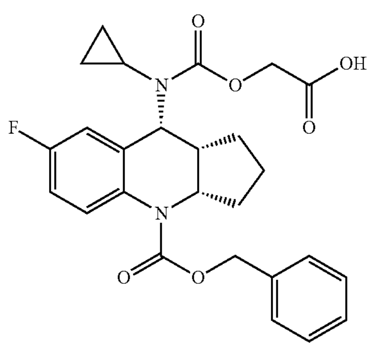 [SMILES: O=C(O)COC(=O)N(C1CC1)[C@H]1c2cc(F)ccc2N(C(=O)OCc2ccccc2)[C@H]2CCC[C@H]21] | 3aS,9R,9aR single enantiomer | 4-(phenylmethyl)(3aS,9R,9aR)-[[(carboxymethoxy)carbonyl] cyclopropylamino]-7-fluoro-1,2,3,3a,9,9a-hexahydro-4H-cyclopenta[b]quinoline-4-carboxylate | 505.0 [M + Na]+ |
| 32G | 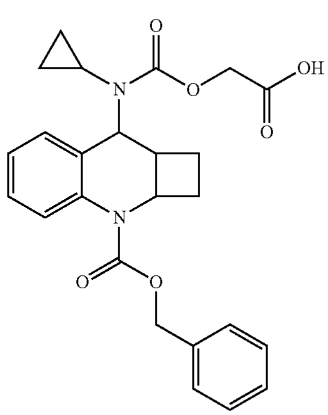 [SMILES: O=C(O)COC(=O)N(C1CC1)C1c2ccccc2N(C(=O)OCc2ccccc2)C2CCC21] | cis, cis single enantiomer | 3-(phenylmethyl) cis, cis-[[(carboxymethoxy)carbonyl] cyclopropylamino]-2,2a,8,8a-tetrahydrocyclobuta[b] quinoline-3(1H)-carboxylate | 472.6 [M + Na]+ |

The compounds in the following table were prepared by similar synthetic processes as those described in Examples 32 and 14. The enantiomerically pure final products were prepared from enantiomerically pure tetraquinoline amides (prepared from chiral tetrahydroquinolin-9(9aH)-one).

| # | Structure | Stereo designation | Name | [M + H]$^+$ |
|---|---|---|---|---|
| 32H | 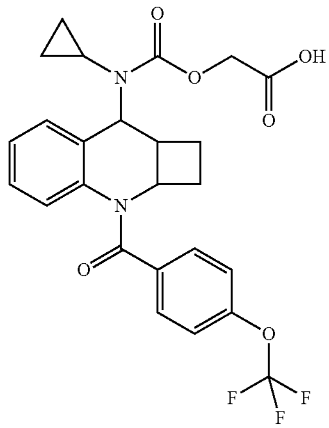 [SMILES: O=C(O)COC(=O)N(C1CC1)C1c2ccccc2N(C(=O)c2ccc(OC(F)(F)F)cc2)C2CCC21] | cis, cis, single enantiomer | [[[cyclopropyl[cis,cis-1,2,2a,3,8,8a-hexahydro-3-[4-(trifluoromethoxy)benzoyl]cyclobuta[b]quinolin-8-yl]amino]carbonyl]oxy]acetic acid | 505.1 |
| 32i | 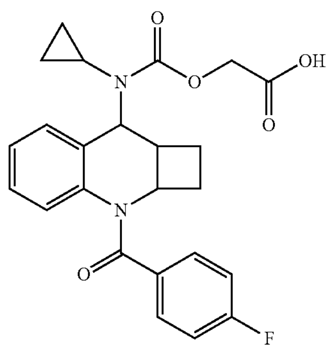 [SMILES: O=C(O)COC(=O)N(C1CC1)C1c2ccccc2N(C(=O)c2ccc(F)cc2)C2CCC21] | cis, cis, single enantiomer r | [[[cyclopropyl[cis, cis-3-(4-fluorobenzoyl)-1,2,2a,3,8,8a-hexahydrocyclobuta[b]quinolin-8-yl]amino]carbonyl]oxy]acetic acid | 439.2 |
| 32J | 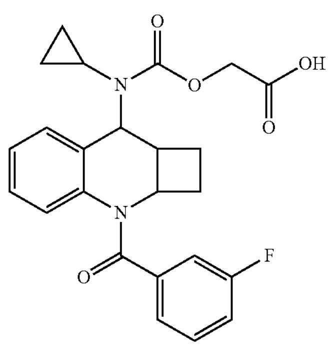 [SMILES: O=C(O)COC(=O)N(C1CC1)C1c2ccccc2N(C(=O)c2cccc(F)c2)C2CCC21] | cis, cis single enantiomer | [[[cyclopropyl[cis, cis-3-(3-fluorobenzoyl)-1,2,2a,3,8,8a-hexahydrocyclobuta[b]quinolin-8-yl]amino]carbonyl]oxy] acetic acid | 439.2 |
| 32K | 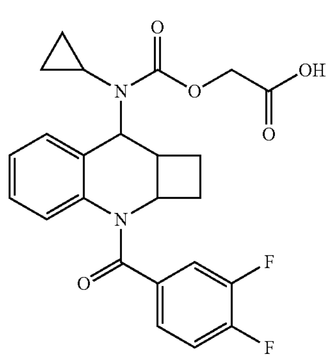 [SMILES: O=C(O)COC(=O)N(C1CC1)C1c2ccccc2N(C(=O)c2ccc(F)c(F)c2)C2CCC21] | cis, cis, single enantiomer | [[[cyclopropyl[cis, cis-3-(3,4-difluorobenzyl)-1,2,2a,3,8,8a-hexahydrocyclobuta[b]quinolin-8-yl]amino]carbonyl]oxy] acetic acid | 457.3 |

| # | Structure | Stereo designation | Name | [M + H]+ |
|---|---|---|---|---|
| 32L | 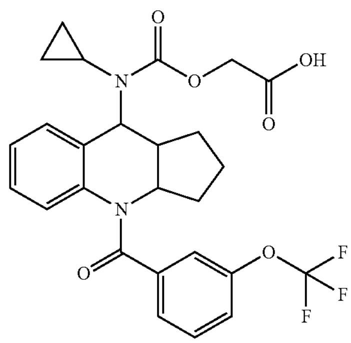 [SMILES: O=C(O)COC(=O)N(C1CC1)C1c2ccccc2N(C(=O)c2cccc(OC(F)(F)F)c2)C2CCCC21] | racemic, cis, cis | [[[cyclopropyl[cis,cis-2,3,3a,4,9,9a-hexahydro-4-[3-(trifluoromethoxy)benzoyl]-1H-cyclopenta[b]quinolin-9-yl]amino]carbonyl]oxy]acetic acid | 519.3 |
| 32M | 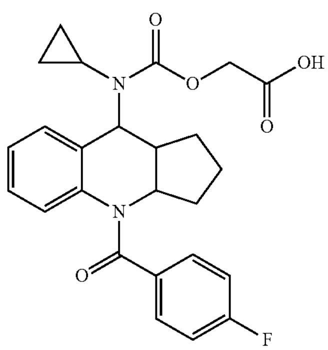 [SMILES: O=C(O)COC(=O)N(C1CC1)C1c2ccccc2N(C(=O)c2ccc(F)cc2)C2CCCC21] | cis, cis, single enantiomer | [[[cyclopropyl[cis, cis-4-(4-fluorobenzoyl)-2,3,3a,4,9,9a-hexahydro-1H-cyclopenta[b]quinolin-9-yl]amino]carbonyl]oxy]acetic acid | 452.7 |
| 32N | 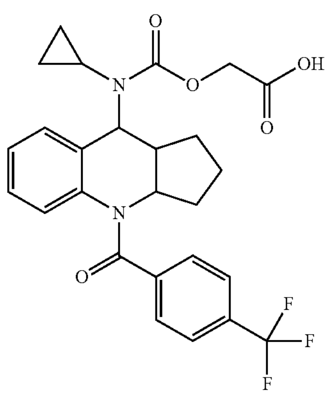 [SMILES: O=C(O)COC(=O)N(C1CC1)C1c2ccccc2N(C(=O)c2ccc(C(F)(F)F)cc2)C2CCCC21] | cis, cis, single enantiomer | [[[cyclopropyl[cis, cis-2,3,3a,4,9,9a-hexahydro-4-[4-(trifluoromethyl)benzoyl]-1H-cyclopenta[b]quinolin-9-yl]amino]carbonyl]oxy]acetic acid | 524.6 |
| 32o | 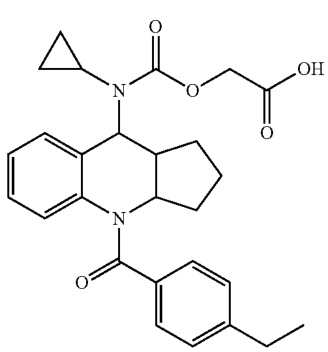 [SMILES: CCc1ccc(C(=O)N2c3ccccc3C(N(C(=O)OCC(=O)O)C3CC3)C3CCCC32)cc1] | cis, cis, single enantiomer | [[[cyclopropyl[cis, cis-4-(4-ethylbenzoyl)-2,3,3a,4,9,9a-hexahydro-1H-cyclopenta[b]quinolin-9-yl]amino]carbonyl]oxy]acetic acid | 462.7 |

-continued

| # | Structure | Stereo designation | Name | [M + H]+ |
|---|---|---|---|---|
| 32P | 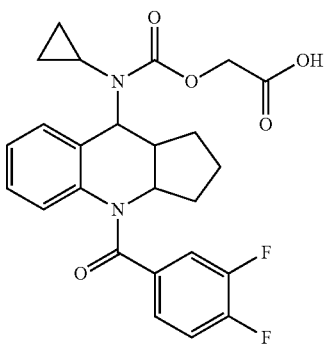 [SMILES: O=C(O)COC(=O)N(C1CC1)C1c2ccccc2N(C(=O)c2ccc(F)c(F)c2)C2CCCC21] | cis, cis, single enantiomer | [[[cyclopropyl[cis, cis-4-(3,4-difluorobenzoyl)-2,3,3a,4,9,9a-hexahydro-1H-cyclopenta[b]quinolin-9-yl]amino]carbonyl]oxy]acetic acid | 470.7 |
| 32Q | 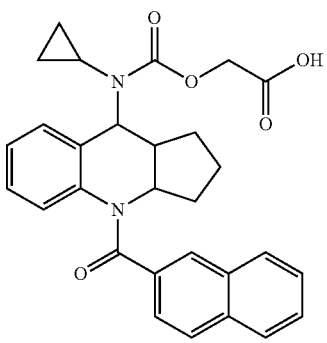 [SMILES: O=C(O)COC(=O)N(C1CC1)C1c2ccccc2N(C(=O)c2ccc3ccccc3c2)C2CCCC21] | cis, cis, single enantiomer | [[[cyclopropyl[cis, cis-2,3,3a,4,9,9a-hexahydro-4-(2-naphthalenylcarbonyl)-1H-cyclopenta[b]quinolin-9-yl]amino]carbonyl]oxy]acetic acid | 484.7 |
| 32R | 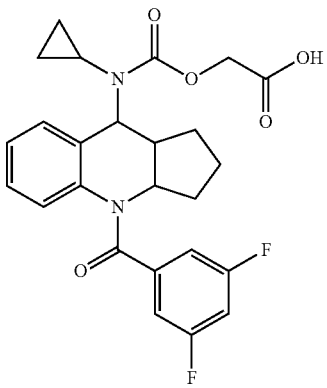 [SMILES: O=C(O)COC(=O)N(C1CC1)C1c2ccccc2N(C(=O)c2cc(F)cc(F)c2)C2CCCC21] | cis, cis, single enantiomer | [[[cyclopropyl[cis, cis-4-(3,5-difluorobenzoyl)-2,3,3a,4,9,9a-hexahydro-1H-cyclopenta[b]quinolin-9-yl]amino]carbonyl]oxy]acetic acid | 470.6 |
| 32S | 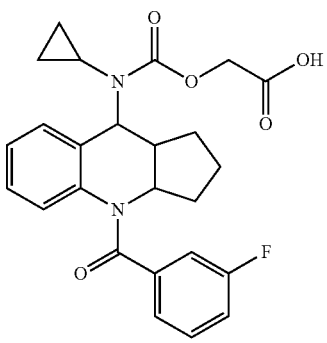 [SMILES: O=C(O)COC(=O)N(C1CC1)C1c2ccccc2N(C(=O)c2cccc(F)c2)C2CCCC21] | cis, cis, single enantiomer | [[[cyclopropyl[cis, cis-4-(3-fluorobenzoyl)-2,3,3a,4,9,9a-hexahydro-1H-cyclopenta[b]quinolin-9-yl]amino]carbonyl]oxy]acetic acid | 453.7 |

US 8,592,383 B2

231                                                                                                                         232

-continued

| # | Structure | Stereo designation | Name | [M + H]+ |
|---|---|---|---|---|
| 32T | 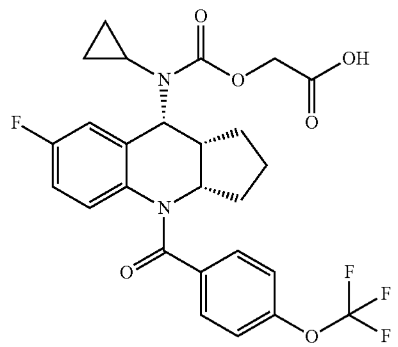 [SMILES: O=C(O)COC(=O)N(C1CC1)[C@H]1c2cc(F)ccc2N(C(=O)c2ccc(OC(F)(F)F)cc2)[C@H]2CCC[C@H]21] | 3aS,9R,9aR, single enantiomer | [[[cyclopropyl[(3aS,9R,9aR)-7-fluoro-2,3,3a,4,9,9a-hexahydro-4-[4-(trifluoromethoxy)benzoyl]-1H-cyclopenta[b]quinolin-9-yl]amino]carbonyl]oxy]acetic acid | 536.6 |
| 32U | 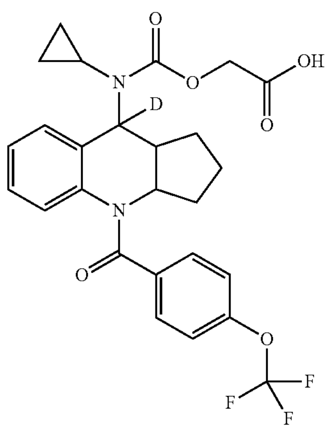 [SMILES: [2H]C1(N(C(=O)OCC(=O)O)C2CC2)c2ccccc2N(C(=O)c2ccc(OC(F)(F)F)cc2)C2CCCC21] | cis, cis, single enantiomer | deuterated-[[[cyclopropyl[cis,cis-2,3,3a,4,9,9a-hexahydro-4-[4-(trifluoromethoxy)benzoyl]-1H-cyclopenta[b]quinolin-9-yl-(d)]amino]carbonyl]oxy]acetic acid | 520 |

Example 33

Preparation of Enantiopure 4-(Phenylmethyl)cis,cis-[[[(2(S)-carboxy-1-azetidinyl)carbonyl]cyclopropylamino]-1,2,3,3a,9,9a-hexahydro-4H-cyclopenta[b]quinoline-4-carboxylate (33)

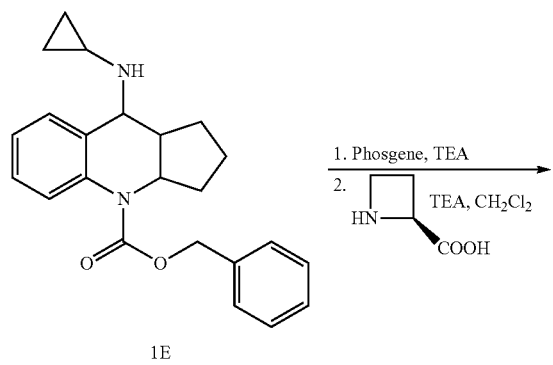

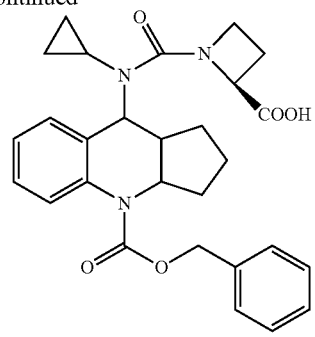

33

To a solution of the enantiopure amine 1E (0.05 g, 0.138 mmol) in anhydrous dichloromethane (5 mL) was added phosgene (0.1 mL, 1 M solution) and triethylamine (0.04 mL). The reaction mixture was stirred for two hours and evaporated to dryness. The residue was redissolved in dichloromethane (5 mL) and treated with the amino acid (S)-azetidine-2-carboxylic acid (28 mg) and triethylamine (0.074 mL) and stirred over night. The reaction mixture was acidified with 1 N HCl, extracted with ethyl acetate, and purified by reversed phase HPLC to give compound 33 (0.055 g, 82%). [M+H]+=490.3.

Example 34

Preparation of Enantiopure 4-(phenylmethyl)(3aS, 9R,9aR)-[[(3-carboxy-1-azetidinyl)carbonyl]cyclopropylamino]-7-fluoro-1,2,3,3a,9,9a-hexahydro-4H-cyclopenta[b]quinoline-4-carboxylate (34)

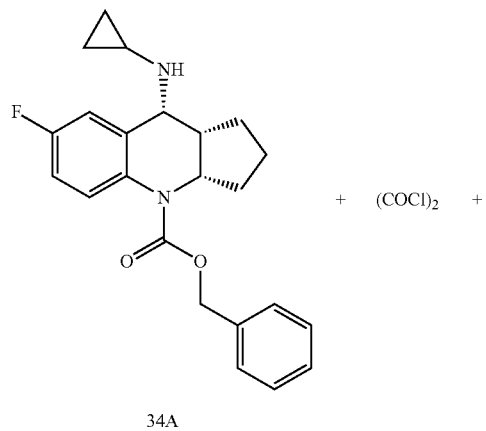

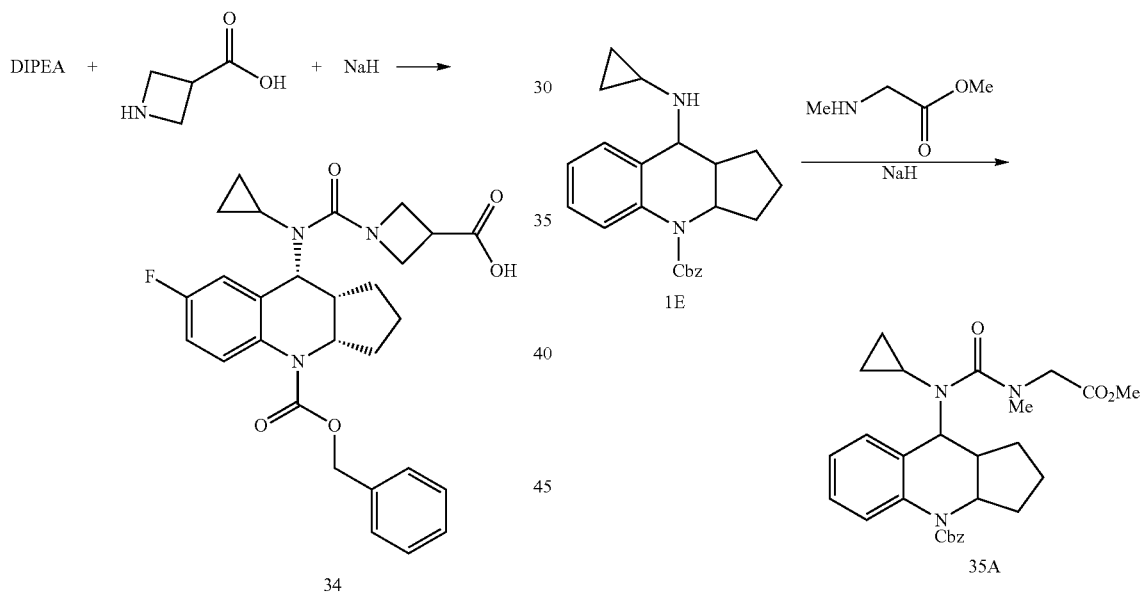

The enantiopure amine 34A was prepared from compound 17C (after chiral HPLC, the stereochemistry was confirmed by conversion to 17D) using a similar procedure as Example 22 to introduce the Cbz group and Example 1, step 5. The solution of amine 34A (38 mg, 0.1 mmol) and DIPEA (40 µL, 0.2 mmol) in $CH_2Cl_2$ (1 mL) was cooled in an ice —$H_2O$ bath, $(COCl)_2$ in toluene (20% solution) (86 µL, 0.15 mmol) was added. The mixture was kept stirring at 0° C. for 2 hrs, then rt for 15 mins, the mixture was concentrated, the residue was taken up in THF (2 mL), azetidine-3-carboxylic acid (30 mg, 0.3 mmol) and NaH (24 mg, 0.6 mmol) were added, respectively. The resultant mixture was kept stirring at rt overnight. EtOAc (10 mL) was added to the mixture, followed by the $H_2O$ (5 mL). The organic layer was washed with $H_2O$ (2 mL), and the combined aqueous layer was acidified with 2 N HCl to pH ~2-3, extracted with $Et_2O$ (2×5 mL). The combined ether layer was dried over $MgSO_4$ and concentrated. The residue was purified via reverse phase HPLC, to obtain 4-(phenylmethyl)(3aS,9R,9aR)-[[(3-carboxy-1-azetidinyl)carbonyl]cyclopropylamino]-7-fluoro-1,2,3,3a,9,9a-hexahydro-4H-cyclopenta[b]quinoline-4-carboxylate 34 as a white solid, 25 mg; $[M+H]^+$ 508.1. $^1H$ NMR (500 MHz, $CDCl_3$) δ ppm: 7.36 (m, 5H); 6.86 (m, 1H); 6.69 (m, 1H); 5.26 (d, J=13 Hz, 1H); 5.17 (d, J=13 Hz, 1H); 5.02 (m, 1H); 4.86 (m, 1H); 4.26 (m, 4H); 3.41 (m, 1H); 2.97 (m, 1H); 2.52 (m, 1H); 2.10 (m, 1H); 1.93 (m, 1H); 1.55 (m, 1H); 1.42 (m, 2H); 1.20–0.97 (m, 4H); 0.79 (m, 1H).

Example 35

Preparation of N-[[Cyclopropyl[cis,cis-2,3,3a,4,9,9a-hexahydro-4-[4-(trifluoromethoxy)benzoyl]-1H-cyclopenta[b]quinolin-9-yl]amino]carbonyl]-N-methylglycine (35)

Step 1

Triphosgene (1.8 g, 6.1 mmol) was added to a mixture of amine 1E (2.0 g, 5.5 mmol), and triethylamine (0.92 mL, 6.6 mmol) in dry DCM (18 mL) at 0° C. The reaction mixture was stirred at room temperature under nitrogen for 15 minutes, and concentrated to dryness. NaH (0.27 g, 10.6 mmol) was added to a mixture of sarcosine methyl ester hydrochloride (1.54 g, 11.0 mmol) in THF (18 mL) at 0° C. under nitrogen. The resulting mixture was stirred at 0° C. for 2 hours, and at room temperature overnight. Water and EtOAc were added. The aqueous layer was separated and extracted with EtOAc. The organic extracts were combined, washed with brine, dried ($MgSO_4$), filtered and concentrated. The residue was purified by silica gel column chromatography (eluted with 10% ethyl acetate-hexane, to 40% ethyl acetate in hexane) to afford pure product urea ester 35A (2.57 g, 5.23 mmol).

Step 2

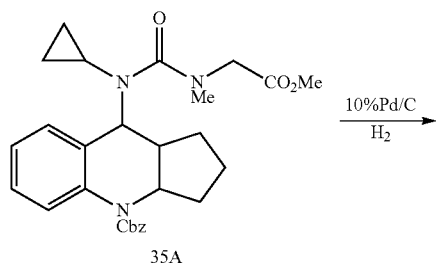

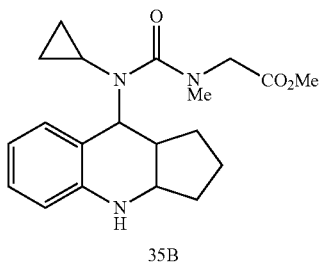

10% Pd on carbon (2.0 g) was added to the solution of urea ester 35A (2.57 g, 5.22 mmol) in EtOH (17 mL). The reaction mixture was stirred under a balloon of hydrogen at room temperature for 1 h. The reaction mixture was filtered though a pad of Celite®, and the filtrate was concentrated. The residue was purified by silica gel column chromatography (eluted with 10% ethyl acetate in hexane) to afford pure urea amine 35B (0.43 g, 1.2 mmol).

Step 3

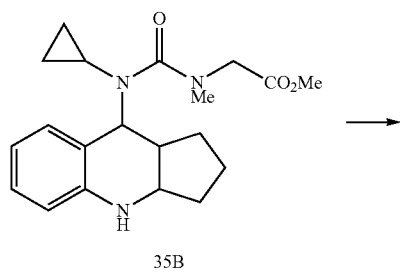

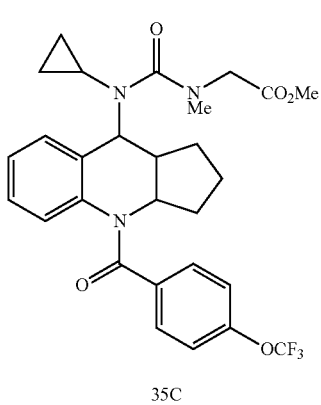

4-(Trifluoromethoxy)benzoyl chloride (50 mg, 0.22 mmol) was added to a solution of urea amine 35B (40 mg, 0.11 mmol) and triethylamine (34 mg, 0.34 mmol) in DCM (2 mL). The reaction mixture was stirred at room temperature for 1 h. Water was added. The aqueous layer was separated and extracted with DCM. The organic extracts were combined, washed with brine, dried (MgSO$_4$), filtered and concentrated. The residue was purified by preparative thin layer chromatography (eluted with 50% ethyl acetate-hexane) to afford the urea amide 35C (30 mg, 0.055 mmol).

Step 4

N-[[Cyclopropyl[cis,cis-2,3,3a,4,9,9a-hexahydro-4-[4-(trifluoromethoxy)benzoyl]-1H-cyclopenta[b]quinolin-9-yl]amino]carbonyl]-N-methylglycine (35)

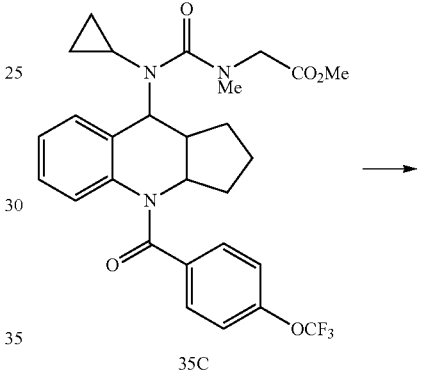

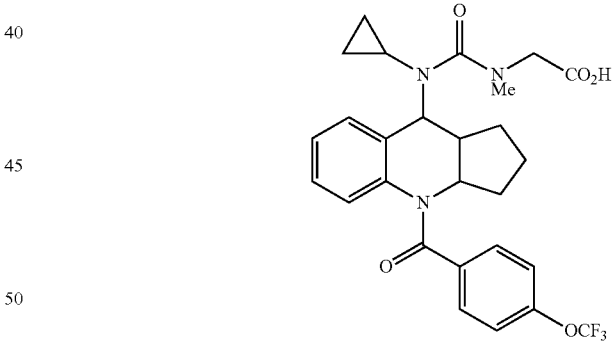

Lithium hydroxide monohydrate (18.2 mg, 0.43 mmol) was added to a solution of urea amide (30 mg, 0.055 mmol) in THF (0.5 mL) and H$_2$O (0.5 mL). The reaction mixture was stirred at room temperature over night. 1 N HCl (aq.) was added to the reaction mixture. The aqueous layer was separated and extracted with EtOAc. The organic extracts were combined, washed with brine, dried (MgSO$_4$), filtered and concentrated to give acid 35 (20 mg, 0.038 mmol). [M+H]$^+$= 532.3.

The compounds in the following table were prepared following protocols similar to those described in Example 35.

| # | Structure | Stereo designation | Name | [M + H]+ |
|---|---|---|---|---|
| 35D | 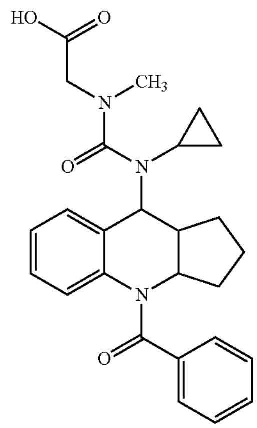 [SMILES: CN(CC(=O)O)C(=O)N(C1CC1)C1c2ccccc2N(C(=O)c2ccccc2)C2CCCC21] | racemic, cis, cis | N-[[[cis,cis-4-benzoyl-2,3,3a,4,9,9a-hexahydro-1H-cyclopenta[b]quinolin-9-yl]cyclopropylamino]carbonyl]-N-methylglycine | 448.2 |
| 35E | 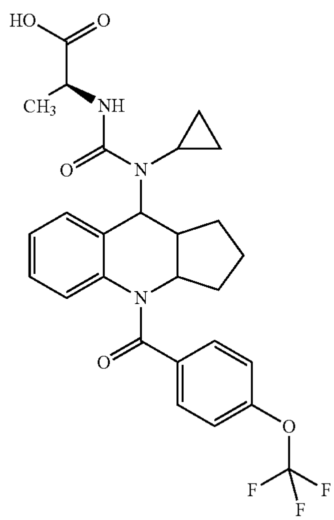 [SMILES: C[C@H](NC(=O)N(C1CC1)C1c2ccccc2N(C(=O)c2ccc(OC(F)(F)F)cc2)C2CCCC21)C(=O)O] | racemic, cis, cis<br>S at acid side chain | N-[[cyclopropyl[cis,cis-2,3,3a,4,9,9a-hexahydro-4-[4-(trifluoromethoxy)benzoyl]-1H-cyclopenta[b]quinolin-9-yl]amino]carbonyl]-l-alanine | 532.3 |
| 35F | 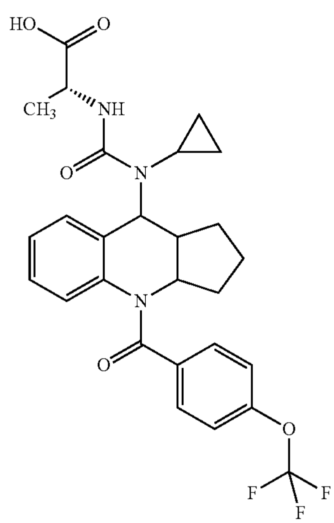 [SMILES: C[C@@H](NC(=O)N(C1CC1)C1c2ccccc2N(C(=O)c2ccc(OC(F)(F)F)cc2)C2CCCC21)C(=O)O] | racemic, cis, cis<br>R at acid side chain | N-[[cyclopropyl[cis,cis-2,3,3a,4,9,9a-hexahydro-4-[4-(trifluoromethoxy)benzoyl]-1H-cyclopenta[b]quinolin-9-yl]amino]carbonyl]-D-alanine | 532.3 |

-continued

| # | Structure | Stereo designation | Name | [M + H]+ |
|---|---|---|---|---|
| 35G | 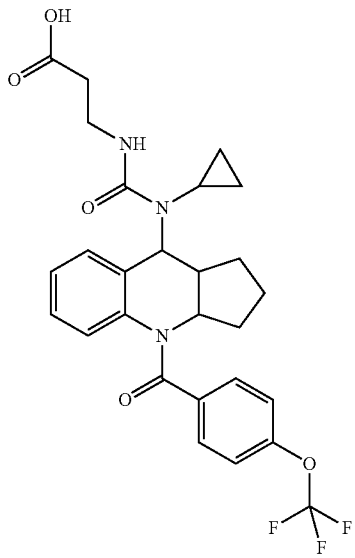 [SMILES: O=C(O)CCNC(=O)N(C1CC1)C1c2ccccc2N(C(=O)c2ccc(OC(F)(F)F)cc2)C2CCCC21] | racemic, cis, cis | N-[[cyclopropyl[cis,cis-2,3,3a,4,9,9a-hexahydro-4-[4-(trifluoromethoxy)benzoyl]-1H-cyclopenta[b]quinolin-9-yl]amino]carbonyl]-beta-alanine | 532.3 |
| 35H | 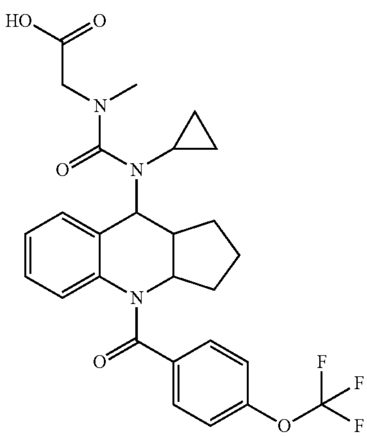 [SMILES: CN(CC(=O)O)C(=O)N(C1CC1)C1c2ccccc2N(C(=O)c2ccc(OC(F)(F)F)cc2)C2CCCC21] | cis, cis, single enantiomer HPLC peak 1 | N-[[cyclopropyl[cis, cis-2,3,3a,4,9,9a-hexahydro-4-[4-(trifluoromethoxy)benzoyl]-1H-cyclopenta[b]quinolin-9-yl]amino]carbonyl]-N-methylglycine | 532.3 |
| 35i | 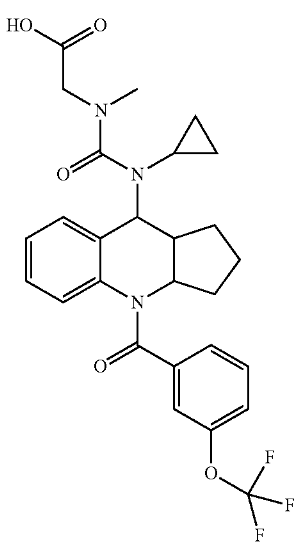 [SMILES: CN(CC(=O)O)C(=O)N(C1CC1)C1c2ccccc2N(C(=O)c2cccc(OC(F)(F)F)c2)C2CCCC21] | cis, cis, single enantiomer HPLC peak 2 | N-[[cyclopropyl[cis, cis-2,3,3a,4,9,9a-hexahydro-4-[3-(trifluoromethoxy)benzoyl]-1H-cyclopenta[b]quinolin-9-yl]amino]carbonyl]-N-methylglycine | 532.3 |

| # | Structure | Stereo designation | Name | [M + H]+ |
|---|---|---|---|---|
| 35J | 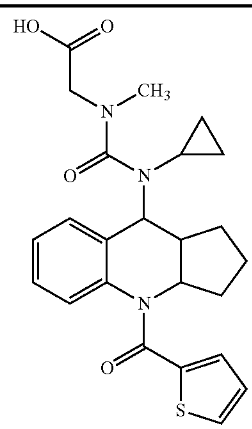 | cis, cis,, single enantiomer | N-[[cyclopropyl[cis, cis-2,3,3a,4,9,9a-hexahydro-4-(2-thienylcarbonyl)-1H-cyclopenta[b]quinolin-9-yl]amino]carbonyl]-N-methylglycine | 454.2 |
| 35K | 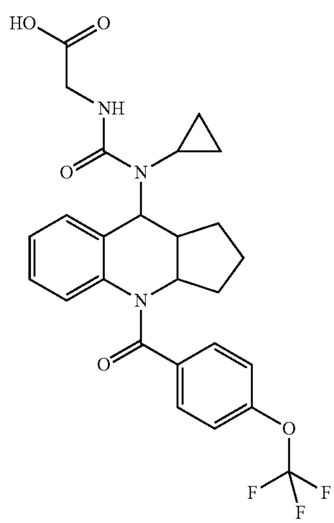 [SMILES: O=C(O)CNC(=O)N(C1CC1)C1c2ccccc2N(C(=O)c2ccc(OC(F)(F)F)cc2)C2CCCC21] | cis, cis racemic | N-[[cyclopropyl[cis,cis-2,3,3a,4,9,9a-hexahydro-4-[4-(trifluoromethoxy)benzoyl]-1H-cyclopenta[b]quinolin-9-yl]amino]carbonyl]glycine | 518.3 |

Example 36

Preparation of Racemic 4-{[cis-4-(5-Benzyl-1,3,4-oxadiazol-2-yl)-2,3,3a,4,9,9a-hexahydro-1H-cyclopenta[b]quinolin-9-yl](cyclopropyl)amino}-4-oxobutanoic acid (36)

Step 1

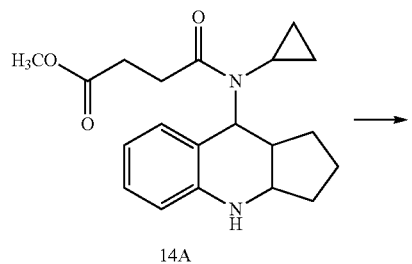

14A

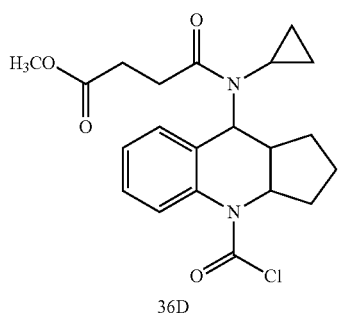

36D

Triphosgene (589 mg, 1.99 mmo, 0.40 equiv) was added to a solution of methyl 4-{cyclopropyl[cis,cis-2,3,3a,4,9,9a-hexahydro-1H-cyclopenta[b]quinolin-9-yl]amino}-4-oxobutanoate 14A (1.7 g, 5.0 mmol, 1 equiv) and N,N-diisopropylethylamine (1.04 mL, 5.96 mmol, 1.2 equiv) in dichloromethane (25 mL) at 23° C. The reaction mixture was stirred at 23° C. for 15 min, and then was partitioned between ethyl acetate and saturated aqueous sodium bicarbonate solution. The organic layer was washed with saturated aqueous sodium chloride solution, and the washed solution was dried over sodium sulfate. The dried solution was filtered, and the filtrate was concentrated to afford methyl 4-[[cis,cis-4-(chlorocarbonyl)-2,3,3a,4,9,9a-hexahydro-1H-cyclopenta[b]quinolin-9-yl](cyclopropyl)amino]-4-oxobutanoate, which was used in subsequent steps without further purification. [M+H]$^+$: 405.1.

Step 2

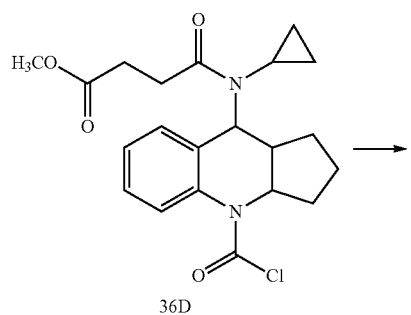

36D

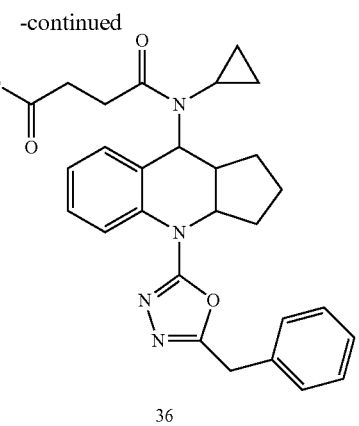

36

2-Phenylacetohydrazide (26.5 mg, 0.177 mmol, 1.1 equiv) was added to a solution of methyl 4-[[cis,cis-4-(chlorocarbonyl)-2,3,3a,4,9,9a-hexahydro-H-cyclopenta[b]quinolin-9-yl](cyclopropyl)amino]-4-oxobutanoate 36D (65 mg, 0.16 mmol, 1 equiv) and N,N-diisopropylethylamine (0.033 mL, 0.19 mmol, 1.2 equiv) in tetrahydrofuran (0.80 mL), and the reaction mixture was warmed to 60° C. After stirring for 2 h at 60° C., the reaction mixture was cooled to 23° C., and 3,3,3-triethyl-1-(methoxycarbonyl)diazathian-3-ium-1-ide 2,2-dioxide (Burgess reagent, 77 mg, 0.32 mmol, 2.0 equiv) was added. The reaction vessel was sealed, and heated in a microwave at 120° C. for 15 min. The reaction mixture was then cooled to 23° C., and aqueous sodium hydroxide solution (1 N, 8 equiv) was added. The reaction mixture was then heated in a microwave at 110° C. for 30 min. After cooling to 23° C., dimethyl sulfoxide (1 mL) was added, and the mixture was purified by reverse-phase HPLC (10% acetonitrile-water, grading to 90% acetonitrile-water, with 0.1% trifluoroacetic acid in both the acetonitrile and water) to afford 36 as a white solid. [M+H]$^+$: 487.3.

The following examples were prepared from methyl 4-[[cis,cis-4-(chlorocarbonyl)-2,3,3a,4,9,9a-hexahydro-1H-cyclopenta[b]quinolin-9-yl](cyclopropyl)amino]-4-oxobutanoate using procedures similar to Example 36, Step 2, and the appropriate hydrazides:

| # | Structure | Stereo designation | Name | [M + H]$^+$ |
|---|-----------|--------------------|------|-------------|
| 36A | 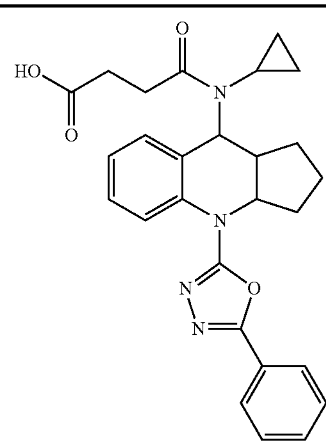 | racemic, cis, cis | racemic 4-{cyclopropyl[cis, cis-4-(5-phenyl-1,3,4-oxadiazol-2-yl)-2,3,3a,4,9,9a-hexahydro-1H-cyclopenta[b]quinolin-9-yl]amino}-4-oxobutanoic acid | 473.2 |

-continued

| # | Structure | Stereo designation | Name | [M + H]+ |
|---|---|---|---|---|
| 36B | 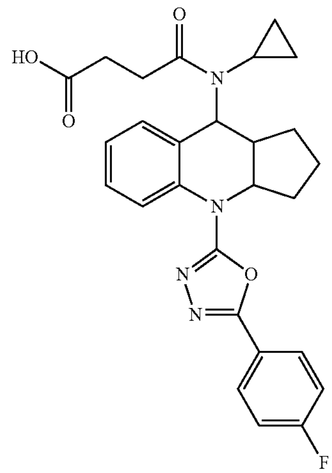 [SMILES: O=C(O)CCC(=O)N(C1CC1)C1c2ccccc2N(c2nnc(-c3ccc(F)cc3)o2)C2CCCC21] | racemic, cis, cis | racemic 4-(cyclopropyl{cis, cis-4-[5-(4-fluorophenyl)-1,3,4-oxadiazol-2-yl]-2,3,3a,4,9,9a-hexahydro-1H-cyclopenta[b]quinolin-9-yl}amino)-4-oxobutanoic acid | 491.2 |
| 36C | 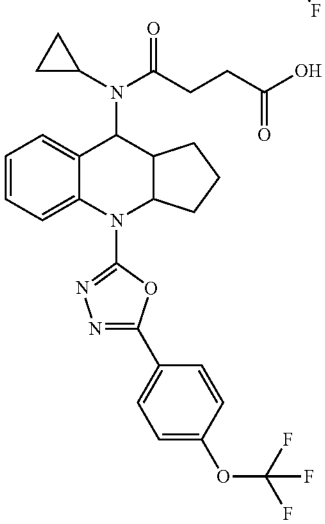 | racemic, cis, cis | racemic 4-{cyclopropyl[cis, cis-4-{5-[4-trifluoro-(methoxy)phenyl]-1,3,4-oxadiazol-2-yl}-2,3,3a,4,9,9a-hexahydro-1H-cyclopenta[b]quinolin-9-yl]amino}-4-oxobutanoic acid | 557.2 |

Example 37

Preparation of Racemic ({Cyclopropyl[cis,cis-4-(5-phenyl-1,3,4-oxadiazol-2-yl)-2,3,3a,4,9,9a-hexahydro-1H-cyclopenta[b]quinolin-9-yl]carbamoyl}oxy)acetic acid (37)

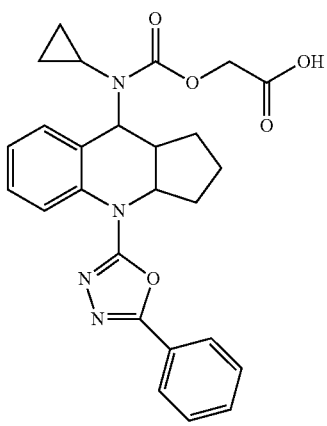

Compound 37 was prepared from 2-(benzyloxy)ethyl cyclopropyl[cis,cis-2,3,3a,4,9,9a-hexahydro-1H-cyclopenta[b]quinolin-9-yl]carbamate 29B, using a sequence of procedures similar to Example 36, Step 1, Example 36, Step 2 (without the hydrolysis step), Example 29, Step 4, and Example 30. [M+H]+: 475.2.

Example 38

Preparation of Racemic [[[Cyclopropyl[cis,cis-2,3,3a,4,9,9a-hexahydro-4-[5-[3-(trifluoromethoxy)phenyl]-1,3,4-oxadiazol-2-yl]-1H-cyclopenta[b]quinolin-9-yl]amino]carbonyl]oxy]acetic acid (38)

Step 1

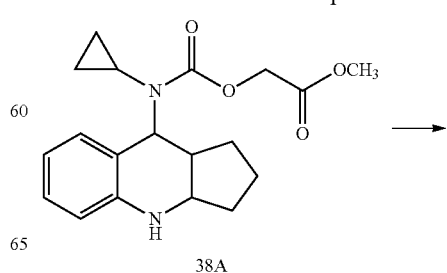

-continued

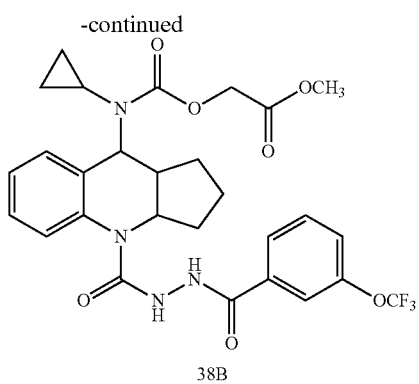

38B

Triphosgene (41 mg, 0.32 mmol) was added to a mixture of amine 38A (0.23 g, 0.67 mmol, prepared from 1E following a similar procedure as in Example 32, steps 1 and 2, and Example 14, step 1) and i-Pr₂NEt (0.14 mL, 0.80 mmol) in DCM (4 mL). The resulting mixture was stirred at room temperature for 1.5 h, and partitioned in EtOAc and water. The organic layer was separated, washed with brine, dried (MgSO₄), filtered and concentrated in vacuo. The residue was taken up with THF (2 mL), and treated with Hünigs base (0.14 mL, 0.80 mmol) and anhydrous hydrazine (0.05 mL, 1.59 mmol). The resulting mixture was stirred at room temperature overnight. The volatiles were removed. The residue was taken up with DCM (4 mL), and treated with Et₃N (0.14 mL, 1.0 mmol), DMAP (30 mg, 0.21 mmol), followed by 3-(trifluoromethoxy)benzoyl chloride (185 mg, 0.82 mmol). The resulting mixture was stirred at room temperature overnight. DCM was added and washed with 1 N HCl. The aqueous layer was separated and extracted with DCM. The organic extracts were combined, washed with brine, dried (MgSO₄), and concentrated. The residue was purified by a silica gel chromatography (eluted with EtOAc-hexanes, 1:1 to 2:1) to give the desired product hydrazine amide 38B.

Step 2

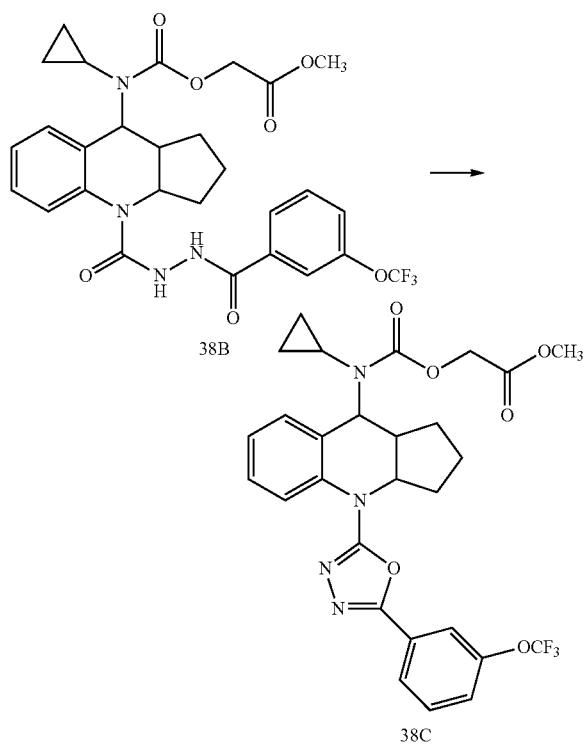

Starting material hydrazine amide 38B (50 mg) was treated with POCl₃ (1.5 mL) and heated at 120° C. for 2 h. The reaction mixture was cooled to room temperature and poured into DCM and washed with 1 N NaOH. The aqueous layer was extracted with DCM. The organic extracts were combined, washed with brine, and dried (MgSO₄), filtered and concentrated in vacuo. The residue was purified by preparative thin-layer-chromatography (eluted with 1:30 7 N NH₃/MeOH-DCM), to give desired product oxadiazole ester 38C (27 mg).

Step 3

[[[Cyclopropyl[cis,cis-2,3,3a,4,9,9a-hexahydro-4-[5-[3-(trifluoromethoxy)phenyl]-1,3,4-oxadiazol-2-yl]-1H-cyclopenta[b]quinolin-9-yl]amino]carbonyl]oxy] acetic acid (38)

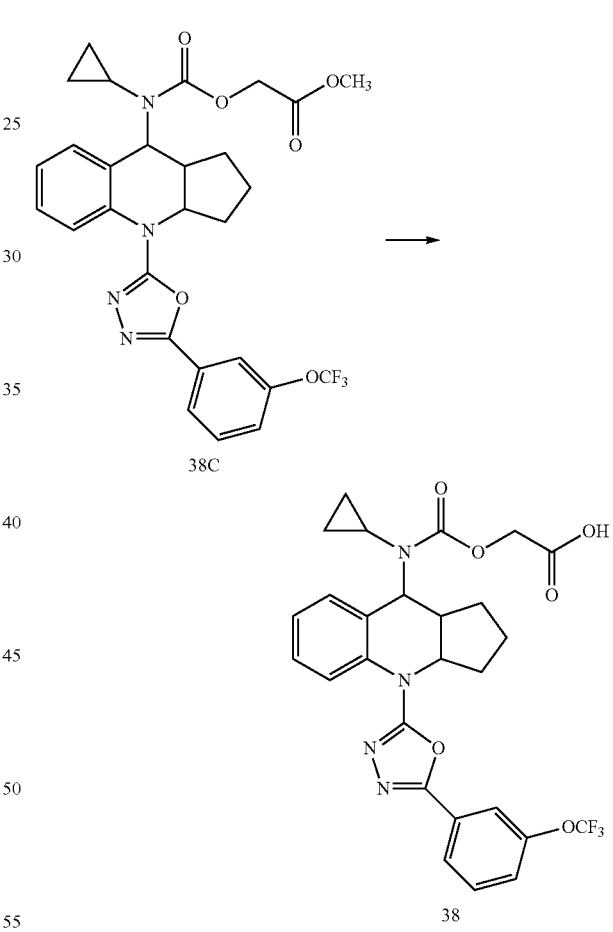

Starting material oxadiazole ester 38C (29 mg) in THF (0.5 mL) was treated with 2 N LiOH (0.5 mL). The resulting mixture was stirred at room temperature for 3 h. The reaction mixture was treated with 1 N HCl (aq.) until pH reached 6, and was extracted with DCM. The organic extracts were combined, washed with brine, dried (MgSO₄), filtered and concentrated in vacuo to give desired product 38, [M+H]⁺= 559.3.

The compounds in the following table were prepared following a similar protocol as described in Example 38.

| # | Structure | Stereo designation | Name | [M + H]+ |
|---|---|---|---|---|
| 38D | 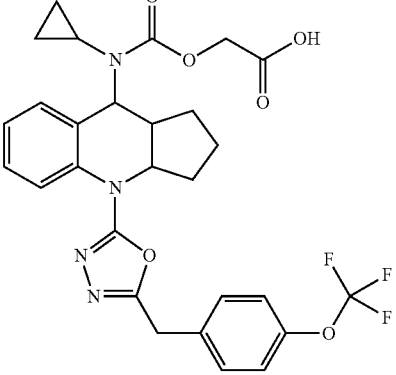 | racemic, cis, cis | [[[cyclopropyl[cis,cis-2,3,3a,4,9,9a-hexahydro-4-[5-[[4-(trifluoromethoxy)phenyl]methyl]-1,3,4-oxadiazol-2-yl]-1H-cyclopenta[b]quinoline-9-yl]amino]carbonyl]oxy]acetic acid | 573.2 |
| 38E | 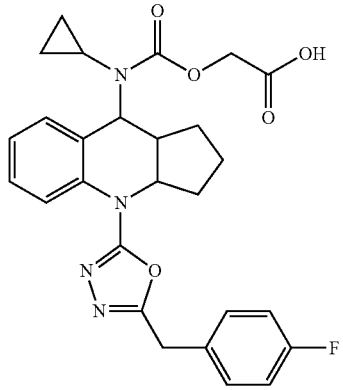 [SMILES: O=C(O)COC(=O)N(C1CC1)C1c2ccccc2N(c2nnc(Cc3ccc(F)cc3)o2)C2CCCC21] | racemic, cis, cis | [[[cyclopropyl[cis,cis-4-[5-[(4-fluorophenyl)methyl]-1,3,4-oxadiazol-2-yl]-2,3,3a,4,9,9a-hexahydro-1H-cyclopenta[b]quinoline-9-yl]amino]carbonyl]oxy]acetic acid | 507.2 |
| 38F | 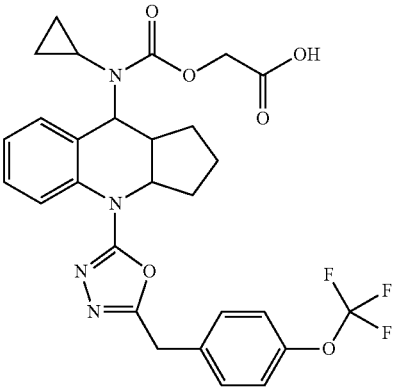 [SMILES: O=C(O)COC(=O)N(C1CC1)C1c2ccccc2N(c2nnc(Cc3ccc(OC(F)(F)F)cc3)o2)C2CCCC21] | single enantiomer, cis, cis peak 1 from chiral HPLC | [[[cyclopropyl[cis,cis 2,3,3a,4,9,9a-hexahydro-4-[5-[[4-(trifluoromethoxy)phenyl]methyl]-1,3,4-oxadiazol-2-yl]-1H-cyclopenta[b]quinoline-9-yl]amino]carbonyl]oxy]acetic acid | 573 |
| 38G | 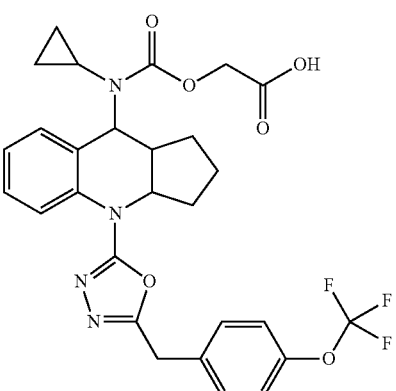 | single enantiomer, cis, cis peak 2 from chiral HPLC | [[[cyclopropyl[cis,cis-2,3,3a,4,9,9a-hexahydro-4-[5-[[4-(trifluoromethoxy)phenyl]methyl]-1,3,4-oxadiazol-2-yl]-1H-cyclopenta[b]quinoline-9-yl]amino]carbonyl]oxy]acetic acid | 573 |

Example 39

Preparation of Racemic 2-[{cis,cis-4-[(Benzyloxy)carbonyl]-2,3,3a,4,9,9a-hexahydro-1H-cyclopenta[b]quinolin-9-yl}(ethyl)amino]-1,3-thiazole-4-carboxylic acid (39)

Step 1

Benzyl cis,cis-9-{[4-(ethoxycarbonyl)-1,3-thiazol-2-yl]amino}-1,2,3,3a,9,9a-hexahydro-4H-cyclopenta[b]quinoline-4-carboxylate (39A)

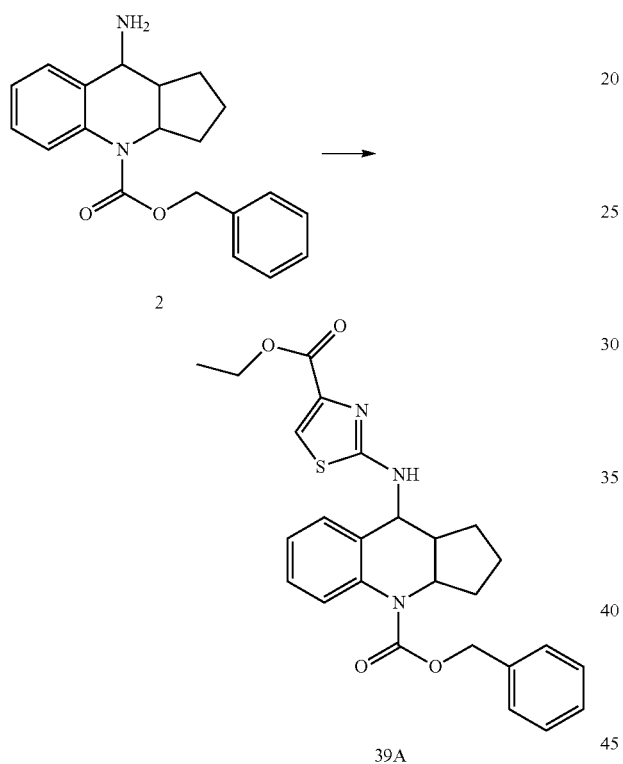

Benzyl cis,cis-9-amino-1,2,3,3a,9,9a-hexahydro-4H-cyclopenta[b]quinoline-4-carboxylate (2, 104 mg, 0.323 mmol, 1 equiv), Tris(dibenzylideneacetone)dipalladium (44 mg, 0.048 mmol, 0.15 equiv), dicyclohexylphosphino-2'-(N,N-dimethylamino)biphenyl (57 mg, 0.15 mmol, 0.45 equiv), and ethyl 2-bromo-1,3-thiazole-4-carboxylate (152 mg, 0.645 mg, 2.0 equiv) were combined in a microwave tube. Dioxane (3.2 mL) was added to the microwave tube, and nitrogen gas was bubbled through the reaction mixture for 5 min. Lithium bis(trimethylsilyl)amide in tetrahydrofuran (1.0 M, 0.484 mL, 0.484 mmol, 1.5 equiv) was then added, and the reaction mixture was heated to 110° C. After stirring at 110° C. for 25 min, the heating bath was removed and the reaction mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (5% ethyl acetate-hexanes, grading to 65% ethyl acetate-hexanes) to afford 39A [M+H]$^+$: 478.1.

Step 2

Benzyl cis,cis-9-[[4-(ethoxycarbonyl)-1,3-thiazol-2-yl](ethyl)amino]-1,2,3,3a,9,9a-hexahydro-4H-cyclopenta[b]quinoline-4-carboxylate (39B)

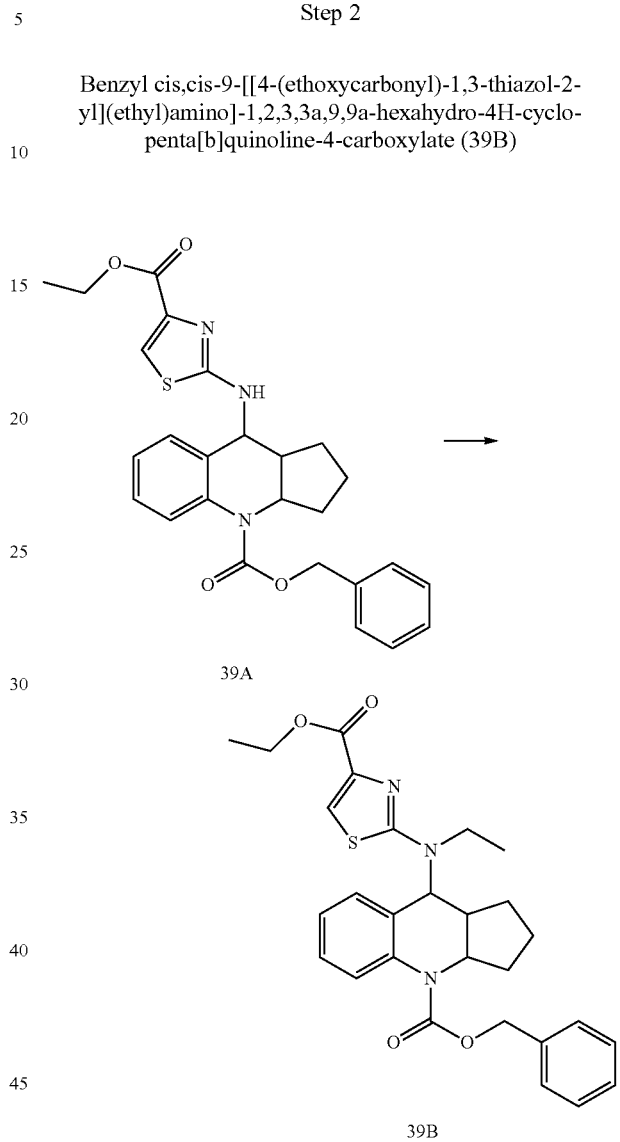

Lithium bis(trimethylsilyl)amide in tetrahydrofuran (1.0 M, 0.095 mL, 0.095 mmol, 1.0 equiv) was added to a solution of 39A (38 mg, 0.080 mmol, 1 equiv) in tetrahydrofuran (0.80 mL) at 0° C. The reaction mixture was stirred at 0° C. for 10 min, and then iodoethane (0.026 mL, 0.32 mmol, 4.0 equiv) was added. The cooling bath was removed, and the reaction mixture was stirred at 23° C. After stirring at 23° C. for 3 h, the temperature was increased to 40° C., and the reaction mixture was stirred for 16 h. After cooling to 23° C., the reaction mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (10% ethyl acetate-hexanes, grading to 40% ethyl acetate-hexanes) to afford 39B. [M+H]$^+$: 506.2.

Step 3

2-[{cis,cis-4-[(benzyloxy)carbonyl]-2,3,3a,4,9,9a-hexahydro-1H-cyclopenta[b]quinolin-9-yl}(ethyl)amino]-1,3-thiazole-4-carboxylic acid (39)

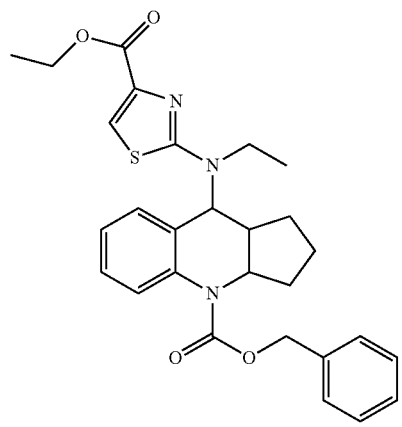

39B

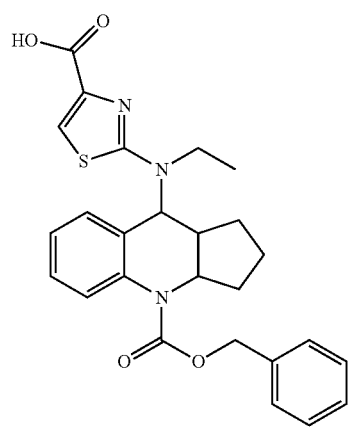

39

Compound 39 was prepared from benzyl cis,cis-9-[[4-(ethoxycarbonyl)-1,3-thiazol-2-yl](ethyl)amino]-1,2,3,3a,9,9a-hexahydro-4H-cyclopenta[b]quinoline-4-carboxylate 39B using a procedure similar to that used in Example 14, Step 3. [M+H]$^+$: 478.1.

Example 40

Preparation of Racemic 2-[Ethyl[cis,cis-2,3,3a,4,9,9a-hexahydro-4-[4-(trifluoromethoxy)benzoyl]-1H-cyclopenta[b]quinolin-9-yl]amino]-4-oxazolecarboxylic acid (40)

Step 1

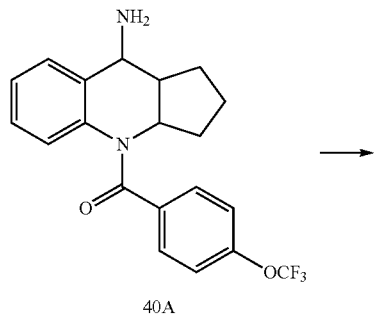

40A

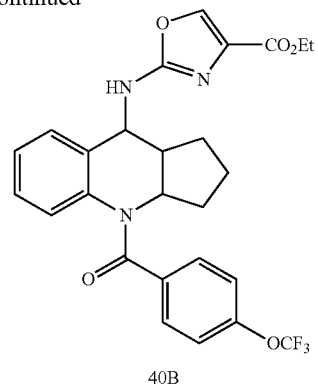

40B

Amine 40A (100 mg, 0.26 mmol, prepared from 1D following a similar procedure as in Example 14, step 1 and 2, and Example 2), ethyl 2-chlorooxazole-4-carboxylate (120 mg, 0.68 mmol) and iPr$_2$NEt were dissolved in dioxane (8 mL) and heated in a sealed tube at 130° C. overnight. The resulting mixture was cooled to room temperature, diluted with EtOAc and washed with 1 N HCl. The aqueous layer was separated and extracted with EtOAc. The organic extracts were combined and washed with brine, dried (MgSO$_4$), filtered and concentrated in vacuo. The residue was purified with preparative thin-layer-chromatography (eluted with 1:30 7 N NH$_3$/MeOH:DCM), to give the desired product amino oxazole 40B (71 mg).

Step 2

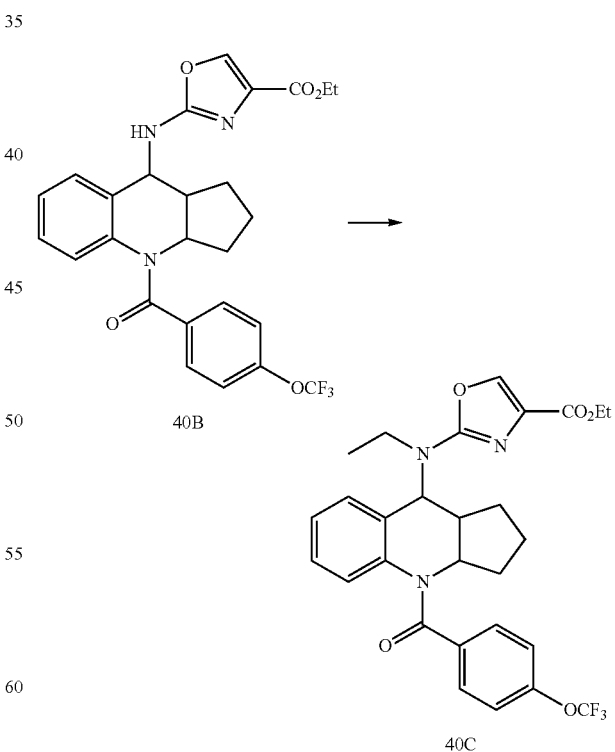

Starting material amino oxazole 40B (40 mg, 0.078 mmol) was dissolved in DMF (1 mL), treated with NaH (20 mg, 10 mmol). The mixture was stirred at room temperature for 1 h, and EtI (0.06 mL, 0.75 mmol) was added. The resulting mixture was stirred at room temperature overnight, and diluted with EtOAc and washed with water. The aqueous layer was separated and extracted with EtOAc. The organic extracts were combined and washed with brine, dried (MgSO₄), filtered and concentrated in vacuo. The residue was purified with preparative thin-layer-chromatography (eluted with 1:4 EtOAc-hexanes), to give the desired product ethyl amino oxazole 40C (28 mg).

Step 3: 2-[Ethyl[cis,cis-2,3,3a,4,9,9a-hexahydro-4-[4-(trifluoromethoxy)benzoyl]-1H-cyclopenta[b]quinolin-9-yl]amino]-4-oxazolecarboxylic acid (40)

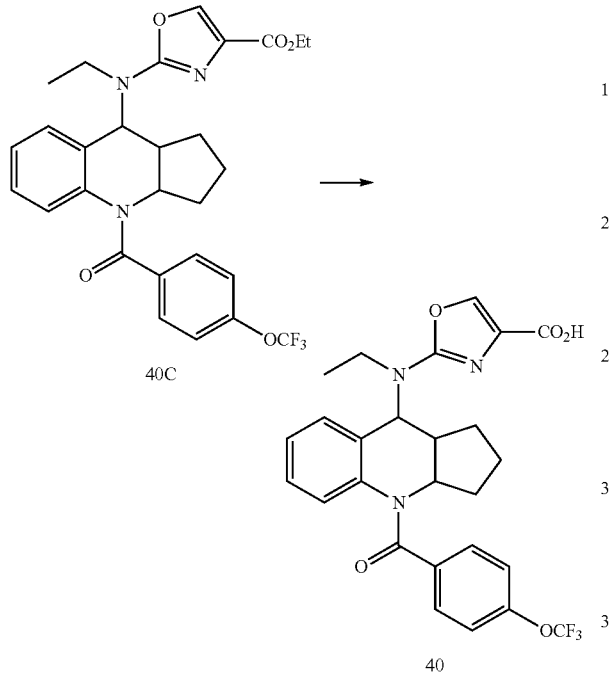

Starting material ethyl amino oxazole 40C (28 mg) in THF (0.5 mL) was treated with 2 N LiOH (0.5 mL). The resulting mixture was stirred at room temperature for 3 h. The reaction mixture was treated with 1 N HCl (aq.) until pH reached 6, and was extracted with DCM. The organic extracts were combined, washed with brine, dried (MgSO₄), filtered and concentrated in vacuo to give the desired product 40, [M+H]⁺=516.

Example 41

Preparation of Racemic 5-[Cyclopropyl[cis,cis-2,3,3a,4,9,9a-hexahydro-4-[4-(trifluoromethoxy)benzoyl]-1H-cyclopenta[b]quinolin-9-yl]amino]-1,3,4-oxadiazole-2-acetic acid (41)

Step 1

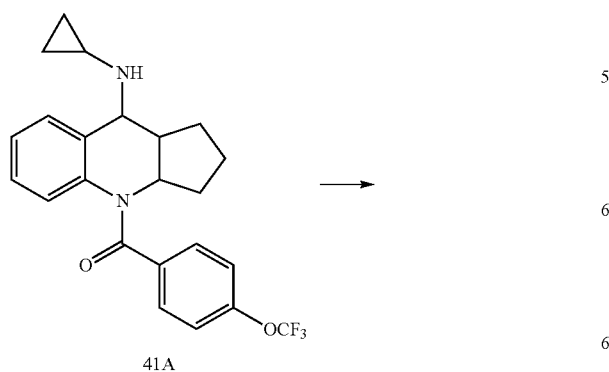

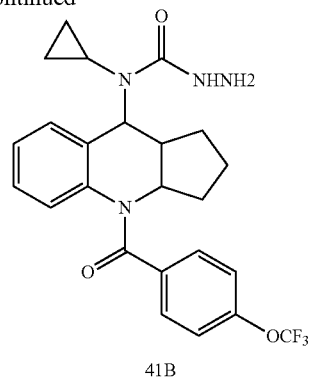

Triphosgene (148 mg, 0.50 mmol) was added to a mixture of starting amine 41A (200 mg, 0.48 mmol, prepared from 1D following a similar procedure as in Example 14, step 1 and 2, and Example 6, step 4) and iPr₂NEt (0.1 mL, 0.57 mmol) in DCM (4 mL). The resulting mixture was stirred at room temperature overnight. iPr₂NEt (0.1 mL, 0.57 mmol) was added followed by anhydrous hydrazine (0.1 mL. 3.2 mmol). The resulting mixture was stirred at room temperature for 2 h and concentrated in vacuo. The residue was purified with silica gel chromatography (eluted with 1:50 7 N NH₃/MeOH-DCM), to give N-cyclopropyl-N-[cis,cis-2,3,3a,4,9,9a-hexahydro-4-[4-(trifluoromethoxy)benzoyl]-1H-cyclopenta[b]quinolin-9-yl]hydrazine carboxamide 41B.

Step 2

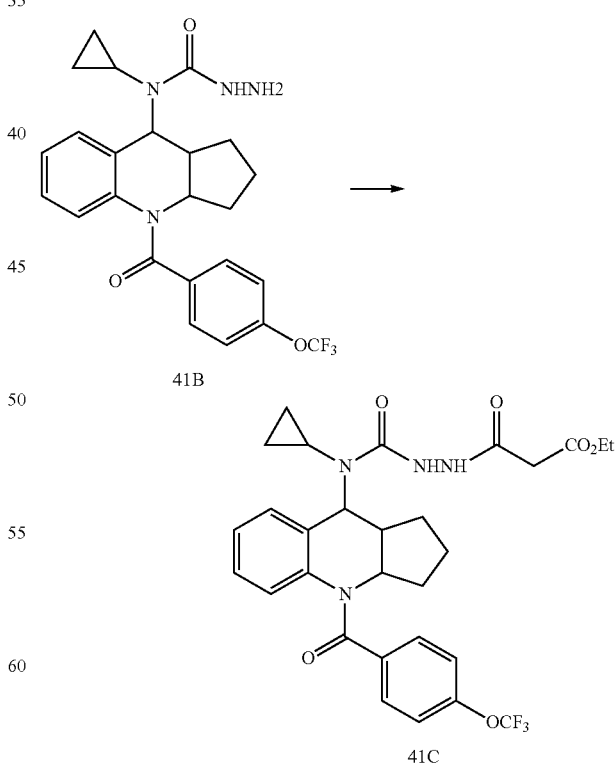

Starting material hydrazine 41B (170 mg, 0.36 mmol) and iPr₂NEt (0.1 mL, 0.57 mmol) were dissolved in DCM (4 mL)

and cooled to −4° C. To the mixture, ethyl malonyl chloride (136 mg, 0.90 mmol) was added. The resulting mixture was stirred at room temperature overnight. DCM and 0.1 N HCl were added. The aqueous layer was separated and extracted with DCM. The organic extracts were combined and washed with brine, dried (MgSO$_4$), filtered and concentrated in vacuo. The residue was purified with preparative thin-layer-chromatography (eluted with 1:50 7 N NH$_3$/MeOH-DCM), to give desired product hydrazine amide 41C (200 mg).

Step 3

5-[Cyclopropyl[cis,cis-2,3,3a,4,9,9a-hexahydro-4-[4-(trifluoromethoxy)benzoyl]-1H-cyclopenta[b]quinolin-9-yl]amino]-1,3,4-oxadiazole-2-acetic acid (41)

The starting material hydrazine amide 41C (214 mg, 0.36 mmol) was treated with POCl$_3$ (2 mL), and heated at 120° C. for 2 h. The reaction mixture was cooled to room temperature and poured into 4 N NaOH. The aqueous layer was separated and extracted with DCM. The organic extracts were combined and washed with brine, dried (MgSO$_4$), filtered and concentrated in vacuo. The residue was purified with preparative thin-layer-chromatography (eluted with 1:50 7 N NH$_3$/MeOH-DCM), to give desired product 41D (36 mg). The oxadiazole ester 41D (31 mg) in THF (0.5 mL) was treated with 2 N LiOH (0.5 mL). The resulting mixture was stirred at room temperature for 3 h and then treated with 1N HCl (aq.) until the pH turned 6. The aqueous layer separated and extracted with DCM. The organic extracts were combined, washed with brine, dried (MgSO$_4$), filtered and concentrated in vacuo to give desired product 41, [M+H]$^+$=543.3.

Example 42

Preparation of Racemic N-Cyclopropyl-N-[cis,cis-2,3,3a,4,9,9a-hexahydro-4-[4-(trifluoromethoxy)benzoyl]-1H-cyclopenta[b]quinolin-9-yl]-2H-tetrazole-5-propanamide (42)

Step 1

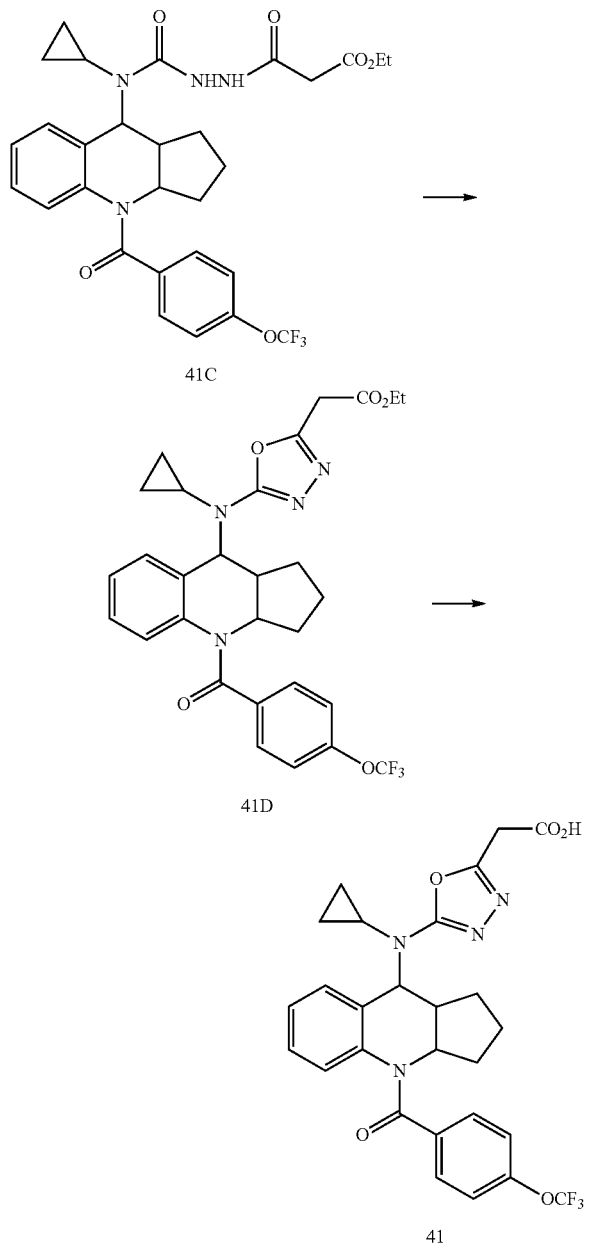

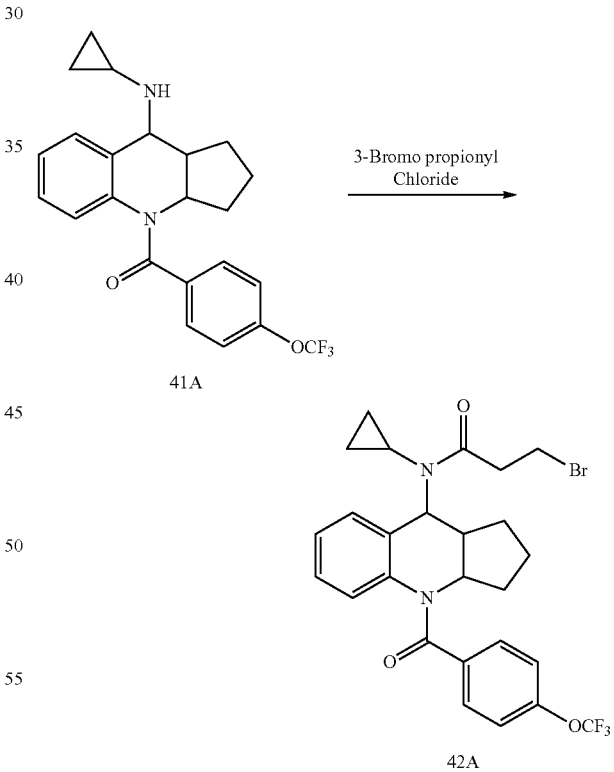

To a solution of the amine 41A (0.050 g, 0.119 mmol) in anhydrous dioxane (5 mL) was added 3-bromopropionyl-chloride (0.81 mg, 0.48 mmol) and Hunigs base (0.084 mL, 0.48 mmol) at 0° C. The mixture was stirred at room temperature for two hours. Removal of solvent and chromatographic purification using ethyl acetate/hexane gave the bromoamide 42A as a white solid (0.04 g, 71%)

Step 2

3-Cyano-N-cyclopropyl-N-[cis,cis-2,3,3a,4,9,9a-hexahydro-4-[4-(trifluoromethoxy)benzoyl]-1H-cyclopenta[b]quinolin-9-yl]propanamide (42B)

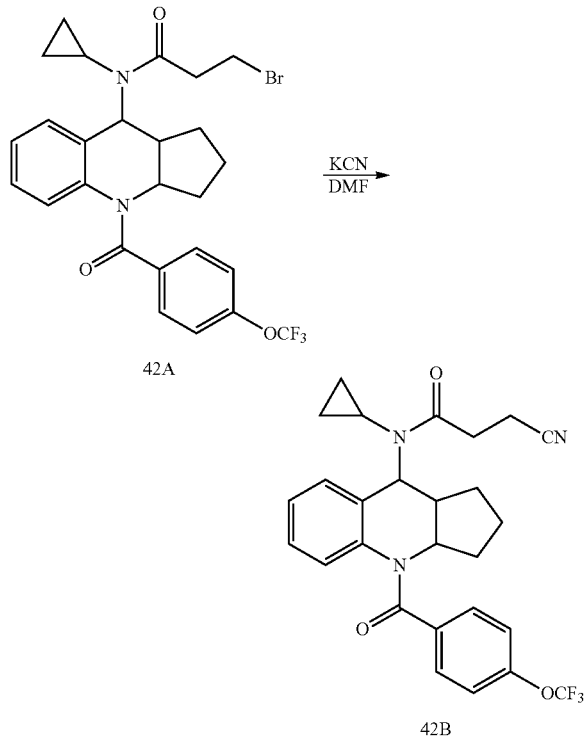

A mixture of bromo amide 42A and potassium cyanide in DMF was stirred at room temperature and heated to 65° C. overnight. The reaction mixture was taken into a separation funnel, washed with water, brine and dried over anhydrous sodium sulfate. Filtration and removal of the solvent gave the crude cyanide (42B), which was used in the next step without purification (0.032 mg, 76%).

Step 3: N-Cyclopropyl-N-[cis,cis-2,3,3a,4,9,9a-hexahydro-4-[4-(trifluoromethoxy)benzoyl]-1H-cyclopenta[b]quinolin-9-yl]-2H-tetrazole-5-propanamide (42)

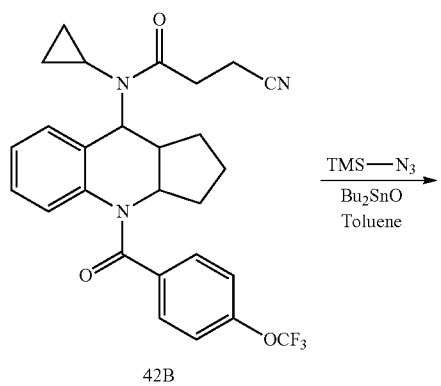

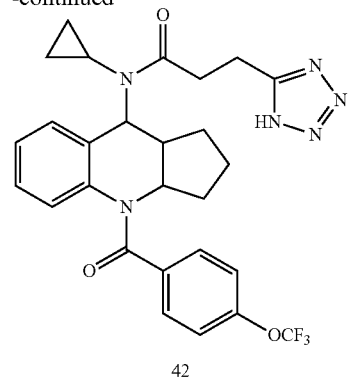

To a solution of the nitrile (42B) (0.08 g, 0.16 mmol) and trimethylsilylazide (0.32 mmol) in toluene (5 mL) was added dibutyltin oxide (0.016 mmol), and the mixture was heated for two days until the nitrile was consumed. The reaction mixture was concentrated and the residue was dissolved in methanol and concentrated. The residue was partitioned between ethyl acetate and 10% sodium bicarbonate solution. The organic phase was extracted with an additional 10% sodium bicarbonate solution. The combined aquous phase was acidified to pH 2 with 10% HCl and then extracted with ethyl acetate. The tetrazole product 42 was purified by reverse phase HPLC. (0.040 g, 45%), $[M+H]^+=541.3$.

Example 43

Preparation of Enantiopure 4-(Phenylmethyl)deuterated-cis,cis-9-[(3-carboxypropyl)cyclopropylamino]-1,2,3,3a,9,9a-hexahydro-4H-cyclopenta[b]quinoline-4-carboxylate-(9D) (43)

Step 1

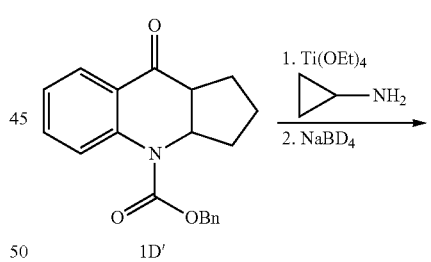

Titanium (IV) ethoxide (4.84 mL, 23.3 mmol, 2.50 equiv) was added to a solution of enantiopure benzyl cis,cis-9-oxo-1,2,3,3a,9,9a-hexahydro-4H-cyclopenta[b]quinoline-4-carboxylate 1D' (3.00 g, 9.34 mmol, 1 equiv, enantiomer of 1D after chiral HPLC) and cyclopropylamine (1.83 mL, 23.3 mmol, 2.50 equiv) in tetrahydrofuran. The reaction vessel was sealed and heated to 60° C. After stirring for 16 h, the reaction mixture was cooled to 23° C. and poured over saturated aqueous sodium chloride solution (50 mL). The biphasic mixture was stirred for 5 min, then filtered through Celite® with the aid of ethyl acetate. The filtrate was partitioned between ethyl acetate and brine, and the organic phase was then dried over sodium sulfate. The dried solution was filtered, and the filtrate was concentrated. The residue was dissolved in methanol (30 mL) and tetrahydrofuran (60 mL), and the solution was cooled to 0° C. Sodium borodeuteride (855 mg, 22.6 mmol, 2.50 equiv) was added to the cooled solution. After stirring for 15 min at 0° C., the cooling bath was removed, and the reaction mixture was partitioned between ethyl acetate and saturated aqueous sodium bicarbonate solution. The organic layer was washed with saturated aqueous sodium chloride solution, and the washed solution was dried over sodium sulfate. The dried solution was filtered, and the filtrate was concentrated to afford the desired product 43A. [M+H]$^+$: 364.3.

Step 2: Enantiopure 4-(Phenylmethyl)deuterated-cis, cis-9-[(3-carboxypropyl)cyclopropylamino]-1,2,3,3a, 9,9a-hexahydro-4H-cyclopenta[b]quinoline-4-carboxylate-(9D) (43)

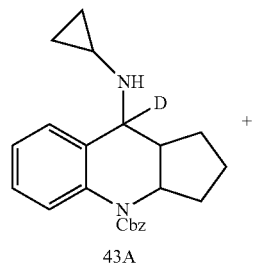

43A

+

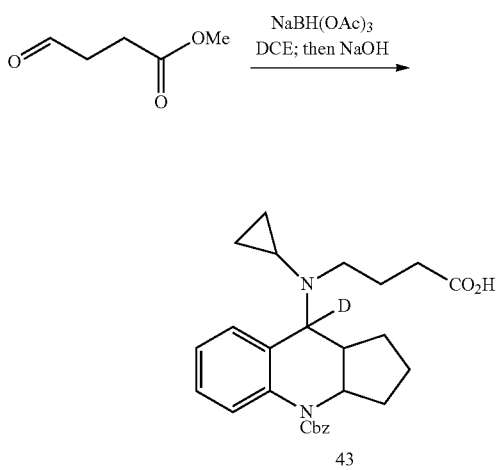

43

Enantiopure amine 43A (100 mg) and aldehyde (200 mg) in DCE were treated with NaBH(OAc)$_3$ (500 mg) at room temperature overnight. The reaction mixture was then diluted with EtOAc (50 mL), washed with aq. NaHCO$_3$ (30 mL) and brine (30 mL). The organic layer was dried with Na$_2$SO$_4$, concentrated by rotovap. The residue was dissolved in MeOH/THF (3/3 mL) and treated with 1 N aq. NaOH (3 mL) and the reaction mixture was stirred at room temperature for 3 hours. The crude product was directly purified by reverse phase HPLC to give the product 43 (100 mg, 85%) as white foam, [M+H]$^+$=450. $^1$H NMR (500 MHz, CD$_3$OD) δ ppm: 7.52-7.30 (m, 9H), 5.28 (d, J=12.0 Hz, 1H), 5.23 (d, J=12.5 Hz, 1H), 5.06 (m, 1H), 3.69-3.59 (m, 3H), 3.33 (m, 1H), 3.17 (m, 1H), 2.46 (dd, J=6.5, 7.0 Hz, 2H), 2.34 (m, 1H), 2.26 (m, 1H), 2.12 (m, 1H), 1.76 (m, 1H), 1.54-1.42 (m, 2H), 1.35 (m, 1H), 1.25-1.10 (m, 4H), 0.99 (m, 1H).

The compounds in following table were synthesized by as similar route as that described in Example 43, wherein the reducing agent in Step 1 was NaBH$_4$, instead of NaBD$_4$.

| # | Structure | Stereo designation | Name | [M + H]$^+$ |
|---|---|---|---|---|
| 43B | (structure shown) | cis, cis, single enantiomer | 4-((cis, cis-3-(benzyloxycarbonyl)-5-fluoro-1,2,2a,3,8,8a-hexahydrocyclobuta[b]quinolin-8-yl)(cyclopropyl)amino)butanoic acid | 453 |

| # | Structure | Stereo designation | Name | [M + H]+ |
|---|---|---|---|---|
| 43C | 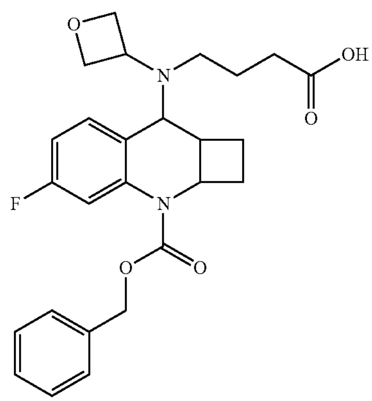 [SMILES: O=C(O)CCCN(C1COC1)C1c2ccc(F)cc2N(C(=O)OCc2ccccc2)C2CCC21] | cis, cis, single enantiomer | 4-((cis, cis-3-(benzyloxycarbonyl)-5-fluoro-1,2,2a,3,8,8a-hexahydrocyclobuta[b]quinolin-8-yl)(oxetan-3-yl)amino) butanoic acid | 491 [M + Na]+ |

Example 44

Preparation of Racemic 4-[Cyclopropyl[cis,cis-2,3,3a,4,9,9a-hexahydro-4-[4-(trifluoromethoxy)benzoyl]-1H-cyclopenta[b]quinolin-9-yl]amino]butanoic acid (44)

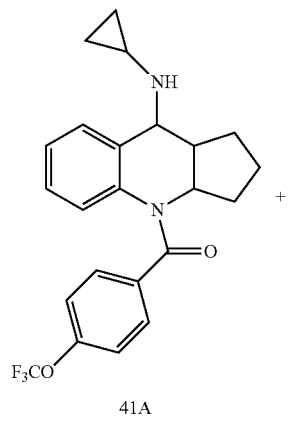

41A

+

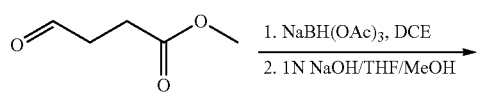

1. NaBH(OAc)₃, DCE
2. 1N NaOH/THF/MeOH

-continued

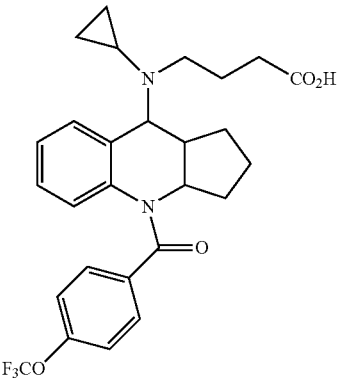

44

Amine 41A (100 mg, racemic) and aldehyde (200 mg) in DCE were treated with NaBH(OAc)₃ (500 mg) at room temperature overnight. The reaction mixture was then diluted with EtOAc (50 mL), washed with aq. NaHCO₃ (30 mL) and brine (30 mL). The organic layer was dried with Na₂SO₄, and then concentrated on a rotary evaporator. The residue was dissolved in MeOH/THF (3/3 mL) and treated with 1 N aq. NaOH (3 mL) and the reaction mixture was stirred at room temperature for 3 hours. The crude was directly purified by reverse phase HPLC to give the product 44 (100 mg, 85%) as a white foam, [M+H]+=503. ¹H NMR (500 MHz, CD₃OD) δ ppm: 7.56 (d, J=8.5 Hz, 2H), 7.51 (d, J=8.0 Hz, 1H), 7.29 (dd, J=7.5, 7.5 Hz), 7.23 (d, J=7.5 Hz, 2H), 7.16 (d, J=7.5 Hz, 1H), 7.12 (dd, J=7.0, 7.5 Hz, 1H), 5.26 (br, 1H), 5.09 (s, 1H), 3.83-3.64 (m, 3H), 3.32 (m, 1H), 3.19 (m, 1H), 2.59 (ddd, J=5.5, 6.0, 18 Hz, 1H), 2.48-2.24 (m, 3H), 1.80 (m, 1H), 1.49-1.38 (m, 3H), 1.32-1.27 (m, 2H), 1.22-1.10 (m, 3H), 0.99 (m, 1H).

The compounds in following table were synthesized by a similar route as described in Example 44.

| # | Structure | Stereo designation | Name | [M + H]+ |
|---|---|---|---|---|
| 44B | 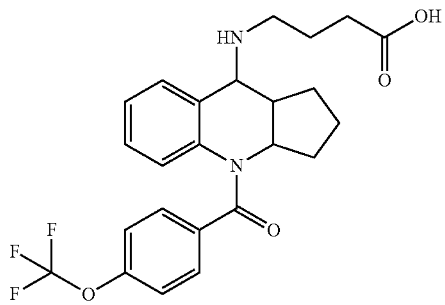 [SMILES: O=C(O)CCCNC1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl]amino]butanoic acid | 463 |
| 44C | 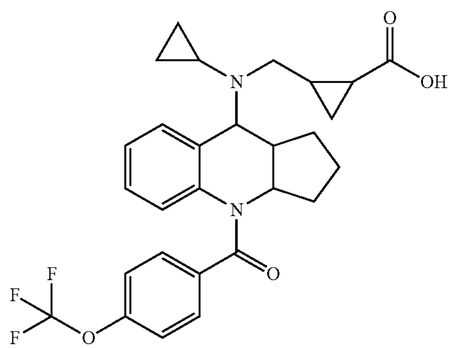 [SMILES: O=C(O)C1CC1CN(C1CC1)C1c2ccccc2N(C(=O)c2ccc(OC(F)(F)F)cc2)C2CCCC21] | (racemic) cis, cis at 3a,9,9a, (racemic) trans at cyclopropyl, | trans-2-[[cyclopropyl[cis,cis-2,3,3a,4,9,9a-hexahydro-4-[4-(trifluoromethoxy)benzoyl]-1H-cyclopenta[b]quinolin-9-yl]amino]methyl]cyclopropane-carboxylic acid | 515 |
| 44D | 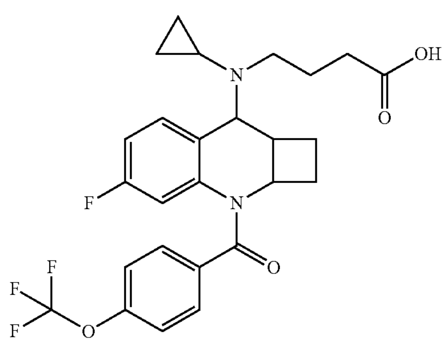 [SMILES: O=C(O)CCCN(C1CC1)C1c2ccc(F)cc2N(C(=O)c2ccc(OC(F)(F)F)cc2)C2CCC21] | cis, cis, single enantiomer | 4-(cyclopropyl(cis, cis-5-fluoro-3-(4-(trifluoromethoxy)benzoyl)-1,2,2a,3,8,8a-hexahydrocyclobuta[b]quinolin-8-yl)amino)butanoic acid | 507 |
| 44E | 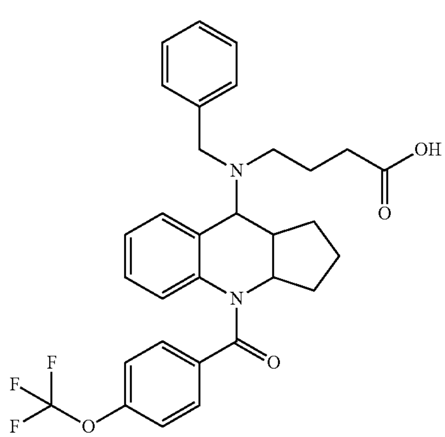 [SMILES: O=C(O)CCCN(Cc1ccccc1)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl](phenylmethyl)amino]butanoic acid | 553 |

| # | Structure | Stereo designation | Name | [M + H]+ |
|---|---|---|---|---|
| 44F | 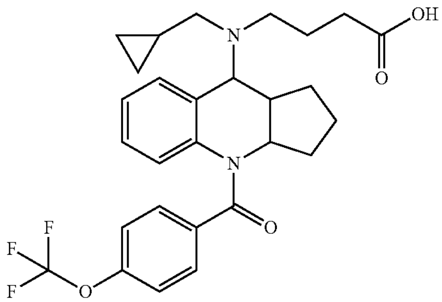 [SMILES: O=C(O)CCCN(CC1CC1)C1c2ccccc2N(C(=O)c2ccc(OC(F)(F)F)cc2)C2CCCC12] | racemic, cis, cis | 4-[(cyclopropylmethyl)[cis,cis-2,3,3a,4,9,9a-hexahydro-4-[4-(trifluoromethoxy)benzoyl]-1H-cyclopenta[b]quinolin-9-yl]amino]butanoic acid | 517 |

Example 45

Preparation of Racemic 4-[[cis,cis-2,3,3a,4,9,9a-Hexahydro-4-[4-(trifluoromethoxy)benzoyl]-1H-cyclopenta[b]quinolin-9-yl]amino]-4-oxobutanoic acid (45)

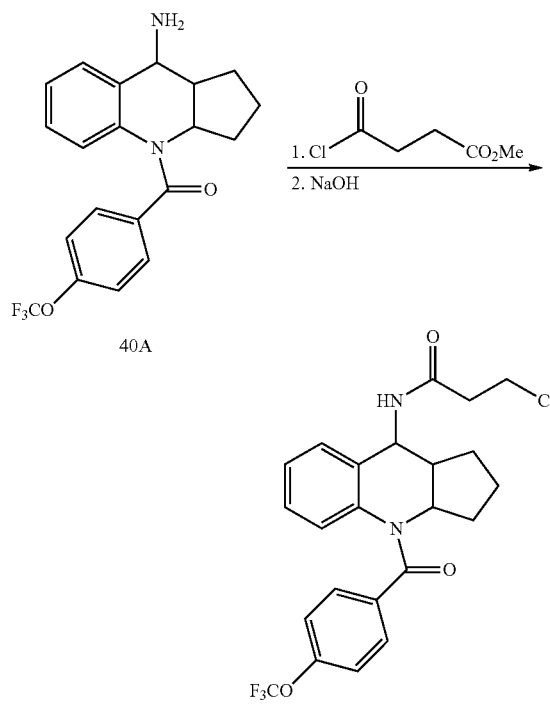

Methyl 4-chloro-4-oxobutanoate (0.2 mL, 2.2 equiv) was added to a solution of amine 40A (200 mg, 1 equiv) and N,N-diisopropylethylamine (0.2 mL, 3.00 equiv) in DCM (8 mL) at 23° C. (used a 23° C. water bath to control the exotherm that was observed during the addition). The reaction mixture was stirred for 1 h, and then it was partitioned between ethyl acetate and aqueous hydrochloric acid solution (1 N). The organic layer was washed sequentially with aqueous sodium hydroxide solution (1N) and saturated aqueous sodium chloride solution, and the washed organic layer was dried over sodium sulfate. The dried solution was filtered, and the filtrate was concentrated. The residue was purified by flash-column chromatography (20% ethyl acetate-hexanes, grading to ethyl acetate) to afford the methyl ester of the desired product.

Aqueous sodium hydroxide solution (1 N, 3 mL) was added to a solution of the ester (80 mg,) in THF/MeOH (3/3 mL). The reaction was stirred at room temperature overnight. The mixture was purified by reverse phase HPLC to give the desired acid 45, [M+H]+: =477.

Example 46

Preparation of Enantiopure 4-[Cyclopropyl[cis,cis-4-[2-[(4-fluorophenyl)amino]-2-oxoethyl]-2,3,3a,4,9,9a-hexahydro-1H-cyclopenta[b]quinolin-9-yl]amino]-4-oxobutanoic acid (46)

Step 1

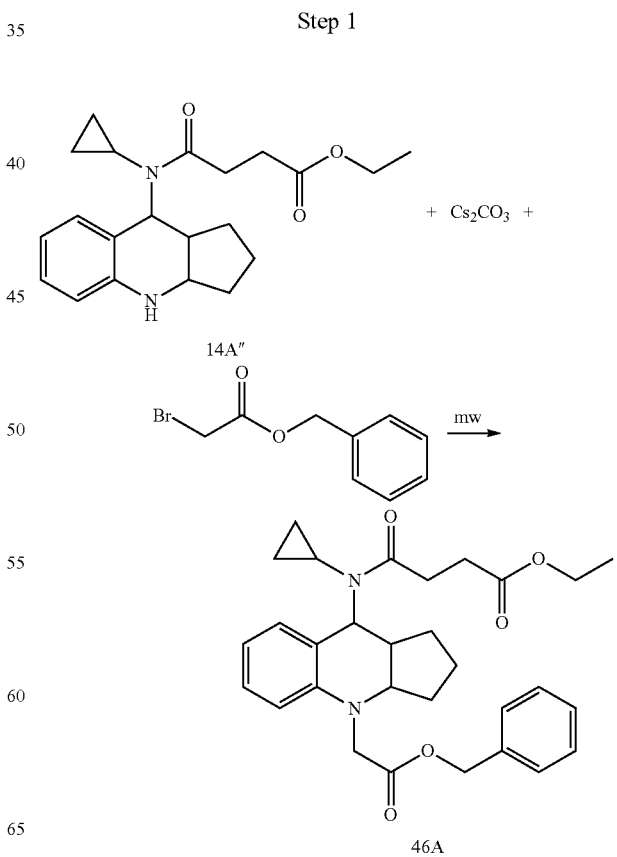

Cs₂CO₃ (110 mg, 0.337 mmol) was added to a solution of enantiopure amine 14A" (60 mg, 0.168 mmol, prepared in the same manner as compound 14A' with an ethyl ester.) in DMF (2 mL), and the mixture was stirred at rt for 30 mins. Benzyl 2-bromoacetate (170 µL, 0.84 mmol) was added. The resultant mixture was placed in a Biotage microwave reactor: T=120° C. t=1 h, Absorption=High. EtOAc (10 mL) was added to the cooled mixture, followed by H₂O (10 mL). The organic layer was washed with brine (10 mL), dried over MgSO₄ and concentrated. The residue was purified via silica gel column chromatography (EtOAc/Hexane=1:2), to obtain enantiopure benzyl ester 46A as a brown syrup, 32 mg; [M+H]⁺=505.

Step 2

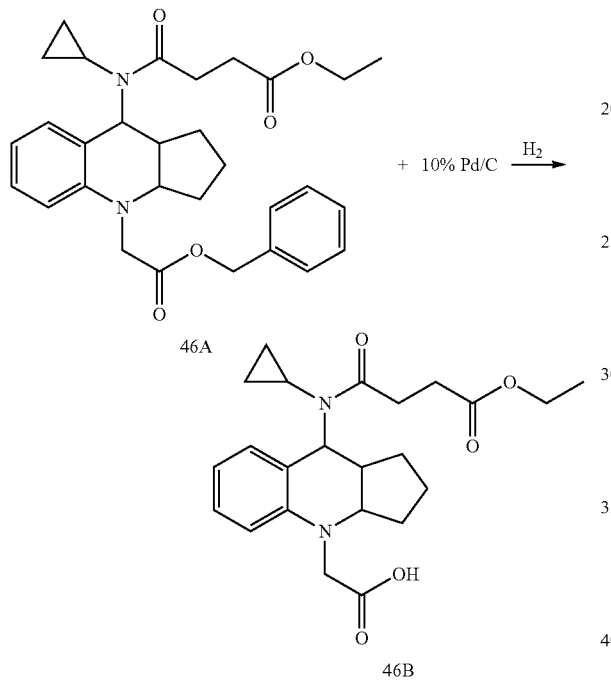

46A

46B

10% Pd on C (6 mg) was added to a solution of benzyl ester (26 mg, 0.05 mmol) in a mixed solvent of EtOH (3 mL)-EtOAc (1 mL). The resultant mixture was degassed and filled with H₂ (balloon, 3 times), the mixture was kept under H₂, stirring at rt for 2 h. The catalyst was filtered off and washed with EtOH. The filtrate was concentrated to obtain a clear syrup as the acid, 17 mg; [M+H]⁺=415.

Step 3

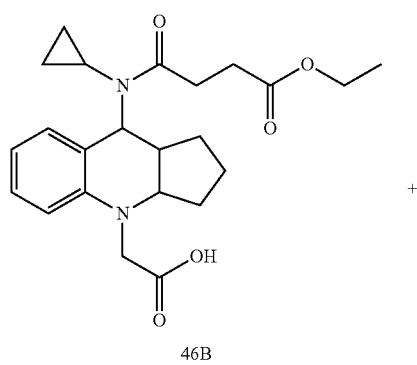

46B

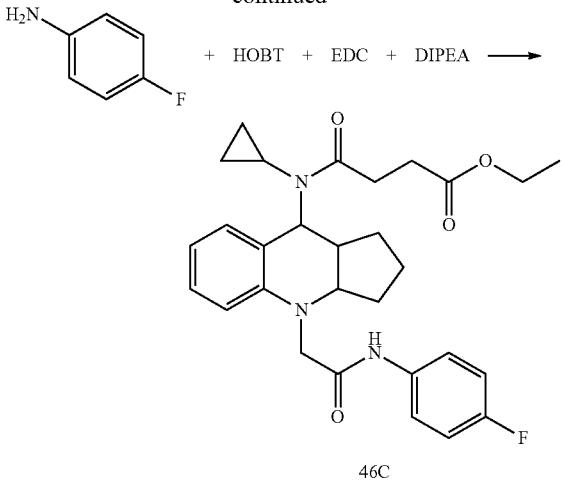

46C

The above obtained enantiopure acid 46B (17 mg, 0.041 mmol), 4-fluoroaniline (7 µL, 0.082 mmol), HOBt (11 mg, 0.082 mmol), EDC (16 mg, 0.082 mmol) and DIPEA (22 µL, 0.123 mmol) were mixed in CH₂Cl₂ (1 mL), and the resultant mixture was kept stirring at rt overnight. The mixture was concentrated, and the residue was purified via silica gel column chromatography (EtOAc/Hexane=1:1) to obtain amide 46C as a clear syrup, 17 mg; [M+H]⁺=508.

Step 4

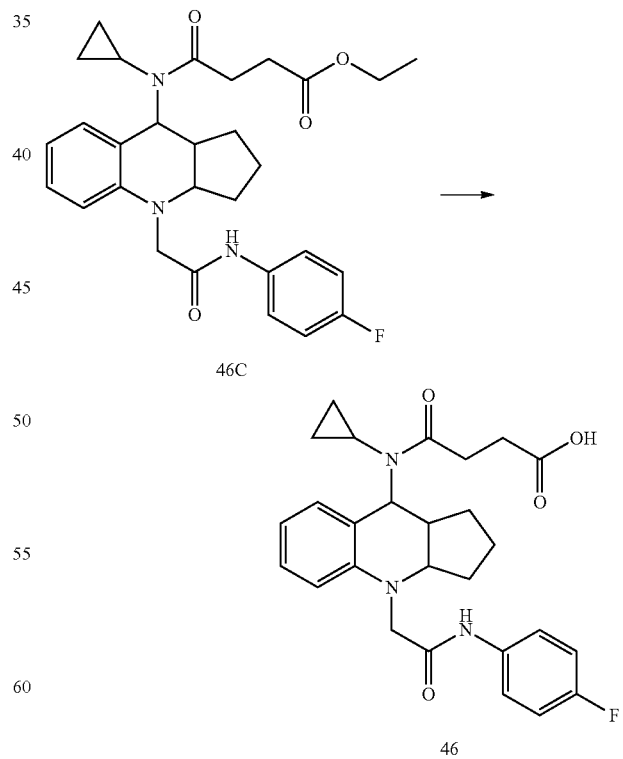

46C

46

The above obtained amide was converted to the desired enantiopure acid 46 using a similar procedure to that described in Example 14, [M+H]⁺=479.7. ¹H NMR (500

MHz, CDCl₃) δ ppm: 7.54 (m, 2H); 7.10 (m, 1H); 7.01 (m, 2H); 6.75 (m, 1H); 6.52 (m, 1H); 3.93 (s, 2H); 3.76 (m, 2H); 3.05 (m 1H); 2.75~2.63 (m, 5H); 1.86 (m, 6H); 1.12~0.90 (m, 4H).

Example 47

Preparation of Racemic 4-[Acetyl[cis,cis-2,3,3a,4,9,9a-hexahydro-4-[4-(trifluoromethoxy)benzoyl]-1H-cyclopenta[b]quinolin-9-yl]amino]butanoic acid (47)

Step 1: Cis,cis-2,3,3a,4,9,9a-hexahydro-n-(4-hydroxybutyl)-4-[4-(trifluoromethoxy)benzoyl]-1H-cyclopenta[b]quinolin-9-amine (47A)

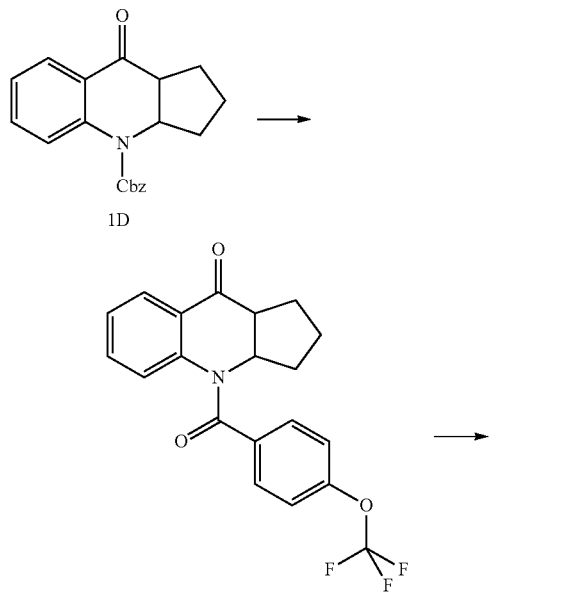

Cis,cis-2,3,3a,4,9,9a-hexahydro-n-(4-hydroxybutyl)-4-[4-(trifluoromethoxy)benzoyl]-1H-cyclopenta[b]quinolin-9-amine 47A was obtained from 1D following the similar procedure as Example 14, step 1, 2 to obtain ketone amide 47A' which was reacted with 4-hydroxybutyl amine following similar procedure as Example 6, step 4.

Step 2: N-[4-(Acetyloxy)butyl]-N-[cis,cis-2,3,3a,4,9,9a-hexahydro-4-[4-(trifluoromethoxy)benzoyl]-1H-cyclopenta[b]quinolin-9-yl]acetamide (47B)

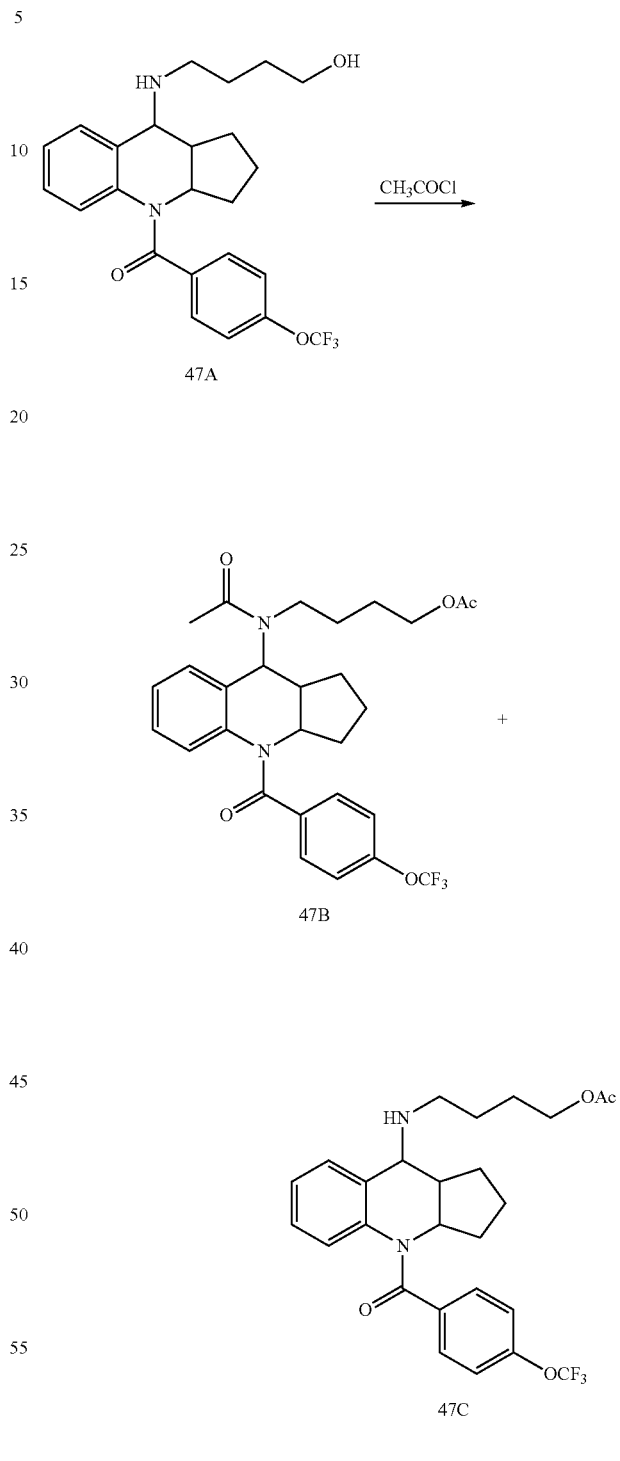

To a solution of the amino alcohol 47A (0.312 g, 0.696 mmol) in anhydrous dichloromethane (10 mL) was added acetyl chloride (0.19 mL, 2.78 mmol) and Hunigs base (0.61 mL, 3.48 mmol) at 0° C. The mixture was stirred at room temperature for six hours. Removal of solvent and chromatographic purification using ethyl acetate/hexane gave the amide 47B as the major product as a white solid (0.3 g, 81%) and small amount of 47C.

Step 3: N-[cis,cis-2,3,3a,4,9,9a-hexahydro-4-[4-(trifluoromethoxy)benzoyl]-1H-cyclopenta[b]quinolin-9-yl]-N-(4-hydroxybutyl)acetamide (47D)

Step 4: 4-[Acetyl[cis,cis-2,3,3a,4,9,9a-hexahydro-4-[4-(trifluoromethoxy)benzoyl]-1H-cyclopenta[b]quinolin-9-yl]amino]butanoic acid (47)

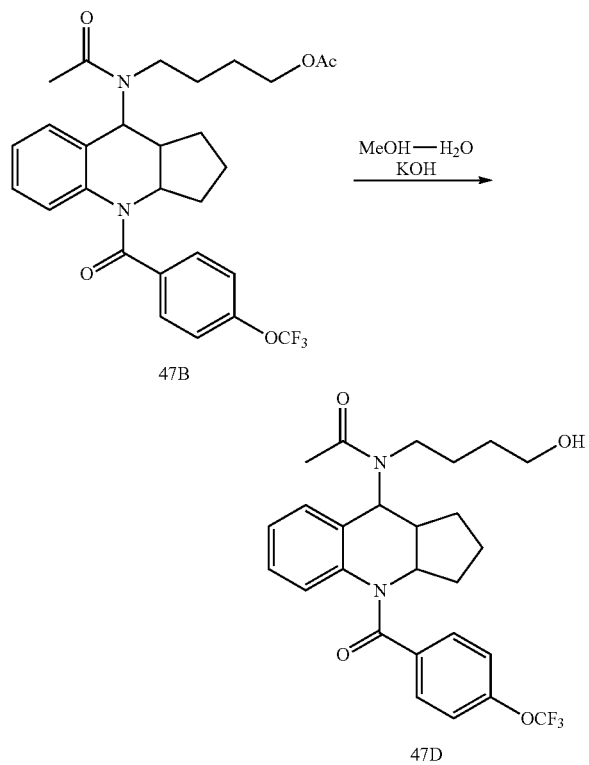

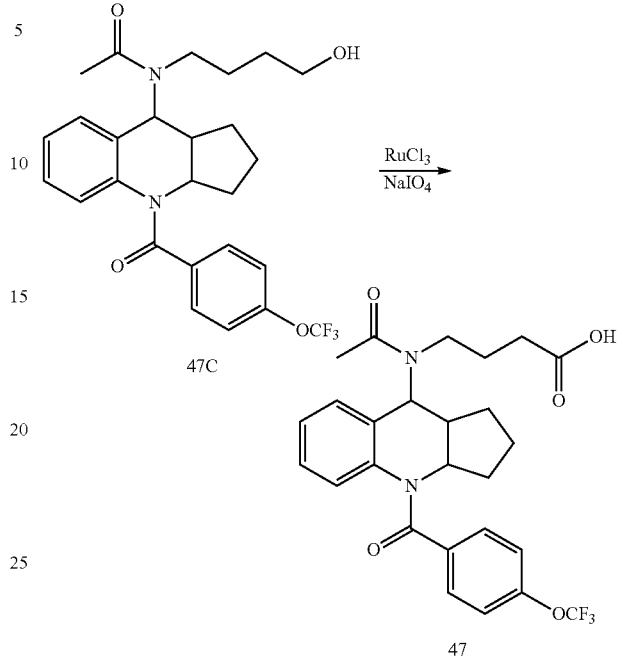

A solution of the acetate 47B (0.102 g, 0.19 mmol) in methanol (5 mL) and water (1 mL) was treated with potassium hydroxide (0.76 mmol) and refluxed for one hour. The reaction mixture was concentrated and extracted with ethyl acetate, washed with water, brine and dried over anhydrous sodium sulfate. Filtration and removal of the solvent gave the crude alcohol 47D which was used for the next step without purification (0.070 g, 75%).

To a solution of the alcohol 47C (0.051 mmol) in carbon tetrachloride/acetonitrile/water (2 mL, 2 mL, 3 mL) was treated with sodium periodate followed by catalytic amount of rutheniumchloride.trihydrate. The reaction mixture was stirred at room temperature for two hours, 1 mL of saturated ammonium chloride solution was added and filtered. The filtrate diluted with ethyl acetate and taken into a separatory funnel, was washed with water, brine and dried over anhydrous sodium sulfate. Removal of the solvent gave the crude acid 47 which was purified by using reverse phase HPLC. (0.015 mg, 60%). [M+H]$^+$=505.3.

The compounds in the following table were prepared in a similar procedure as showed above in Example 47.

| # | Structure | Stereo designation | Name | [M + H]$^+$ |
|---|---|---|---|---|
| 47D | 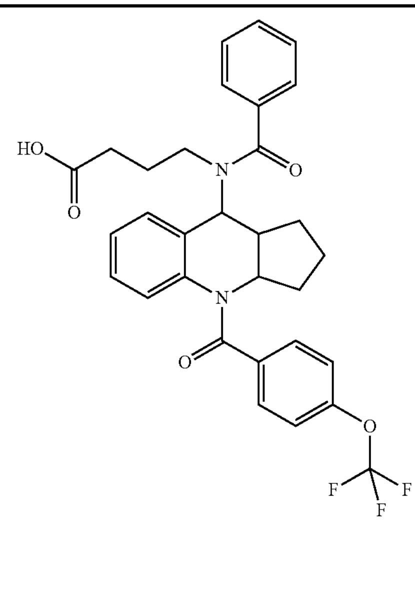 | racemic, cis, cis | 4-[benzoyl[cis,cis-2,3,3a,4,9,9a-hexahydro-4-[4-(trifluoromethoxy)benzoyl]-1H-cyclopenta[b]quinolin-9-yl]amino]butanoic acid | 567.3 |

-continued

| # | Structure | Stereo designation | Name | [M + H]+ |
|---|---|---|---|---|
| 47E | 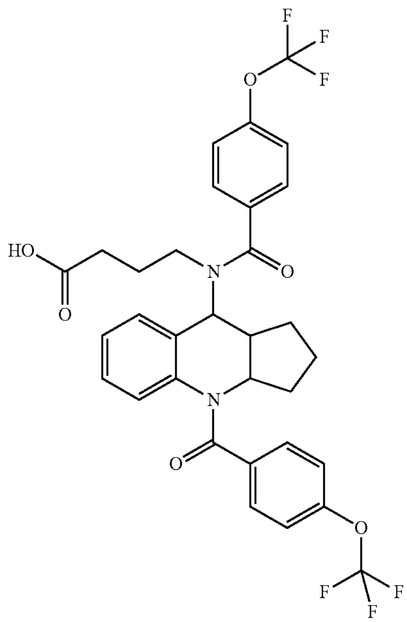 [SMILES: O=C(O)CCCN(C(=O)c1ccc(OC(F)(F)F)cc1)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl][4-(trifluoromethoxy)benzoyl]amino]butanoic acid | 651.4 |
| 47F | 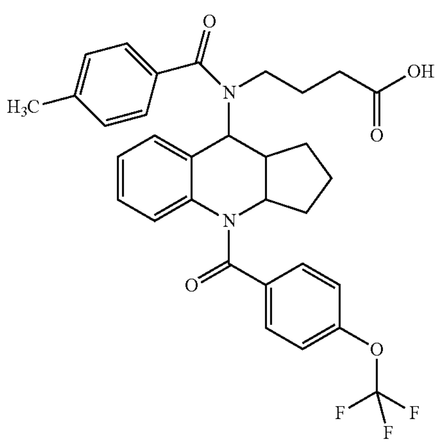 [SMILES: Cc1ccc(C(=O)N(CCCC(=O)O)C2c3ccccc3N(C(=O)c3ccc(OC(F)(F)F)cc3)C3CCCC23)cc1] | racemic, cis, cis | 4-[[cis,cis-2,3,3a,4,9,9a-hexahydro-4-[4-(trifluoromethoxy)benzoyl]-1H-cyclopenta[b]quinolin-9-yl](4-methylbenzoyl)amino]butanoic acid | 581.3 |
| 47G | 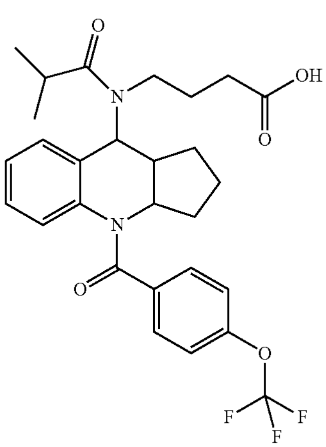 [SMILES: CC(C)C(=O)N(CCCC(=O)O)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl](2-methyl-1-oxopropyl)amino]butanoic acid | 533.3 |

Example 48

Preparation of Enantiopure Ketone Intermediate Containing a Bridgehead Methyl Group for Compounds 48 and 48C

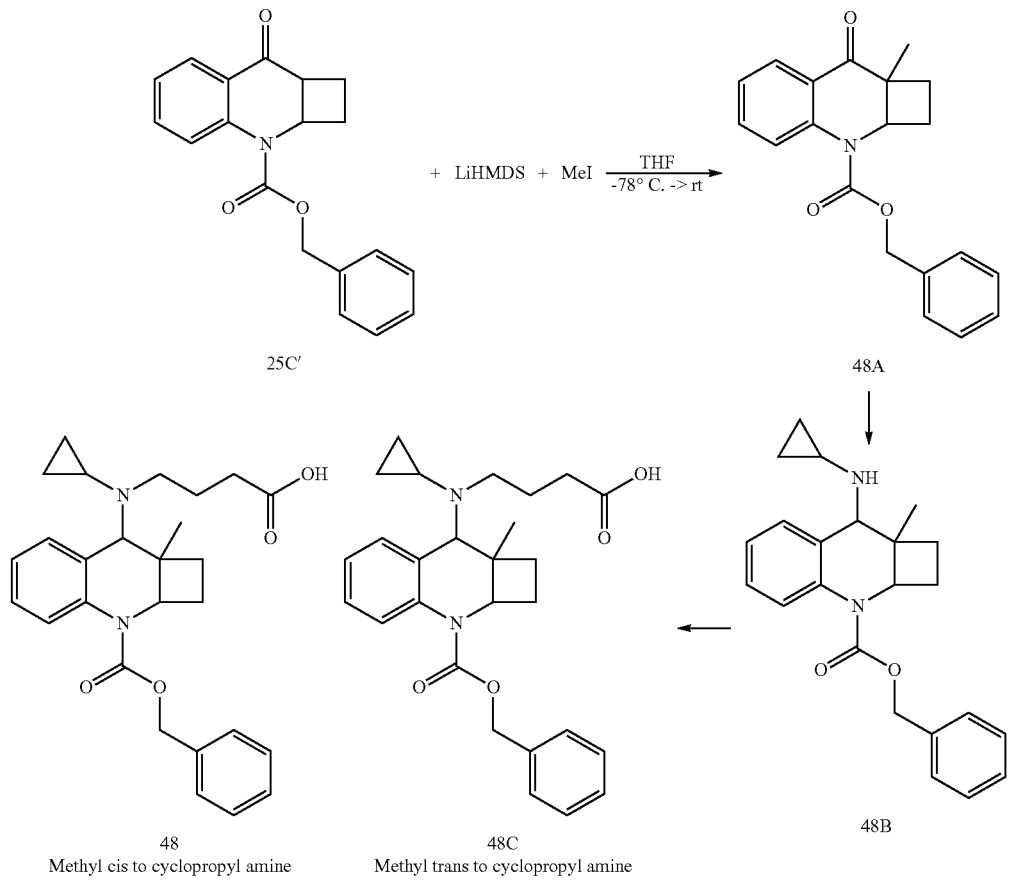

The ketone 25C' (0.5 g, 1.62 mmol, single enantiomer after resolution of the racemate 25C via chiral HPLC) was taken up in 5 mL of THF, and cooled to −78° C. To this mixture, LiHMDS was slowly added and the resulting solution stirred for one hour. Excess methyl iodide was then slowly added at −78° C., and the ice bath was removed. The reaction mixture was stirred at room temperature for an additional hour. The solution was quenched with aqueous NH$_4$Cl and extracted with ethyl acetate (20 mL) three times. The combined organic layers were then dried over anhydrous sodium sulfate. The filtrate was concentrated in vacuo to afford the product 48A (0.480 g) in 92% yield.

The ketone 48A was converted to a mixture of the enantiopure acids 48 and 48C using procedures similar to those used for Example 1, Step 5 and Example 43, Steps 2. The acids 48 and 48C were separated at the last stage.

| # | Structure | Stereo designation | Name | [M + H]$^+$ |
|---|-----------|--------------------|----|-----|
| 48 | 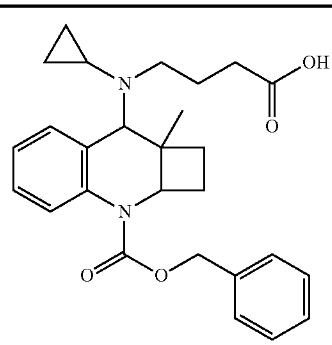 | cis, cis (cyclobutyl ring and cyclopropyl amine), methyl trans to cyclopropyl amine, single enantiomer | 4-((cis, cis-3-(benzyloxycarbonyl)-8a-methyl-1,2,2a,3,8,8a-hexahydrocyclobuta[b]quinolin-8-yl)(cyclopropyl)amino) butanoic acid | 449 |

| # | Structure | Stereo designation | Name | [M + H]+ |
|---|---|---|---|---|
| 48C | 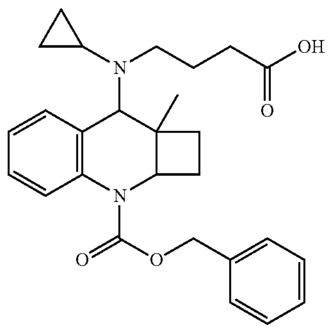 [SMILES: CC12CCC1N(C(=O)OCc1ccccc1)c1ccccc1C2N(CCCC(=O)O)C1CC1] | Cyclobutyl ring cis fused which is trans to cyclopropyl amine, methyl cis to cyclopropyl amine, single enantiomer | 4-((cis, trans-3-(benzyloxycarbonyl)-8a-methyl-1,2,2a,3,8,8a-hexahydrocyclobuta[b]quinolin-8-yl)(cyclopropyl)amino)butanoic acid | 449 |

Example 49

Preparation of Ketone Intermediate for enantiopure 4-[(2,4-Difluorophenyl)methyl]cis,cis-7-bromo-9-[(3-carboxy-1-oxopropyl)cyclopropylamino]-1,2,3,3a,9,9a-hexahydro-4H-cyclopenta[b]quinoline-4-carboxylate (49) and enantiopure 4-[[cis,cis-7-bromo-2,3,3a,4,9,9a-hexahydro-4-[4-(trifluoromethoxy)benzoyl]-1H-cyclopenta[b]quinolin-9-yl]cyclopropylamino]-4-oxobutanoic acid (49B)

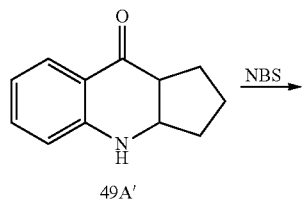

49A'

-continued

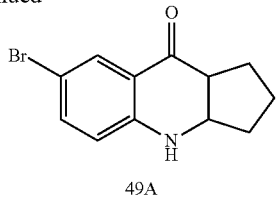

49A

To a stirring solution of enantiomerically pure compound cis-49A' (800 mg, 4.27 mmol, prepared in a similar sequence in Example 17, steps 1, 2, 3 where the racemic ketone was resolved by chiral HPLC.) in DMF (40 mL) was added NBS (760 mg, 4.27 mmol). The resulting solution was stirred at room temperature overnight. The mixture was diluted with EtOAc. The organic layer was washed with water, brine, dried (MgSO$_4$), filtered and concentrated in vacuo to give desired enantiomerically pure cis product 49A (1.14 g) as a yellow solid.

Following procedures similar to those described in Examples 22 without hydrolysis (for 49) or Example 14, step 2 (for 49B), and Example 6, step 4, and Example 7, enantiopure cis ketone 49A was converted into compounds 49 and 49B below.

| # | Structure | Stereo designation | Name | [M + H]+ |
|---|---|---|---|---|
| 49 | 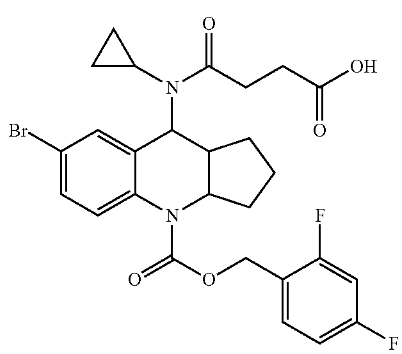 [SMILES: O=C(O)CCC(=O)N(C1CC1)C1c2cc(Br)ccc2N(C(=O)OCc2ccc(F)cc2F)C2CCCC21] | cis, cis, single enantiomer | 4-[(2,4-difluorophenyl)methyl] cis,cis-7-bromo-9-[(3-carboxy-1-oxopropyl)cyclopropylamino]-1,2,3,3a,9,9a-hexahydro-4H-cyclopenta[b]quinoline-4-carboxylate | 579.3 |

-continued

| # | Structure | Stereo designation | Name | [M + H]+ |
|---|---|---|---|---|
| 49B | 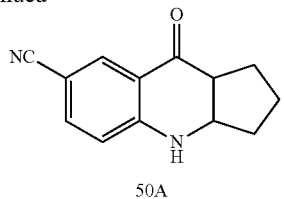 | cis, cis,, single enantiomer | 4-[[cis, cis-7-bromo-2,3,3a,4,9,9a-hexahydro-4-[4-(trifluoromethoxy)benzoyl]-1H-cyclopenta[b]quinolin-9-yl]cyclopropylamino]-4-oxobutanoic acid | 597.3 |

Example 50

Preparation of Ketone Intermediate for enantiopure 4-[[cis,cis-7-cyano-2,3,3a,4,9,9a-hexahydro-4-[4-(trifluoromethoxy)benzoyl]-1H-cyclopenta[b]quinolin-9-yl]cyclopropylamino]-4-oxobutanoic acid (50)

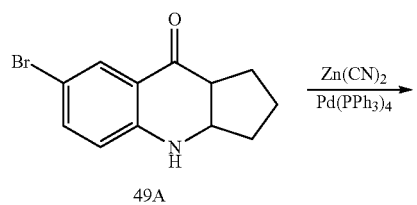

49A

-continued

50A

Starting material enantiopure cis 49A (100 mg, 0.376 mmol), Zn(CN)$_2$ (44 mg, 0.376 mmol), Pd(PPh$_3$)$_4$ (43 mg, 0.0037 mmol) were mixed in DMF (1.3 mL) and heated in a microwave oven at 110° C. for 30 min. The reaction mixture was diluted with EtOAc and washed with water. The organic layer was separated and washed with brine, dried (MgSO$_4$), filtered, and concentrated. The residue was purified with preparative TLC, eluting with EtOAc-hexanes, 1:1, to give desired product enantiopure cis 50A (10 mg).

Following procedures similar to those described in Examples 14, step 2, Example 6, step 4, Example 7, ketone 50A was converted into enantiopure compound 50. [M+H]+: 542.3

| # | Structure | Stere designation | Name | [M + H]+ |
|---|---|---|---|---|
| 50 | 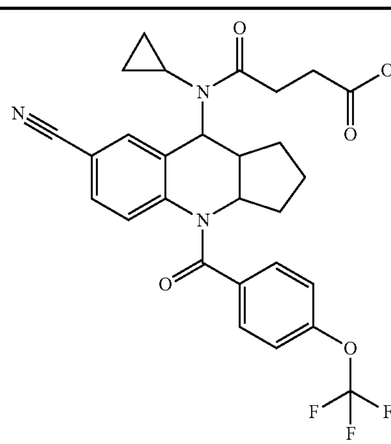 | cis, cis,, single enantiomer | 4-[[cis, cis-7-cyano-2,3,3a,4,9,9a-hexahydro-4-[4-(trifluoromethoxy)benzoyl]-1H-cyclopenta[b]quinolin-9-yl]cyclopropylamino]-4-oxobutanoic acid | 542.3 |

Example 51

Preparation of enantiopure cis Ketone Intermediate for enantiopure Compound 4-[Cyclopropyl[cis,cis-2,3,3a,4,9,9a-hexahydro-7-methyl-4-[4-(trifluoromethoxy)benzoyl]-1H-cyclopenta[b]quinolin-9-yl]amino]-4-oxobutanoic acid (51)

Example 52

Preparation of Intermediate (52B) for enantiopure 4-(Cyclopropyl(cis,cis-5,6-difluoro-3-(4-(trifluoromethoxy)benzoyl)-1,2,2a,3,8,8a-hexahydrocyclobuta[b]quinolin-8-yl)amino)-4-oxobutanoic acid (52)

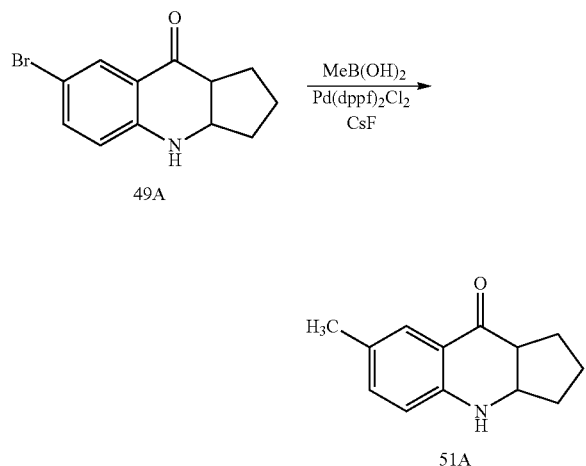

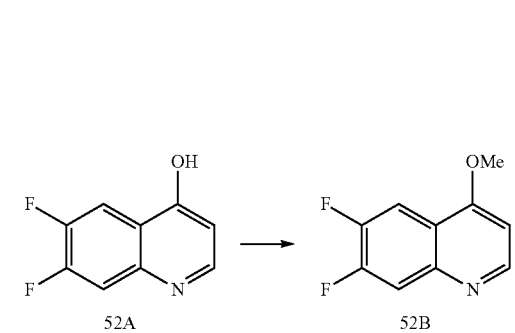 [SMILES: Oc1ccnc2cc(F)c(F)cc12 ; COc1ccnc2cc(F)c(F)cc12]

Starting material enantiopure cis 49A (100 mg, 0.376 mmol), methylboronic acid (45 mg, 0.752 mmol), CsF (171 mg, 1.13 mmol), Pd(dppf)$_2$Cl$_2$ (31 mg, 0.0038 mmol) were mixed in DMF (1.3 mL), and heated in a microwave oven at 110° C. for 80 min. The reaction mixture was diluted with DCM and filtered through a pad of Celite®. The filtrate concentrated under reduced pressure. The residue was purified with preparative TLC, eluting with EtOAc-hexanes, 1:3, to give desired enantiopure cis product 51A (30 mg).

Following procedures similar to those described in Examples 14, step 2, Example 6, step 4, Example 7, ketone 51A was converted into enantiopure compound 51 below.

To a stirring mixture of compound 52A (10 g, 55.2 mmol, Beta Pharma, Inc., Branford, Conn.) in 200 mL toluene in a sealed reaction vessel Ag$_2$CO$_3$ (75 g, 273 mmol) and MeI (3.75 mL, 59.9 mmol) was added. The resulting mixture was heated at 120° C. overnight. The mixture was cooled to room temperature and filtered through a pad of Celite®. The filtrate was concentrated, and the residue was loaded on a pad of silica gel, eluting with EtOAc, to give 7.9 g (73%) desired product 52B as a white solid.

Following procedures similar to those described in Example 1, Step 1, Example 25, Steps 1-3 (where chiral ketone was obtained via chiral HPLC resolution of the racemic ketone), Example 25, Step 4, Example 26, and Example 2527, compound 52B was converted into enantiopure compound 52 below.

| # | Structure | Stereo designation | Name | [M + H]+ |
|---|-----------|--------------------|------|----------|
| 51 | 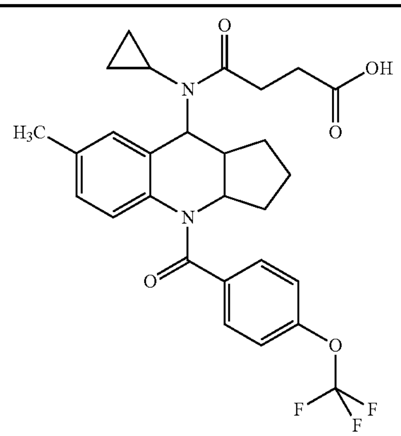 | cis, cis, single enantiomer | 4-[cyclopropyl[cis, cis-2,3,3a,4,9,9a-hexahydro-7-methyl-4-[4-(trifluoromethoxy)benzoyl]-1H-cyclpenta[b]quinolin-9-yl]amino]-4-oxobutanoic acid | 531.3 |

| # | Structure | Stereo designation | Name | [M + H]+ |
|---|---|---|---|---|
| 52 | 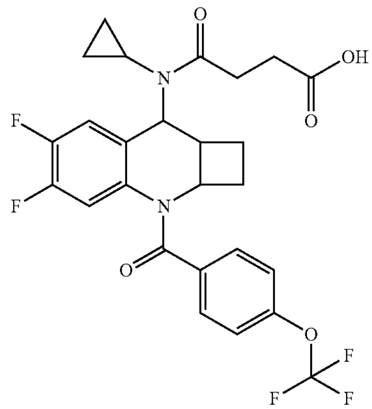 [SMILES: O=C(O)CCC(=O)N(C1CC1)C1c2cc(F)c(F)cc2N(C(=O)c2ccc(OC(F)(F)F)cc2)C2CCC21] | cis, cis, single enantiomer | 4-(cyclopropyl(cis, cis-5,6-difluoro-3-(4-(trifluoromethoxy)benzoyl)-1,2,2a,3,8,8a-hexahydrocyclobuta[b]quinolin-8-yl)amino)-4-oxobutanoic acid | 539.8 |

Example 53

Preparation of Enantiopure 4-(Cyclopropyl((cis,cis,)-4-(4-(trifluoromethoxy)benzoyl)-7-vinyl-2,3,3a,4,9,9a-hexahydro-1H-cyclopenta[b]quinolin-9-yl)amino)-4-oxobutanoic acid (53)

Step 1

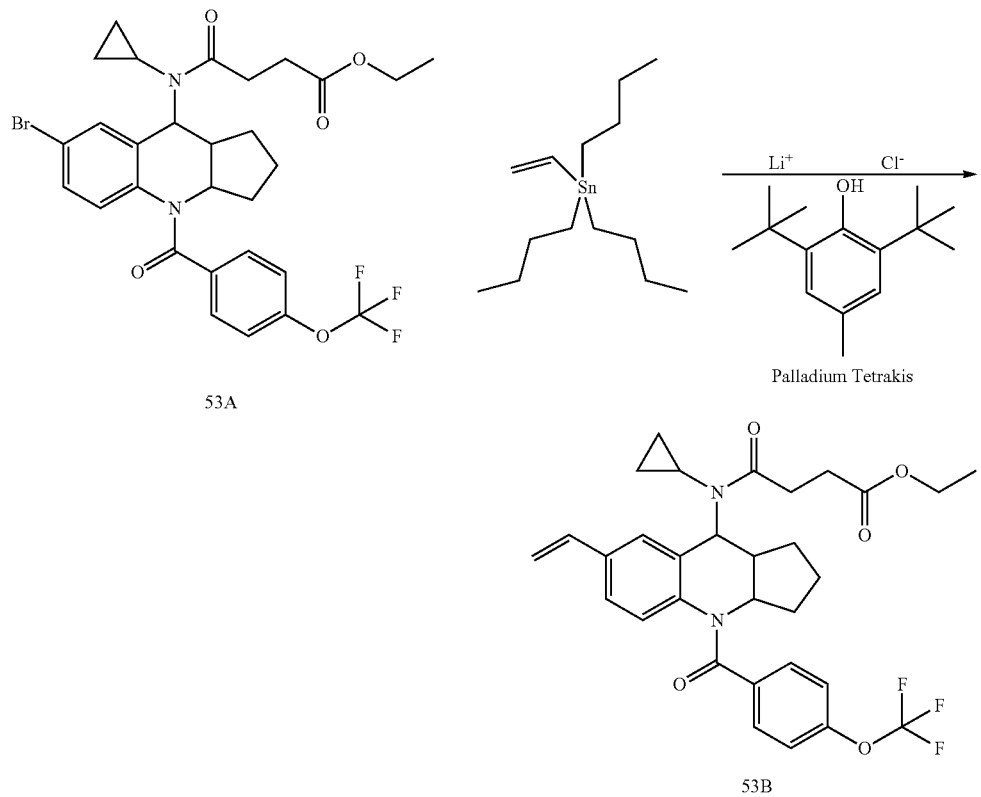

Enantiopure 53A (180 mg, 0.289 mmol), 2,6-di-tert-butyl-4-methylphenol (6.36 mg, 0.029 mmol) and Palladium Tetrakis (16.7 mg, 0.014 mmol), tributyl(vinyl)stannane (110 mg, 0.346 mmol) and lithium chloride (36.7 mg, 0.866 mmol) were mixed in a microwave vial, degassed and refilled with nitrogen (3 times). The vial was placed in an oil bath at 100°

C. overnight. The mixture was diluted with ethyl acetate (15 mL) and water (6 mL). The mixture was filtered through Celite®, and the filtrate was separated. The organic layer was washed with brine (1×5 mL), dried (MgSO₄), filtered and the solvent was evaporated under reduced pressure. The residue was purified by column chromatography on silica gel silica gel (Si; 40 g prepacked), eluting with EtOAc/isohexane=1:3 to give 53B (120 mg, 72% yield, [M+H]⁺: 571) as a white foam.

Step 2

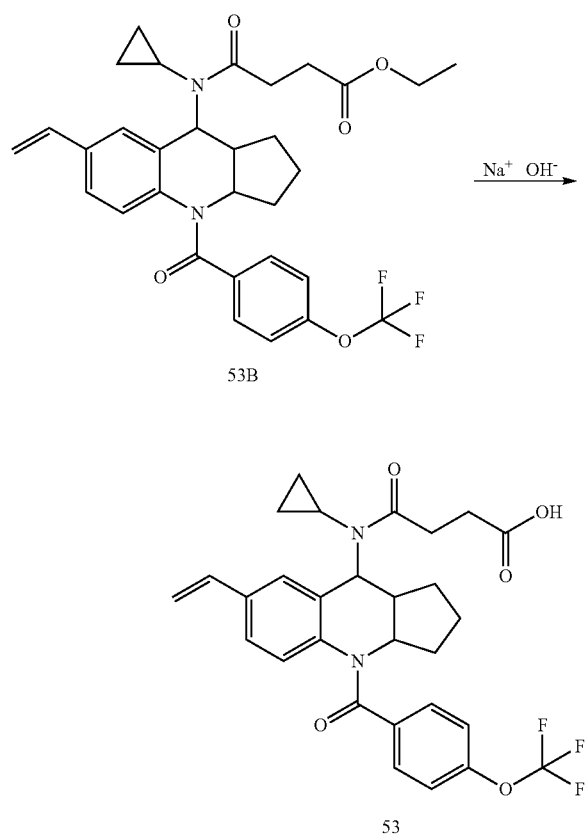

53B

53

NaOH (1 M aq) (0.5 mL, 0.500 mmol) was added to a stirred mixture of enantiopure 53B (30 mg, 0.053 mmol) in MeOH (0.5 mL) and THF (0.500 mL), and the mixture was stirred at room temperature for 2 h. The reaction mixture was diluted with diethyl ether (3 mL), and water (2 mL) was added. The aqueous layer was separated, acidified with to pH 2-3, extracted with diethyl ether (3×2 mL), the combined organic was dried MgSO₄, filtered and concentrated. The residue was purified by preparative HPLC (reverse phase C-18), eluting with acetonitrile/water+0.1% TFA, to give 53 (15 mg, 0.028 mmol, 52.6% yield, [M+H]⁺: 543.1) as a white foam. $^1$H NMR (500 MHz, CDCl₃) δ ppm: 7.31 (d, J=8.5 Hz, 2H); 7.06 (d, J=8.5 Hz, 2H); 6.94 (d, 1H); 6.85 (s, 1H); 6.61 (dd, J1=11 Hz, J2=17 Hz, 1H); 6.38 (d, J=8.5 Hz, 1H); 5.62 (d, J=17 Hz, 1H); 5.22 (d, J=11 Hz 1H); 5.14 (m, 1H); 3.15 (m, 2H); 3.06 (m, 1H); 2.84 (m, 3H); 2.44 (m, 1H); 2.04 (m, 1H); 1.59 (m, 1H); 1.41 (m, 2H); 1.23 (m, 3H); 1.06 (m, 1H); 0.97 (m, 1H).

Example 54

Preparation of enantiopure 4-(Cyclopropyl((cis,cis,)-7-ethyl-4-(4-(trifluoromethoxy)benzoyl)-2,3,3a,4,9,9a-hexahydro-1H-cyclopenta[b]quinolin-9-yl)amino)-4-oxobutanoic acid (54)

Step 1

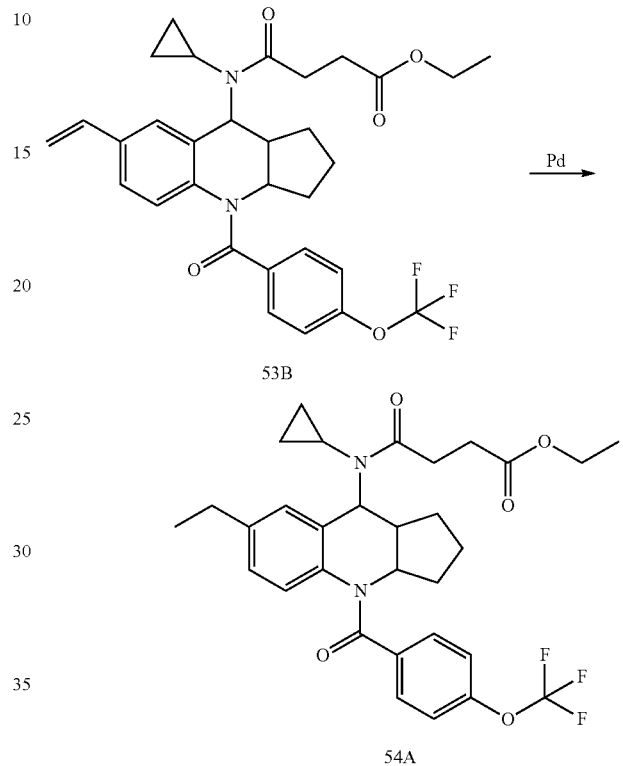

53B

54A

Palladium on carbon 10% (5.0 mg, 4.70 μmol) was added to a stirred, room temperature mixture of enantiopure 53B (25 mg, 0.044 mmol) in EtOH (1.500 mL) and EtOAc (0.5 mL). The mixture was stirred under hydrogen (using a balloon filled with hydrogen) at room temperature for overnight. The mixture was filtered, washing with ethanol. The filtrate was concentrated to obtain a white foam 54A (16 mg, 64% yield, [M+Na]⁺=595), which was used in the next step directly.

Step 2

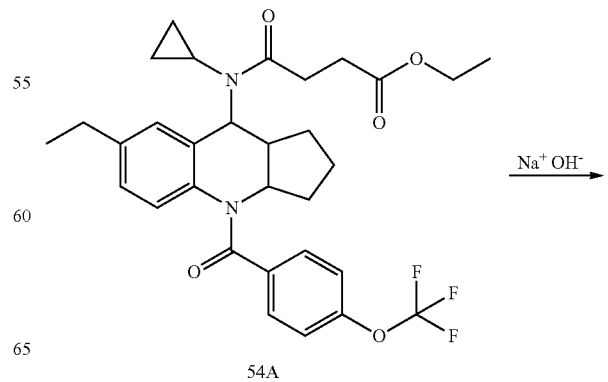

54A

-continued

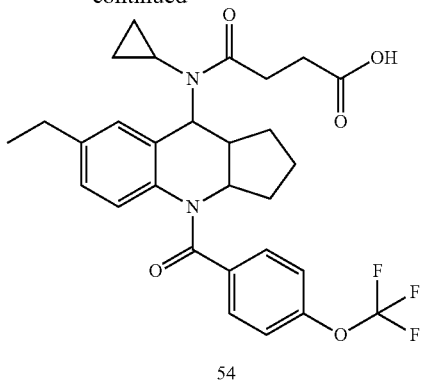

54

NaOH (1 M aq) (0.028 mL, 0.028 mmol) was added to a stirred mixture of enantiopure 54A (16 mg, 0.028 mmol) in MeOH (0.3 mL) and THF (0.3 mL) and the mixture was stirred at room temperature for 2 h. The mixture was concentrated, and the residue was purified by preparative HPLC (C-18 reverse phase solid phase), eluting with acetonitrile/water+0.1% TFA, to give 54 (10 mg, 0.018 mmol, 65.7% yield, [M+H]$^+$=544.8) as a white solid. $^1$H NMR (500 MHz, CDCl$_3$) δ ppm: 7.28 (d, J=8 Hz, 2H); 7.04 (d, J=8 Hz, 2H); 6.71 (d, J=8 Hz, 1H); 6.61 (s, 1H); 6.33 (d J=8 Hz, 1H); 5.16 (m, 1H); 3.13 (m, 2H); 3.05 (m, 1H); 2.83 (m, 3H); 2.55 (q, J=8 Hz, 2H); 2.434 (m, 1H); 2.03 (m, 1H); 2.60 (m, 1H); 1.40 (m, 2H); 1.22 (m, 2H); 1.17 (t, J=8 Hz, 3H); 1.19~0.93 (m, 3H).

Example 55

Preparation of Enantiopure 4-(Cyclopropyl((cis,cis,)-7-(hydroxymethyl)-4-(4-(trifluoromethoxy)benzoyl)-2,3,3a,4,9,9a-hexahydro-1H-cyclopenta[b]quinolin-9-yl)amino)-4-oxobutanoic acid (55)

Step 1

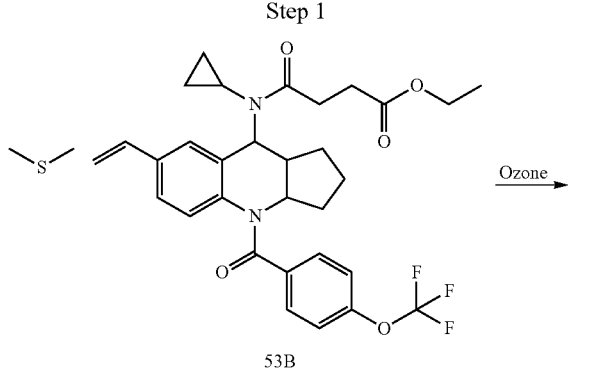

53B

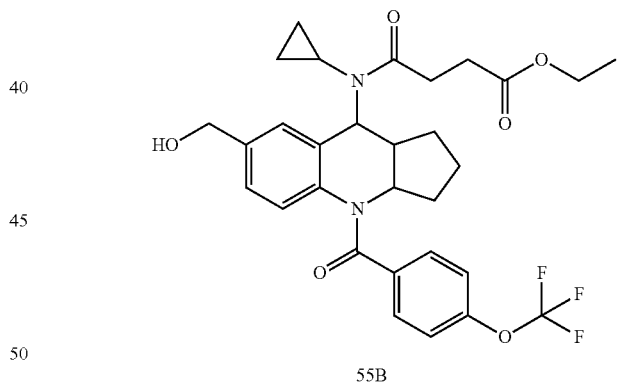

55A

Ozone was bubbled into a stirred, cooled −78° C. mixture of enantiopure 53B (235 mg, 0.412 mmol) in DCM (2 mL) and MeOH (1.000 mL). The mixture was stirred at −78° C. for min. until the mixture turned blue. Oxygen was bubbled in to remove the excess ozone, until the blue color disappeared. Dimethyl sulfide (0.2 mL, 2.70 mmol) was added, and the mixture was kept stirring at room temperature for 1 h. The mixture was diluted with DCM (10 mL), washed with water (5 mL), dried MgSO$_4$, filtered and the solvent was evaporated under reduced pressure to obtain a white foam. The residue was purified by column chromatography on silica gel (Si; 40 g prepacked), eluting with EtOAc/isohexane=1:1 to give 55A (184 mg, 0.321 mmol, 78% yield, [M+H]$^+$=573) as a white foam.

Step 2

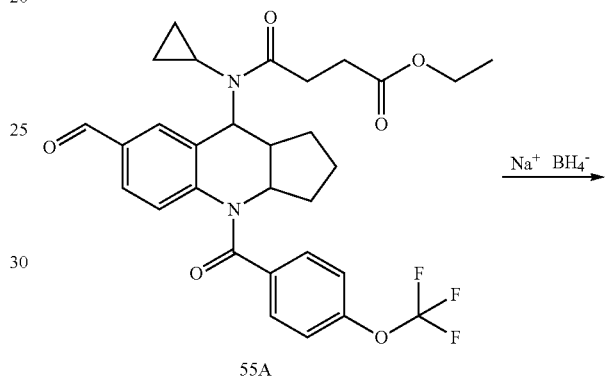

55A

55B

Sodium borohydride (10.57 mg, 0.279 mmol) was added to a stirred, room temperature mixture of enantiopure 55A (80 mg, 0.140 mmol) in DCM (1 mL) and MeOH (1 mL), and the mixture was stirred at room temperature overnight.

An LCMS analysis revealed that starting material along with product was present in the mixture. In addition, the ethyl ester was partially replaced by methyl ester. The mixture was cooled, diluted with dichloromethane (5 mL), washed with aqueous sodium hydrogen carbonate (saturated, 2×3 mL), dried (MgSO$_4$), filtered and the solvent was evaporated under reduced pressure. The residue was purified by column chromatography on silica gel (Si; 24 g prepacked), eluting with EtOAc/isohexane=1:1 to 3:1 to give 55B (34 mg, 0.059 mmol, 42.4% yield [M+Na]$^+$=597) as a white solid.

Step 3

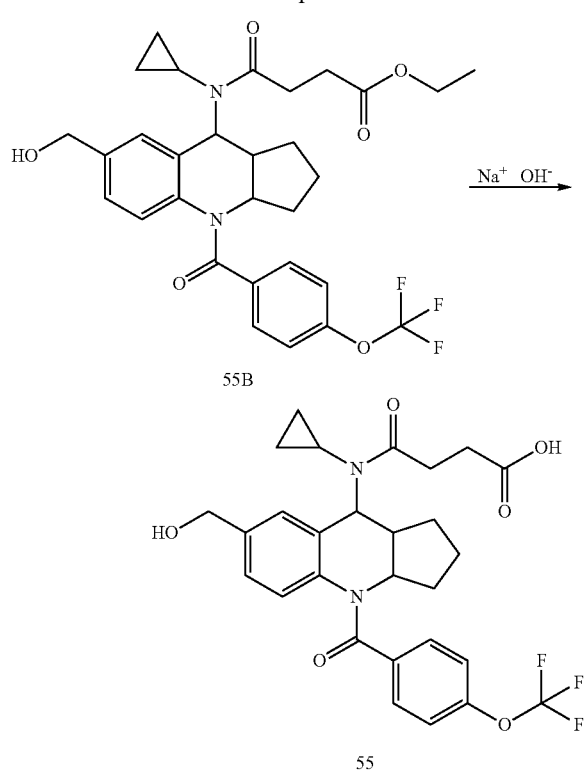

NaOH (1 M aq) (0.5 mL, 0.500 mmol) was added to a stirred mixture of enantiopure 55B (10 mg, 0.017 mmol) in tetrahydrofuran (0.500 mL) and MeOH (0.5 mL), and the mixture was stirred at room temperature for 2 h. The reaction mixture was diluted with water (1 mL), diethyl ether (1 mL) was added, the aqueous layer was separated, acidified with 2 M hydrochloric acid to pH 2-3, extracted with diethyl ether (2×2 mL), the combined organic was dried Na$_2$SO$_4$, filtered and concentrated to give 55 (8.3 mg, 0.015 mmol, 87% yield [M+Na]$^+$=568.8) as a white solid. $^1$H NMR (500 MHz, CDCl$_3$) δ ppm: 7.32 (d, J=8 Hz, 2H); 7.06 (d, J=8 Hz, 2H); 6.76 (d, J=8 Hz, 1H); 6.63 (d, J=8 Hz, 1H); 5.16 (m, 1H); 4.60 (d, J=12.5 Hz, 1H); 4.51 (d, J=12.5 Hz, 1H); 3.12~2.70 (m, 5H); 2.37 (m, 1H); 1.95 (m, 1H); 1.46 (m, 2H); 1.24~1.07 (m, 5H).

Example 56

Preparation of enantiopure 4-(Cyclopropyl((cis,cis,)-7-(fluoromethyl)-4-(4-(trifluoromethoxy)benzoyl)-2,3,3a,4,9,9a-hexahydro-1H-cyclopenta[b]quinolin-9-yl)amino)-4-oxobutanoic acid (56)

Step 1

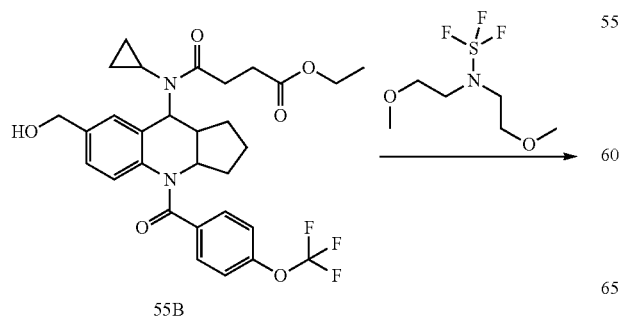

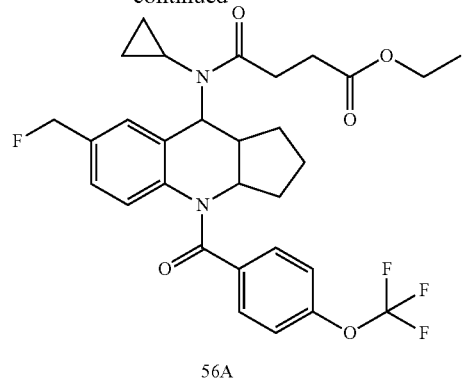

DEOXO-FLUOR (bis(2-methoxyethyl)aminosulfur trifluoride) (0.2 mL, 1.085 mmol) was added to a stirred, room temperature mixture of enantiopure 55B (24 mg, 0.042 mmol) in tetrahydrofuran (1 mL) and the mixture was stirred at 80° C. for 6 h. The mixture was cooled, poured into icy water (1 mL), diluted with ethyl acetate (5 mL), and basified with NaHCO$_3$ (saturated 3 mL). The organic layer was separated, washed with brine (saturated, 1×3 mL), dried (MgSO$_4$), filtered and the solvent was evaporated under reduced pressure obtained a light brown foam, 56A (27 mg, 0.047 mmol, [M+Na]=599), which was used directly in the hydrolysis step.

Step 2

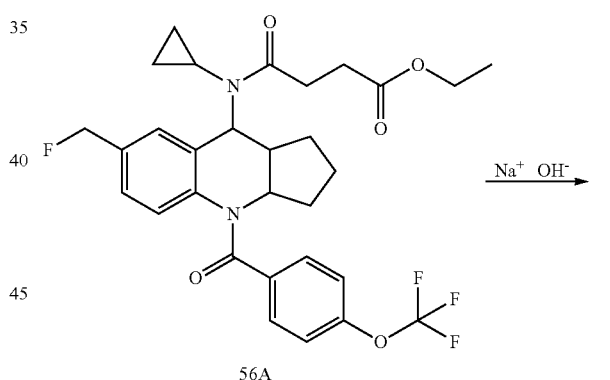

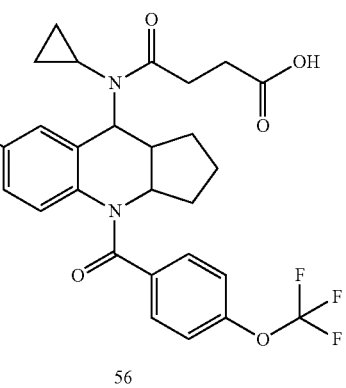

NaOH (1M aq) (1 mL, 1.000 mmol) was added to a stirred mixture of enantiopure 56A (27 mg, 0.047 mmol) in MeOH (1.000 mL) and tetrahydrofuran (1 mL), and the mixture was stirred at room temperature for 2 h. The reaction mixture was diluted with water (1 mL), and diethyl ether (2 mL) was added. The aqueous layer was separated, acidified to pH 2-3, extracted with diethyl ether (3×2 mL). The combined organic were dried over MgSO$_4$, filtered and concentrated. The reaction mixture was concentrated and the residue was purified by preparative TLC with CH$_2$Cl$_2$/isohexane/MeOH/AcOH (1%), to give 56 (15 mg, 0.027 mmol, 58.4% yield, [M+H]$^+$=549.1) as a white solid. $^1$H NMR (500 MHz, CDCl$_3$) δ ppm: 7.30 (d, J=8 Hz, 2H); 7.06 (d, J=8 Hz, 2H); 6.87 (m, 2H); 6.45 (d, J=8 Hz, 1H); 5.33 (dd, J1=6 Hz, J2=17 Hz, 1H); 5.23 (dd, J1=6 Hz, J2=17 Hz, 1H); 5.14 (m, 1H); 3.10 (m, 3H); 2.85 (m, 1H); 2.81 (m, 2H); 2.44 (m, 1H); 2.02 (m, 1H); 1.56 (m, 1H); 1.41 (m, 2H); 1.21~1.07 (m, 7H).

Example 57

Preparation of enantiopure 4-(cyclopropyl((cis,cis,)-7-(difluoromethyl)-4-(4-(trifluoromethoxy)benzoyl)-2,3,3a,4,9,9a-hexahydro-1H-cyclopenta[b]quinolin-9-yl)amino)-4-oxobutanoic acid (57)

Step 1

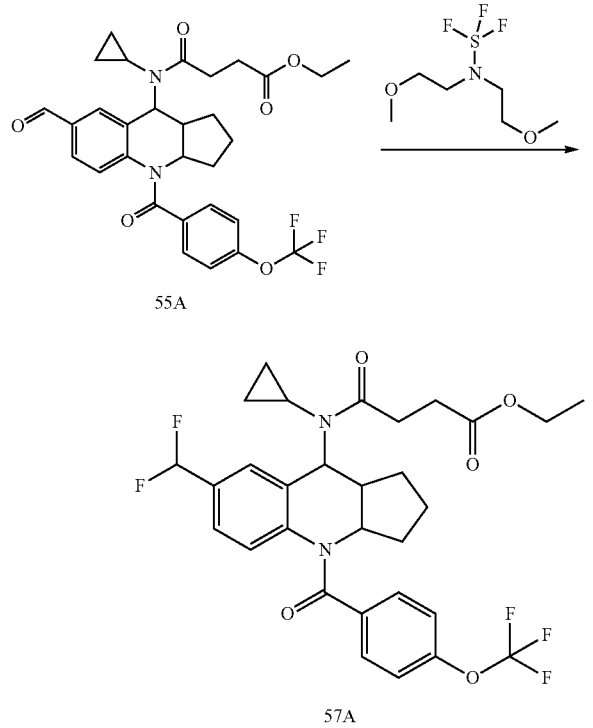

DEOXO-FLUOR (bis(2-methoxyethyl)aminosulfur trifluoride) (0.077 mL, 0.419 mmol) was added to a stirred, room temperature mixture of enantiopure 55A (60 mg, 0.105 mmol) in THF (1 mL) and the mixture was stirred at 80° C. overnight. LCMS check revealed that both starting material and product were present in the mixture. More DEOXO-FLUOR (0.077 mL, 0.419 mmol) was added. The reaction mixture was heated at 80° C. overnight. The mixture was cooled, poured into icy water (3 mL), diluted with ethyl acetate (10 mL), basified with saturated NaHCO$_3$ (5 mL), the organic was separated, washed with brine (1×5 mL), dried (MgSO$_4$), filtered and the solvent was evaporated under reduced pressure to obtain a light brown foam. The residue was purified by preparative HPLC (Reverse phase C-18), eluting with acetonitrile/water+0.1% TFA, to give 57A (25 mg, 0.032 mmol, 30.1% yield, [M+H]$^+$=595) as a yellow gum.

Step 2

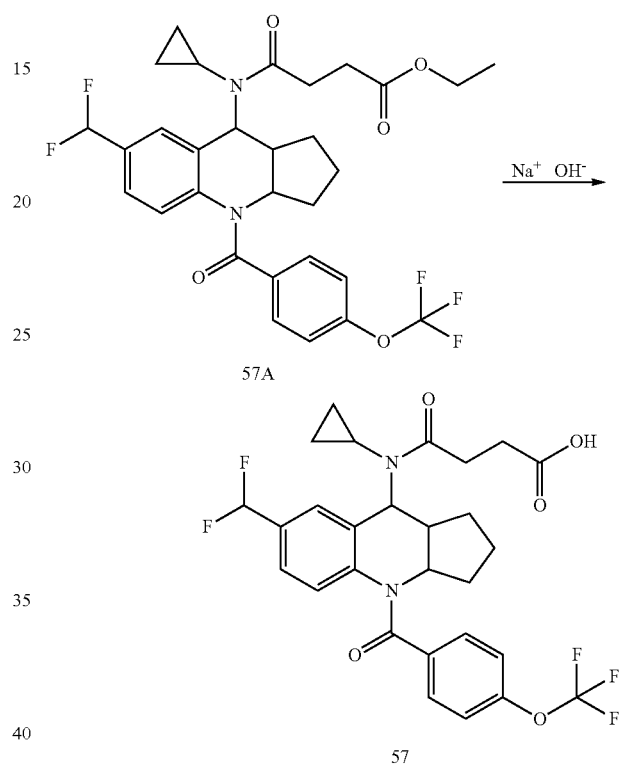

NaOH (1 M aq) (0.042 mL, 0.042 mmol) was added to a stirred mixture of enantiopure 57A (25 mg, 0.042 mmol) in MeOH (1 mL) and tetrahydrofuran (1.000 mL). The mixture was stirred at room temperature for 2 h. The reaction mixture was diluted with water (1 mL), and diethyl ether (2 mL) was added. The aqeuous layer was separated, acidified with hydrochloric acid 2 M to pH 2-3, and extracted with diethyl ether (3×2 mL). The combined organic layer was dried (MgSO$_4$), filtered and concentrated. The residue was purified by preparative TLC, CH$_2$Cl$_2$/isohexane/MeOH/AcOH (1%)=2:1:0.4. The residue was further purified by preparative HPLC (reverse phase C-18), eluting with acetonitrile/water+0.1% TFA, to give 57 (8.3 mg, 0.015 mmol, 34.8% yield, [M+H]$^+$=567) as a white foam. $^1$H NMR (500 MHz, CDCl$_3$) δ ppm: 7.29 (d, J=8 Hz, 2H); 7.07 (d, J=8 Hz, 2H); 7.04 (d, J=8 Hz, 1H); 6.98 (m, 1H); 6.57 (t, J=11.5 Hz, 1H); 6.51 (d, J=8 Hz, 1H); 5.13 (m, 1H); 3.11 (m, 3H); 2.87 (m, 1H); 2.81 (m, 2H); 2.44 (m, 1H); 2.02 (m, 1H); 1.55 (m, 1H); 1.41 (m, 2H); 1.23 (m, 1H); 1.12~0.98 (m, 4H).

The following compounds were prepared following procedures similar to those described in the examples above.

| # | Structure | Stereo designation | Name | [M + H]⁺ |
|---|---|---|---|---|
| 58 | 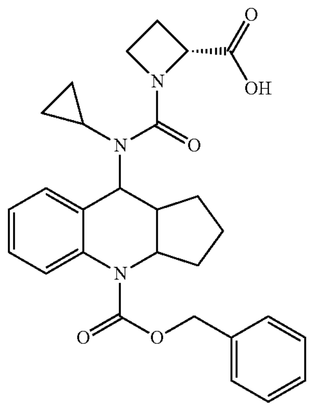 [SMILES: O=C(O)[C@H]1CCN1C(=O)N(C1CC1)C1c2ccccc2N(C(=O)OCc2ccccc2)C2CCCC21] | cis, cis (enentiopure), R-configuration at azetidine, single enantiomer | 4-(phenylmethyl) cis, cis-[[(2(R)-carboxy-1-azetidinyl)carbonyl] cyclopropylamino]-1,2,3,3a,9,9a-hexahydro-4H-cyclopenta[b]quinoline-4-carboxylate | 490.3 |
| 59 | 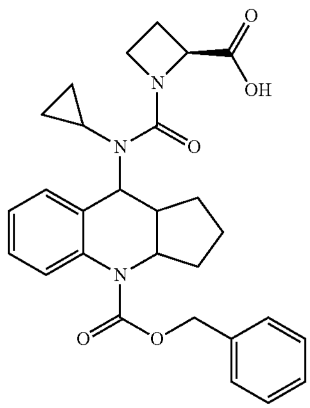 [SMILES: O=C(O)[C@@H]1CCN1C(=O)N(C1CC1)C1c2ccccc2N(C(=O)OCc2ccccc2)C2CCCC21] | cis, cis (enentiopure), S-configuration at azetidine, single enantiomer | 4-(phenylmethyl) cis, cis-[[(2(S)-carboxy-1-azetidinyl)carbonyl] cyclopropylamino]-1,2,3,3a,9,9a-hexahydro-4H-cyclopenta[b]quinoline-4-carboxylate | 490.3 |
| 60 | 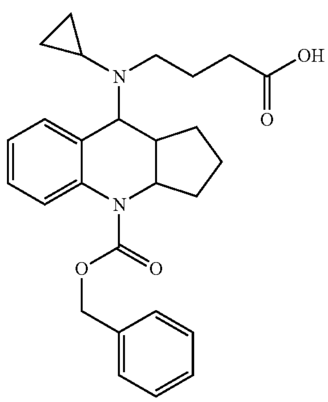 [SMILES: O=C(O)CCCN(C1CC1)C1c2ccccc2N(C(=O)OCc2ccccc2)C2CCCC21] | cis, cis, single enantiomer | 4-(phenylmethyl) cis, cis-[(3-carboxypropyl) cyclopropylamino]-1,2,3,3a,9,9a-hexahydro-4H-cyclopenta[b]quinoline-4-carboxylate | 449.2 |
| 61 | 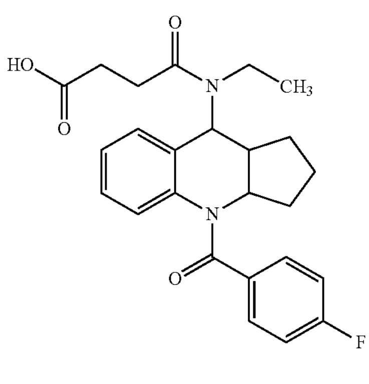 [SMILES: CCN(C(=O)CCC(=O)O)C1c2ccccc2N(C(=O)c2ccc(F)cc2)C2CCCC12] | cis, cis, single enantiomer | 4-[ethyl[cis, cis-4-(4-fluorobenzoyl)-2,3,3a,9,9a-hexahydro-1H-cyclopenta[b]quinolin-9-yl]amino]-4-oxobutanoic acid | 439.2 |

-continued

| # | Structure | Stereo designation | Name | [M + H]+ |
|---|---|---|---|---|
| 62 | 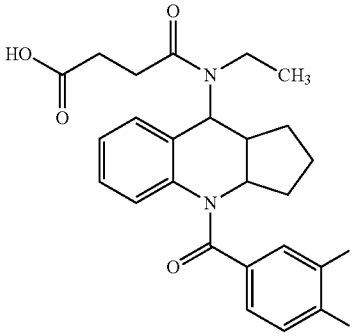 | cis, cis, single enantiomer | 4-[[cis, cis-4-(3,4-difluorobenzoyl)-2,3,3a,4,9,9a-hexahydro-1H-cyclopenta[b]quinolin-9-yl]ethylamino]-4-oxobutanoic acid | 457.3 |
| 63 | 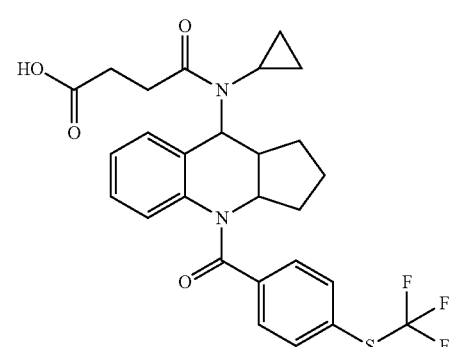 | cis, cis, single enantiomer | 4-[cyclopropyl[cis, cis-2,3,3a,4,9,9a-hexahydro-4-[4-[(trifluoromethyl)thio]benzoyl]-1H-cyclopenta[b]quinolin-9-yl]amino]-4-oxobutanoic acid | 533.3 |
| 64 | 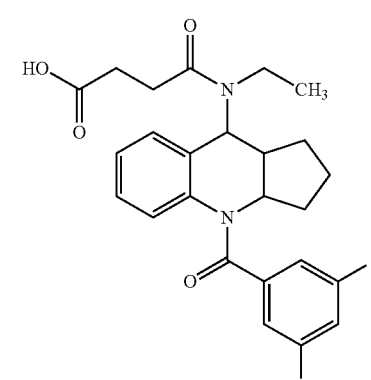 | cis, cis, single enantiomer | 4-[[cis, cis-4-(3,5-difluorobenzoyl)-2,3,3a,4,9,9a-hexahydro-1H-cyclopenta[b]quinolin-9-yl]ethylamino]-4-oxobutanoic acid | 457.3 |
| 65 | 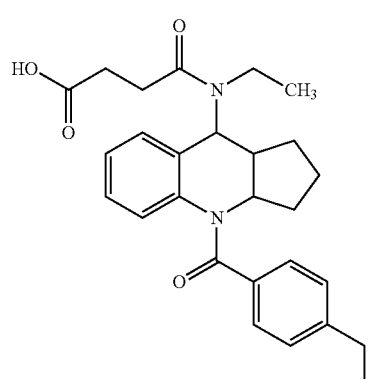 | cis, cis, single enantiomer | 4-[ethyl[cis, cis-4-(4-ethylbenzoyl)-2,3,3a,4,9,9a-hexahydro-1H-cyclopenta[b]quinolin-9-yl]amino]-4-oxobutanoic acid | 449.2 |

| # | Structure | Stereo designation | Name | [M + H]+ |
|---|---|---|---|---|
| 66 | 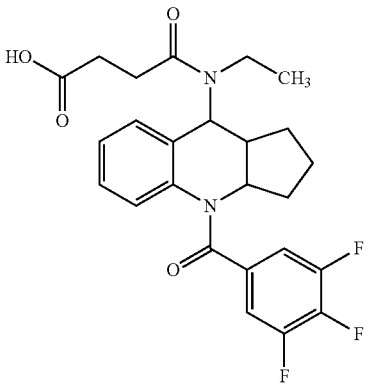 [SMILES: CCN(C(=O)CCC(=O)O)C1c2ccccc2N(C(=O)c2cc(F)c(F)c(F)c2)C2CCCC12] | cis, cis, single enantiomer | 4-[ethyl[cis, cis-2,3,3a,4,9,9a-hexahydro-4-(3,4,5-trifluorobenzoyl)-1H-cyclopenta[b]quinolin-9-yl]amino]-4-oxobutanoic acid | 475.3 |
| 67 | 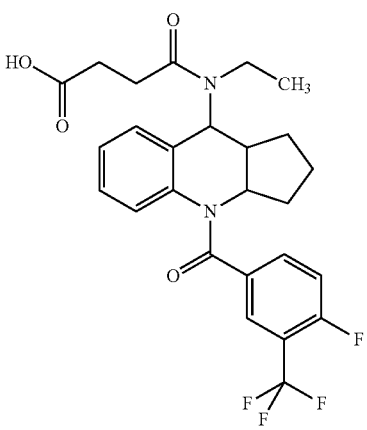 [SMILES: CCN(C(=O)CCC(=O)O)C1c2ccccc2N(C(=O)c2ccc(F)c(C(F)(F)F)c2)C2CCCC12] | cis, cis, single enantiomer | 4-[ethyl[cis, cis-4-[4-fluoro-3-(trifluoromethyl)benzoyl]-2,3,3a,4,9,9a-hexahydro-1H-cyclopenta[b]quinolin-9-yl]amino]-4-oxobutanoic acid | 507.3 |
| 68 | 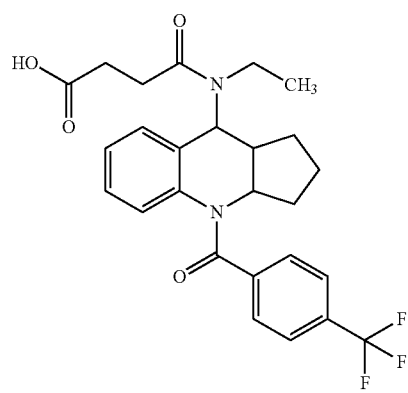 [SMILES: CCN(C(=O)CCC(=O)O)C1c2ccccc2N(C(=O)c2ccc(C(F)(F)F)cc2)C2CCCC12] | cis, cis, single enantiomer | 4-[ethyl[cis, cis-2,3,3a,4,9,9a-hexahydro-4-[4-(trifluoromethyl)benzoyl]-1H-cyclopenta[b]quinolin-9-yl]amino]-4-oxobutanoic acid | 489.3 |

| # | Structure | Stereo designation | Name | [M + H]⁺ |
|---|---|---|---|---|
| 69 | 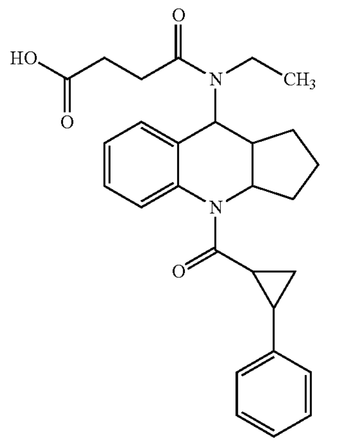 [SMILES: CCN(C(=O)CCC(=O)O)C1c2ccccc2N(C(=O)C2CC2c2ccccc2)C2CCCC12] | (cis, cis,); trans at cyclopropyl (enantiopure); single enantiomer | 4-[ethyl[cis, cis-2,3,3a,4,9,9a-hexahydro-4-[(2-phenyl-1-cyclopropyl)carbonyl]-1H-cyclopenta[b]quinolin-9-yl]amino]-4-oxobutanoic acid | 461.3 |
| 70 | 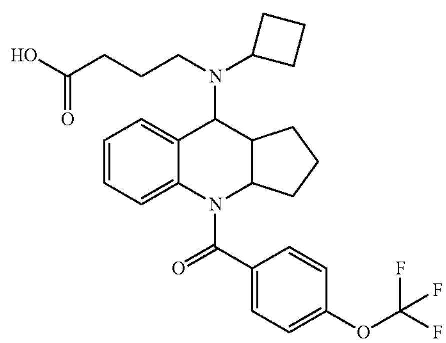 [SMILES: O=C(O)CCCN(C1CCC1)C1c2ccccc2N(C(=O)c2ccc(OC(F)(F)F)cc2)C2CCCC21] | cis, cis, single enantiomer | 4-[cyclobutyl[cis, cis-2,3,3a,4,9,9a-hexahydro-4-[4-(trifluoromethoxy)benzoyl]-1H-cyclopenta[b]quinolin-9-yl]amino]butanoic acid | 517.3 |
| 71 | 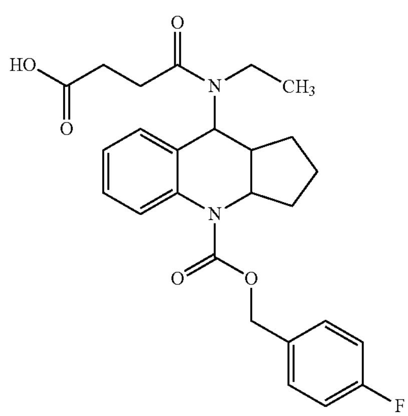 [SMILES: CCN(C(=O)CCC(=O)O)C1c2ccccc2N(C(=O)OCc2ccc(F)cc2)C2CCCC12] | cis, cis, single enantiomer | 4-[(4-fluorophenyl)methyl] cis, cis-[(3-carboxy-1-oxopropyl)ethylamino]-1,2,3,3a,9,9a-hexahydro-4H-cyclopenta[b]quinoline-4-carboxylate | 469.3 |
| 72 | 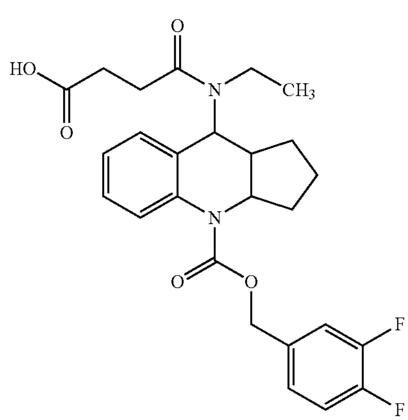 [SMILES: CCN(C(=O)CCC(=O)O)C1c2ccccc2N(C(=O)OCc2ccc(F)c(F)c2)C2CCCC12] | cis, cis, single enantiomer | 4-[(3,4-difluorophenyl)methyl] cis, cis-[(3-carboxy-1-oxopropyl)ethylamino]-1,2,3,3a,9,9a-hexahydro-4H-cyclopenta[b]quinoline-4-carboxylate | 487.3 |

| # | Structure | Stereo designation | Name | [M + H]+ |
|---|---|---|---|---|
| 73 | 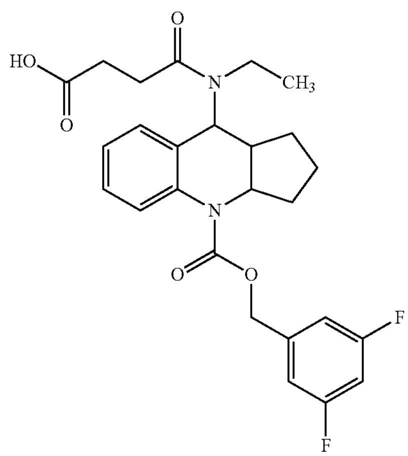 [SMILES: CCN(C(=O)CCC(=O)O)C1c2ccccc2N(C(=O)OCc2cc(F)cc(F)c2)C2CCCC12] | cis, cis, single enantiomer | 4-[(3,5-difluorophenyl)methyl] cis, cis-[(3-carboxy-1-oxopropyl)ethylamino]-1,2,3,3a,9,9a-hexahydro-4H-cyclopenta[b]quinoline-4-carboxylate | 487.3 |
| 74 | 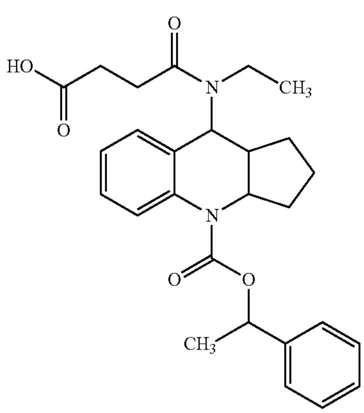 [SMILES: CCN(C(=O)CCC(=O)O)C1c2ccccc2N(C(=O)OC(C)c2ccccc2)C2CCCC12] | cis, cis (enantiopure), racemic at benzylic methyl. | 4-(1-phenylethyl) cis, cis-[(3-carboxy-1-oxopropyl)ethylamino]-1,2,3,3a,9,9a-hexahydro-4H-cyclopenta[b]quinoline-4-carboxylate | 465.3 |
| 75 | 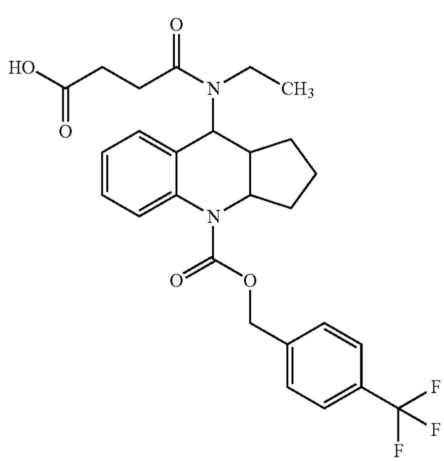 [SMILES: CCN(C(=O)CCC(=O)O)C1c2ccccc2N(C(=O)OCc2ccc(C(F)(F)F)cc2)C2CCCC12] | cis, cis, single enantiomer | 4-[[4-(trifluoromethyl)phenyl]methyl] cis, cis-[(3-carboxy-1-oxopropyl)ethylamino]-1,2,3,3a,9,9a-hexahydro-4H-cyclopenta[b]quinoline-4-carboxylate | 519.3 |

-continued

| # | Structure | Stereo designation | Name | [M + H]$^+$ |
|---|---|---|---|---|
| 76 | 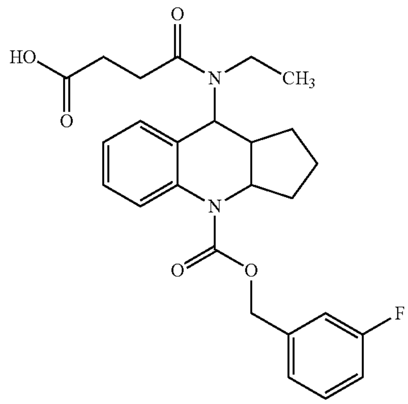 [SMILES: CCN(C(=O)CCC(=O)O)C1c2ccccc2N(C(=O)OCc2cccc(F)c2)C2CCCC12] | cis, cis, single enantiomer | 4-[(3-fluorophenyl)methyl] cis, cis-[(3-carboxy-1-oxopropyl)ethylamino]-1,2,3,3a,9,9a-hexahydro-4H-cyclopenta[b]quinoline-4-carboxylate | 469.3 |
| 77 | 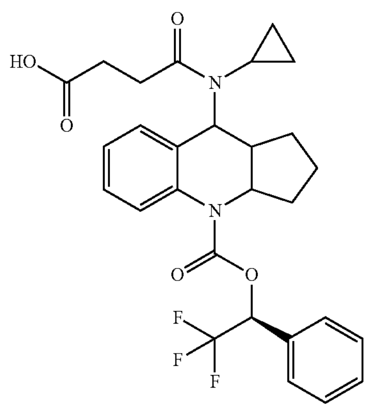 [SMILES: O=C(O)CCC(=O)N(C1CC1)C1c2ccccc2N(C(=O)O[C@@H](c2ccccc2)C(F)(F)F)C2CCCC21] | (cis, cis), S configuration at benzylic carbon atom, single enantiomer | 4-(2,2,2-trifluoro-1(S)-phenylethyl) cis, cis-[(3-carboxy-1-oxopropyl)cyclopropylamino]-1,2,3,3a,9,9a-hexahydro-4H-cyclopenta[b]quinoline-4-carboxylate | 531.3 |
| 78 | 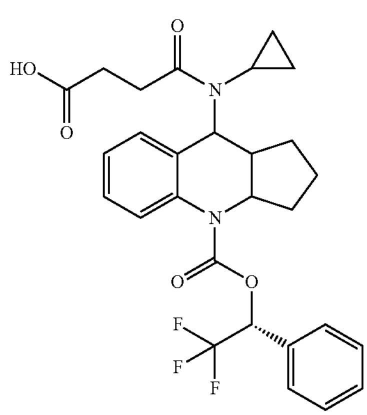 [SMILES: O=C(O)CCC(=O)N(C1CC1)C1c2ccccc2N(C(=O)O[C@H](c2ccccc2)C(F)(F)F)C2CCCC21] | (cis, cis), R configuration at benzylic carbon atom, single enantiomer | 4-(2,2,2-trifluoro-1(R)-phenylethyl) cis, cis-[(3-carboxy-1-oxopropyl)cyclopropylamino]-1,2,3,3a,9,9a-hexahydro-4H-cyclopenta[b]quinoline-4-carboxylate | 531.3 |

-continued

| # | Structure | Stereo designation | Name | [M + H]+ |
|---|---|---|---|---|
| 79 | 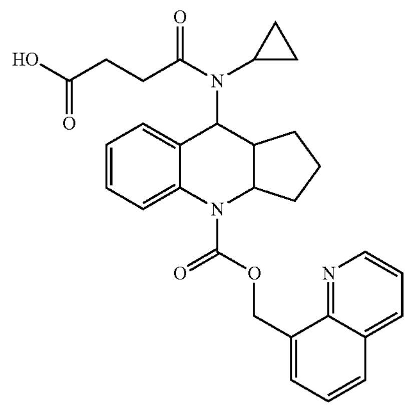 [SMILES: O=C(O)CCC(=O)N(C1CC1)C1c2ccccc2N(C(=O)OCc2cccc3cccnc23)C2CCCC21] | cis, cis, single enantiomer | (cis, cis)-4H-cyclopenta[b]quinoline-4-carboxylic acid, 9-[(3-carboxy-1-oxopropyl) cyclopropylamino]-1,2,3,3a,9,9a-hexahydro-, 4-(8-quinolinylmethyl) ester | 514.3 |
| 80 | 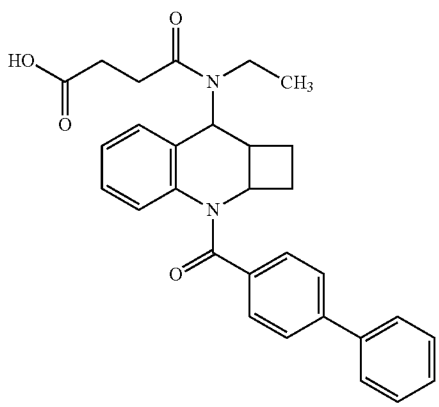 [SMILES: CCN(C(=O)CCC(=O)O)C1c2ccccc2N(C(=O)c2ccc(-c3ccccc3)cc2)C2CCC12] | cis, cis, single enantiomer | 4-((cis, cis-3-(biphenylcarbonyl)-1,2,2a,3,8,8a-hexahydrocyclobuta[b] quinolin-8-yl)(ethyl)amino)-4-oxobutanoic acid | 483.2 |
| 81 | 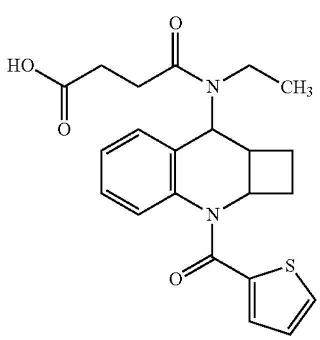 [SMILES: CCN(C(=O)CCC(=O)O)C1c2ccccc2N(C(=O)c2cccs2)C2CCC12] | cis, cis, single enantiomer | 4-(ethyl(cis, cis-3-(thiophene-2-carbonyl)-1,2,2a,3,8,8a-hexahydrocyclobuta[b] quinolin-8-yl)amino)-4-oxobutanoic acid | 413.2 |
| 82 | 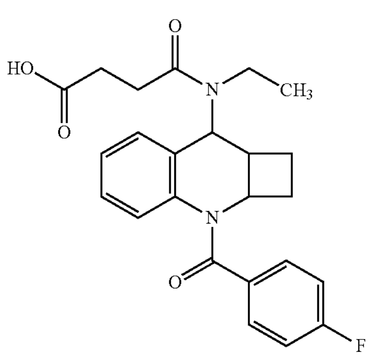 [SMILES: CCN(C(=O)CCC(=O)O)C1c2ccccc2N(C(=O)c2ccc(F)cc2)C2CCC12] | cis, cis, single enantiomer | 4-(ethyl(cis, cis-3-(4-fluorobenzoyl)-1,2,2a,3,8,8a-hexahydrocyclobuta[b] quinolin-8-yl)amino)-4-oxobutanoic acid | 425.2 |

| # | Structure | Stereo designation | Name | [M + H]+ |
|---|---|---|---|---|
| 83 | 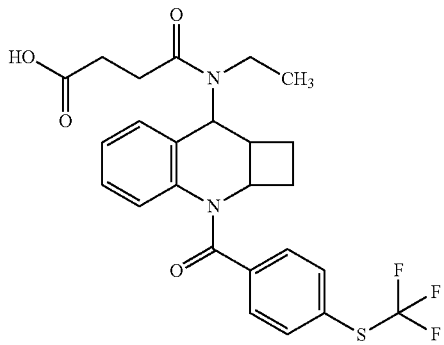 [SMILES: CCN(C(=O)CCC(=O)O)C1c2ccccc2N(C(=O)c2ccc(SC(F)(F)F)cc2)C2CCC12] | cis, cis, single enantiomer | 4-(ethyl(cis, cis-3-(4-(trifluoromethylthio)benzoyl)-1,2,2a,3,8,8a-hexahydrocyclobuta[b]quinolin-8-yl)amino)-4-oxobutanoic acid | 507.2 |
| 84 | 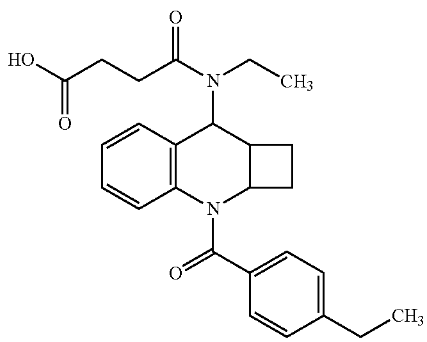 [SMILES: CCc1ccc(C(=O)N2c3ccccc3C(N(CC)C(=O)CCC(=O)O)C3CCC32)cc1] | cis, cis, single enantiomer | 4-(ethyl(cis, cis-3-(4-ethylbenzoyl)-1,2,2a,3,8,8a-hexahydrocyclobuta[b]quinolin-8-yl)amino)-4-oxobutanoic acid | 435.2 |
| 85 | 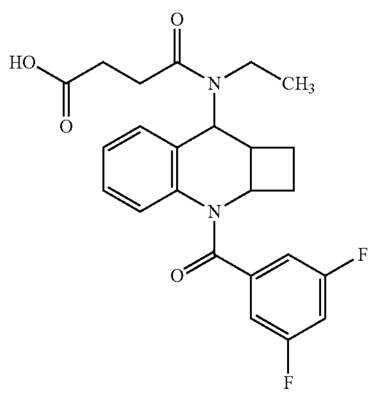 | cis, cis, single enantiomer | 4-((cis, cis-3-(3,5-difluorobenzoyl)-1,2,2a,3,8,8a-hexahydrocyclobuta[b]quinolin-8-yl)(ethyl)amino)-4-oxobutanoic acid | 443.2 |
| 86 | 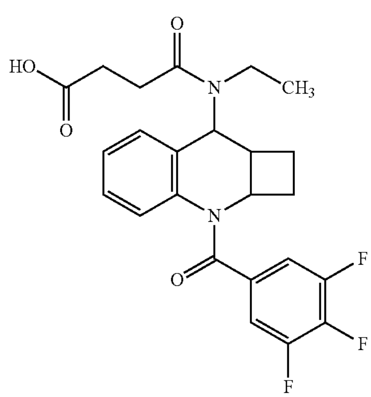 [SMILES: CCN(C(=O)CCC(=O)O)C1c2ccccc2N(C(=O)c2cc(F)c(F)c(F)c2)C2CCC12] | cis, cis, single enantiomer | 4-(ethyl(cis, cis-3-(3,4,5-trifluorobenzoyl)-1,2,2a,3,8,8a-hexahydrocyclobuta[b]quinolin-8-yl)amino)-4-oxobutanoic acid | 461.2 |

-continued

| # | Structure | Stereo designation | Name | [M + H]+ |
|---|---|---|---|---|
| 87 | 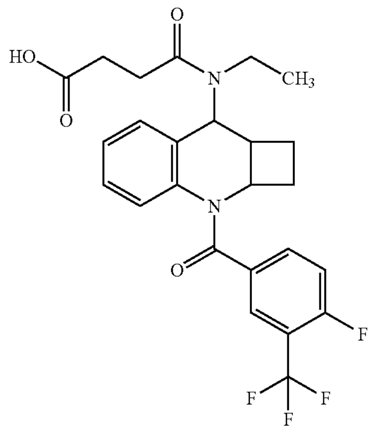 [SMILES: CCN(C(=O)CCC(=O)O)C1c2ccccc2N(C(=O)c2ccc(F)c(C(F)(F)F)c2)C2CCC12] | cis, cis, single enantiomer | 4-(ethyl(cis, cis-3-(4-fluoro-3-(trifluoromethyl)benzoyl)-1,2,2a,3,8,8a-hexahydrocyclobuta[b]quinolin-8-yl)amino)-4-oxobutanoic acid | 493.2 |
| 88 | 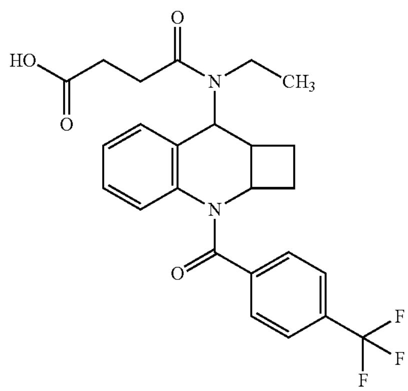 [SMILES: CCN(C(=O)CCC(=O)O)C1c2ccccc2N(C(=O)c2ccc(C(F)(F)F)cc2)C2CCC12] | cis, cis, single enantiomer | 4-(ethyl(cis, cis-3-(4-(trifluoromethyl)benzoyl)-1,2,2a,3,8,8a-hexahydrocyclobuta[b]quinolin-8-yl)amino)-4-oxobutanoic acid | 475.2 |
| 89 | 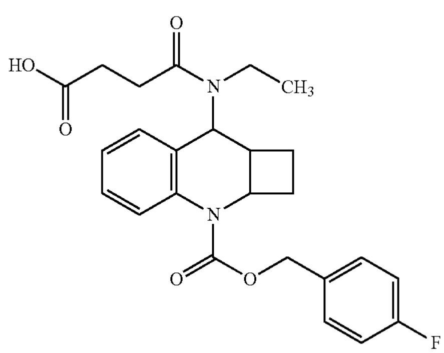 [SMILES: CCN(C(=O)CCC(=O)O)C1c2ccccc2N(C(=O)OCc2ccc(F)cc2)C2CCC12] | cis, cis, single enantiomer | 4-(ethyl(cis, cis-3-((4-fluorobenzyloxy)carbonyl)-1,2,2a,3,8,8a-hexahydrocyclobuta[b]quinolin-8-yl)amino)-4-oxobutanoic acid | 455.1 |
| 90 | 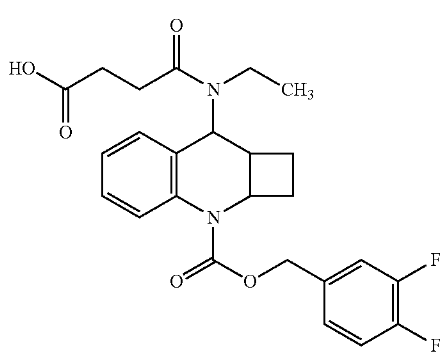 [SMILES: CCN(C(=O)CCC(=O)O)C1c2ccccc2N(C(=O)OCc2ccc(F)c(F)c2)C2CCC12] | cis, cis, single enantiomer | 4-((cis, cis-3-((3,4-difluorobenzyloxy)carbonyl)-1,2,2a,3,8,8a-hexahydrocyclobuta[b]quinolin-8-yl)(ethyl)amino)-4-oxobutanoic acid | 473.1 |

| # | Structure | Stereo designation | Name | $[M + H]^+$ |
|---|-----------|--------------------|------|-------------|
| 91 | 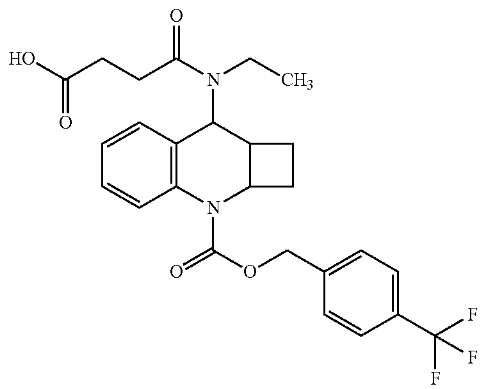 [SMILES: CCN(C(=O)CCC(=O)O)C1c2ccccc2N(C(=O)OCc2ccc(C(F)(F)F)cc2)C2CCC12] | cis, cis, single enantiomer | 4-(ethyl(cis, cis-3-((4-(trifluoromethyl)benzyloxy)carbonyl)-1,2,2a,3,8,8a-hexahydrocyclobuta[b]quinolin-8-yl)amino)-4-oxobutanoic acid | 505.1 |
| 92 | 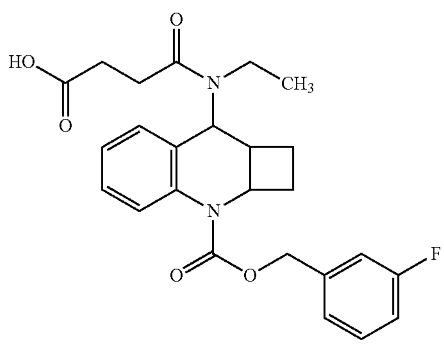 [SMILES: CCN(C(=O)CCC(=O)O)C1c2ccccc2N(C(=O)OCc2cccc(F)c2)C2CCC12] | cis, cis, single enantiomer | 4-(ethyl(cis, cis-3-((3-fluorobenzyloxy)carbonyl)-1,2,2a,3,8,8a-hexahydrocyclobuta[b]quinolin-8-yl)amino)-4-oxobutanoic acid | 455.1 |
| 93 | 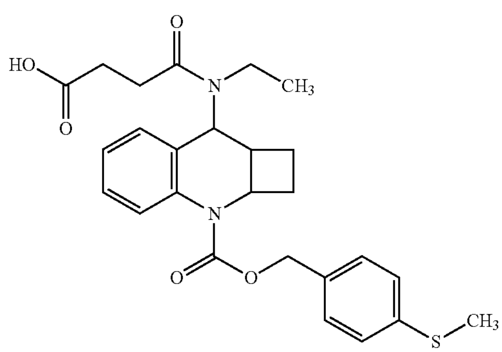 [SMILES: CCN(C(=O)CCC(=O)O)C1c2ccccc2N(C(=O)OCc2ccc(SC)cc2)C2CCC12] | cis, cis, single enantiomer | 4-(ethyl(cis, cis-3-((4-(methylthio)benzyloxy)carbonyl)-1,2,2a,3,8,8a-hexahydrocyclobuta[b]quinolin-8-yl)amino)-4-oxobutanoic acid | 483.1 |
| 94 | 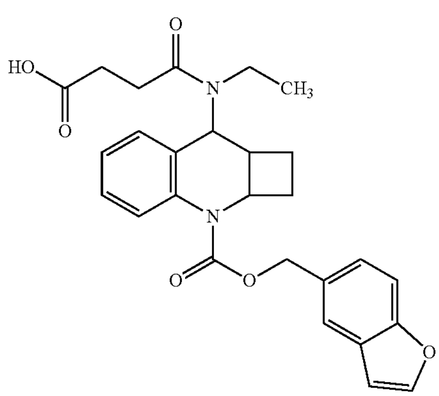 [SMILES: CCN(C(=O)CCC(=O)O)C1c2ccccc2N(C(=O)OCc2ccc3occc3c2)C2CCC12] | cis, cis, single enantiomer | 4-((cis, cis-3-((benzofuran-5-ylmethoxy)carbonyl)-1,2,2a,3,8,8a-hexahydrocyclobuta[b]quinolin-8-yl)(ethyl)amino)-4-oxobutanoic acid | 477.2 |

| # | Structure | Stereo designation | Name | [M + H]+ |
|---|---|---|---|---|
| 95 | 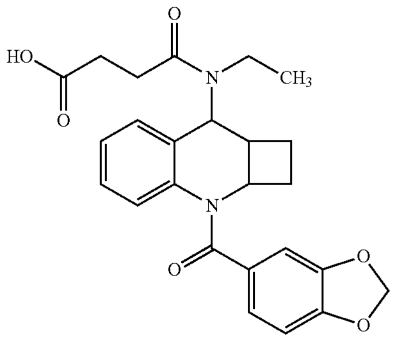 [SMILES: CCN(C(=O)CCC(=O)O)C1c2ccccc2N(C(=O)c2ccc3c(c2)OCO3)C2CCC12] | cis, cis, single enantiomer | 4-((cis, cis-3-(benzo[d][1,3]dioxole-5-carbonyl)-1,2,2a,3,8,8a-hexahydrocyclobuta[b]quinolin-8-yl)(ethyl)amino)-4-oxobutanoic acid | 451.2 |
| 96 | 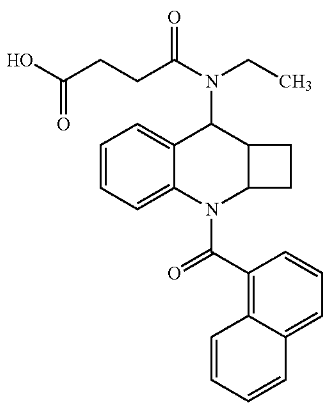 [SMILES: CCN(C(=O)CCC(=O)O)C1c2ccccc2N(C(=O)c2cccc3ccccc23)C2CCC12] | cis, cis, single enantiomer | 4-((cis, cis-3-(1-naphthoyl)-1,2,2a,3,8,8a-hexahydrocyclobuta[b]quinolin-8-yl)(ethyl)amino)-4-oxobutanoic acid | 457.2 |
| 97 | 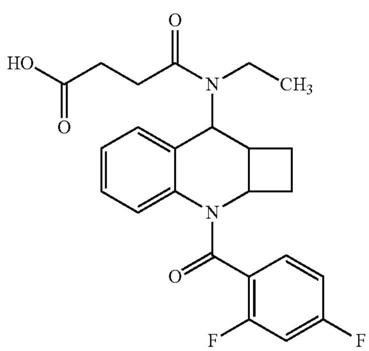 [SMILES: CCN(C(=O)CCC(=O)O)C1c2ccccc2N(C(=O)c2ccc(F)cc2F)C2CCC12] | cis, cis, single enantiomer | 4-((cis, cis-3-(2,4-difluorobenzoyl)-1,2,2a,3,8,8a-hexahydrocyclobuta[b]quinolin-8-yl)(ethyl)amino)-4-oxobutanoic acid | 443.2 |
| 98 | 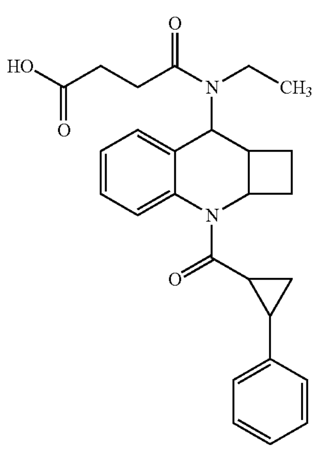 [SMILES: CCN(C(=O)CCC(=O)O)C1c2ccccc2N(C(=O)C2CC2c2ccccc2)C2CCC12] | cis, cis (enantiopure), trans at cyclopropyl ring racemic | 4-(ethyl(cis, cis-3-(2-phenylcyclopropanecarbonyl)-1,2,2a,3,8,8a-hexahydrocyclobuta[b]quinolin-8-yl)amino)-4-oxobutanoic acid | 447.2 |

-continued

| # | Structure | Stereo designation | Name | [M + H]+ |
|---|---|---|---|---|
| 99 | 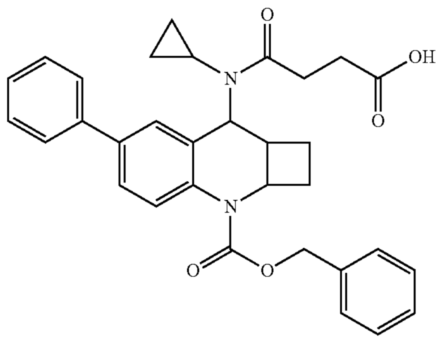 [SMILES: O=C(O)CCC(=O)N(C1CC1)C1c2cc(-c3ccccc3)ccc2N(C(=O)OCc2ccccc2)C2CCC21] | cis, cis, single enantiomer | 4-((cis, cis-3-(benzyloxycarbonyl)-6-phenyl-1,2,2a,3,8,8a-hexahydrocyclobuta[b]quinolin-8-yl)(cyclopropyl)amino)-4-oxobutanoic acid | 525.2 |
| 100 | 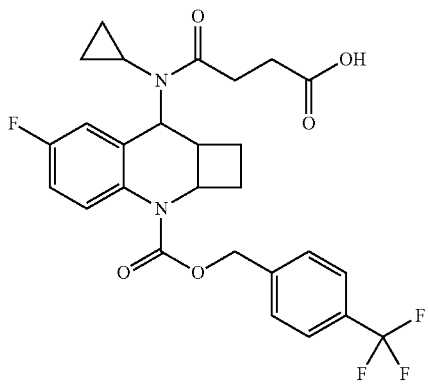 [SMILES: O=C(O)CCC(=O)N(C1CC1)C1c2cc(F)ccc2N(C(=O)OCc2ccc(C(F)(F)F)cc2)C2CCC21] | cis, cis, single enantiomer | 3-[[4-(trifluoromethyl)phenyl]methyl] cis, cis-[(3-carboxy-1-oxopropyl)cyclopropylamino]-6-fluoro-2,2a,8,8a-tetrahydrocyclobuta[b]quinoline-3(1H)-carboxylate | 535 |
| 101 | 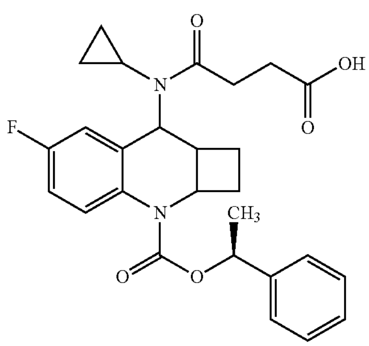 [SMILES: C[C@H](OC(=O)N1c2ccc(F)cc2C(N(C(=O)CCC(=O)O)C2CC2)C2CCC21)c1ccccc1] | cis, cis (enantiopure), single enantiomer | 3-(1(S)-phenylethyl) cis, cis-[(3-carboxy-1-oxopropyl)cyclopropylamino]-6-fluoro-2,2a,8,8a-tetrahydrocyclobuta[b]quinoline-3(1H)-carboxylate | 481 |
| 102 | 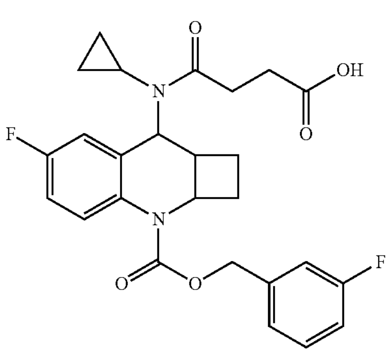 [SMILES: O=C(O)CCC(=O)N(C1CC1)C1c2cc(F)ccc2N(C(=O)OCc2cccc(F)c2)C2CCC21] | cis, cis, single enantiomer | 3-[(3-fluorophenyl)methyl] cis, cis-[(3-carboxy-1-oxopropyl)cyclopropylamino]-6-fluoro-2,2a,8,8a-tetrahydrocyclobuta[b]quinoline-3(1H)-carboxylate | 485 |

-continued

| # | Structure | Stereo designation | Name | [M + H]+ |
|---|---|---|---|---|
| 103 | 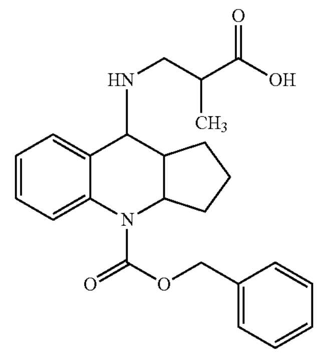 [SMILES: CC(CNC1c2ccccc2N(C(=O)OCc2ccccc2)C2CCCC12)C(=O)O] | cis, cis (racemic), racemic at alpha carbon of acid chain | 4-(phenylmethyl) cis, cis-[(2(RS)-carboxypropyl)amino]-1,2,3,3a,9,9a-hexahydro-4H-cyclopenta[b]quinoline-4-carboxylate | 409 |
| 104 | 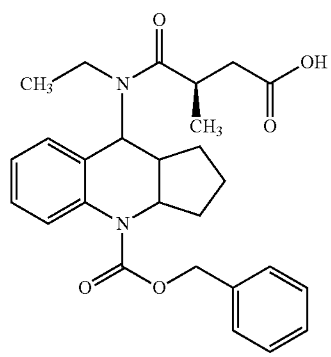 [SMILES: CCN(C(=O)[C@H](C)CC(=O)O)C1c2ccccc2N(C(=O)OCc2ccccc2)C2CCCC12] | cis, cis, racemic; R configuration at beta carbon of acid chain | 4-(phenylmethyl) cis,cis-9-[(3-carboxy-2(R)-methyl-1-oxopropyl)ethylamino]-1,2,3,3a,9,9a-hexahydro-4H-cyclopenta[b]quinoline-4-carboxylate | 465 |
| 105 | 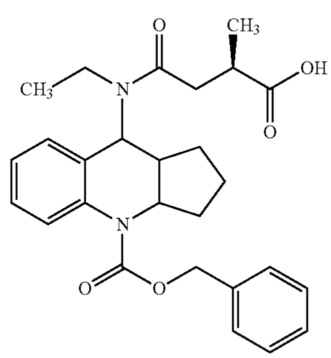 [SMILES: CCN(C(=O)C[C@@H](C)C(=O)O)C1c2ccccc2N(C(=O)OCc2ccccc2)C2CCCC12] | all cis, racemic; R configuration at alpha carbon of acid chain | 4-(phenylmethyl) cis,cis-9-[(3(R)-carboxy-1-oxobutyl)ethylamino]-1,2,3,3a,9,9a-hexahydro-4H-cyclopenta[b]quinoline-4-carboxylate | 465 |
| 106 | 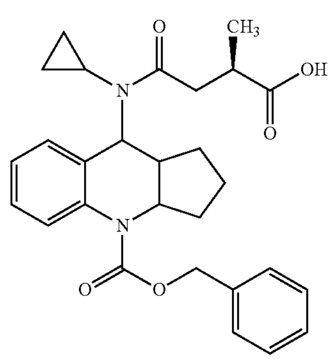 [SMILES: C[C@H](CC(=O)N(C1CC1)C1c2ccccc2N(C(=O)OCc2ccccc2)C2CCCC21)C(=O)O] | cis, cis, (enantiopure), single enantiomer, R configuration at alpha carbon of acid chain | (R)-4-(((cis, cis)-4-(benzyloxycarbonyl)-2,3,3a,4,9,9a-hexahydro-1H-cyclopenta[b]quinolin-9-yl)(cyclopropyl)amino)-2-methyl-4-oxobutanoic acid | 477 |

-continued

| # | Structure | Stereo designation | Name | [M + H]+ |
|---|---|---|---|---|
| 107 | 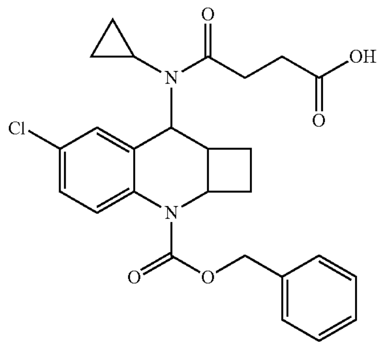 [SMILES: O=C(O)CCC(=O)N(C1CC1)C1c2cc(Cl)ccc2N(C(=O)OCc2ccccc2)C2CCC21] | cis, cis, single enantiomer | 4-((cis, cis-3-(benzyloxycarbonyl)-6-chloro-1,2,2a,3,8,8a-hexahydrocyclobuta[b]quinolin-8-yl)(cyclopropyl)amino)-4-oxobutanoic acid | 484 |
| 108 | 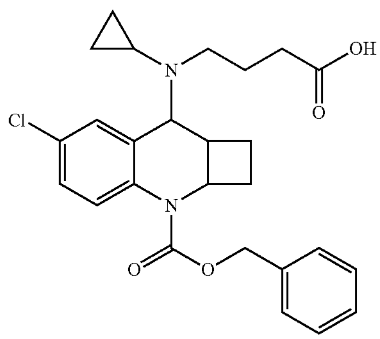 [SMILES: O=C(O)CCCN(C1CC1)C1c2cc(Cl)ccc2N(C(=O)OCc2ccccc2)C2CCC21] | cis, cis, single enantiomer | 4-((cis, cis-3-(benzyloxycarbonyl)-6-chloro-1,2,2a,3,8,8a-hexahydrocyclobuta[b]quinolin-8-yl)(cyclopropyl)amino)butanoic acid | 470 |
| 109 | 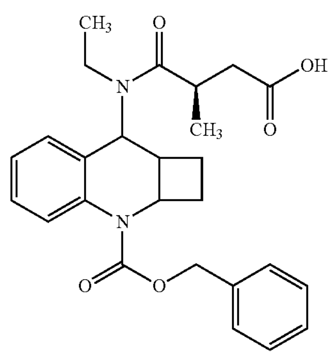 [SMILES: CCN(C(=O)[C@H](C)CC(=O)O)C1c2ccccc2N(C(=O)OCc2ccccc2)C2CCC12] | cis, cis (enantiopure), single enantiomer | (R)-4-((cis, cis-3-(benzyloxycarbonyl)-1,2,2a,3,8,8a-hexahydrocyclobuta[b]quinolin-8-yl)(ethyl)amino)-3-methyl-4-oxobutanoic acid | 451 |
| 110 | 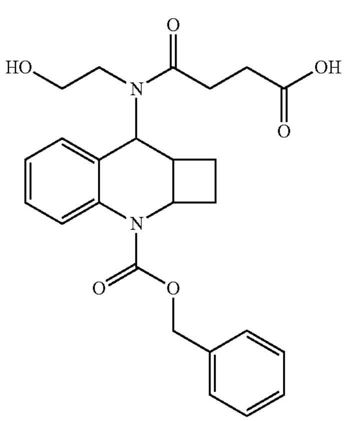 [SMILES: O=C(O)CCC(=O)N(CCO)C1c2ccccc2N(C(=O)OCc2ccccc2)C2CCC12] | cis, cis, single enantiomer | 3-(phenylmethyl) cis, cis-[(3-carboxy-1-oxopropyl)(2-hydroxyethyl)amino]-2,2a,8,8a-tetrahydrocyclobuta[b]quinoline-3(1H)-carboxylate | 474.9 [M + Na]+ |

-continued

| # | Structure | Stereo designation | Name | [M + H]+ |
|---|---|---|---|---|
| 111 | 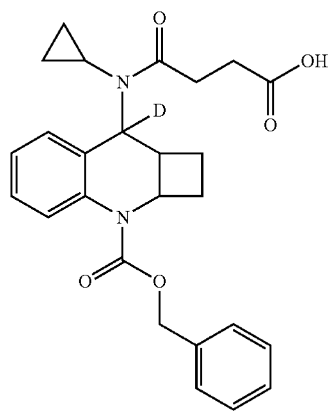 [SMILES: [2H]C1(N(C(=O)CCC(=O)O)C2CC2)c2ccccc2N(C(=O)OCc2ccccc2)C2CCC21] | cis, cis, single enantiomer | 3-(phenylmethyl) deuterated-cis, cis-[(3-carboxy-1-oxopropyl)cyclopropylamino]-2,2a,8,8a-tetrahydrocyclobuta[b]quinoline-3(1H)-carboxylate-(8D) | 449.9 |
| 112 | 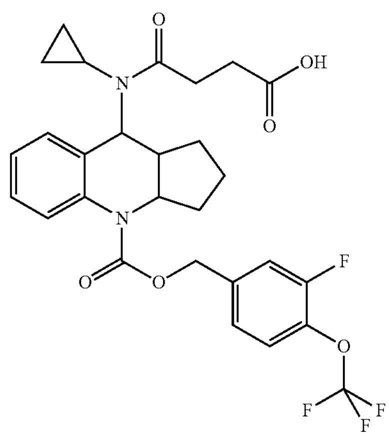 [SMILES: O=C(O)CCC(=O)N(C1CC1)C1c2ccccc2N(C(=O)OCc2ccc(OC(F)(F)F)c(F)c2)C2CCCC21] | cis, cis, single enantiomer | 4-[[3-fluoro-4-(trifluoromethoxy)phenyl]methyl] cis, cis-[(3-carboxy-1-oxopropyl)cyclopropylamino]-1,2,3,3a,9,9a-hexahydro-4H-cyclopenta[b]quinoline-4-carboxylate | 565.3 |
| 113 | 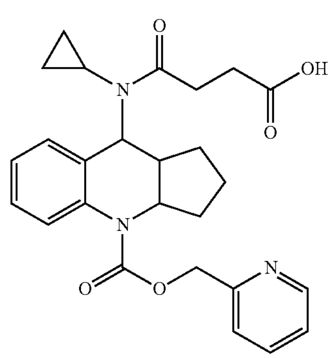 | cis, cis, single enantiomer | 4-(2-pyridinylmethyl) cis, cis-[(3-carboxy-1-oxopropyl)cyclopropylamino]-1,2,3,3a,9,9a-hexahydro-4H-cyclopenta[b]quinoline-4-carboxylate | 464.3 |
| 114 | 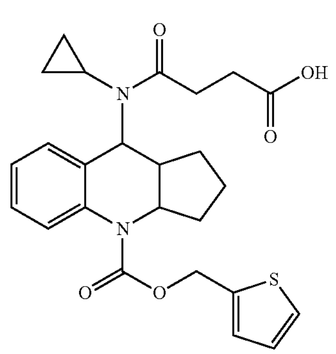 [SMILES: O=C(O)CCC(=O)N(C1CC1)C1c2ccccc2N(C(=O)OCc2cccs2)C2CCCC21] | cis, cis, single enantiomer | 4-(2-thienylmethyl) cis, cis-[(3-carboxy-1-oxopropyl)cyclopropylamino]-1,2,3,3a,9,9a-hexahydro-4H-cyclopenta[b]quinoline-4-carboxylate | 469 |

| # | Structure | Stereo designation | Name | [M + H]$^+$ |
|---|---|---|---|---|
| 115 | 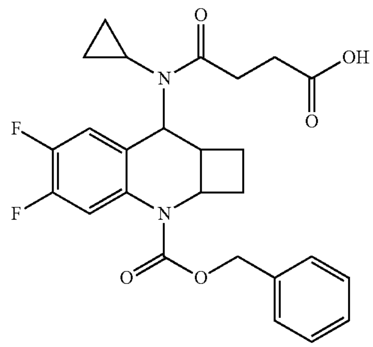 [SMILES: O=C(O)CCC(=O)N(C1CC1)C1c2cc(F)c(F)cc2N(C(=O)OCc2ccccc2)C2CCC21] | cis, cis, single enantiomer 1 | 3-(phenylmethyl) 8-[(3-carboxy-1-oxopropyl)cyclopropylamino]-5,6-difluoro-2,2a,8,8a-tetrahydro-cyclobuta[b]quinoline-3(1H)-carboxylate | 485.2 |
| 116 | 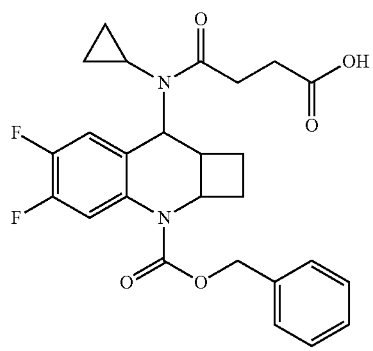 [SMILES: O=C(O)CCC(=O)N(C1CC1)C1c2cc(F)c(F)cc2N(C(=O)OCc2ccccc2)C2CCC21] | cis, cis, single enantiomer 2 | 3-(phenylmethyl) 8-[(3-carboxy-1-oxopropyl)cyclopropylamino]-5,6-difluoro-2,2a,8,8a-tetrahydro-cyclobuta[b]quinoline-3(1H)-carboxylate | 485.2 |
| 117 | 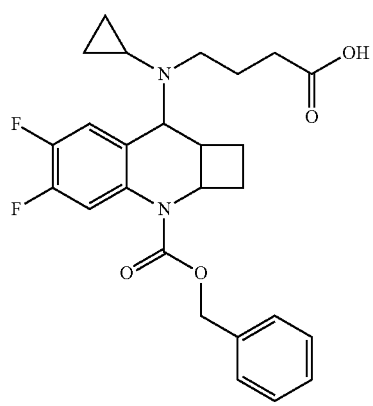 [SMILES: O=C(O)CCCN(C1CC1)C1c2cc(F)c(F)cc2N(C(=O)OCc2ccccc2)C2CCC21] | cis, cis, single enantiomer | 4-((cis, cis-3-(benzyloxycarbonyl)-5,6-difluoro-1,2,2a,3,8,8a-hexahyclrocyclobuta[b]quinolin-8-yl)(cyclopropyl)amino) butanoic acid | 470.8 |
| 118 | 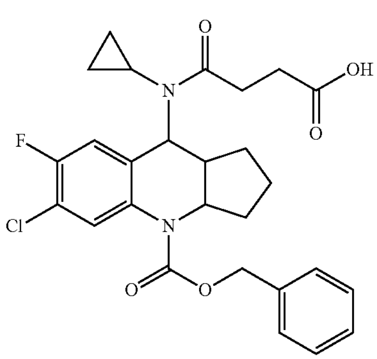 [SMILES: O=C(O)CCC(=O)N(C1CC1)C1c2cc(F)c(Cl)cc2N(C(=O)OCc2ccccc2)C2CCCC21] | cis, cis, single enantiomer | 4-(phenylmethyl) cis, cis-[(3-carboxy-1-oxopropyl)cyclopropylamino]-6-chloro-7-fluoro-1,2,3,3a,9,9a-hexahydro-4H-cyclopenta[b]quinoline-4-carboxylate | 515.3 |

| # | Structure | Stereo designation | Name | [M + H]⁺ |
|---|---|---|---|---|
| 119 | 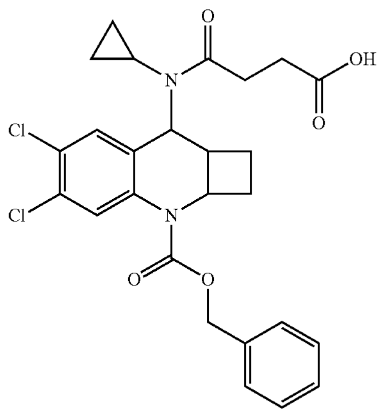 [SMILES: O=C(O)CCC(=O)N(C1CC1)C1c2cc(Cl)c(Cl)cc2N(C(=O)OCc2ccccc2)C2CCC21] | cis, cis, single enantiomer | 3-(phenylmethyl) cis,cis-8-[(3-carboxy-1-oxopropyl)cyclopropylamino]-5,6-dichloro-2,2a,8,8a-tetrahydrocyclobuta[b]quinoline-3(1H)-carboxylate | 519.3 |
| 120 | 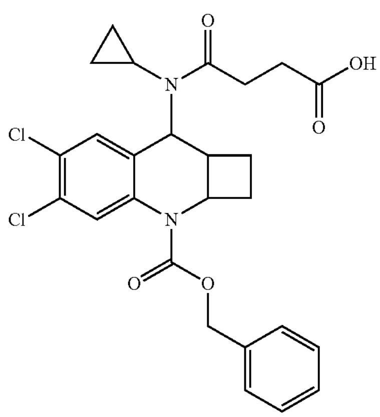 [SMILES: O=C(O)CCC(=O)N(C1CC1)C1c2cc(Cl)c(Cl)cc2N(C(=O)OCc2ccccc2)C2CCC21] | cis, cis, single enantiomer | 3-(phenylmethyl) cis,cis-8-[(3-carboxy-1-oxopropyl)cyclopropylamino]-5,6-dichloro-2,2a,8,8a-tetrahydrocyclobuta[b]quinoline-3(1H)-carboxylate | 519.3 |
| 121 | 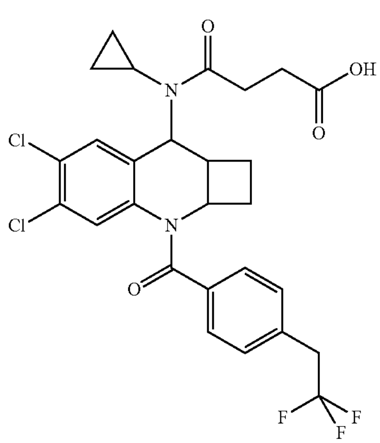 [SMILES: O=C(O)CCC(=O)N(C1CC1)C1c2cc(Cl)c(Cl)cc2N(C(=O)c2ccc(CC(F)(F)F)cc2)C2CCC21] | cis, cis, single enantiomer | 4-[cyclopropyl[cis, cis-5,6-dichloro-1,2,2a,3,8,8a-hexahydro-3-[4-(trifluoromethoxy)benzoyl]cyclobuta[b]quinolin-8-yl]amino]-4-oxobutanoic acid | 573.3 |

| # | Structure | Stereo designation | Name | [M + H]+ |
|---|---|---|---|---|
| 122 | 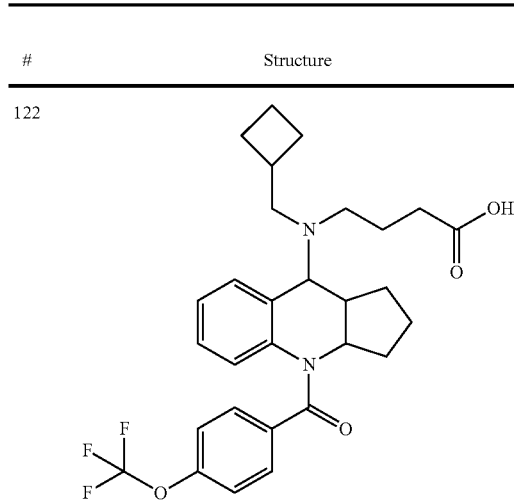 | racemic, cis, cis | 4-[(cyclobutylmethyl)[cis,cis-2,3,3a,4,9,9a-hexahydro-4-[4-(trifluoromethoxy)benzoyl]-1H-cyclopenta[b]quinolin-9-yl]amino]butanoic acid | 531 |
| 123 | 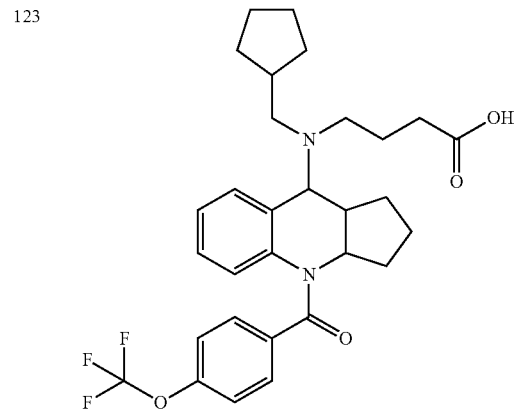 | racemic, cis, cis | 4-[(cyclopentylmethyl)[cis-2,3,3a,4,9,9a-hexahydro-4-[4-(trifluoromethoxy)benzoyl]-1H-cyclopenta[b]quinolin-9-yl]amino]butanoic acid | 545 |
| 124 | 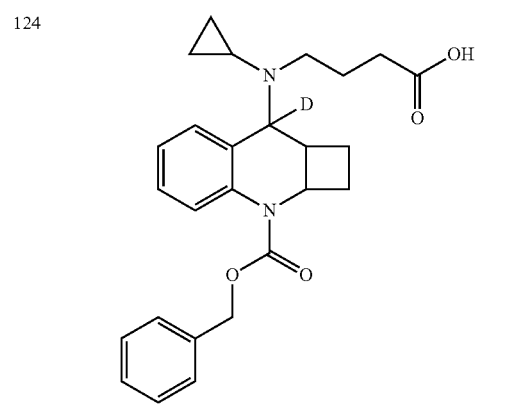 | cis, cis, single enantiomer | 3-(phenylmethyl) deuterated-cis,cis-8-[(3-carboxypropyl)cyclopropyl amino]-2,2a,8,8a-tetrahydrocyclobuta[b] quinoline-3(1H)-carboxylate-(8D) | 436 |

-continued

| # | Structure | Stereo designation | Name | [M + H]+ |
|---|---|---|---|---|
| 125 | 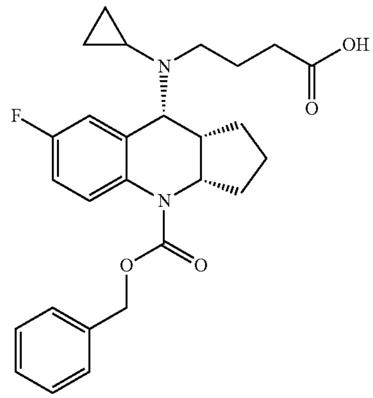 [SMILES: O=C(O)CCCN(C1CC1)[C@H]1c2cc(F)ccc2N(C(=O)OCc2ccccc2)[C@H]2CCC[C@H]21] | 3aS,9R,9aR, single enantiomer | 4-(phenylmethyl) (3aS,9R,9aR)-9-[(3-carboxypropyl)cyclopropyl amino]-7-fluoro-1,2,3,3a,9,9a-hexahydro-4H-cyclopenta[b]quinoline-4-carboxylate | 467 |
| 126 | 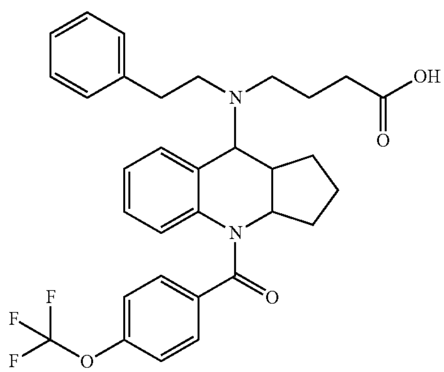 [SMILES: O=C(O)CCCN(CCc1ccccc1)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl](2-phenylethyl)amino]butanoic acid | 567 |
| 127 | 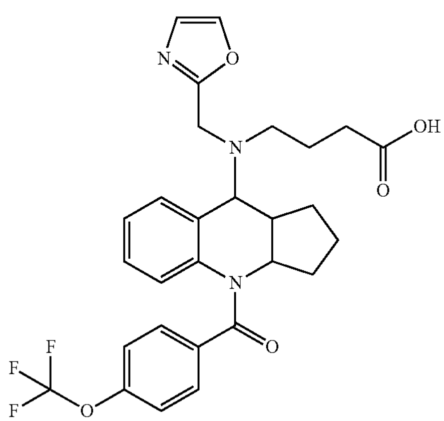 [SMILES: O=C(O)CCCN(Cc1ncco1)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl](2-oxazolylmethyl)amino] butanoic acid | 544 |
| 128 | 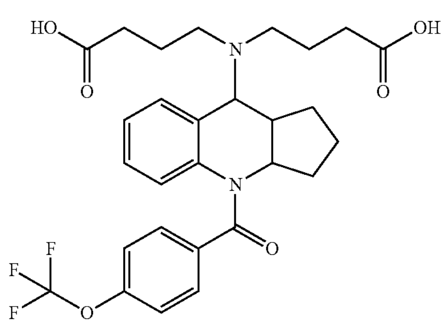 [SMILES: O=C(O)CCCN(CCCC(=O)O)C1c2ccccc2N(C(=O)c2ccc(OC(F)(F)F)cc2)C2CCCC12] | racemic, cis, cis | 4,4'-[[cis,cis-2,3,3a,4,9,9a-hexahydro-4-[4-(trifluoromethoxy)benzoyl]-1H-cyclopenta[b]quinolin-9-yl]imino]bisbutanoic acid | 549 |

| # | Structure | Stereo designation | Name | [M + H]⁺ |
|---|---|---|---|---|
| 129 | 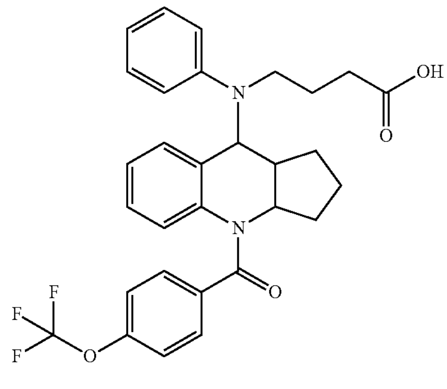 [SMILES: O=C(O)CCCN(c1ccccc1)C1c2ccccc2N(C(=O)c2ccc(OC(F)(F)F)cc2)C2CCCC12] | racemic, cis, cis | 4-[[cis,cis-2,3,3a,4,9,9a-hexahydro-4-[4-(trifluoromethoxy)benzoyl]-1H-cyclopenta[b]quinolin-9-yl]phenylamino]butanoic acid | 561 |
| 130 | 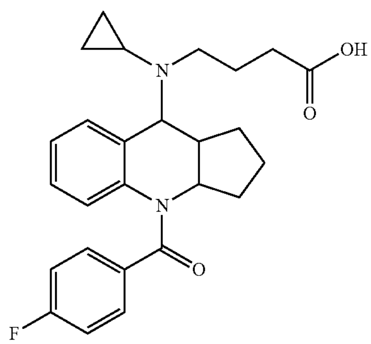 [SMILES: O=C(O)CCCN(C1CC1)C1c2ccccc2N(C(=O)c2ccc(F)cc2)C2CCCC21] | cis, cis, single enantiomer | 4-[cyclopropyl[cis,cis-4-(4-fluorobenzoyl)-2,3,3a,4,9,9a-hexahydro-1H-cyclopenta[b]quinolin-9-yl]amino]butanoic acid | 437 |
| 131 | 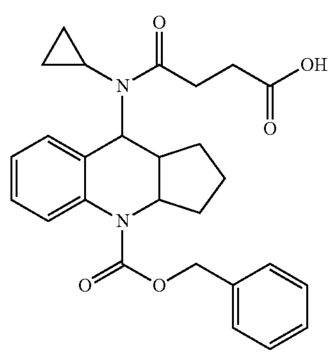 [SMILES: O=C(O)CCC(=O)N(C1CC1)C1c2ccccc2N(C(=O)OCc2ccccc2)C2CCCC21] | cis, cis, single enantiomer | 4-(phenylmethyl) cis, cis-[(3-carboxy-1-oxopropyl)cyclopropylamino]-1,2,3,3a,9,9a-hexahydro-4H-cyclopenta[b]quinoline-4-carboxylate | 462.9 |
| 132 | 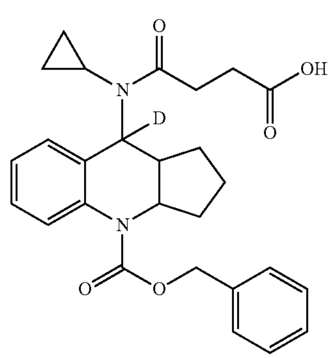 [SMILES: [2H]C1(N(C(=O)CCC(=O)O)C2CC2)c2ccccc2N(C(=O)OCc2ccccc2)C2CCCC21] | cis, cis, single enantiomer | 4-(phenylmethyl) deuterated-cis, cis-[(3-carboxy-1-oxopropyl)cyclopropylamino]-1,2,3,3a,9,9a-hexahydro-4H-cyclopenta[b]quinoline-4-carboxylate-(9D) | 463.9 |

| # | Structure | Stereo designation | Name | [M + H]+ |
|---|---|---|---|---|
| 133 | 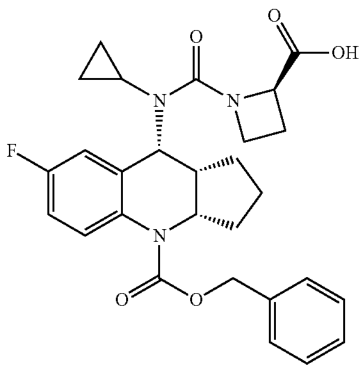 [SMILES: O=C(O)[C@H]1CCN1C(=O)N(C1CC1)[C@H]1c2cc(F)ccc2N(C(=O)OCc2ccccc2)[C@H]2CCC[C@H]21] | 3aS,9R,9aR, single enantiomer, R configuration at azetidine carbon atom | 4-(phenylmethyl) (3aS,9R,9aR)-[[[2(R)-carboxy-1-azetidinyl]carbonyl] cyclopropylamino]-7-fluoro-1,2,3,3a,9,9a-hexahydro-4H-cyclopenta[b]quinoline-4-carboxylate | 507.9 |
| 134 | 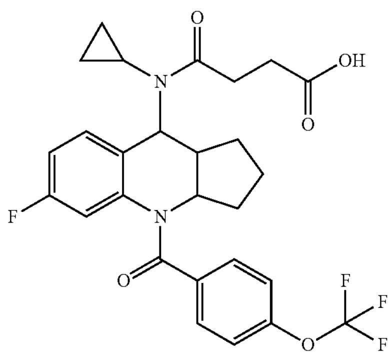 [SMILES: O=C(O)CCC(=O)N(C1CC1)C1c2ccc(F)cc2N(C(=O)c2ccc(OC(F)(F)F)cc2)C2CCCC21] | cis, cis, single enantiomer | 4-[cyclopropyl[cis, cis-7-fluoro-2,3,3a,4,9,9a-hexahydro-4-[4-(trifluoromethoxy)benzoyl]-1H-cyclopenta[b]quinolin-9-yl]amino]-4-oxobutanoic acid | 534.8 |
| 135 | 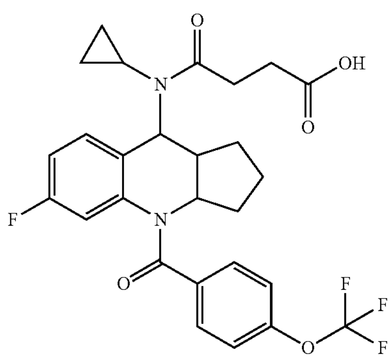 [SMILES: O=C(O)CCC(=O)N(C1CC1)C1c2ccc(F)cc2N(C(=O)c2ccc(OC(F)(F)F)cc2)C2CCCC21] | cis, cis, single enantiomer | 4-[cyclopropyl[cis, cis-6-fluoro-2,3,3a,4,9,9a-hexahydro-4-[4-(trifluoromethoxy)benzoyl]-1H-cyclopenta[b]quinolin-9-yl]amino]-4-oxo-butanoic acid | 534.8 |
| 136 | 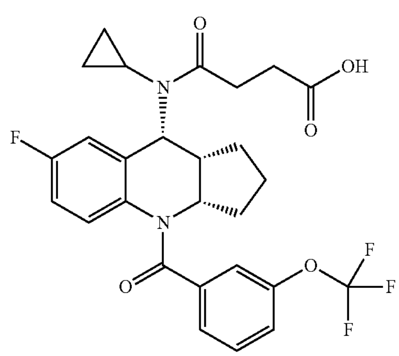 [SMILES: O=C(O)CCC(=O)N(C1CC1)[C@H]1c2cc(F)ccc2N(C(=O)c2cccc(OC(F)(F)F)c2)[C@H]2CCC[C@H]21] | 3aS,9R,9aR, single enantiomer | 4-[cyclopropyl[(3aS,9R,9aR)-7-fluoro-2,3,3a,9,9a-hexahydro-4-[3-(trifluoromethoxy)benzoyl]-1H-cyclopenta[b]quinolin-9-yl]amino]-4-oxobutanoic acid | 534.8 |

-continued

| # | Structure | Stereo designation | Name | [M + H]+ |
|---|---|---|---|---|
| 137 | 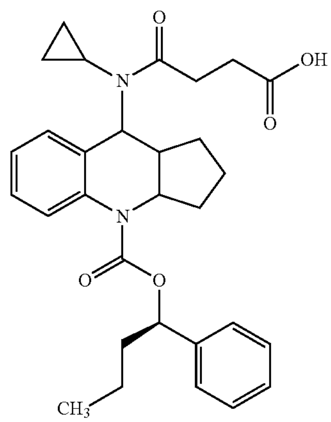 [SMILES: CCC[C@@H](OC(=O)N1c2ccccc2C(N(C(=O)CCC(=O)O)C2CC2)C2CCCC21)c1ccccc1] | cis, cis single enantiomer, R configuration at benzylic carbamate | 4-(1(R)-phenylbutyl) cis, cis-[(3-carboxy-1-oxopropyl)cyclopropylamino]-1,2,3,3a,9,9a-hexahydro-4H-cyclopenta[b]quinoline-4-carboxylate | 526.8 [M + Na]+ |
| 138 | 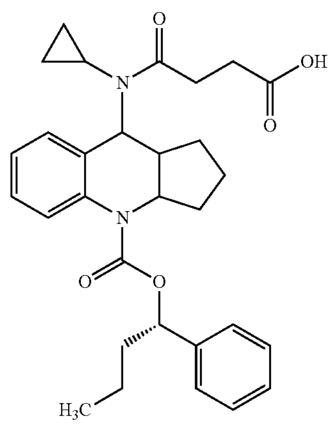 [SMILES: CCC[C@H](OC(=O)N1c2ccccc2C(N(C(=O)CCC(=O)O)C2CC2)C2CCCC21)c1ccccc1] | cis, cis single enantiomer, S configuration at benzylic carbon of carbamate | 4-(1(S)-phenylbutyl) cis, cis-[(3-carboxy-1-oxopropyl)cyclopropylamino]-1,2,3,3a,9,9a-hexahydro-4H-cyclopenta[b]quinoline-4-carboxylate | 526.8 [M + Na]+ |
| 139 | 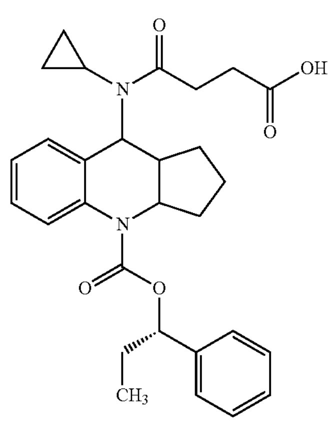 [SMILES: CC[C@H](OC(=O)N1c2ccccc2C(N(C(=O)CCC(=O)O)C2CC2)C2CCCC21)c1ccccc1] | cis, cis single enantiomer, S configuration at benzylic carbamate | 4-(1(S)-phenylpropyl) cis, cis-[(3-carboxy-1-oxopropyl)cyclopropylamino]-1,2,3,3a,9,9a-hexahydro-4H-cyclopenta[b]quinoline-4-carboxylate | 512.8 [M + Na]+ |

-continued

| # | Structure | Stereo designation | Name | [M + H]+ |
|---|---|---|---|---|
| 140 | 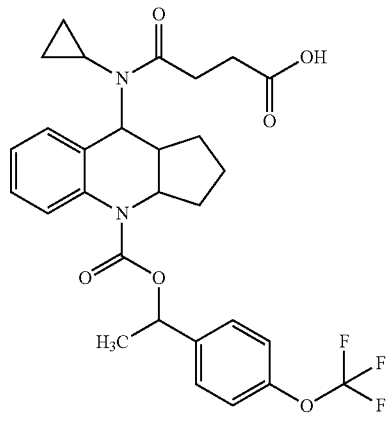 [SMILES: CC(OC(=O)N1c2ccccc2C(N(C(=O)CCC(=O)O)C2CC2)C2CCCC21)c1ccc(OC(F)(F)F)cc1] | cis, cis (enantiopure), racemic at benzylic carbamate | 4-[1-[4-(trifluoromethoxy)phenyl]ethyl] cis, cis-[(3-carboxy-1-oxopropyl)cyclopropylamino]-1,2,3,3a,9,9a-hexahydro-4H-cyclopenta[b]quinoline-4-carboxylate | 582.7 [M + Na]+ |
| 141 | 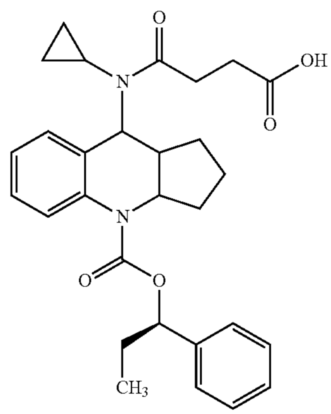 [SMILES: CC[C@@H](OC(=O)N1c2ccccc2C(N(C(=O)CCC(=O)O)C2CC2)C2CCCC21)c1ccccc1] | cis, cis single enantiomer, R at benzylic carbamate | 4-(1(R)-phenylpropyl) cis, cis-[(3-carboxy-1-oxopropyl)cyclopropylamino]-1,2,3,3a,9,9a-hexahydro-4H-cyclopenta[b]quinoline-4-carboxylate | 512.8 [M + Na]+ |
| 142 | 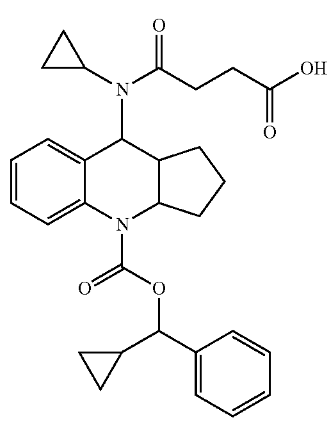 [SMILES: O=C(O)CCC(=O)N(C1CC1)C1c2ccccc2N(C(=O)OC(c2ccccc2)C2CC2)C2CCCC21] | cis, cis single enantiomer, racemic at benzylic carbamate | 4-(cyclopropylphenylmethyl) cis, cis-[(3-carboxy-1-oxopropyl)cyclopropylamino]-1,2,3,3a,9,9a-hexahydro-4H-cyclopenta[b]quinoline-4-carboxylate | 502.8 |

-continued

| # | Structure | Stereo designation | Name | [M + H]+ |
|---|---|---|---|---|
| 143 | 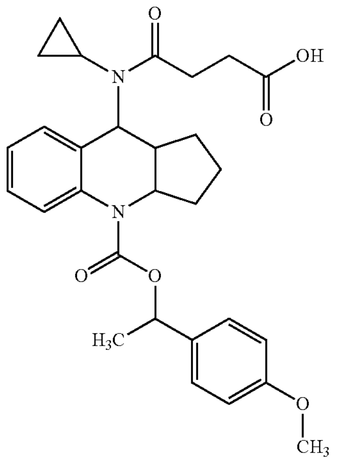 [SMILES: COc1ccc(C(C)OC(=O)N2c3ccccc3C(N(C(=O)CCC(=O)O)C3CC3)C3CCCC32)cc1] | cis, cis (enantiopure), racemic at benzylic carbamate | 4-[1-(4-methoxyphenyl)ethyl] cis, cis-[(3-carboxy-1-oxopropyl)cyclopropylamino]-1,2,3,3a,9,9a-hexahydro-4H-cyclopenta[b]quinoline-4-carboxylate | 529.2 [M + Na]+ |
| 144 | 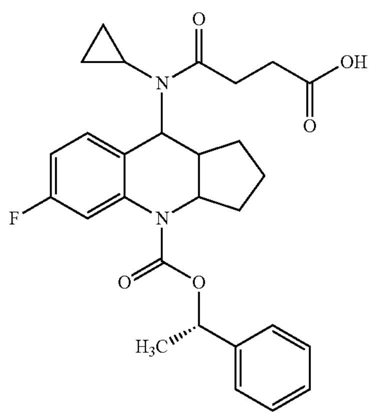 [SMILES: C[C@H](OC(=O)N1c2cc(F)ccc2C(N(C(=O)CCC(=O)O)C2CC2)C2CCCC21)c1ccccc1] | cis, cis single enantiomer, S configuration at benzylic carbamate | 4-(1(S)-phenylethyl) cis, cis-[(3-carboxy-1-oxopropyl)cyclopropylamino]-6-fluoro-1,2,3,3a,9,9a-hexahydro-4H-cyclopenta[b]quinoline-4-carboxylate | 516.8 [M + Na]+ |
| 145 | 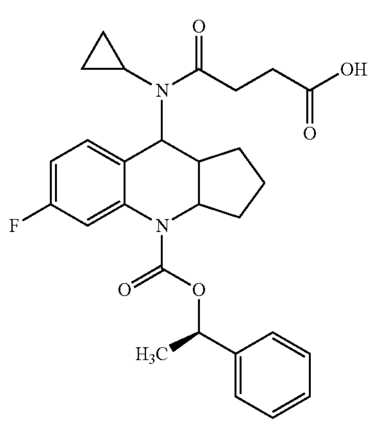 [SMILES: C[C@@H](OC(=O)N1c2cc(F)ccc2C(N(C(=O)CCC(=O)O)C2CC2)C2CCCC21)c1ccccc1] | cis, cis single enantiomer, R configuration at benzylic carbamate | 4-(1(R)-phenylethyl) cis, cis-[(3-carboxy-1-oxopropyl)cyclopropylamino]-6-fluoro-1,2,3,3a,9,9a-hexahydro-4H-cyclopenta[b]quinoline-4-carboxylate | 516.8 [M + Na]+ |

-continued

| # | Structure | Stereo designation | Name | [M + H]⁺ |
|---|---|---|---|---|
| 146 | 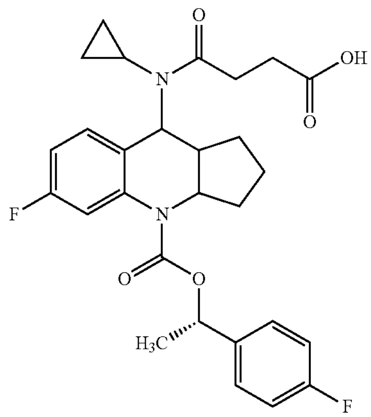 [SMILES: C[C@H](OC(=O)N1c2cc(F)ccc2C(N(C(=O)CCC(=O)O)C2CC2)C2CCCC21)c1ccc(F)cc1] | cis, cis single enantiomer, S configuration at benzylic carbamate | 4-[1(S)-(4-fluorophenyl)ethyl] cis, cis-[(3-carboxy-1-oxopropyl)cyclopropylamino]-6-fluoro-1,2,3,3a,9,9a-hexahydro-4H-cyclopenta[b]quinoline-4-carboxylate | 534.8 [M + Na]⁺ |
| 147 | 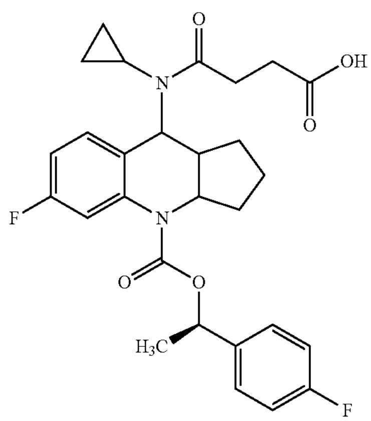 [SMILES: C[C@@H](OC(=O)N1c2cc(F)ccc2C(N(C(=O)CCC(=O)O)C2CC2)C2CCCC21)c1ccc(F)cc1] | cis, cis single enantiomer, R configuration at benzylic carbamate | 4-[1(R)-(4-fluorophenyl)ethyl] cis, cis-[(3-carboxy-1-oxopropyl)cyclopropylamino]-6-fluoro-1,2,3,3a,9,9a-hexahydro-4H-cyclopenta[b]quinoline-4-carboxylate | 534.7 [M + Na]⁺ |
| 148 | 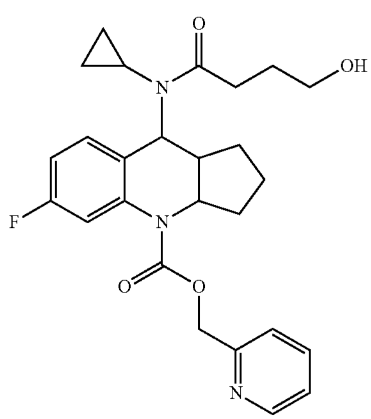 [SMILES: O=C(OCc1ccccn1)N1c2cc(F)ccc2C(N(C(=O)CCCO)C2CC2)C2CCCC21] | cis, cis, single enantiomer | 4-(2-pyridinylmethyl) cis, cis-[(3-carboxy-1-oxopropyl)cyclopropylamino]-6-fluoro-1,2,3,3a,9,9a-hexahydro-4H-cyclopenta[b]quinoline-4-carboxylate | 481.8 |

| # | Structure | Stereo designation | Name | [M + H]+ |
|---|---|---|---|---|
| 149 | 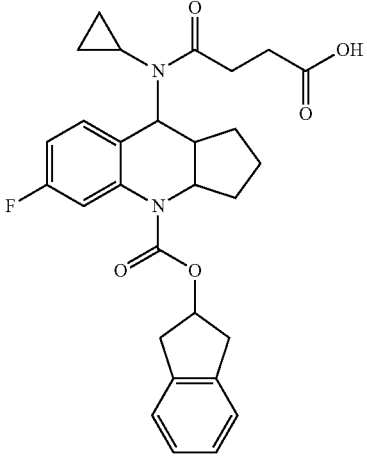 [SMILES: O=C(O)CCC(=O)N(C1CC1)C1c2ccc(F)cc2N(C(=O)OC2Cc3ccccc3C2)C2CCCC21] | cis, cis, single enantiomer | 4-(2,3-dihydro-1H-inden-2-yl) cis, cis-[(3-carboxy-1-oxopropyl)cyclopropylamino]-6-fluoro-1,2,3,3a,9,9a-hexahydro-4H-cyclopenta[b]quinoline-4-carboxylate | 506.8 |
| 150 | 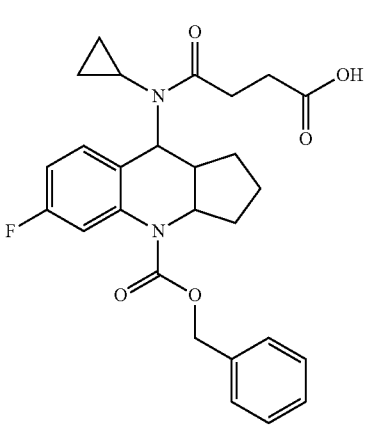 [SMILES: O=C(O)CCC(=O)N(C1CC1)C1c2ccc(F)cc2N(C(=O)OCc2ccccc2)C2CCCC21] | cis, cis, single enantiomer | 4-(phenylmethyl) cis, cis-[(3-carboxy-1-oxopropyl)cyclopropylamino]-6-fluoro-1,2,3,3a,9,9a-hexahydro-4H-cyclopenta[b]quinoline-4-carboxylate | 480.8 |
| 151 | 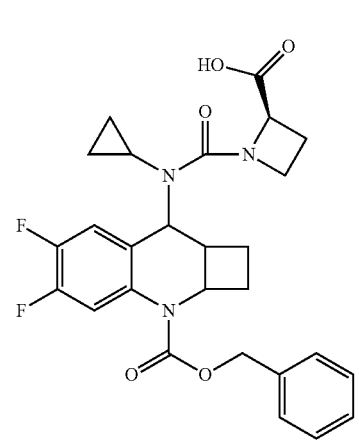 [SMILES: O=C(O)[C@H]1CCN1C(=O)N(C1CC1)C1c2cc(F)c(F)cc2N(C(=O)OCc2ccccc2)C2CCC21] | cis, cis single enantiomer, R at acid side chain | (R)-1-((cis, cis-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid | 533.7 [M + Na]+ |

| # | Structure | Stereo designation | Name | [M + H]+ |
|---|---|---|---|---|
| 152 | 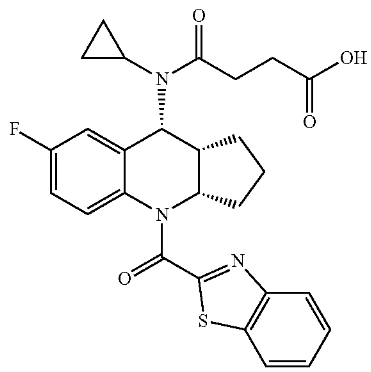 [SMILES: O=C(O)CCC(=O)N(C1CC1)[C@H]1c2cc(F)ccc2N(C(=O)c2nc3ccccc3s2)[C@H]2CCC[C@H]21] | 3aS,9R,9aR single enantiomer | 4-(((3aS,9R,9aR)-4-(benzo[d]thiazole-2-carbonyl)-7-fluoro-2,3,3a,4,9,9a-hexahydro-1H-cyclopenta[b]quinolin-9-yl)(cyclopropyl)amino)-4-oxobutanoic acid | 507.8 |
| 153 | 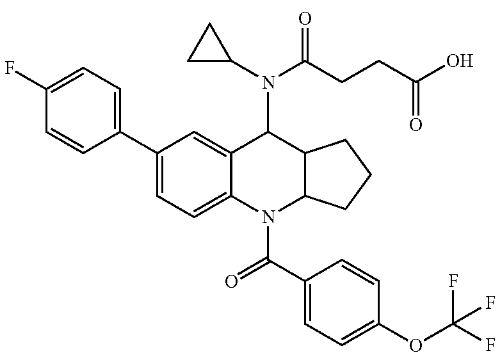 [SMILES: O=C(O)CCC(=O)N(C1CC1)C1c2cc(-c3ccc(F)cc3)ccc2N(C(=O)c2ccc(OC(F)(F)F)cc2)C2CCCC21] | cis, cis, single enantiomer | 4-(cyclopropyl((cis, cis)-7-(4-fluorophenyl)-4-(4-(trifluoromethoxy)benzoyl)-2,3,3a,4,9,9a-hexahydro-1H-cyclopenta[b]quinolin-9-yl)amino)-4-oxobutanoic acid | 610.6 |
| 154 | 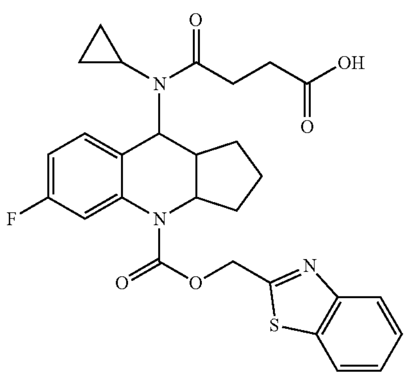 [SMILES: O=C(O)CCC(=O)N(C1CC1)C1c2ccc(F)cc2N(C(=O)OCc2nc3ccccc3s2)C2CCCC21] | cis, cis, single enantiomer | 4-(((cis, cis)-4-((benzo[d]thiazol-2-ylmethoxy)carbonyl)-6-fluoro-2,3,3a,4,9,9a-hexahydro-1H-cyclopenta[b]quinolin-9-yl)(cyclopropyl)amino)-4-oxobutanoic acid | 537.8 |
| 155 | 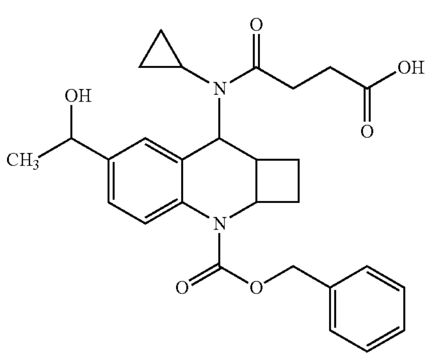 [SMILES: CC(O)c1ccc2c(c1)C(N(C(=O)CCC(=O)O)C1CC1)C1CCC1N2C(=O)OCc1ccccc1] | cis, cis single enantiomer, racemic at benzylic carbon of the alcohol | 4-((cis, cis-3-((benzyloxy)carbonyl)-6-(1-hydroxyethyl)-1,2,2a,3,8,8a-hexahydrocyclobuta[b]quinolin-8-yl)(cyclopropyl)amino)-4-oxobutanoic acid | 515 [M + Na]+ |

| # | Structure | Stereo designation | Name | [M + H]+ |
|---|---|---|---|---|
| 156 | 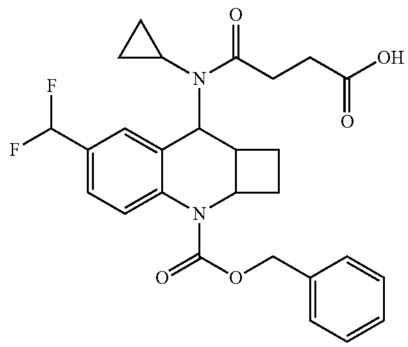 [SMILES: O=C(O)CCC(=O)N(C1CC1)C1c2cc(C(F)F)ccc2N(C(=O)OCc2ccccc2)C2CCC21] | cis, cis, single enantiomer | 4-((cis, cis-3-((benzyloxy)carbonyl)-6-(difluoromethyl)-1,2,2a,3,8,8a-hexahydrocyclobuta[b]quinolin-8-yl)(cyclopropyl)amino)-4-oxobutanoic acid | 499 |
| 157 | 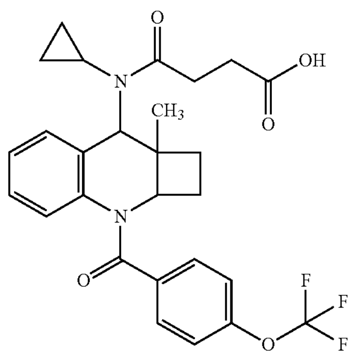 [SMILES: CC12CCC1N(C(=O)c1ccc(OC(F)(F)F)cc1)c1ccccc1C2N(C(=O)CCC(=O)O)C1CC1] | single enantiomer, cyclopropylamine trans to cyclobutyl ring, cyclobutyl ring cis fused | 4-(cyclopropyl(cis, trans-8a-methyl-3-(4-(trifluoromethoxy)benzoyl)-1,2,2a,3,8,8a-hexahydrocyclobuta[b]quinolin-8-yl)amino)-4-oxobutanoic acid | 517 |
| 158 | 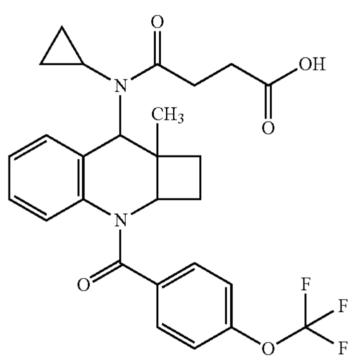 [SMILES: CC12CCC1N(C(=O)c1ccc(OC(F)(F)F)cc1)c1ccccc1C2N(C(=O)CCC(=O)O)C1CC1] | single enantiomer, cyclobutyl ring cis fused, cyclopropylamine cis to cyclobutyl ring | 4-(cyclopropyl(cis, cis-8a-methyl-3-(4-(trifluoromethoxy)benzoyl)-1,2,2a,3,8,8a-hexahydrocyclobuta[b]quinolin-8-yl)amino)-4-oxobutanoic acid | 517 |
| 159 | 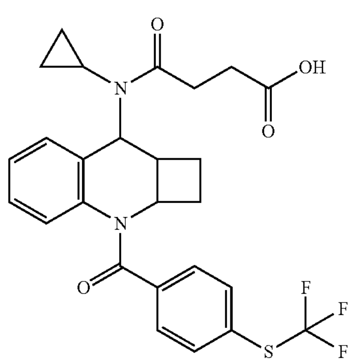 [SMILES: O=C(O)CCC(=O)N(C1CC1)C1c2ccccc2N(C(=O)c2ccc(SC(F)(F)F)cc2)C2CCC21] | cis, cis, single enantiomer | 4-(cyclopropyl(cis, cis-3-(4-((trifluoromethyl)thio)benzoyl)-1,2,2a,3,8,8a-hexahydrocyclobuta[b]quinolin-8-yl)amino)-4-oxobutanoic acid | 519 |

| # | Structure | Stereo designation | Name | [M + H]+ |
|---|---|---|---|---|
| 160 | 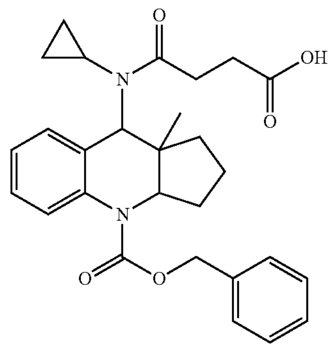 [SMILES: CC12CCCC1N(C(=O)OCc1ccccc1)c1ccccc1C2N(C(=O)CCC(=O)O)C1CC1] | single enantiomer, cyclopentyl ring cis fused, cyclopropylamine cis to cyclopentyl ring | 4-((cis, cis-4-((benzyloxy)carbonyl)-9a-methyl-2,3,3a,4,9,9a-hexahydro-1H-cyclopenta[b]quinolin-9-yl)(cyclopropyl)amino)-4-oxobutanoic acid | 477 |
| 161 | 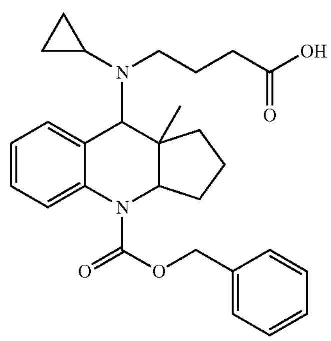 [SMILES: CC12CCCC1N(C(=O)OCc1ccccc1)c1ccccc1C2N(CCCC(=O)O)C1CC1] | single enantiomer, cyclopentyl ring cis fused, cyclopropylamine cis to cyclopentyl ring | 4-((cis, cis-4-((benzyloxy)carbonyl)-9a-methyl-2,3,3a,4,9,9a-hexahydro-1H-cyclopenta[b]quinolin-9-yl)(cyclopropyl)amino) butanoic acid | 463 |
| 162 | 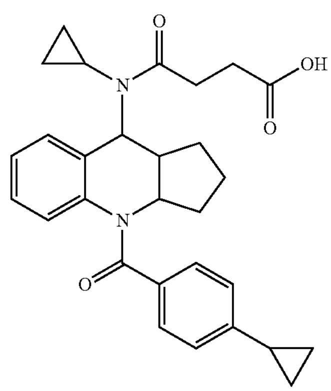 [SMILES: O=C(O)CCC(=O)N(C1CC1)C1c2ccccc2N(C(=O)c2ccc(C3CC3)cc2)C2CCCC21] | cis, cis, single enantiomer | 4-(cyclopropyl(cis, cis-4-(4-cyclopropylbenzoyl)-2,3,3a,4,9,9a-hexahydro-1H-cyclopenta[b]quinolin-9-yl)amino)-4-oxobutanoic acid | 473 |
| 163 | 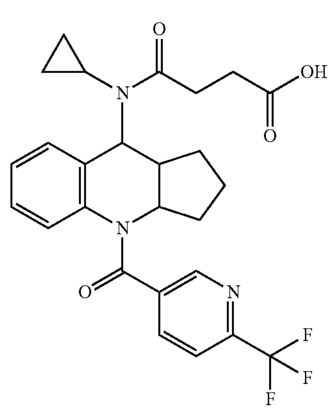 [SMILES: O=C(O)CCC(=O)N(C1CC1)C1c2ccccc2N(C(=O)c2ccc(C(F)(F)F)nc2)C2CCCC21] | cis, cis, single enantiomer | 4-(cyclopropyl(cis, cis-4-(6-(trifluoromethyl)nicotinoyl)-2,3,3a,4,9,9a-hexahydro-1H-cyclopenta[b]quinolin-9-yl)amino)-4-oxobutanoic acid | 502 |

| # | Structure | Stereo designation | Name | [M + H]⁺ |
|---|---|---|---|---|
| 164 | 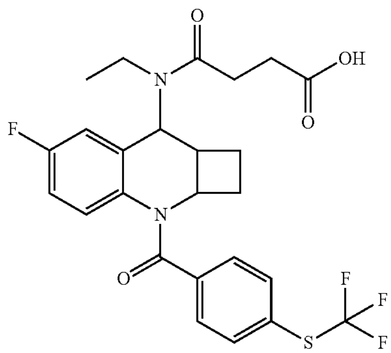 [SMILES: CCN(C(=O)CCC(=O)O)C1c2cc(F)ccc2N(C(=O)c2ccc(SC(F)(F)F)cc2)C2CCC12] | cis, cis, single enantiomer | 4-(ethyl(cis, cis-6-fluoro-3-(4-((trifluoromethyl)thio)benzoyl)-1,2,2a,3,8,8a-hexahydrocyclobuta[b]quinolin-8-yl)amino)-4-oxobutanoic acid | 525 |
| 165 | 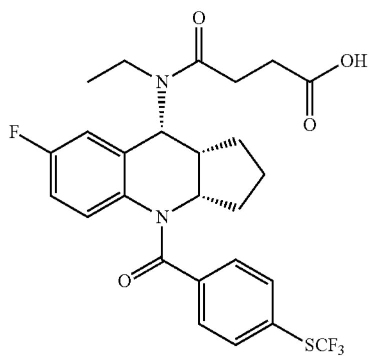 | 3aS,9R,9aR, single enantiomer | 4-(ethyl((3aS,9R,9aR)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid | 539 |
| 166 | 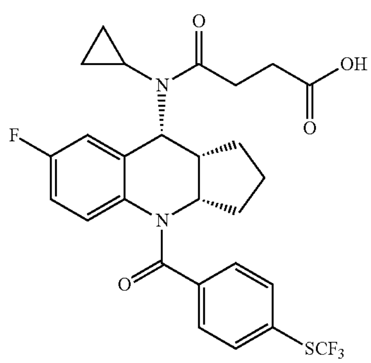 | 3aS,9R,9aR, single enantiomer | 4-(cyclopropyl((3aS,9R,9aR)-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid | 551 |
| 167 | 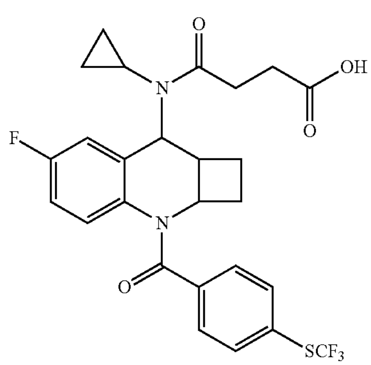 | cis, cis, single enantiomer | 4-(cyclopropyl(cis, cis-6-fluoro-3-(4-((trifluoromethyl)thio)benzoyl)-1,2,2a,3,8,8a-hexahydrocyclobuta[b]quinolin-8-yl)amino)-4-oxobutanoic acid | 537 |

-continued

| # | Structure | Stereo designation | Name | [M + H]+ |
|---|---|---|---|---|
| 168 | 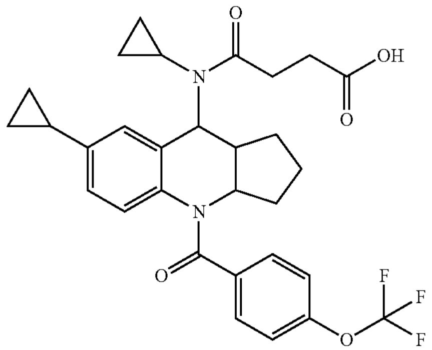 [SMILES: O=C(O)CCC(=O)N(C1CC1)C1c2cc(C3CC3)ccc2N(C(=O)c2ccc(OC(F)(F)F)cc2)C2CCCC21] | cis, cis, single enantiomer | 4-(cyclopropyl(cis, cis-7-cyclopropyl-4-(4-(trifluoromethoxy)benzoyl)-2,3,3a,4,9,9a-hexahydro-1H-cyclopenta[b]quinolin-9-yl)amino)-4-oxobutanoic acid | 557 |
| 169 | 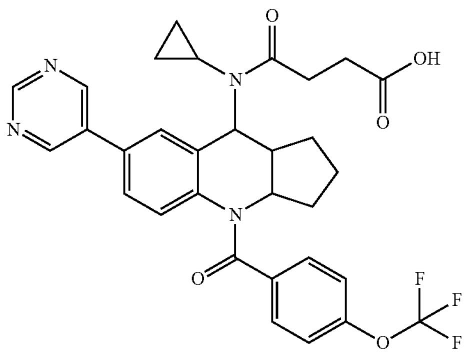 [SMILES: O=C(O)CCC(=O)N(C1CC1)C1c2cc(-c3cncnc3)ccc2N(C(=O)c2ccc(OC(F)(F)F)cc2)C2CCCC21] | cis, cis, single enantiomer | 4-(cyclopropyl(cis, cis-7-(pyrimidin-5-yl)-4-(4-(trifluoromethoxy)benzoyl)-2,3,3a,4,9,9a-hexahydro-1H-cyclopenta[b]quinolin-9-yl)amino)-4-oxobutanoic acid | 595 |
| 170 | 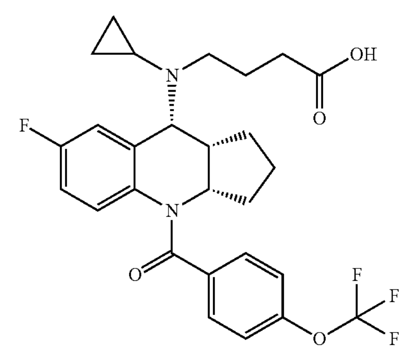 [SMILES: O=C(O)CCCN(C1CC1)[C@H]1c2cc(F)ccc2N(C(=O)c2ccc(OC(F)(F)F)cc2)[C@H]2CCC[C@H]21] | 3aS,9R,9aR, Single enantiomer | 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)butanoic acid | 521 |

Example 171

Preparation of 4-(Cyclopropyl-(3aS,9R,9aR)-7-fluoro-4-(2-hydroxy-4-(trifluoromethoxy)benzoyl)-2,3,3a,4,9,9a-hexahydro-1H-cyclopenta[b]quinolin-9-yl)amino)-4-oxobutanoic acid (171)

Step 1

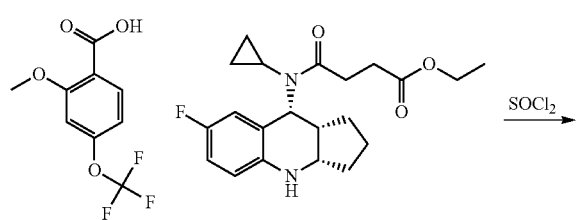

-continued

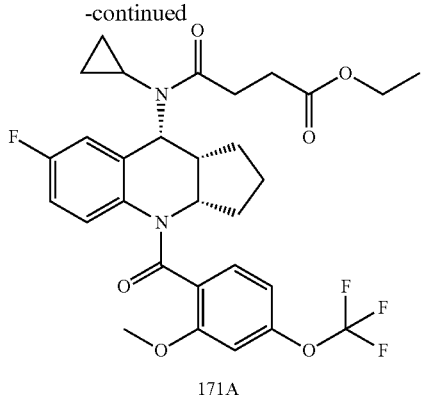

171A

A mixture of 2-methoxy-4-(trifluoromethoxy)benzoic acid (70.9 mg, 0.300 mmol) in thionyl chloride (2 mL, 27.4 mmol) was heated up 40° C. for 2 h before the mixture was cooled and then concentrated under reduced pressure to remove the excess thionyl chloride. The residue was taken up in dichloromethane (2 mL), the solution was added to a stirred, room temperature mixture of ethyl 4-(cyclopropyl((3aS,9R,9aR)-7-fluoro-2,3,3a,4,9,9a-hexahydro-H-cyclopenta[b]quinolin-9-yl)amino)-4-oxobutanoate (75 mg, 0.200 mmol), DMAP (4.89 mg, 0.040 mmol) and Hunig's Base (0.105 mL, 0.601 mmol) in dichloromethane (2 mL) and the mixture was stirred at room temperature for overnight before it was diluted with dichloromethane (10 mL), washed with aqueous sodium hydroxide (0.5 M, 2×6 mL), dried (MgSO$_4$), filtered and the solvent was evaporated under reduced pressure. The residue was purified by column chromatography on silica gel 40 g prepacked column, eluting with EtOAc/isohexane=50% to give ethyl 4-(cyclopropyl((3aS,9R,9aR)-7-fluoro-4-(2-methoxy-4-(trifluoromethoxy)benzoyl)-2,3,3a,4,9,9a-hexahydro-1H-cyclopenta[b]quinolin-9-yl)amino)-4-oxobutanoate 171A (73 mg, 0.123 mmol, 61.5% yield) as a white foam.

Step 2

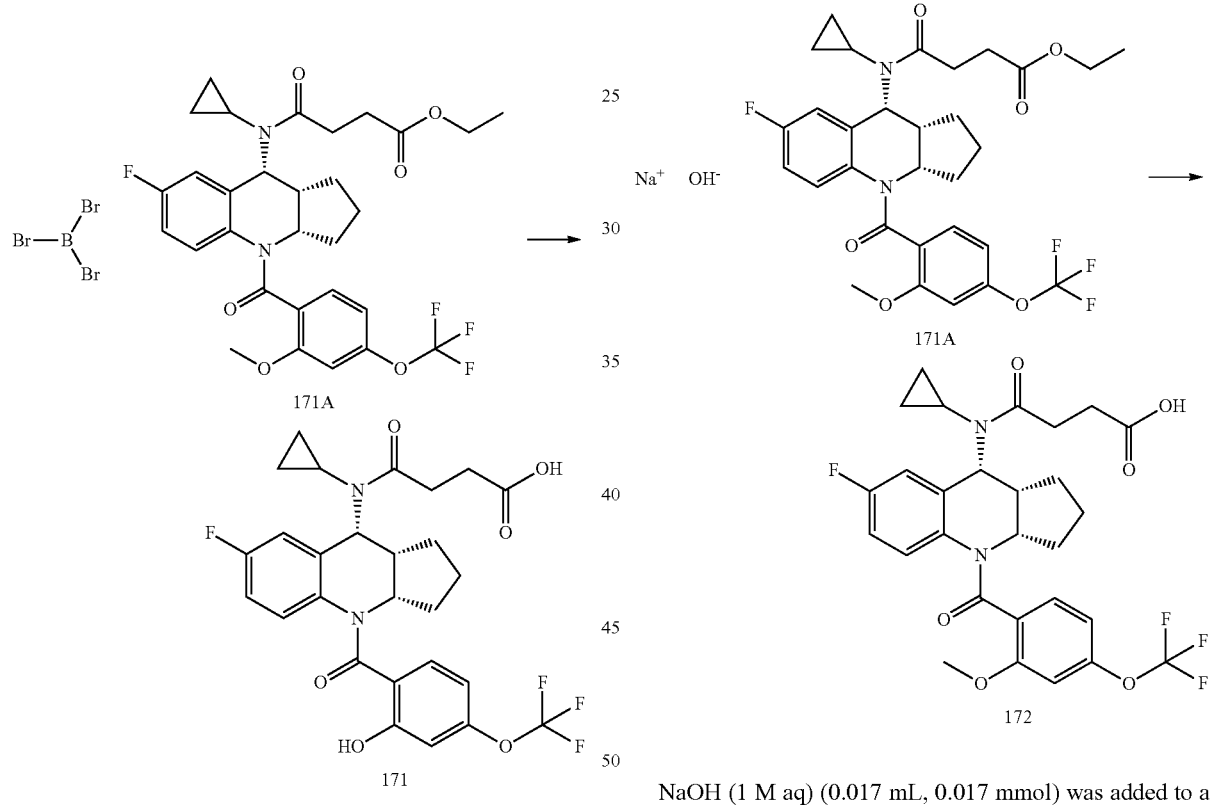

171A

171

1 M BBr$_3$ (0.089 mL, 0.089 mmol) in dichloromethane was added to a stirred mixture of ethyl 4-(cyclopropyl((3aS,9R,9aR)-7-fluoro-4-(2-methoxy-4-(trifluoromethoxy)benzoyl)-2,3,3a,4,9,9a-hexahydro-1H-cyclopenta[b]quinolin-9-yl)amino)-4-oxobutanoate (42 mg, 0.071 mmol) in dichloromethane (5 mL) at −78° C. and the mixture was stirred at −78° C. for 30 min. then room temperature for 1 h. LCMS showed the reaction was complete. The mixture was concentrated, the residue was taken up in MeOH (1.0 mL) and tetrahydrofuran (1.0 mL), NaOH (1 M aq) (0.284 mL, 0.284 mmol) was added, the mixture was kept stirring at room temperature for 2 h. The reaction mixture was diluted with water (5 mL), diethyl ether (20 mL) was added. The aqeuous layer was separated, acidified with 2 M hydrochloric acid to pH ~3, extracted with dichloromethane (2×10 mL), the combined organic was dried MgSO$_4$, filtered and concentrated. The residue was purified by column chromatography on silica gel; 24 g prepacked column, eluting with CH$_2$Cl$_2$/MeOH=6% to 4-(Cyclopropyl-(3aS,9R,9aR)-7-fluoro-4-(2-hydroxy-4-(trifluoromethoxy)benzoyl)-2,3,3a,4,9,9a-hexahydro-H-cyclopenta[b]quinolin-9-yl)amino)-4-oxobutanoic acid 171 (35 mg, 0.064 mmol, 90% yield) as a white solid; [M+H$^+$]=551.2.

Example 172

Preparation of 4-(Cyclopropyl-(3aS,9R,9aR)-7-fluoro-4-(2-methoxy-4-(trifluoromethoxy)benzoyl)-2,3,3a,4,9,9a-hexahydro-1H-cyclopenta[b]quinolin-9-yl)amino)-4-oxobutanoic acid (172)

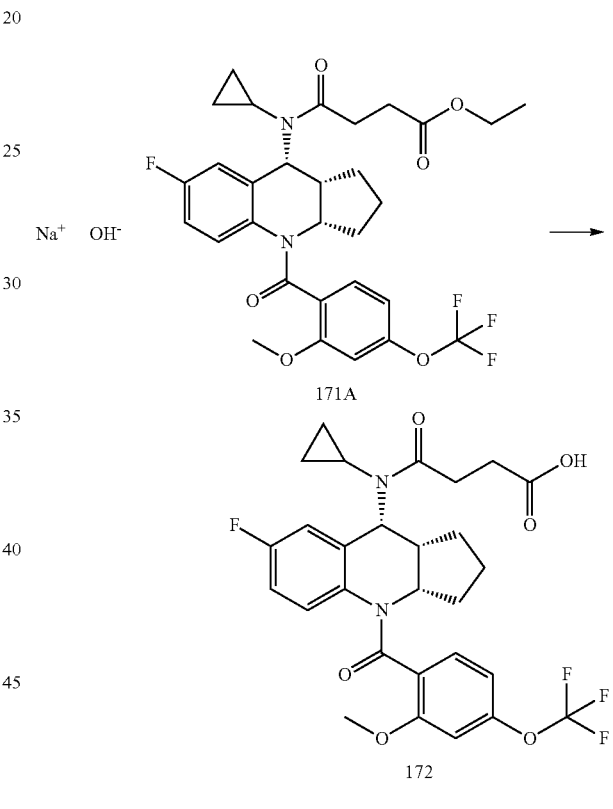

171A

172

NaOH (1 M aq) (0.017 mL, 0.017 mmol) was added to a stirred, room temperature mixture of ethyl 4-(cyclopropyl ((3aS,9R,9aR)-7-fluoro-4-(2-methoxy-4-(trifluoromethoxy) benzoyl)-2,3,3a,4,9,9a-hexahydro-1H-cyclopenta[b]quinolin-9-yl)amino)-4-oxobutanoate (10 mg, 0.017 mmol) in MeOH (1 mL) and tetrahydrofuran (1.0 mL), and the mixture was stirred at room temperature for 2 h. The reaction mixture was diluted with water (2 mL), diethyl ether (2 mL) was added. The aqeuous layer was separated, acidified with hydrochloric acid (1 M) to pH ~3, extracted with dichloromethane (2×3 mL), the combined organic was dried (MgSO$_4$), filtered and concentrated to give 4-(cyclopropyl (3aS,9R,9aR)-7-fluoro-4-(2-methoxy-4-(trifluoromethoxy) benzoyl)-2,3,3a,4,9,9a-hexahydro-1H-cyclopenta[b]quinolin-9-yl)amino)-4-oxobutanoic acid 172 (4.5 mg, 7.97 μmol, 47.2% yield) as a white foam; [M+H$^+$]=565.2

Example 173

Preparation of 4-(Cyclopropyl-(3aS,9R,9aR)-7-fluoro-4-(3-hydroxy-4-(trifluoromethoxy)benzoyl)-2,3,3a,4,9,9a-hexahydro-1H-cyclopenta[b]quinolin-9-yl)amino)-4-oxobutanoic acid (173)

Step 1

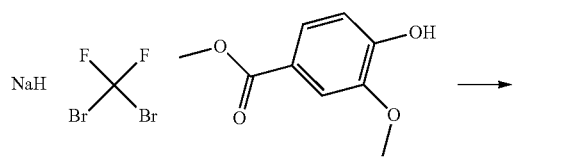

173A

NaH (1.647 g, 41.2 mmol) was added to a stirred, 0° C. mixture of methyl vanillate (5 g, 27.4 mmol) in DMF (30 mL) and the mixture was stirred at 0° C. for 30 min. Dibromofluoromethane (14.96 mL, 165 mmol) in DMF (30 mL) was then added via an additional funnel, the resultant mixture was allowed to warm up to 50° C. and kept stirring at 50° C. for 16 h. The mixture was cooled, diluted with ethyl acetate (150 mL), washed with water (100 mL), the organic was washed with brine (100 mL), dried (MgSO$_4$), filtered and the solvent was evaporated under reduced pressure. The residue was purified by column chromatography on; 120 g prepacked column, eluting with 10% EtOAc/isohexane to give methyl 4-(bromodifluoromethoxy)-3-methoxybenzoate 173A (1.5 g, 4.82 mmol, 17.57% yield) as a colorless liquid.

Step 2

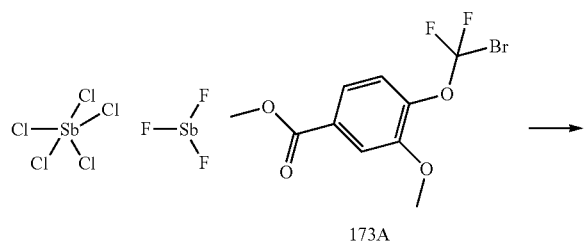

173A

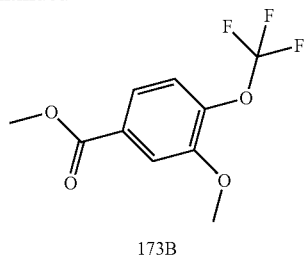

173B

Antimony (V) Chloride (26.4 mg, 0.088 mmol) was added to a stirred, room temperature mixture of 173A (550 mg, 1.768 mmol) and antimony trifluoride (221 mg, 1.238 mmol) in a sealed tube, and the mixture was stirred at 170° C. for 4 h. The mixture was cooled, diluted with diethyl ether (50 mL), washed with water (50 mL), dried (MgSO$_4$), filtered and the solvent was evaporated under reduced pressure. The residue was purified by column chromatography on silica gel; 24 g prepacked column, eluting with EtOAc/isohexane=10% to give methyl 3-methoxy-4-(trifluoromethoxy)benzoate 173B (240 mg, 0.959 mmol, 54.3% yield) as a white solid.

Step 3

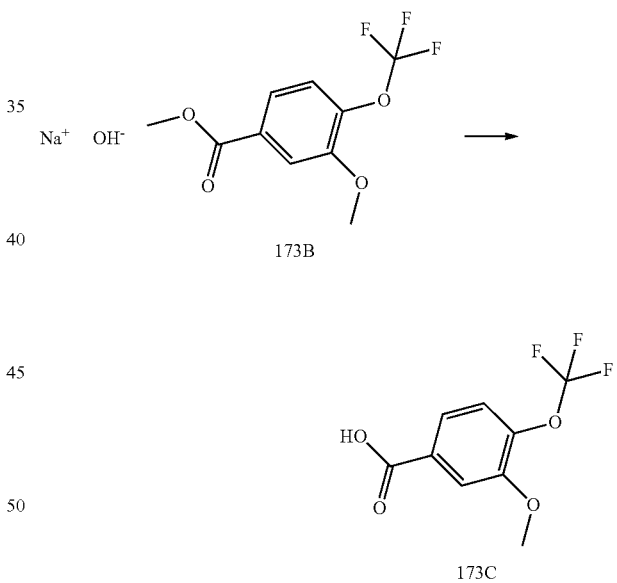

173B

173C

NaOH (1M aq) (1 mL, 1.000 mmol) was added to a stirred, room temperature mixture of 179B (120 mg, 0.480 mmol) in tetrahydrofuran (2 mL) MeOH (2.000 mL), and the mixture was stirred at room temperature for 1 h. The reaction mixture was diluted with diethyl ether (10 mL), water (2 mL) was added, the aqueous layer was separated, acidified with hydrochloric acid (2 M) to pH 2-3, extracted with dichloromethane (3×6 mL). The combined organic layers were dried (MgSO$_4$), filtered and concentrated to give 3-methoxy-4-(trifluoromethoxy)benzoic acid 173C (110 mg, 0.466 mmol, 97% yield) as a white solid.

Steps 4 and 5

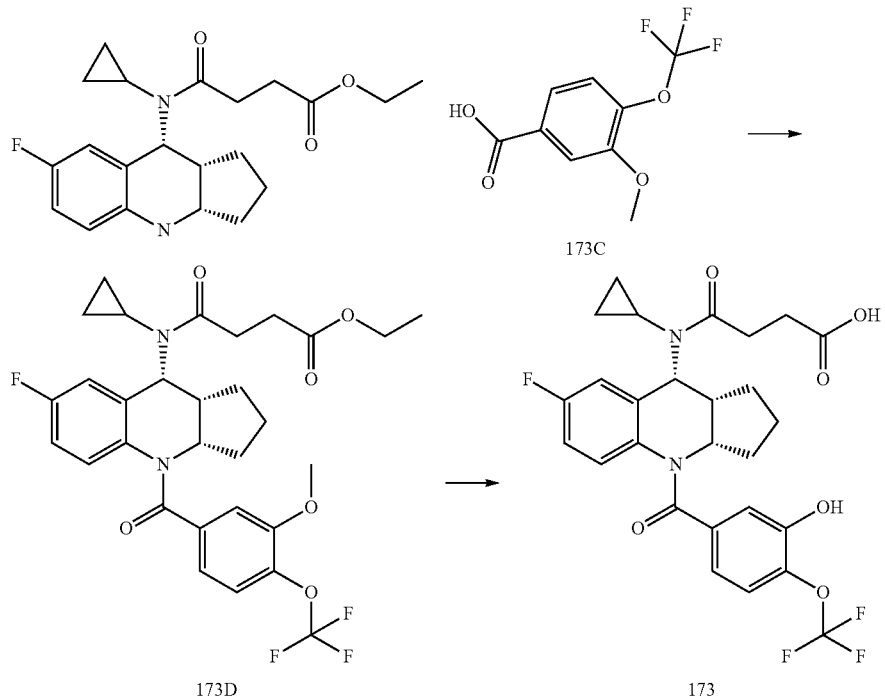

3-methoxy-4-(trifluoromethoxy)benzoic acid was converted to 4-(cyclopropyl-(3aS,9R,9aR-7-fluoro-4-(3-hydroxy-4-(trifluoromethoxy)benzoyl)-2,3,3a,4,9,9a-hexahydro-1H-cyclopenta[b]quinolin-9-yl)amino)-4-oxobutanoic acid 173 as a white solid ([M+H]$^+$=551.2) by following similar procedure as described in Steps 1 and 2 of Example 171.

Example 172

Preparation of 6-((4-(Cyclopropyl-(3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoyl)oxy)-3,4,5-trihydroxytetrahydro-2H-pyran-2-carboxylic acid (174)

Step 1

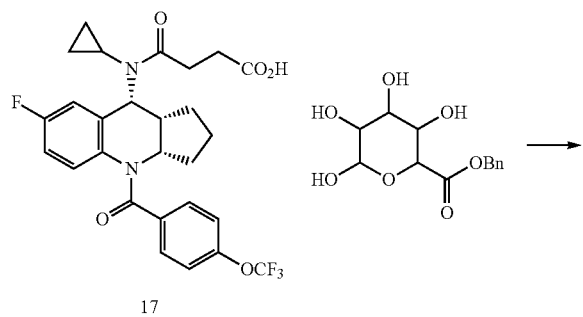

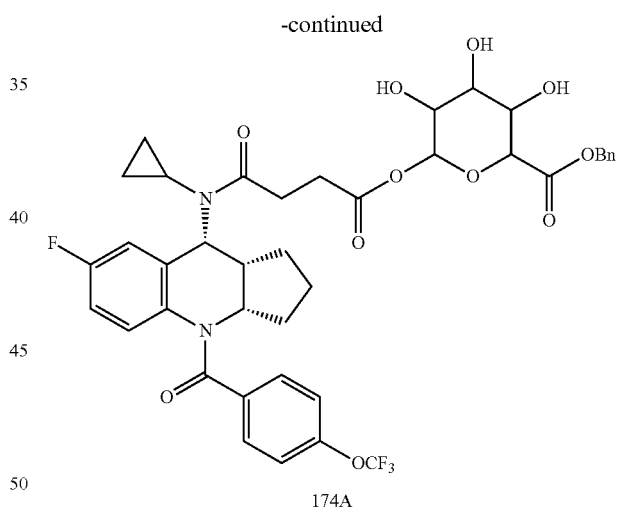

N-methylmorpholine (0.077 mL, 0.702 mmol) was added to a stirred mixture of 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoic acid (150 mg, 0.281 mmol), HATU (133 mg, 0.351 mmol) and benzyl 3,4,5,6-tetrahydroxytetrahydro-2H-pyran-2-carboxylate (100 mg, 0.351 mmol) in acetonitrile (3 mL) and the mixture was stirred at room temperature for 3 h. TLC showed clean reaction (MeOH in DCM 10%). Solvent was removed and the residue was purified by column chromatography on silica gel (24 g prepacked column) eluting with DCM/MeOH gradient up to 20% MeOH to give benzyl 6-((4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoyl)oxy)-3,4,5-trihydroxytetrahydro-2H-pyran-2-carboxylate 174A (0.23 g).

Step 2

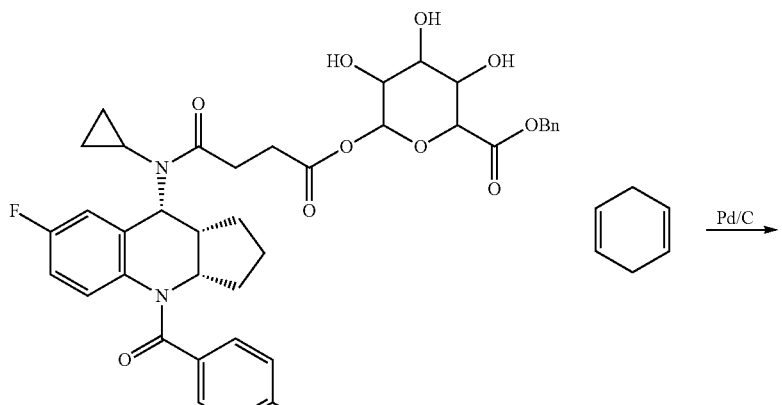

174A

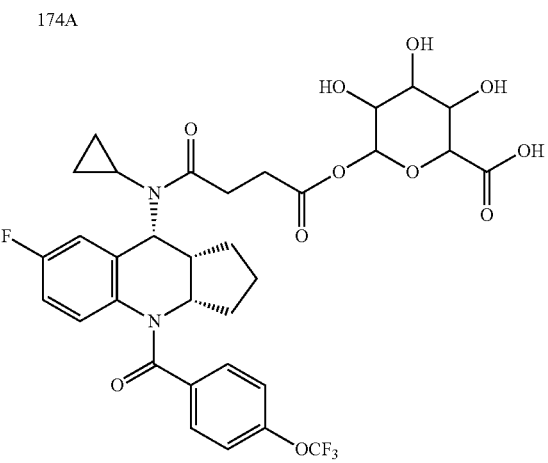

174

Palladium on carbon (80 mg, 0.752 mmol) was added to a stirred mixture of benzyl 6-((4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoyl)oxy)-3,4,5-trihydroxytetrahydro-2H-pyran-2-carboxylate (0.23 g, 0.29 mmol) and cyclohexadiene (1.5 mL, 0.293 mmol) in isopropanol (7.5 mL) and cyclopentylmethyl ether (7.50 mL) and the mixture was stirred at 60° C. for 1 h. The mixture was filtered through a Celite® pad and washed with ether/isopropanol (1/1). Solvent was removed to give crude product which was purified using reverse phase HPLC to give 6-((4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoyl)oxy)-3,4,5-trihydroxytetrahydro-2H-pyran-2-carboxylic acid 174 (140 mg), $[M+H]^+$=710.1.

Biological Assays
Radioligand Binding Assays

Certain representative compounds of the invention were tested in Radioligand Binding Assay A and others were tested in Radioligand Binding Assay B.

Radioligand Binding Assay A.

Radioligand Binding Assay A was performed at room temperature in 50 mM Tris-HCl pH 7.4, 1 mM EDTA containing 2 mM $MnCl_2$ and 3.0 nM $[^3H]PGD_2$ (New England Nuclear, Boston, Mass.) (171 Ci $mmol^{-1}$), in a final volume of 0.2 mL. Competing ligands were diluted in dimethylsulfoxide ($Me_2SO$) that was kept constant at 1% (v/v) of the final incubation volume. The reaction was initiated by the addition of 8-20 g of membrane protein prepared from a human embryonic kidney (HEK)-$hCRTH_2$ cell line. Total and non-specific binding were determined in the absence and the presence of 10 μM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted (0.3% polyethyleneimine) 96-well printed Filtermate™ (Wallac) using a Tomtec® harvester (Hamden, Conn.). After washing with cold buffer, the filter was dried for 2 minutes in microwave, and Meltilex Scintillator sheet (Wallac) was melted on for 2 min. The radioactivity was measured with Betaplate model 1205 (Wallac). Table A below lists representative compounds of the invention with binding data which were tested in Radioligand Binding Assay A whereby the Ki values are rated "A", "B," "C," or "D." The Ki values are rated "A" for Ki values in the range of 1.0 to 5.0 nM, "B" for Ki values in the range from 5.1-20.0 nM, "C" for Ki values in the range from 20.1-200 nM, and "D" for Ki values in the range from 201-7500 nM. The designation "N.A." indicates that data is unavailable for that entry.

TABLE A

| No. | Ki (nM) |
|---|---|
| 9 | B |
| 9A | A |
| 9B | B |
| 11 | D |
| 11A | C |
| 11B | C |
| 11C | B |
| 17 | B |
| 17G | B |
| 17i | C |
| 17J | D |
| 17K | B |
| 17L | B |
| 17M | C |
| 17R | D |
| 17S | B |
| 17T | C |
| 17U | D |
| 17V | C |
| 17W | B |
| 17X | C |
| 17Y | C |
| 17Z | C |
| 17AA | C |
| 17AB | C |
| 17AC | B |
| 17AD | B |
| 17AE | D |
| 17AF | D |
| 17AG | C |
| 17AH | B |
| 17Ai | B |
| 17AJ | C |
| 17AK | A |
| 17AL | B |
| 17AM | C |
| 17AN | C |
| 17Ao | C |
| 17AP | B |
| 17AQ | C |
| 17AR | B |
| 17AS | C |
| 17AT | B |
| 17AU | B |
| 17AV | B |
| 17AW | B |
| 17AX | B |
| 17AY | C |
| 17AZ | C |
| 17BA | C |
| 17BB | C |
| 17BC | C |
| 17BD | C |
| 17BE | B |
| 17BF | C |
| 17BG | B |
| 17BH | B |
| 17Bi | B |
| 17BJ | C |
| 17BK | B |
| 17BL | C |
| 17BM | A |
| 17BN | B |
| 17Bo | A |
| 17BP | B |
| 17BQ | B |
| 17BR | B |
| 17BS | B |
| 17BT | A |
| 17BU | A |
| 17BV | B |
| 17BW | B |
| 17BX | D |
| 17BY | A |
| 17BZ | D |
| 17CA | A |
| 17CB | B |
| 17CC | A |

TABLE A-continued

| No. | Ki (nM) |
|---|---|
| 17CD | A |
| 17CE | A |
| 17CF | B |
| 17CG | B |
| 17CH | B |
| 17Ci | D |
| 17CJ | D |
| 17CK | A |
| 17CL | B |
| 17CM | B |
| 17CN | B |
| 17Co | B |
| 17CP | B |
| 18CQ | A |
| 17CR | A |
| 17CS | B |
| 17CT | A |
| 17CU | A |
| 17CV | A |
| 17CW | B |
| 17CX | A |
| 17CY | A |
| 17CZ | B |
| 17DA | C |
| 17DB | C |
| 17DC | C |
| 17DD | C |
| 17DE | B |
| 17DF | D |
| 17DG | D |
| 17DH | B |
| 17Di | C |
| 17DJ | B |
| 17DK | B |
| 17DL | A |
| 17DN | B |
| 17Do | D |
| 18 | C |
| 18C | A |
| 18D | B |
| 18E | B |
| 18F | C |
| 18G | B |
| 18H | C |
| 18i # | C |
| 18J | B |
| 18K | B |
| 18L | A |
| 18M | A |
| 18N | C |
| 18o | B |
| 18P | C |
| 18Q | C |
| 18R | B |
| 18S | B |
| 18T | C |
| 19 | D |
| 20 | C |
| 22 | B |
| 22A | D |
| 22D | A |
| 22E | B |
| 22F | B |
| 22G | B |
| 22H | B |
| 22i | A |
| 22J | D |
| 22K | B |
| 22L | B |
| 22M | B |
| 22N | C |
| 22O | C |
| 22P | C |
| 22Q | B |
| 22R | B |
| 22S | B |
| 22T | B |
| 22U | A |

TABLE A-continued

| No. | Ki (nM) |
|---|---|
| 22V | A |
| 22W | B |
| 22X | B |
| 22Y | B |
| 23E | C |
| 23F | C |
| 23G | C |
| 23H | C |
| 23i | D |
| 24B | C |
| 24C | C |
| 27A | B |
| 27B | A |
| 27C | B |
| 27D | D |
| 27E | D |
| 27F | D |
| 27G | B |
| 27H | D |
| 27i | D |
| 27J | D |
| 27K | A |
| 27L | A |
| 27M | B |
| 27N | B |
| 27o | A |
| 27Q | B |
| 27R | B |
| 27S | A |
| 32 | C |
| 32C | C |
| 32D | C |
| 32E | A |
| 32F | A |
| 32G | A |
| 32H | A |
| 32i | A |
| 32J | A |
| 32K | A |
| 32L | A |
| 32M | A |
| 32N | A |
| 32O | A |
| 32P | B |
| 32Q | A |
| 32R | B |
| 32S | A |
| 32T | A |
| 32U | A |
| 33 | D |
| 34 | D |
| 35 | B |
| 35D | B |
| 35E | C |
| 35F | D |
| 35G | D |
| 35H | B |
| 35i | B |
| 35J | B |
| 35K | B |
| 38 | C |
| 38D | B |
| 38E | C |
| 38F | B |
| 38G | D |
| 40 | C |
| 41 | D |
| 42 | C |
| 43 | B |
| 43B | A |
| 43C | C |
| 44 | A |
| 44B | D |
| 44C | C |
| 44D | A |
| 44E | B |
| 44F | C |
| 45 | C |

TABLE A-continued

| No. | Ki (nM) |
|---|---|
| 46 | D |
| 47 | D |
| 47D | B |
| 47E | N.A. |
| 47F | D |
| 47G | D |
| 48 | B |
| 48C | D |
| 49 | C |
| 49B | B |
| 50 | C |
| 51 | B |
| 52 | A |
| 53 | B |
| 54 | C |
| 55 | C |
| 56 | B |
| 57 | B |
| 58 | C |
| 59 | D |
| 60 | C |
| 61 | B |
| 62 | B |
| 63 | B |
| 64 | B |
| 65 | B |
| 66 | B |
| 67 | B |
| 68 | B |
| 69 | A |
| 70 | C |
| 71 | A |
| 72 | B |
| 73 | C |
| 74 | C |
| 75 | B |
| 76 | B |
| 77 | C |
| 78 | B |
| 79 | C |
| 80 | B |
| 81 | A |
| 82 | B |
| 83 | A |
| 84 | B |
| 85 | C |
| 86 | C |
| 87 | B |
| 88 | B |
| 89 | C |
| 90 | C |
| 91 | C |
| 92 | C |
| 93 | C |
| 94 | C |
| 95 | C |
| 96 | B |
| 97 | C |
| 98 | B |
| 99 | D |
| 100 | A |
| 101 | D |
| 102 | D |
| 103 | D |
| 104 | D |
| 105 | D |
| 106 | D |
| 107 | B |
| 108 | B |
| 109 | C |
| 110 | D |
| 111 | B |
| 112 | C |
| 113 | C |
| 114 | C |
| 115 | D |
| 116 | A |
| 117 | A |

TABLE A-continued

| No. | Ki (nM) |
|---|---|
| 118 | B |
| 119 | A |
| 120 | D |
| 121 | A |
| 122 | C |
| 123 | C |
| 124 | B |
| 125 | B |
| 126 | B |
| 127 | C |
| 128 | D |
| 129 | C |
| 130 | B |
| 131 | C |
| 132 | B |
| 133 | B |
| 134 | D |
| 135 | A |
| 136 | B |
| 137 | C |
| 138 | B |
| 139 | B |
| 140 | C |
| 141 | C |
| 142 | C |
| 143 | C |
| 144 | A |
| 145 | B |
| 146 | A |
| 147 | B |
| 148 | B |
| 149 | A |
| 150 | A |
| 151 | B |
| 152 | B |
| 153 | C |
| 154 | B |
| 155 | D |
| 156 | C |
| 157 | C |
| 158 | C |
| 159 | A |
| 160 | D |
| 161 | C |
| 162 | B |
| 163 | C |
| 164 | B |
| 165 | A |
| 166 | B |
| 167 | B |
| 168 | C |
| 169 | D |
| 170 | A |
| 171 | B |
| 172 | B |
| 173 | B |
| 174 | D |

Representative compounds of the invention had the Ki values specified in parentheses immediately following the compound number in Radioligand Binding Assay A: 9A (4.7 nM), 17 (5.1 nM), 17U (604.9 nM), 17BL (36.0 nM), 17Co (10.9 nM), 17Ci (838.0), 18CQ (2.4 nM), 17DA (34.2 nM), 18o (9.8 nM), 18 P (28.5 nM), 22A (1083.5 nM), 27K (1.5 nM), 38G (637.5 nM), 44 (2.541 nM), 51 (6.9 nM), 55 (37.7 nM), 60 (21.2 nM), 69 (4.972), 72 (15.7 nM), and 134 (236.4 nM).

Radioligand Binding Assay B.

Radioligand Binding Assay B was performed at room temperature in 10 mM HEPES/KOH pH 7.4, 1 mM EDTA containing 10 mM $MnCl_2$ and 0.7 nM [$^3$H]$PGD_2$ (NEN, 171 Ci $mmol^{-1}$), in a final volume of 0.2 mL. Competing ligands were diluted in dimethylsulfoxide ($Me_2SO$) that was kept constant at 1% (v/v) of the final incubation volume. The reaction was initiated by the addition of 8-20 µg of membrane protein prepared from a HEK-hCRTH2 cell line. Total and non-specific binding were determined in the absence and the presence of 10 µM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted Unifilters GF/C (Packard), using a Tomtec MachIII semi-automated harvester (for HEK-$hCRTH_2$). The filters were then washed with 4 mL of the same buffer and residual radioligand bound to the filter was determined by liquid scintillation counting following equilibration in 25 µl Ultima Gold F™ (Unifilter) (Packard). Table B below lists representative compounds of the invention with binding data which were tested in Radioligand Binding Assay B whereby the Ki values are rated "A", "B," "C," or "D." The Ki values are rated "A" for Ki values in the range of 1.0 to 5.0 nM, "B" for Ki values in the range from 5.1-20.0 nM, "C" for Ki values in the range from 20.1-200 nM, and "D" for Ki values in the range from 201-7500 nM.

TABLE B

| No. | Ki (nM) |
|---|---|
| 7 | A |
| 10 | D |
| 12 | D |
| 12B | C |
| 12C | B |
| 12D | B |
| 12E | B |
| 13 | B |
| 13C | B |
| 13D | B |
| 13E | C |
| 14 | B |
| 14C | B |
| 14D | B |
| 14E | B |
| 14F | B |
| 14G | C |
| 14H | C |
| 14i | C |
| 14K | B |
| 14L | C |
| 14N | D |
| 14o | D |
| 14P | D |
| 15 | C |
| 16 | A |
| 16A | D |
| 16B | B |
| 16C | C |
| 16D | C |
| 16E | A |
| 17H | D |
| 17N | D |
| 17o | D |
| 17P | D |
| 17Q | D |
| 21 | C |
| 21A | C |
| 21B | D |
| 21C | C |
| 21D | C |
| 21E | C |
| 21F | C |
| 21G | C |
| 21H | D |
| 21i | C |
| 21J | D |
| 21K | D |
| 21L | C |
| 23 | C |

TABLE B-continued

| No. | Ki (nM) |
|---|---|
| 23B | C |
| 23C | C |
| 23D | C |
| 24 | C |
| 24D | C |
| 25 | C |
| 26 | C |
| 27 | B |
| 28 | C |
| 29 | D |
| 30 | B |
| 31 | B |
| 36 | C |
| 36A | C |
| 36B | C |
| 36C | D |
| 37 | B |
| 39 | C |

Representative compounds of the invention had the Ki values specified in parentheses immediately following the compound number in Radioligand Binding Assay B: 7 (3.1 nM), 10 (514.5 nM), 13E (122.6 nM), 14E (9.9 nM), 14K (18.4 nM), 14P (413.6 nM), 16 (2.7 nM), 16C (140.3 nM), 21A (45.7 nM), 21K (905.4 nM), and 27 (7.7 nM).

i[cAMP] Measurements.

The ability of the compounds to antagonize the formation of cAMP can be assayed using the ELISA-based assay described in this example. HEK-hCRTH$_2$ cells are grown to 80-90% confluency. On the day of the assay, the cells are washed with phosphate buffered saline (PBS), incubated for 2 min in cell dissociation buffer, harvested by centrifugation at 300 g for 7 min at room temperature and resuspended at 1.25e10$^6$ cells mL$^{-1}$ in Hanks' balanced salt solution containing 20 mM HEPES pH 7.4 and 0.75 mM IBMX (HBSS/HEPES/IBMX). The assay is performed in 384-plate format with 0.01 mL HBSS/HEPES/IBMX per well containing 12 500 cells and 70 to 75 nl of the test compound and DK-PGD$_2$ at various concentrations. Following a 0 to 10 to min pre-incubation of the cells with the test compound at 37° C., 0.005 mL of 30 µM Forskolin dilute in HBSS 20 mM HEPES, is added at a final concentration of 10 uM to initiate the reaction. After 10 to 60 min incubation at room temperature or 37° C., the cAMP content was quantified using the cAMP XS+ HitHunter chemiluminescence assay (GE Healthcare 90-0075). Percent inhibition is calculated using the Forskolin and EC85 DK-PGD$_2$ controls.

β-Arrestin Assay:

CHO-K1 cells obtained from DiscoverX are stably transfected with human CRTH$_2$ (propagation medium: F-12, 10% FBS, 300 ug/mL hygB and 800 ug/mL G418). Cells are grown in T175 cm$^2$ flask. While in log phase, cells are collected via 0.05% trypsin treatment. Triturated cells are filtered and 40 uL (10K cells) are plated per well in a 384-well white clear bottom plate and incubated O/N. Cell plate is emptied via inversion and blotted dry. Each well is filled with 35 uL of HBSS (with Ca$^{++}$ and Mg$^{++}$) and incubated for 5 min. Compounds are added in volumes of 1 µL and the plate is gently shaken for 2 min., followed by incubation at 37° C. for 20 min. All compounds and controls are diluted in HBSS assay buffer (with Ca$^{++}$ and Mg$^{++}$) with a final concentration range of 10$^{-5}$ M to 3×10$^{-11}$ M, 11 point Dose response curves at appropriate half-log increments. Final DMSO % is ≤0.3%. Agonist Assay: 1 µl/well of compound is added into cell plate and left to incubate at 37° C. for 90 min. Antagonist Assay: 1 µl/well of compounds are added into a cell plate. Incubate 30 minutes at 37° C. Stimulate cells with 1 ul/well of PGD$_2$ [100 nM] final. Incubate plate for 60 minutes at 37° C. Resulting luminescent signal is detected via Discoverx PathHunter Detection Kit per manufacturer's instructions. A total of 12 µl/well is added to each well. The plate is covered and incubated for 60 min. with gentle shaking. Chemiluminescent detection is done by a SpectraMax plate reader.

Eosinophil Shape Change Assay in Human Whole Blood:

Blood is collected in vacutainers containing EDTA. The antagonist is added to blood and incubated for 10 min at room temperature. DK-PGD$_2$ (13,14-dihydro-15-keto prostaglandin D$_2$) are then added to blood for 4 min at 37° C. in a running water bath. Blood cells are then fixed in presence of cold 0.25% (v/v) paraformaldehyde prepared in 75% (v/v) DPBS without Ca$^+$ and Mg$^{++}$ for 1 min on ice. 175 µL of fixed blood is transferred into 870 µL of cold 155 mM NH$_4$Cl lysis solution and incubated at 4° C. for at least 40 min. The solution is then centrifuged at 430 g for 5 min and the supernatant is discarded. Centrifuged cells are resuspended in residual supernatant and sodium azide is added (1% final concentration). Samples are analyzed with a FACs Calibur flow cytometer (Becton Dickinson). Flow cytometry raw data is analyzed with Diva software by isolating the eosinophils from the neutrophils based on their high autofluorescence and determining the percent of total eosinophils with increased forward light scatter. Maximum (100%) and minimum (0%) shape change is determined in the presence of 10 µM DK-PGD$_2$ and DPBS, respectively. A dose response curve with DK-PGD$_2$ is performed with every assay to determine the EC$_{50}$ for each blood donor. Compounds are tested in 11-dose titration curves in the presence of 50 nM DK-PGD$_2$ to determine an antagonist IC$_{50}$.

Compounds of the present invention are selective for the CRTH$_2$ receptor over the DP receptor. Assays on the DP, as well as other prostanoid, receptors are described in WO2003/06220.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the Formula (I)

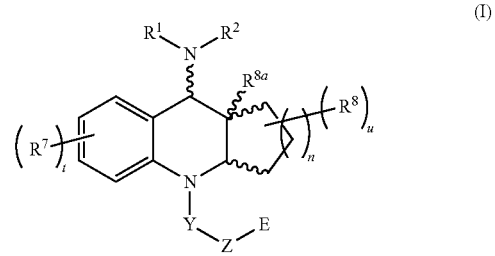

or a pharmaceutically acceptable salt or ester thereof, wherein

R$^1$ is
(i) H,
(ii) C$_1$-C$_4$ alkyl,
(iii) C$_2$-C$_4$ alkenyl,
(iv) C$_3$-C$_7$ cycloalkyl, (v) —(C$_1$-C$_3$ alkylene)-R$^9$ wherein R$^9$ is C$_3$-C$_7$ cycloalkyl, phenyl or a 5- to 6-membered heteroaryl containing 1 to 2 heteroatoms selected from the group consisting of N, O, and S, (vi) phenyl, (vii) —C(O)—R$^5$, wherein R$^5$ is C$_1$-C$_6$ alkyl, C$_3$-C$_6$ cycloalkyl, phenyl, (viii) or a group of the formula

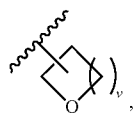

wherein v is 1, 2, or 3;

R$^2$ is (i) -Q-W—V, wherein

Q is —C(O)—, —C(O)O—, —C(O)N(H)—, —C(O)N(C$_1$-C$_6$ alkyl)-, —CH$_2$—, or —S(O)$_2$—;

W is (a) C$_1$-C$_8$ alkylene, wherein said alkylene of W is unsubstituted or substituted by 1 to 2 fluoro;

(b) —CH=CH—, or (c) a phenylene of the formula

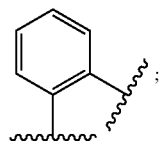

wherein said phenylene is unsubstituted or substituted by 1 to 2 halo;

V is (a) —CO$_2$H, (b) tetrazolyl, or (c) a group of the formula

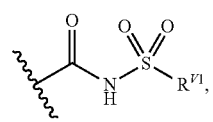

wherein R$^{V1}$ is selected from the group consisting of C$_1$-C$_6$ alkyl, C$_3$-C$_6$ cycloalkyl, and phenyl;

(ii) -M-CO$_2$H, wherein

M is

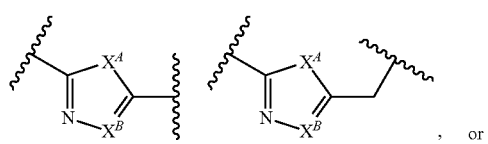
, or

-continued

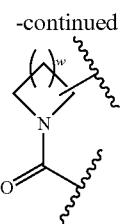

wherein w is 0, 1, 2, or 3;

X$^A$ is S or O;

X$^B$ is N or C(H);

with the proviso that when R$^1$ is —C(O)—R$^5$, then R$^2$ is —CH$_2$—W—V;

Y is —C(O)—, —S(O)$_2$—, or a group of the formula

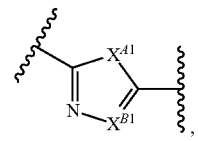

wherein X$^{A1}$ is S or O; and

X$^{B1}$ is N or C(H);

Z is (i) absent, (ii) —(C$_1$-C$_6$) alkylene-, (iii) —O—, (iv) —O—(C$_1$-C$_6$ alkylene)-, wherein said —O—(C$_1$-C$_6$ alkylene)- of Z is unsubstituted or substituted by 1 to 3 fluoro, (v) —N(H)—, or (vi) a group of the formula

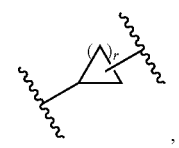

wherein r is 1, 2, 3, or 4;

E is (i) phenyl, (ii) naphthyl, (iii) tetrahydronapthyl, (iv) indanyl, (v) 5- to 10-membered mono- or bicyclic heteroaryl containing one to three heteroatoms selected from the group consisting of N, O, and S, (vi) 5- to 10-membered mono- or bicyclic heterocyclenyl containing one to three heteroatoms selected from the group consisting of N, O, and S, wherein said phenyl, napthyl, tetrahydronapthyl, indanyl, 5- to 10-membered heteroaryl, or 5- to 10-membered heterocyclenyl of E is unsubstituted or substituted by one to three R$^4$ moieties, wherein each R$^4$ is selected from the group consisting of C$_1$-C$_6$ alkyl, C$_1$-C$_3$ alkoxy, —CN, halo, hydroxyl, C$_1$-C$_3$ fluoroalkyl, —O—(C$_1$-C$_3$ fluoroalkyl), —S—(C$_1$-C$_3$ alkyl), —S—(C$_1$-C$_3$ fluoroalkyl), C$_3$-C$_7$ cycloalkyl, R$^{4a}$, —O—R$^{4a}$, or 5- to 6-membered heterocyclyl containing 1 or 2 heteroatom selected from the group consisting of N, O, and S;

$R^{4a}$ is phenyl or a 5 to 6-membered heteroaryl ring containing one to two heteroatoms selected from the group consisting of N, O, and S;

wherein $R^{4a}$ is unsubstituted or substituted by one to two moieties independently selected from the group consisting of $C_1$-$C_6$ alkyl, $C_1$-$C_3$ alkoxy, halo, —CN, $C_1$-$C_3$ fluoroalkyl, —O—($C_1$-$C_3$ fluoroalkyl), —S—($C_1$-$C_3$ fluoroalkyl), and —SO$_2$—($C_1$-$C_3$ alkyl), or, wherein two $R^4$ moieties are substituted on vicinal carbon atoms of E, the two $R^4$ moieties together with the carbon atoms to which they are attached form a dioxolane ring;

(vii) $C_3$-$C_7$ cycloalkyl, or (viii) $C_1$-$C_6$ alkyl, n is 0, 1, or 2;

each occurrence of $R^7$ is independently halo, $C_1$-$C_3$ fluoroalkyl, hydroxy($C_1$-$C_3$ alkyl), —CN, phenyl, or a 5- to 6-membered heteroaryl containing 1 to 2 heteroatoms selected from the group consisting of N, O, and S, wherein said phenyl or heteroaryl of $R^7$ is independently unsubstituted or substituted with 1 to 2 halo;

t is 0, 1, 2, or 3;

each occurrence of $R^8$ is independently $C_1$-$C_3$ alkyl, $C_2$-$C_3$ alkenyl, or fluoro;

u is 0, 1, or 2; and $R^{8a}$ is H or $C_1$-$C_6$ alkyl.

2. The compound of claim 1 or a pharmaceutically acceptable salt thereof, wherein $R^2$ is

-Q-W—V;

Q is —C(O)—, —C(O)O—, —C(O)N(CH$_3$)— or —CH$_2$—;

W is $C_1$-$C_4$ alkylene; and

V is —CO$_2$H.

3. The compound of claim 2 or a pharmaceutically acceptable salt thereof, wherein the group -Q-W—V is selected from the group consisting of:

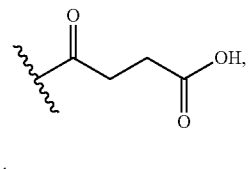 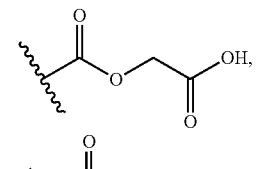

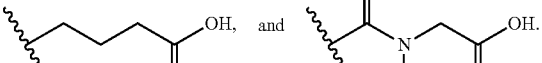

4. The compound of claim 1 or a pharmaceutically acceptable salt thereof, wherein $R^1$ is $C_1$-$C_4$ alkyl, $C_3$-$C_7$ cycloalkyl, —CH$_2$—($C_3$-$C_7$ cycloalkyl), or phenyl.

5. The compound of claim 4 or a pharmaceutically acceptable salt thereof, wherein $R^1$ is methyl, ethyl, cyclopropyl, cyclobutyl, —CH$_2$-cyclopropyl, or phenyl.

6. The compound of claim 1 or a pharmaceutically acceptable salt thereof, wherein Y is —C(O)— or

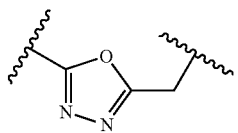

7. The compound of claim 6 or a pharmaceutically acceptable salt thereof, wherein Y is —C(O)—.

8. The compound of claim 7 or a pharmaceutically acceptable salt thereof, wherein the group —Y—Z is selected from the group consisting of —C(O)—, —C(O)O—CH$_2$—, —C(O)O—C(H)(CH$_3$)—, and

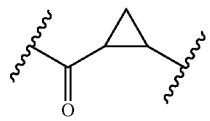

9. The compound of claim 1 or a pharmaceutically acceptable salt thereof, wherein E is phenyl, thienyl,

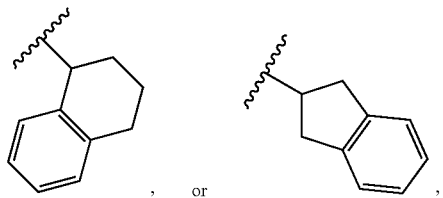

wherein E is unsubstituted or substituted by one to two moieties independently selected from the group consisting of methyl, fluoro, trifluoromethoxy, —O-phenyl, and thiazolyl.

10. The compound of claim 1 or a pharmaceutically acceptable salt thereof, wherein the compound has the Formula (IB)

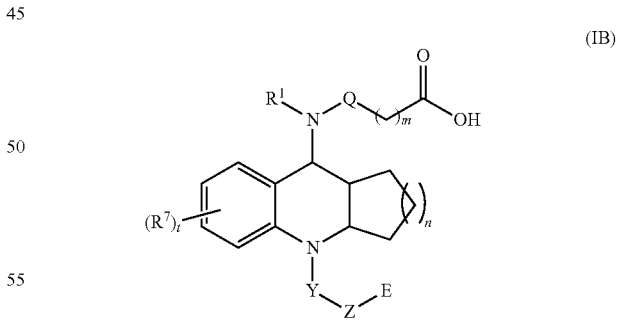

(IB)

wherein $R^1$ is H, $C_1$-$C_4$ alkyl, cyclopropyl, cyclobutyl, —CH$_2$-cyclopropyl, —CH$_2$-cyclobutyl, or phenyl;

Q is —C(O)—, —C(O)O—, —C(O)N(CH$_3$)—, or —CH$_2$—;

m is 1 or 2;

Y is —C(O)— or

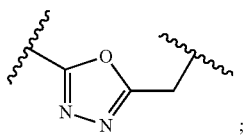 [SMILES: *Cc1nnc(*)o1]

Z is absent, —(C₁-C₃) alkylene-, —OCH₂—, —OCH(CH₃)—, or a group of the formula

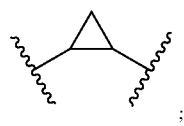 [SMILES: *C1CC1*]

E is phenyl, thienyl,

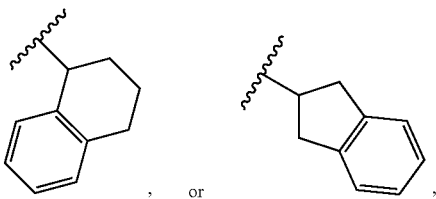

wherein E is unsubstituted or substituted by one to two $R^4$ moieties independently selected from the group consisting of C₁-C₃ alkyl, fluoro, trifluoromethoxy, —S—CF₃, —O-phenyl, and thiazolyl;

n is 0 or 1;

each occurrence of $R^7$ is independently chloro or fluoro; and t is 0, 1, or 2.

11. The compound of claim 10 or a pharmaceutically acceptable salt thereof, wherein the compound has the Formula (IC)

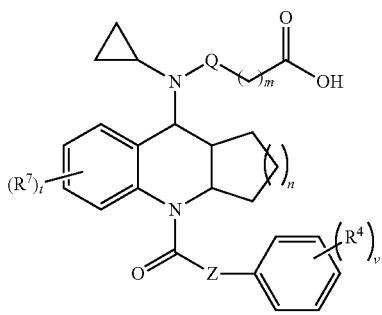

wherein
Q is —C(O)—, —C(O)O—, or —CH₂—;
m is 1 or 2;
Z is absent or —OCH₂—;
each occurrence of $R^4$ is independently C₁-C₃ alkyl, fluoro, trifluoromethoxy, or —S—CF₃;
v is 0, 1, or 2;
n is 0 or 1;
each occurrence of $R^7$ is independently chloro or fluoro; and
t is 0, 1, or 2.

12. The compound of claim 11 or a pharmaceutically acceptable salt thereof, wherein the group

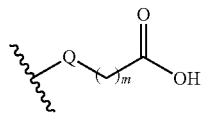

is selected from the group consisting of:

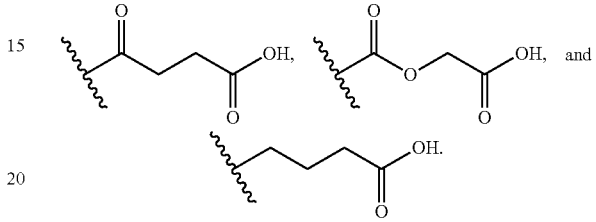

13. The compound of claim 1 or a pharmaceutically acceptable salt thereof, wherein the compound is selected from the group consisting of:

4-[{cis,cis-4-[(Benzyloxy)carbonyl]-2,3,3a,4,9,9a-hexahydro-1H-cyclopenta[b]quinolin-9-yl}(cyclopropyl)amino]-4-oxobutanoic acid;

4-[{cis,cis-4-[(benzyloxy)carbonyl]-2,3,3a,4,9,9a-hexahydro-1H-cyclopenta[b]quinolin-9-yl}(phenyl)amino]-4-oxobutanoic acid;

4-{ethyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-[{cis,cis-4-[(benzyloxy)carbonyl]-6-fluoro-2,3,3a,4,9,9a-hexahydro-1H-cyclopenta[b]quinolin-9-yl}(cyclopropyl)amino]-4-oxobutanoic acid;

4-{cyclopropyl[cis,cis-6-fluoro-4-[(4-phenoxyphenyl)carbonyl]-2,3,3a,4,9,9a-hexahydro-1H-cyclopenta[b]quinolin-9-yl}amino)-4-oxobutanoic acid;

4-{cyclopropyl[cis,cis-3-{[4-(trifluoromethoxy)phenyl]carbonyl}-1,2,2a,3,8,8a-hexahydrocyclobuta[b]quinolin-8-yl]amino}-4-oxobutanoic acid;

({cyclopropyl[cis,cis-4-{[4-(trifluoromethoxy)phenyl]carbonyl}-2,3,3a,4,9,9a-hexahydro-1H-cyclopenta[b]quinolin-9-yl]carbamoyl}oxy)acetic acid;

3-(phenylmethyl)cis,cis-8-[(3-carboxy-1-oxopropyl)cyclopropylamino]-5-fluoro-2,2a,8,8a-tetrahydrocyclobuta[b]quinoline-3(1H)-carboxylate;

4-(phenylmethyl)cis,cis-9-[(3-carboxy-1-oxopropyl)cyclopropylamino]-6-chloro-1,2,3,3a,9,9a-hexahydro-4H-cyclopenta[b]quinoline-4-carboxylate;

4-(phenylmethyl)cis,cis-9-[(3-carboxy-1-oxopropyl)cyclopropylamino]-7-fluoro-1,2,3,3a,9,9a-hexahydro-4H-cyclopenta[b]quinoline-4-carboxylate;

4-[cyclopropyl[(cis,cis)-7-fluoro-2,3,3a,4,9,9a-hexahydro-4-[4-(trifluoromethoxy)benzoyl]-1H-cyclopenta[b]quinolin-9-yl]amino]-4-oxobutanoic acid;

4-[[cis,cis-2,3,3a,4,9,9a-hexahydro-4-[4-(trifluoromethoxy)benzoyl]-1H-cyclopenta[b]quinolin-9-yl]methylamino]-4-oxobutanoic acid;

4-[(cyclobutylmethyl)[cis,cis-2,3,3a,4,9,9a-hexahydro-4-[4-(trifluoromethoxy)benzoyl]-1H-cyclopenta[b]quinolin-9-yl]amino]-4-oxobutanoic acid;

4-[cyclopropyl[cis,cis-2,3,3a,4,9,9a-hexahydro-4-(3-phenoxybenzoyl)-1H-cyclopenta[b]quinolin-9-yl]amino]-4-oxo-butanoic acid;

4-(cyclopropyl(cis,cis-4-(thiophene-2-carbonyl)-2,3,3a,4,9,9a-hexahydro-1H-cyclopenta[b]quinolin-9-yl)amino)-4-oxobutanoic acid;

[[[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]carbonyl]oxy]acetic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]-4-oxobutanoic acid;

deuterated-4-[cyclopropyl[cis,cis-2,3,3a,4,9,9a-hexahydro-4-[4-(trifluoromethoxy)benzoyl]-1H-cyclopenta[b]quinolin-9(R)-yl-(d)]amino]-4-oxobutanoic acid;

4-[[(cis,cis)-6-chloro-2,3,3a,4,9,9a-hexahydro-4-[4-(trifluoromethoxy)benzoyl]-1H-cyclopenta[b]quinolin-9-yl]cyclobutylamino]-4-oxobutanoic acid;

4-[[(cis,cis)-6-chloro-2,3,3a,4,9,9a-hexahydro-4-[4-(trifluoromethoxy)benzoyl]-1H-cyclopenta[b]quinolin-9-yl]cyclopropylamino]-4-oxobutanoic acid;

4-[[(cis,cis)-6-chloro-2,3,3a,4,9,9a-hexahydro-4-[(trans-2-phenylcyclopropyl)carbonyl]-1H-cyclopenta[b]quinolin-9-yl]cyclopropylamino]-4-oxobutanoic acid;

4-[cyclobutyl[(cis,cis)-2,3,3a,4,9,9a-hexahydro-4-[4-(trifluoromethoxy)benzoyl]-1H-cyclopenta[b]quinolin-9-yl]amino]-4-oxobutanoic acid;

4-[[(cis,cis)-6-chloro-2,3,3a,4,9,9a-hexahydro-4-[(1,2,3,4-tetrahydro-1-naphthalenyl)carbonyl]-1H-cyclopenta[b]quinolin-9-yl]cyclopropylamino]-4-oxobutanoic acid;

4-[[(cis,cis)-6-chloro-4-[(2,3-dihydro-1H-inden-2-yl)carbonyl]-2,3,3a,4,9,9a-hexahydro-1H-cyclopenta[b]quinolin-9-yl]cyclopropylamino]-4-oxobutanoic acid;

4-[[(cis,cis)-6-chloro-2,3,3a,4,9,9a-hexahydro-4-[(1,2,3,4-tetrahydro-2-naphthalenyl)carbonyl]-1H-cyclopenta[b]quinolin-9-yl]cyclopropylamino]-4-oxobutanoic acid;

4-[cyclopropyl[cis,cis-2,3,3a,4,9,9a-hexahydro-4-[3-(5-thiazolyl)benzoyl]-1H-cyclopenta[b]quinolin-9-yl]amino]-4-oxobutanoic acid;

4-[(2,4-difluorophenyl)methyl](cis,cis)-9-[[(carboxymethoxy)carbonyl]cyclopropylamino]-1,2,3,3a,9,9a-hexahydro-4H-cyclopenta[b]quinoline-4-carboxylate;

4-[1-(4-fluorophenyl)ethyl](cis,cis)-9-[(3-carboxy-1-oxopropyl)cyclopropylamino]-1,2,3,3a,9,9a-hexahydro-4H-cyclopenta[b]quinoline-4-carboxylate;

4-(1,2,3,4-tetrahydro-2-naphthalenyl)(cis,cis)-9-[(3-carboxy-1-oxopropyl)cyclopropylamino]-7-fluoro-1,2,3,3a,9,9a-hexahydro-4H-cyclopenta[b]quinoline-4-carboxylate;

4-[cyclopropyl[(cis,cis)-6-fluoro-1,2,2a,3,8,8a-hexahydro-3-[4-(trifluoromethoxy)benzoyl]cyclobuta[b]quinolin-8-yl]amino]-4-oxobutanoic acid;

3-(phenylmethyl)(cis,cis)-8-[(3-carboxy-1-oxopropyl)cyclopropylamino]-5-chloro-2,2a,8,8a-tetrahydrocyclobuta[b]quinoline-3(1H)-carboxylate;

4-[[(cis,cis)-5-chloro-1,2,2a,3,8,8a-hexahydro-3-[4-(trifluoromethoxy)benzoyl]cyclobuta[b]quinolin-8-yl]cyclopropylamino]-4-oxobutanoic acid;

3-(phenylmethyl)(cis,cis)-8-[(3-carboxy-1-oxopropyl)cyclopropylamino]-2,2a,8,8a-tetrahydrocyclobuta[b]quinoline-3(1H)-carboxylate;

4-[cyclopropyl[(cis,cis)-1,2,2a,3,8,8a-hexahydro-3-[4-(trifluoromethoxy)benzoyl]cyclobuta[b]quinolin-8-yl]amino]-4-oxobutanoic acid;

4-(phenylmethyl)(cis,cis)-9-[[(carboxymethoxy)carbonyl]cyclopropylamino]-1,2,3,3a,9,9a-hexahydro-4H-cyclopenta[b]quinoline-4-carboxylate;

4-(phenylmethyl)(cis,cis)-9-[[(carboxymethoxy)carbonyl]cyclopropylamino]-7-fluoro-1,2,3,3a,9,9a-hexahydro-4H-cyclopenta[b]quinoline-4-carboxylate;

[[[cyclopropyl[(cis,cis)-1,2,2a,3,8,8a-hexahydro-3-[4-(trifluoromethoxy)benzoyl]cyclobuta[b]quinolin-8-yl]amino]carbonyl]oxy]acetic acid;

[[[cyclopropyl[(cis,cis)-3-(3,4-difluorobenzoyl)-1,2,2a,3,8,8a-hexahydrocyclobuta[b]quinolin-8-yl]amino]carbonyl]oxy]acetic acid;

[[[cyclopropyl[(cis,cis)-7-fluoro-2,3,3a,4,9,9a-hexahydro-4-[4-(trifluoromethoxy)benzoyl]-1H-cyclopenta[b]quinolin-9-yl]amino]carbonyl]oxy]acetic acid;

4-(phenylmethyl)(cis,cis)-9-[[(2(S)-carboxy-1-azetidinyl)carbonyl]cyclopropylamino]-1,2,3,3a,9,9a-hexahydro-4H-cyclopenta[b]quinoline-4-carboxylate;

N-[[cyclopropyl[(cis,cis)-2,3,3a,4,9,9a-hexahydro-4-[4-(trifluoromethoxy)benzoyl]-1H-cyclopenta[b]quinolin-9-yl]amino]carbonyl]-N-methylglycine;

[[[cyclopropyl[cis,cis-2,3,3a,4,9,9a-hexahydro-4-[5-[[4-(trifluoromethoxy)phenyl]methyl]-1,3,4-oxadiazol-2-yl]-1H-cyclopenta[b]quinoline-9-yl]amino]carbonyl]oxy]acetic acid;

2-[ethyl[cis,cis-2,3,3a,4,9,9a-hexahydro-4-[4-(trifluoromethoxy)benzoyl]-1H-cyclopenta[b]quinolin-9-yl]amino]-4-oxazolecarboxylic acid;

3-(phenylmethyl)cis,cis-8-[(3-carboxypropyl)cyclopropylamino]-5-fluoro-2,2a,8,8a-tetrahydrocyclobuta[b]quinoline-3(1H)-carboxylate;

4-[cyclopropyl[cis,cis-2,3,3a,4,9,9a-hexahydro-4-[4-(trifluoromethoxy)benzoyl]-1H-cyclopenta[b]quinolin-9-yl]amino]butanoic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]butanoic acid;

4-[cyclopropyl[(cis,cis)-2,3,3a,4,9,9a-hexahydro-4-[4-[(trifluoromethyl)thio]benzoyl]-1H-cyclopenta[b]quinolin-9-yl]amino]-4-oxobutanoic acid;

4-(ethyl((cis,cis)-3-(4-(trifluoromethylthio)benzoyl)-1,2,2a,3,8,8a-hexahydrocyclobuta[b]quinolin-8-yl)amino)-4-oxobutanoic acid;

4-(ethyl((cis,cis)-3-(4-ethylbenzoyl)-1,2,2a,3,8,8a-hexahydrocyclobuta[b]quinolin-8-yl)amino)-4-oxobutanoic acid;

3-(phenylmethyl) 8-[(3-carboxy-1-oxopropyl)cyclopropylamino]-5,6-difluoro-2,2a,8,8a-tetrahydro-cyclobuta[b]quinoline-3(1H)-carboxylate;

4-[cyclopropyl[(cis,cis)-5,6-dichloro-1,2,2a,3,8,8a-hexahydro-3-[4-(trifluoromethoxy)benzoyl]cyclobuta[b]quinolin-8-yl]amino]-4-oxobutanoic acid;

4-(cyclopropyl((cis,cis)-5,6-difluoro-3-(4-(trifluoromethoxy)benzoyl)-1,2,2a,3,8,8a-hexahydrocyclobuta[b]quinolin-8-yl)amino)-4-oxobutanoic acid;

4-[cyclopropyl[(cis,cis)-6-fluoro-2,3,3a,4,9,9a-hexahydro-4-[4-(trifluoromethoxy)benzoyl]-1H-cyclopenta[b]quinolin-9-yl]amino]-4-oxo-butanoic acid;

(R)-1-(((cis,cis)-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid;

4-(cyclopropyl(cis,cis-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid; and 4-(cyclopropyl(cis,cis-7-fluoro-4-(4-(trifluoromethoxy)benzoyl)-2,3,3a,4,9,9a-hexahydro-1H-cyclopenta[b]quinolin-9-yl)amino)butanoic acid.

14. The compound of claim 1 or a pharmaceutically acceptable salt thereof, wherein the compound is selected from the group consisting of:

4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid;

4-[cyclopropyl[cis,cis-7-fluoro-2,3,3a,4,9,9a-hexahydro-4-[4-(trifluoromethoxy)benzoyl]-1H-cyclopenta[b]quinolin-9-yl]amino]-4-oxobutanoic acid;

4-[[cis,cis-6-chloro-7-fluoro-2,3,3a,4,9,9a-hexahydro-4-[4-(trifluoromethoxy)benzoyl]-1H-cyclopenta[b]quinolin-9-yl]cyclopropylamino]-4-oxobutanoic acid;

4-[cyclopropyl[cis,cis-5-fluoro-1,2,2a,3,8,8a-hexahydro-3-[4-(trifluoromethoxy)benzoyl]cyclobuta[b]quinolin-8-yl]amino]-4-oxobutanoic acid;

4-[cyclopropyl[cis,cis-6-fluoro-1,2,2a,3,8,8a-hexahydro-3-[4-(trifluoromethoxy)benzoyl]cyclobuta[b]quinolin-8-yl]amino]-4-oxobutanoic acid;

3-(phenylmethyl)(cis,cis)-8-[(3-carboxy-1-oxopropyl)cyclopropylamino]-5-chloro-2,2a,8,8a-tetrahydrocyclobuta[b]quinoline-3(1H)-carboxylate;

3-(phenylmethyl)(cis,cis)-8-[(3-carboxy-1-oxopropyl)cyclopropylamino]-2,2a,8,8a-tetrahydrocyclobuta[b]quinoline-3(1H)-carboxylate;

4-[cyclopropyl[cis,cis-1,2,2a,3,8,8a-hexahydro-3-[4-(trifluoromethoxy)benzoyl]cyclobuta[b]quinolin-8-yl]amino]-4-oxobutanoic acid;

[[[cyclopropyl[cis,cis-3-(3,4-difluorobenzoyl)-1,2,2a,3,8,8a-hexahydrocyclobuta[b]quinolin-8-yl]amino]carbonyl]oxy]acetic acid;

3-(phenylmethyl)cis,cis-8-[(3-carboxypropyl)cyclopropylamino]-5-fluoro-2,2a,8,8a-tetrahydrocyclobuta[b]quinoline-3(1H)-carboxylate;

4-[cyclopropyl[cis,cis-2,3,3a,4,9,9a-hexahydro-4-[4-(trifluoromethoxy)benzoyl]-1H-cyclopenta[b]quinolin-9-yl]amino]butanoic acid;

4-[cyclopropyl[cis,cis-2,3,3a,4,9,9a-hexahydro-4-[4-[(trifluoromethyl)thio]benzoyl]-1H-cyclopenta[b]quinolin-9-yl]amino]-4-oxobutanoic acid;

(R)-1-((cis,cis-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid;

4-(cyclopropyl(cis,cis-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-6-fluoro-3-(4-((trifluoromethyl)thio)benzoyl)-1,2,2a,3,8,8a-hexahydrocyclobuta[b]quinolin-8-yl)amino)-4-oxobutanoic acid;

4-(ethyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid;

4-(cyclopropyl(cis,cis-7-fluoro-4-(4-((trifluoromethyl)thio)benzoyl)-2,3,3a,4,9,9a-hexahydro-1H-cyclopenta[b]quinolin-9-yl)amino)-4-oxobutanoic acid; and 4-(cyclopropyl(cis,cis-7-fluoro-4-(4-(trifluoromethoxy)benzoyl)-2,3,3a,4,9,9a-hexahydro-1H-cyclopenta[b]quinolin-9-yl)amino)butanoic acid.

15. A pharmaceutical formulation comprising a therapeutically effective amount of the compound of claim 1 or a pharmaceutically acceptable salt thereof, and a pharmaceutically acceptable carrier.

16. A method for treating a disease or condition associated with uncontrolled or inappropriate stimulation of $CRTH_2$ function, wherein the disease or condition is asthma, allergic rhinitis, or COPD, comprising administering to a patient in need of such treatment a therapeutically amount of a compound of claim 1 or a pharmaceutically acceptable salt thereof.

17. A method for treating a disease or condition associated with uncontrolled or inappropriate stimulation of $CRTH_2$ function, wherein the disease or condition is asthma, allergic rhinitis, or COPD, comprising administering to a patient in need of such treatment a therapeutically amount of a compound of claim 1 or a pharmaceutically acceptable salt thereof and an additional therapeutic agent.

18. A compound which is 4-{cyclopropyl[cis,cis-4-{[4-(trifluoromethoxy)phenyl]carbonyl}-2,3,3a,4,9,9a-hexahydro-1H-cyclopenta[b]quinolin-9-yl]amino}-4-oxobutanoic acid, or a pharmaceutically acceptable salt thereof.

19. A compound which is 4-[cyclopropyl[cis,cis-7-fluoro-2,3,3a,4,9,9a-hexahydro-4-[4-(trifluoromethoxy)benzoyl]-1H-cyclopenta[b]quinolin-9-yl]amino]-4-oxobutanoic acid, or a pharmaceutically acceptable salt thereof.

20. A compound which is 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoic acid, or a pharmaceutically acceptable salt thereof.

21. A compound which is 4-[cyclopropyl[cis,cis-1,2,2a,3,8,8a-hexahydro-3-[4-(trifluoromethoxy)benzoyl]cyclobuta[b]quinolin-8-yl]amino]-4-oxobutanoic acid, or a pharmaceutically acceptable salt thereof.

22. A compound which is (R)-1-((cis,cis-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid, or a pharmaceutically acceptable salt thereof.

23. A pharmaceutical formulation comprising a therapeutically effective amount of the compound of claim 18 or a pharmaceutically acceptable salt thereof, and a pharmaceutically acceptable carrier.

24. A pharmaceutical formulation comprising a therapeutically effective amount of the compound of claim 19 or a pharmaceutically acceptable salt thereof, and a pharmaceutically acceptable carrier.

25. A pharmaceutical formulation comprising a therapeutically effective amount of the compound of claim 20 or a pharmaceutically acceptable salt thereof, and a pharmaceutically acceptable carrier.

26. A pharmaceutical formulation comprising a therapeutically effective amount of the compound of claim 21 or a pharmaceutically acceptable salt thereof, and a pharmaceutically acceptable carrier.

27. A pharmaceutical formulation comprising a therapeutically effective amount of the compound of claim 22 or a pharmaceutically acceptable salt thereof, and a pharmaceutically acceptable carrier.

28. The pharmaceutical formulation of claim 15, further comprising a leukotriene receptor antagonist selected from the group consisting of montelukast, zafirlukast, and pranlukast.

29. The pharmaceutical formulation of claim 28 wherein the leukotriene receptor antagonist is montelukast.

30. The method of claim 16, wherein the disease or condition is asthma.

31. The method of claim 17, wherein the disease or condition is asthma.

32. The method of claim 17, wherein the additional therapeutic agent is a leukotriene receptor antagonist selected from the group consisting of montelukast, zafirlukast, and pranlukast.

33. The method of claim 32, wherein the leukotriene receptor antagonist is montelukast.

34. A method of treating asthma, comprising administering to a patient in need of such treatment a therapeutically amount of a compound of the compound of claim 18 or a pharmaceutically acceptable salt thereof.

35. A method of treating asthma, comprising administering to a patient in need of such treatment a therapeutically amount of a compound of the compound of claim 19 or a pharmaceutically acceptable salt thereof.

36. A method of treating asthma, comprising administering to a patient in need of such treatment a therapeutically amount of a compound of the compound of claim 20 or a pharmaceutically acceptable salt thereof.

37. A method of treating asthma, comprising administering to a patient in need of such treatment a therapeutically amount of a compound of the compound of claim 21 or a pharmaceutically acceptable salt thereof.

38. A method of treating asthma, comprising administering to a patient in need of such treatment a therapeutically amount of a compound of the compound of claim 22 or a pharmaceutically acceptable salt thereof.

39. The method of claim 34, further comprising administering montelukast to the patient.

40. The method of claim 35, further comprising administering montelukast to the patient.

41. The method of claim 36, further comprising administering montelukast to the patient.

42. The method of claim 37, further comprising administering montelukast to the patient.

43. The method of claim 38, further comprising administering montelukast to the patient.

44. The pharmaceutical formulation of claim 23, further comprising montelukast.

45. The pharmaceutical formulation of claim 24, further comprising montelukast.

46. The pharmaceutical formulation of claim 25, further comprising montelukast.

47. The pharmaceutical formulation of claim 26, further comprising montelukast.

48. The pharmaceutical formulation of claim 27, further comprising montelukast.

\* \* \* \* \*